US008884010B2

(12) United States Patent
Jachmann et al.

(10) Patent No.: US 8,884,010 B2

(45) Date of Patent: Nov. 11, 2014

(54) METHOD FOR PRODUCING PYRIDAZINONE COMPOUNDS AND INTERMEDIATE THEREOF

(75) Inventors: Markus Jachmann, Tokyo (JP); Takayuki Wakamatsu, Osaka (JP); Mitsuharu Anryu, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/819,112

(22) PCT Filed: Sep. 7, 2011

(86) PCT No.: PCT/JP2011/070914
§ 371 (c)(1), (2), (4) Date: Mar. 18, 2013

(87) PCT Pub. No.: WO2012/033225
PCT Pub. Date: Mar. 15, 2012

(65) Prior Publication Data

US 2013/0172556 A1 Jul. 4, 2013

(30) Foreign Application Priority Data

Sep. 8, 2010 (JP) ................................ 2010-200669
Jun. 22, 2011 (JP) ................................ 2011-138217

(51) Int. Cl.
*C07D 237/04* (2006.01)
*C07D 237/16* (2006.01)
(Continued)

(52) U.S. Cl.
CPC ............ *C07D 237/16* (2013.01); *C07D 237/18* (2013.01); *C07C 69/738* (2013.01); (Continued)

(58) Field of Classification Search
CPC ..................................................... C07D 237/04
USPC ......................................................... 544/240
See application file for complete search history.

(56) References Cited

U.S. PATENT DOCUMENTS 6,525,053 B1 2/2003 Black
2002/0188018 A1 12/2002 Gong et al.
(Continued)

FOREIGN PATENT DOCUMENTS

CN 1444581 9/2003
CN 1676518 A 10/2005
(Continued)

OTHER PUBLICATIONS

International Search Report issued Oct. 25, 2011 in International (PCT) Application No. PCT/JP2011/070914.
(Continued)

*Primary Examiner* — Brian McDowell

(74) *Attorney, Agent, or Firm* — Wenderoth, Lind & Ponack, L.L.P.

(57) ABSTRACT

The present invention relates to a novel method for producing a pyridazinone compound and an intermediate thereof as shown in the following scheme: wherein the symbols are as defined in the specification.

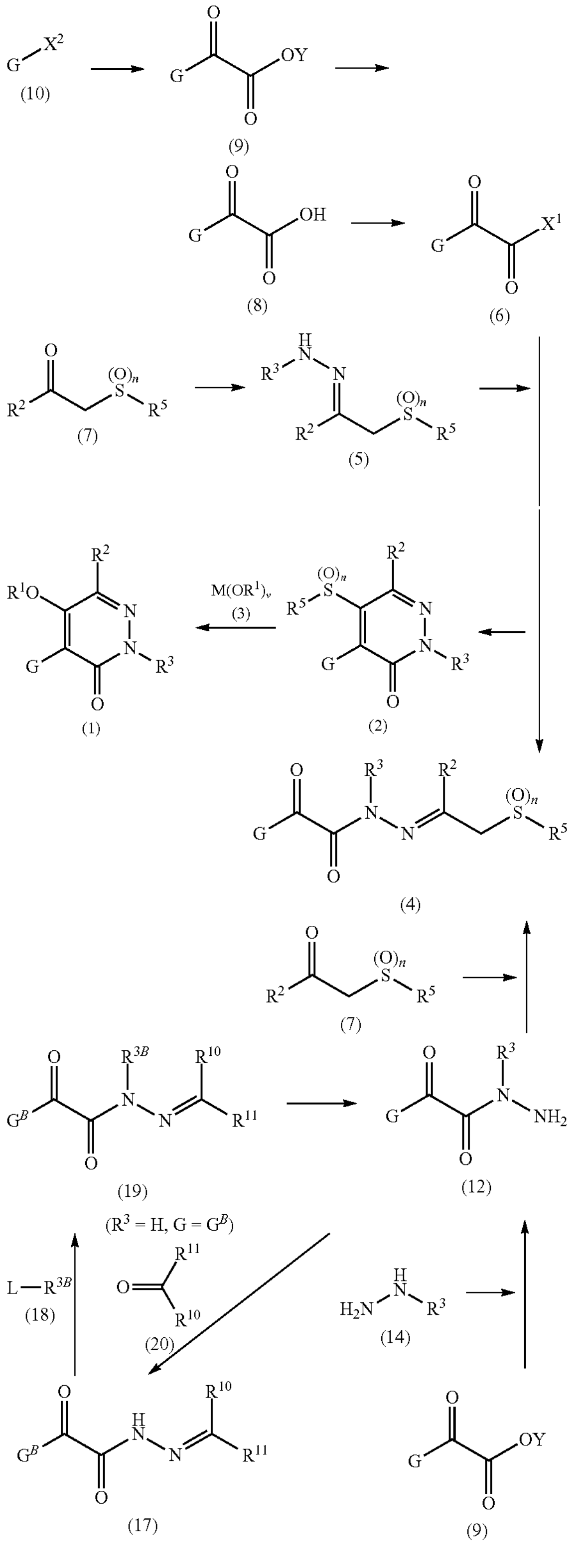

5 Claims, No Drawings

(51) Int. Cl.

| | |
|---|---|
| ***C07D 237/18*** | (2006.01) |
| ***C07C 69/738*** | (2006.01) |
| ***C07C 315/04*** | (2006.01) |
| ***C07C 319/20*** | (2006.01) |
| ***C07C 317/28*** | (2006.01) |
| ***C07D 209/24*** | (2006.01) |
| ***C07C 59/88*** | (2006.01) |
| ***C07C 243/32*** | (2006.01) |
| ***C07C 59/84*** | (2006.01) |
| ***C07C 323/48*** | (2006.01) |
| ***C07C 251/76*** | (2006.01) |
| ***C07D 403/04*** | (2006.01) |

(52) U.S. Cl.

CPC ............. *C07C 315/04* (2013.01); *C07C 319/20* (2013.01); *C07C 317/28* (2013.01); *C07D 209/24* (2013.01); *C07C 59/88* (2013.01); *C07C 243/32* (2013.01); *C07C 59/84* (2013.01); *C07C 323/48* (2013.01); *C07C 251/76* (2013.01); *C07D 403/04* (2013.01)

USPC .......................................................... 544/240

(56) References Cited

U.S. PATENT DOCUMENTS

| | | | |
|---|---|---|---|
| 2003/0176484 | A1 | 9/2003 | Day-Lollini et al. |
| 2005/0020594 | A1 | 1/2005 | Hepperle et al. |
| 2005/0054645 | A1 | 3/2005 | Miyazaki et al. |
| 2008/0280957 | A1 | 11/2008 | Marlow et al. |
| 2009/0011696 | A1 | 1/2009 | Matthews |
| 2009/0111696 | A1 | 4/2009 | Kiji et al. |
| 2009/0156608 | A1 | 6/2009 | Souma et al. |
| 2009/0221832 | A1 | 9/2009 | Cotte et al. |
| 2010/0216642 | A1 | 8/2010 | Fusaka |

FOREIGN PATENT DOCUMENTS

| | | |
|---|---|---|
| CN | 1962642 A | 5/2007 |
| CN | 101443317 | 5/2009 |
| EP | 1 048 667 | 11/2000 |
| EP | 0 835 865 | 3/2003 |
| JP | 52-91883 | 8/1977 |
| JP | 2004-505078 | 2/2004 |
| JP | 2005-519056 | 6/2005 |
| JP | 2007-182430 | 7/2007 |
| JP | 2008-133252 | 6/2008 |
| JP | 2009-84276 | 4/2009 |
| JP | 2009-215312 | 9/2009 |
| JP | 2009-221198 | 10/2009 |
| WO | 02/10158 | 2/2002 |
| WO | 2004/058729 | 7/2004 |
| WO | 2005/007632 | 1/2005 |
| WO | 2005/051301 | 6/2005 |
| WO | 2005/077915 | 8/2005 |
| WO | 2007/061923 | 5/2007 |
| WO | 2007/080720 | 7/2007 |
| WO | 2007/119434 | 10/2007 |
| WO | 2008/002671 | 1/2008 |
| WO | 2008/103277 | 8/2008 |
| WO | 2009/035150 | 3/2009 |
| WO | 2009/086041 | 7/2009 |
| WO | 2009/090039 | 7/2009 |
| WO | 2009/142732 | 11/2009 |

OTHER PUBLICATIONS

International Preliminary Report on Patentability issued Mar. 12, 2013 and Written Opinion of the International Searching Authority issued Oct. 25, 2011 in International Application No. PCT/JP2011/070914.

Ryabtsova, O. et al., "Synthesis of Functionalized Pyridazin-3(2H)-ones via Bromine-Magnesium Exchange on Bromopyridazin-3(2H)-ones", The Journal of Organic Chemistry, 2009, 74(24), pp. 9440-9445.

Datebase CAplus on STN, AN 1994:134399, re: Takahashi, M. et al., "Synthesis of 3-(trifluoromethyl)pyrazoles and 3-(trifluoromethyl)pyridazines from 2-amino-1,1,1-trifluoro-3-(phenylsulfonyl)-2-propanol", Heterocycles, 1993, 35(2), pp. 909-914.

Datebase CAplus on STN, AN 1967:28473, re: Strating J. et al., "Synthesis of β-diazo sulfones", Recueil des Travaux Chimiques des Pays-Bas, 1966, 85(9-10), pp. 1061-1067.

Datebase CAplus on STN, AN 1957:34712, re: Carpino, L., "Oxidative reactions of hydrazines. I. A new synthesis of acid chlorides", Journal of the American Chemical Society, 1957, 79, pp. 96-98.

Datebase CAplus on STN, AN 1999:465384, re: Hu, S. et al., "Photocycloaddition and ortho-hydrogen abstraction reactions of methyl arylglyoxylates: structure dependent reactivities", Journal of the Chemical Society, Perkin Transactions 2: Physical Organic Chemistry, 1999, 8, pp. 1771-1778.

Supplementary European Search Report issued Feb. 26, 2014 in European Application No. 11 82 3693.

Sotelo et al., "Pyridazines. Part XXIX: Synthesis and Platelet Aggregation Inhibition Activity of 5-Substituted-6-phenyl-3(2*H*)-pyridazinones. Novel Aspects of Their Biological Actions", Bioorganic & Medicinal Chemistry, vol. 10, No. 9, Sep. 1, 2002, pp. 2873-2882.

Jelen et al., "Directed Regiospecificity of 1,3-Dipolar Cycloaddition of 2-Diazopropane to 4- and 5-substituted Pyridazin-3(2*H*)-ones", Journal of Heterocyclic Chemistry, vol. 28, No. 2, Feb. 1, 1991, pp. 369-372.

Office Action issued May 26, 2014, in corresponding Chinese Application No. 201180052521.6, with English translation.

METHOD FOR PRODUCING PYRIDAZINONE COMPOUNDS AND INTERMEDIATE THEREOF

TECHNICAL FIELD

The present invention relates to a method for producing pyridazinone compounds and intermediates thereof.

BACKGROUND ART

A certain pyridazinone compound is known to be useful as an active ingredient in a medicine or pesticide or be used as an intermediate of a medicine or pesticide (see, Patent Literatures 1-10).

CITATION LIST

Patent Literature

Patent Literature 1: WO 2007-119434
Patent Literature 2: WO 2009-035150

Patent Literature 3: WO 2009-086041
Patent Literature 4: WO 2007-080720
Patent Literature 5: WO 2009-090039
Patent Literature 6: EP 835 865 A
Patent Literature 7: WO 2004-058729
Patent Literature 8: WO 2005-007632
Patent Literature 9: WO 2005-077915
Patent Literature 10: JP-A-2009-215312

SUMMARY OF INVENTION

Technical Problem

The present invention provides a novel method for producing pyridazinone compounds and the intermediates thereof.

Solution to Problem

The present invention relates to a novel method for producing pyridazinone compounds and the intermediates thereof. The summary is shown below:

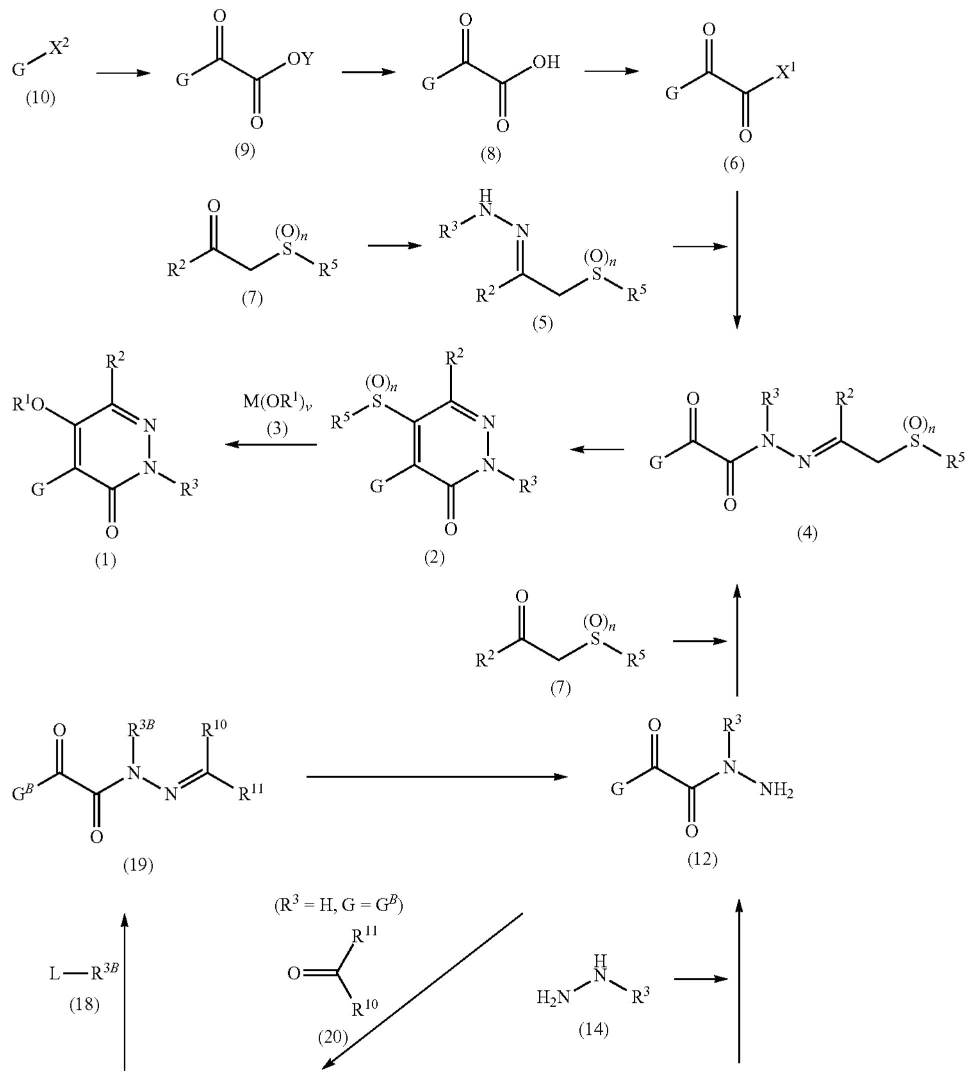

-continued

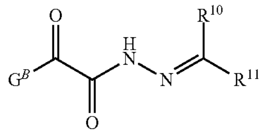

(17)

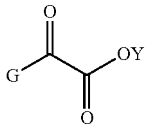

(9)

wherein the symbols in each formula are defined as follows:

$R^1$ represents hydrogen, a C1-C6 alkyl group, or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 1, provided that when it has two or more substituents, then the substituents may be same or different;

the Group 1 consists of halogen, a cyano group, a nitro group, a C1-C6 alkyl group, a C1-C6 alkoxy group, and a (C1-C6 alkoxy)C1-C6 alkyl group;

in the Group 1, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$R^2$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio) C1-C6 alkyl group, a (C1-C6 alkylsulfinyl)C1-C6 alkyl group, a (C1-C6 alkylsulfonyl)C1-C6 alkyl group, a phenyl group, or a 5- or 6-membered heteroaryl group;

wherein the C1-C6 alkyl group, the (C1-C6 alkoxy)C1-C6 alkyl group, the C2-C6 alkenyl group, the C2-C6 alkynyl group, the C3-C6 cycloalkyl group, the (C1-C6 alkylthio)C1-C6 alkyl group, the (C1-C6 alkylsulfinyl)C1-C6 alkyl group, and the (C1-C6 alkylsulfonyl)C1-C6 alkyl group may be optionally substituted with one or more halogens, provided that when they are substituted with two or more halogens, then the halogens may be same or different, the phenyl group and the 5- or 6-membered heteroaryl group may optionally have one or more substituents selected from Group 2, provided that when they have two or more substituents, then the substituents may be same or different, the Group 2 consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 2, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

$R^3$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio) C1-C6 alkyl group, a C1-C6 alkylsulfonyl group, a (C1-C6 alkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a phenyl group, a benzyl group, or a phenylsulfonyl group;

wherein the C1-C6 alkyl group, the (C1-C6 alkoxy)C1-C6 alkyl group, the C2-C6 alkenyl group, the C2-C6 alkynyl group, the C3-C6 cycloalkyl group, the (C1-C6 alkylthio)C1-C6 alkyl group, the C1-C6 alkylsulfonyl group, the (C1-C6 alkyl)carbonyl group, and the (C1-C6 alkoxy)carbonyl group may be optionally substituted with one or more halogens, provided that when they are substituted with two or more halogens, then the halogens may be same or different; and the phenyl group, the benzyl group, and the phenylsulfonyl group may optionally have one or more substituents selected from Group 3, provided that when they have two or more substituents, then the substituents may be same or different;

the Group 3 consists of halogen, a C1-C6 alkyl group, a C1-C6 alkoxy group, and a (C1-C6 alkoxy)C1-C6 alkyl group;

in the Group 3, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$R^5$ represents a C1-C6 alkyl group or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 5, provided that when it has two or more substituents, then the substituents may be same or different, the Group 5 consists of halogen, a C1-C6 alkyl group and a C1-C6 alkoxy group;

in the Group 5, the C1-C6 alkyl group and the C1-C6 alkoxy group may be optionally substituted with one or more halogens, provided that when they are substituted with two or more halogens, then the halogens may be same or different;

G represents a C6-C10 aryl group, a 5- or 6-membered heteroaryl group, or an 8- to 10-membered fused heteroaryl group;

wherein the C6-C10 aryl group, the 5- or 6-membered heteroaryl group, and the 8- to 10-membered fused heteroaryl group may optionally have one or more substituents selected from Group $R^4$, provided that when they have two or more substituents, then the substituents may be same or different, the Group $R^4$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^4$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and in the Group $R^4$, the C6-C10 aryl group and the 5- or 6-membered heteroaryl group may optionally have one or more substituents selected from Group 4, provided that when they have two or more substituents, then the substituents may be same or different;

the Group 4 consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 4, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

n represents an integer of 0, 1 or 2;

V represents an integer of 1 or 2;

M represents an alkali metal when V is an integer of 1, and M represents an alkali earth metal when V is an integer of 2;

$X^1$ represents fluorine, chlorine, bromine, or iodine;

$X^2$ represents chlorine, bromine, or iodine;

Y represents a C1-C6 alkyl group wherein the C1-C6 alkyl group may be optionally substituted with one or more halogens, provided that when it is substituted with two or more halogens, then the halogens may be same or different;

$R^{3B}$ represents a C1-C6 alkyl group, a (C1-C6 alkoxy)C1-C6 alkyl group, a C2-C6 alkenyl group, a C2-C6 alkynyl group, a (C1-C6 alkylthio)C1-C6 alkyl group, a C1-C6 alkylsulfonyl group, a (C1-C6 alkyl)carbonyl group, a (C1-C6 alkoxy)carbonyl group, a di(C1-C6 alkyl)aminocarbonyl group, a benzyl group, or a phenylsulfonyl group;

wherein the C1-C6 alkyl group, the (C1-C6 alkoxy)C1-C6 alkyl group, the C2-C6 alkenyl group, the C2-C6 alkynyl group, the (C1-C6 alkylthio)C1-C6 alkyl group, the C1-C6 alkylsulfonyl group, the (C1-C6 alkyl)carbonyl group, and the (C1-C6 alkoxy)carbonyl group may be optionally substituted with one or more halogens, provided that when they are substituted with two or more halogens, then the halogens may be same or different; and the benzyl group, and the phenylsulfonyl group may optionally have one or more substituents selected from Group 3B, provided that when they have two or more substituents, then the substituents may be same or different, the Group 3B consists of halogen, a C1-C6 alkyl group, a C1-C6 alkoxy group, and a (C1-C6 alkoxy)C1-C6 alkyl group;

in the Group 3B, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$G^B$ represents a phenyl group;

wherein the phenyl group may optionally have one or more substituents selected from Group $R^{4-B}$, provided that when they have two or more substituents, then the substituents may be same or different;

the Group $R^{4-B}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, (C1-C6 alkoxy)carbonyl group, a (C1-C6 alkylamino) carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4-B}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-B, provided that when they have two or more substituents, then the substituents may be same or different;

the Group 4-B consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 4-B, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

$R^{10}$ and $R^{11}$ may be same or different, and each represents hydrogen, C1-C6 alkyl group, a C3-C6 cycloalkyl group or a phenyl group, or $R^{10}$ and $R^{11}$ may be combined to form 5- or 6-membered cyclic group with a carbon atom which is bonded with $R^{10}$ and $R^{11}$, wherein the C1-C6 alkyl group and the C3-C6 cycloalkyl group may be optionally substituted with one or more halogens, provided that when it is substituted with two or more halogens, then the halogens may be same or different; and the phenyl group may optionally have one or more substituents selected from Group 10, provided that when it has two or more substituents, then the substituents may be same or different;

the Group 10 consists of halogen, a C1-C6 alkyl group and a C1-C6 alkoxy group; and L represents halogen, a C1-C6 alkylsulfonyloxy group or a C1-C6 alkoxysulfonyloxy group.

Effects of Invention

According to the present invention, various pyridazinone compounds which are useful as an active ingredient in a medicine or pesticide can be prepared.

In particular, the present invention provides:

[1] A method for producing a compound of the formula (1):

(1)

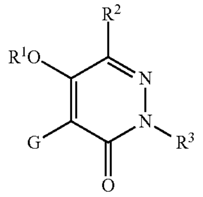

which comprises reacting a compound of the formula (2):

(2)

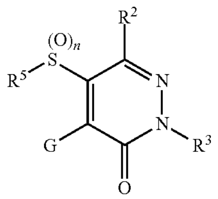

with a compound of the formula (3):

$$M(OR^1)_v \quad (3);$$

wherein the symbols in the formulae (1), (2) and (3) are as defined above.

[2] The method according to the above [1], wherein n is an integer of 2.

[3] The method according to the above [1] or [2], wherein G is a phenyl group wherein the phenyl group may optionally have one or more substituents selected from the Group $R^4$, provided that when it has two or more substituents, then the substituents may be same or different.

[4] The method according to any one of the above [1]-[3], wherein the Group $R^4$ is Group $R^{4-1}$;

wherein the Group $R^{4-1}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group. $R^{4-1}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-1, provided that when it has two or more substituents, then the substituents may be same or different;

the Group 4-1 consists of halogen and a C1-C6 alkyl group;

in the Group 4-1, the C1-C6 alkyl group may be optionally substituted with one or more halogens, provided that when it is substituted with two or more halogens, then the halogens may be same or different.

[5] The method according to the above [4], wherein $R^1$ is hydrogen, a C1-C6 alkyl group or a phenyl group, $R^2$ is hydrogen, a C1-C6 alkyl group or a phenyl group wherein the C1-C6 alkyl group may be optionally substituted with one or more halogens, provided that when it is substituted with two or more halogens, then the halogens may be same or different, and the phenyl group may optionally have one or more halogens, provided that when it has two or more halogens, then the halogens may be same or different;

$R^3$ is hydrogen, a C1-C6 alkyl group, a (C1-C6 alkoxy)C1-C6 alkyl group, or a benzyl group wherein the C1-C6 alkyl group, and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and a C1-C6 alkoxy group, provided that when they have two or more substituents, then the substituents may be same or different;

$R^5$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have one or more a C1-C6 alkyl group, provided that when it has two or more C1-C6 alkyl groups, then the C1-C6 alkyl groups may be same or different; and G is a phenyl group, a pyridyl group, an indolyl group or a pyrazolyl group wherein the phenyl group, the pyridyl group, the indolyl group and the pyrazolyl group may optionally have one or more substituents selected from Group $R^{4-1}$, provided that when they have two or more substituents, then the substituents may be same or different.

[6] The method according to the above [1], wherein $R^1$ is hydrogen, a methyl group, an ethyl group, a n-butyl group or a phenyl group, $R^2$ is a methyl group, a 4-fluorophenyl group or a trifluoromethyl group, $R^3$ is a methyl group or a benzyl group, $R^5$ is a methyl group or a 4-methylphenyl group, and G is a 2,4,6-triethylphenyl group, a 2-ethyl-5-(4-chlorophenyl) phenyl group, a 1-methylindol-3-yl group or a 2,6-diethyl-4-methylphenyl group.

[7] A method for producing a compound of the formula (1):

(1)

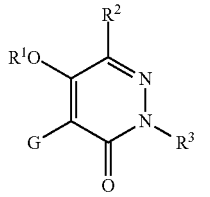

which comprises the steps of:

reacting a compound of the formula (4):

(4)

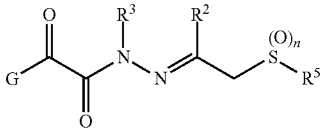

with a base to obtain a compound of the formula (2):

(2)

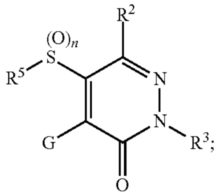

and reacting the compound of the formula (2) with a compound of the formula (3):

$M(OR^1)_v$ (3);

wherein the symbols in the formulae (1), (2), (3) and (4) are as defined above.

[8] A method for producing a compound of the formula (2):

(2)

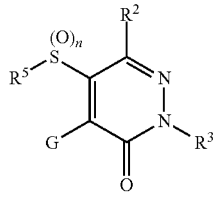

which comprises reacting a compound of the formula (4):

(4)

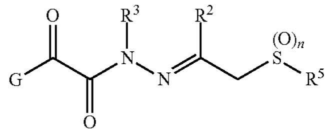

with a base;

wherein the symbols in the formulae (2) and (4) are as defined above.

[9] The method according to the above [8], wherein G is a phenyl group wherein the phenyl group may optionally have one or more substituents selected from the Group $R^4$, provided that when it has two or more substituents, then the substituents may be same or, different.

[10] The method according to the above [8] or [9], wherein the Group $R^4$ is Group $R^{4-3}$;

wherein the Group $R^{4-3}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-3}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-3, provided that when it has two or more substituents, then the substituents may be same or different;

the Group 4-3 consists of halogen and a C1-C6 alkyl group;

in the Group 4-3, the C1-C6 alkyl group may be optionally substituted with one or more halogens, provided that when it is substituted with two or more halogens, then the halogens may be same or different.

[11] The method according to the above [10], wherein $R^2$ is hydrogen, a C1-C6 alkyl group or a phenyl group wherein the C1-C6 alkyl group may be optionally substituted with one or more halogens, provided that when it is substituted with two or more halogens, then the halogens may be same or different, and the phenyl group may optionally have one or more halogens, provided that when it has two or more halogens, then the halogens may be same or different;

$R^3$ is hydrogen, a C1-C6 alkyl group, a (C1-C6 alkoxy)C1-C6 alkyl group, or a benzyl group wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and a C1-C6 alkoxy group, provided that when they have two or more substituents, then the substituents may be same or different;

$R^5$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have a C1-C6 alkyl group, provided that when it has two or more C1-C6 alkyl groups, then the C1-C6 alkyl groups may be same or different; and G is a phenyl group, a pyridyl group, an indolyl group or a pyrazolyl group wherein the phenyl group, the pyridyl group, the indolyl group and the pyrazolyl group may optionally have one or more substituents selected from Group $R^{4-3}$, provided that when they have two or more substituents, then the substituents may be same or different

[12] The method according to the above [8], wherein $R^2$ is a methyl group, a 4-fluorophenyl group or a trifluoromethyl group, $R^3$ is a methyl group or a benzyl group, $R^5$ is a methyl group or a 4-methylphenyl group, and G is a 2,4,6-triethylphenyl group, a 2-ethyl-5-(4-chlorophenyl)phenyl group, a 1-methylindol-3-yl group or a 2,6-diethyl-4-methylphenyl group.

[13] A method for producing a compound of the formula (1):

(1)

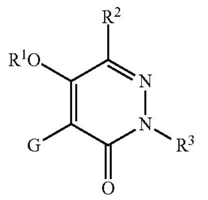

which comprises the steps of:

reacting a compound of the formula (5):

(5)

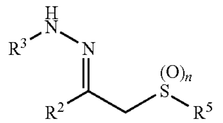

with a compound of the formula (6):

(6)

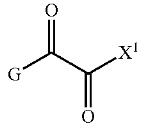

to obtain a compound of the formula (4):

(4)

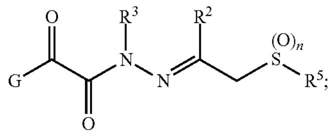

reacting the compound of the formula (4) with a base to obtain a compound of the formula (2):

(2)

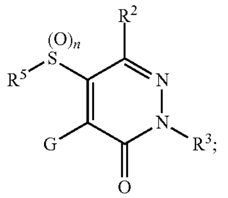

and reacting the compound of the formula (2) with a compound of the formula (3):

$$M(OR^1)_v \quad (3);$$

wherein the symbols in the formulae (1), (2), (3), (4), (5) and (6) are as defined above.

[14] A method for producing a compound of the formula (4):

(4)

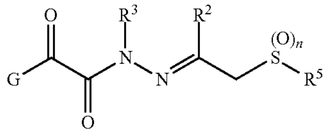

which comprises reacting a compound of the formula (5):

(5)

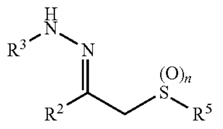

with a compound of the formula (6):

(6)

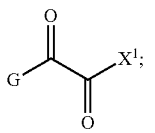

wherein the symbols in the formulae (4), (5) and (6) are as defined above.

[15] The method according to the above [14], wherein G is a phenyl group wherein the phenyl group may optionally have one or more substituents selected from the Group $R^4$, provided that when it has two or more substituents, then the substituents may be same or different.

[16] The method according to the above [14] or [15], wherein the Group $R^4$ is Group $R^{4-5}$;

wherein the Group $R^{4-5}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-5}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-5, provided that when it has two or more substituents, then the substituents may be same or different;

the Group 4-5 consists of halogen and a C1-C6 alkyl group;

in the Group 4-5, the C1-C6 alkyl group may be optionally substituted with one or more halogens, provided that when it is substituted with two or more halogens, then the halogens may be same or different.

[17] The method according to the above [16], wherein $R^2$ is hydrogen, a C1-C6 alkyl group or a phenyl group wherein the C1-C6 alkyl group may be optionally substituted with one or more halogens, provided that when it is substituted with two or more halogens, then the halogens may be same or different, and the phenyl group may optionally have one or more halogens, provided that when it has two or more halogens, then the halogens may be same or different;

$R^3$ is hydrogen, a C1-C6 alkyl group, a (C1-C6 alkoxy)C1-C6 alkyl group, or a benzyl group wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and a C1-C6 alkoxy group, provided that when it has two or more substituents, then the substituents may be same or different;

$R^5$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have one or more a C1-C6 alkyl group, provided that when it has two or more C1-C6 alkyl groups, then the C1-C6 alkyl groups may be same or different; and G is a phenyl group, a pyridyl group, an indolyl group or a pyrazolyl group wherein the phenyl group, the pyridyl group, the indolyl group and the pyrazolyl group may optionally have one or more substituents selected from Group $R^{4-5}$, provided that when they have two or more substituents, then the substituents may be same or different.

[18] The method according to the above [14], wherein $R^2$ is a methyl group or a 4-fluorophenyl group, $R^3$ is a methyl group or a benzyl group, $R^5$ is a methyl group, G is a 2,4,6-triethylphenyl group, a 2-ethyl-5-(4-chlorophenyl)phenyl group, a 5-ethyl-3-(4-trifluoromethylphenyl)pyrazol-1-yl group, a 1-methylindol-3-yl group or a 2,6-diethyl-4-methylphenyl group, and $X^1$ is chlorine.

[19] A method for producing a compound of the formula (1):

(1)

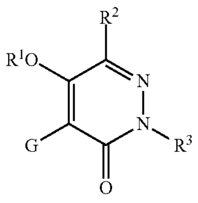

which comprises the steps of:

reacting a compound of the formula (7):

(7)

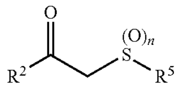

with a compound of the formula (12):

(12)

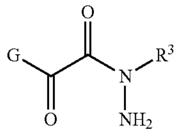

to obtain a compound of the formula (4):

(4)

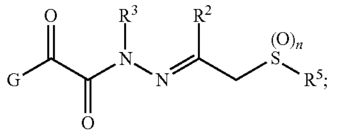

reacting the compound of the formula (4) with a base to obtain a compound of the formula (2):

(2)

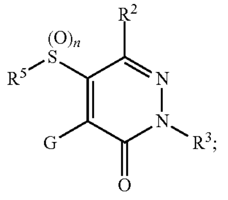

and reacting the compound of the formula (2) with a compound of the formula (3):

$M(OR^1)_v$ (3);

wherein the symbols in the formulae (1), (2), (3), (4), (7) and (12) are as defined above.

[20] A method for producing a compound of the formula (4):

(4)

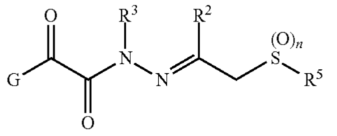

which comprises reacting a compound of the formula (7):

(7)

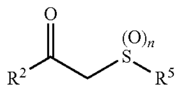

with a compound of the formula (12):

(12)

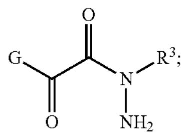

wherein the symbols in the formulae (4), (7) and (12) are as defined above.

[21] The method according to the above [20], wherein G is a phenyl group wherein the phenyl group may optionally have one or more substituents selected from the Group $R^4$, provided that when it has two or more substituents, then the substituents may be same or different.

[22] The method according to the above [20] or [21], wherein the Group $R^4$ is Group $R^{4-7}$;

wherein the Group $R^{4-7}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-7}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-7, provided that when it has two or more substituents, then the substituents may be same or different;

the Group 4-7 consists of halogen and a C1-C6 alkyl group;

in the Group 4-7, the C1-C6 alkyl group may be optionally substituted with one or more halogens, provided that when it is substituted with two or more halogens, then the halogens may be same or different.

[23] The method according to the above [22], wherein $R^2$ is hydrogen or a C1-C6 alkyl group wherein the C1-C6 alkyl group may be optionally substituted with one or more halogens, provided that when it is substituted with two or more halogens, then the halogens may be same or different;

$R^3$ is hydrogen, a C1-C6 alkyl group, or a (C1-C6 alkoxy) C1-C6 alkyl group wherein the C1-C6 alkyl group and the (C1-C6 alkoxy)C1-C6 alkyl group may be optionally substituted with one or more halogens, provided that when they are substituted with two or more halogens, then the halogens may be same or different;

$R^5$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have one or more C1-C6 alkyl groups, provided that when it has two or more C1-C6 alkyl groups, then the C1-C6 alkyl groups may be same or different; and G is a phenyl group, a pyridyl group, an indolyl group or a pyrazolyl group wherein the phenyl group, the pyridyl group, the indolyl group and the pyrazolyl group may optionally have one or more substituents selected from Group $R^{4-7}$, provided that when they have two or more substituents, then the substituents may be same or different.

[24] The method according to the above [20], wherein $R^2$ is a methyl group or a trifluoromethyl group, $R^3$ is a methyl group, $R^5$ is a methyl group or a 4-methylphenyl group, and G is a 2,4,6-triethylphenyl group or a 2,6-diethyl-4-methylphenyl group.

When $R^2$, $R^3$, $R^5$, and G are $R^{2*}$, $R^{3*}$, $R^{5*}$, and G* as defined below, respectively:

[25] A method for producing a compound of the formula (2*-O2):

(2*-O2)

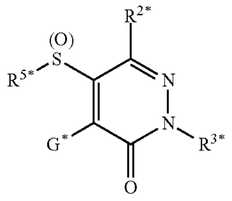

which comprises reacting a compound of the formula (2*-O0):

(2*O0)

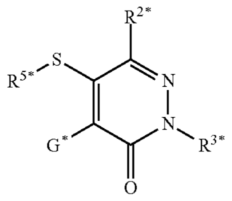

or a compound of the formula (2*-O1):

(2*-O1)

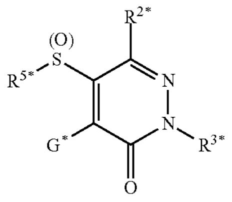

with an oxidizing agent;

wherein the symbols in the formulae (2*-O2), (2*-O0) and (2*-O1) are defined as follows:

$R^{2*}$ represents hydrogen, a C1-C6 alkyl group, a phenyl group, or a 5- or 6-membered heteroaryl group;

wherein the C1-C6 alkyl group may be optionally substituted with one or more halogens, provided that when it is substituted with two or more halogens, then the halogens may be same or different; and the phenyl group and the 5- or 6-membered heteroaryl group may optionally have one or more substituents selected from Group 2*, provided that when they have two or more substituents, then the substituents may be same or different;

the Group 2* consists of halogen and a C1-C6 alkyl group;

in the Group 2*, the C1-C6 alkyl group may be optionally substituted with one or more halogens, provided that when it is substituted with two or more halogens, then the halogens may be same or different;

$R^{3*}$ represents hydrogen, a C1-C6 alkyl group, or a (C1-C6 alkoxy)C1-C6 alkyl group;

wherein the C1-C6 alkyl group and the (C1-C6 alkoxy)C1-C6 alkyl group may be optionally substituted with one or more halogens, provided that when they are substituted with two or more halogens, then the halogens may be same or different;

$R^{5*}$ represents a C1-C6 alkyl group or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 5*, provided that when it has two or more substituents, then the substituents may be same or different;

the Group 5* consists of halogen, a C1-C6 alkyl group, and a C1-C6 alkoxy group;

in the Group 5*, the C1-C6 alkyl group and the C1-C6 alkoxy group may be optionally substituted with one or more halogens, provided that when they are substituted with two or more halogens, then the halogens may be same or different; and G* is a phenyl group;

wherein the phenyl group may optionally have one or more substituents selected from Group $R^{4*}$, provided that when it has two or more substituents, then the substituents may be same or different;

the Group $R^{4*}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4*}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4*, provided that when they have two or more substituents, then the substituents may be same or different;

the Group 4* consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group;

in the Group 4*, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different.

[26] The method according to the above [25], wherein $R^{2*}$ is hydrogen or a C1-C6 alkyl group wherein the C1-C6 alkyl group may be optionally substituted with one or more halogens, provided that when it is substituted with two or more halogens, then the halogens may be same or different;

$R^{3*}$ is hydrogen, a C1-C6 alkyl group, or a (C1-C6 alkoxy)C1-C6 alkyl group wherein the C1-C6 alkyl group and the (C1-C6 alkoxy)C1-C6 alkyl group may be optionally substituted with one or more halogens, provided that when they are substituted with two or more halogens, then the halogens may be same or different; and G* is a phenyl group wherein the phenyl group may optionally have one or more substituents selected from Group $R^{4*-15}$, provided that when it has two or more substituents, then the substituents may be same or different;

the Group $R^{4*-15}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4*-15}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4*-15, provided that when it has two or more substituents, then the substituents may be same or different;

the Group 4*-15 consists of halogen and C1-C6 alkyl group;

in the Group 4*-15, the C1-C6 alkyl group may be optionally substituted with one or more halogens, provided that when it is substituted with two or more halogens, then the halogens may be same or different.

[27] The method according to the above [25], wherein $R^{2*}$ is a methyl group, $R^{3*}$ is a methyl group, $R^{5*}$ is a methyl group, and G* is a 2,4,6-triethylphenyl group or 2,6-diethyl-4-methylphenyl group.

[28] A method for producing a compound of the formula (2*-O1):

(2*-O1)

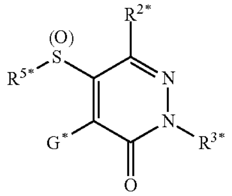

which comprises reacting a compound of the formula (2*-O0):

(2*-O0)

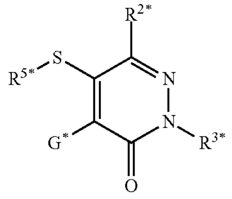

with an oxidizing agent;

wherein the symbols in the formulae (2*-O0) and (2*-O1) are defined above.

[29] The method according to the above [28], wherein $R^{2*}$ is hydrogen or a C1-C6 alkyl group wherein the C1-C6 alkyl group may be optionally substituted with one or more halogens, provided that when it is substituted with two or more halogens, then the halogens may be same or different;

$R^{3*}$ is hydrogen, a C1-C6 alkyl group, or a (C1-C6 alkoxy) C1-C6 alkyl group wherein the C1-C6 alkyl group and the (C1-C6 alkoxy)C1-C6 alkyl group may be optionally substituted with one or more halogens, provided that when they are substituted with two or more halogens, then the halogens may be same or different; and G* is a phenyl group wherein the phenyl group may optionally have one or more substituents selected from Group $R^{4*-16}$, provided that when it has two or more substituents, then the substituents may be same or different;

the Group $R^{4*-16}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4*-16}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4*-16, provided that when it has two or more substituents, then the substituents may be same or different;

the Group 4*-16 consists of halogen and a C1-C6 alkyl group;

in the Group 4*-16, the C1-C6 alkyl group may be optionally substituted with one or more halogens, provided that when it is substituted with two or more halogens, then the halogens may be same or different.

[30] The method according to the above [28], wherein $R^{2*}$ is a methyl group or a trifluoromethyl group, $R^{3*}$ is a methyl group, $R^{5*}$ is a methyl group, and G* is a 2,4,6-triethylphenyl group or a 2,6-diethyl-4-methylphenyl group.

When $R^2$, $R^3$, $R^5$, and G are $R^{2-2A}$, $R^{3-2A}$, $R^{5-2A}$, and $G^{2A}$ as defined below, respectively:

[31] A compound of the formula (2A):

(2A)

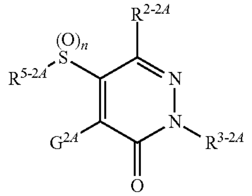

wherein the symbols in the formula (2A) are defined as follows:

$R^{2-2A}$ represents hydrogen, a C1-C6 alkyl group, or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 2-2A, provided that when it has two or more substituents, then the substituents may be same or different;

the Group 2-2A consists of halogen and a C1-C6 alkyl group;

in the Group 2-2A, the C1-C6 alkyl group may be optionally substituted with one or more halogens, provided that when it is substituted with two or more halogens, then the halogens may be same or different;

$R^{3-2A}$ represents hydrogen, a C1-C6 alkyl group, a (C1-C6 alkoxy)C1-C6 alkyl group, or a benzyl group;

wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, C1-C6 alkyl group, and C1-C6 alkoxy group, provided that when it has two or more substituents, then the substituents may be same or different;

$R^{5-2A}$ represents a C1-C6 alkyl group or a phenyl group;

wherein the C1-C6 alkyl group may be optionally substituted with one or more halogens, provided that when it is substituted with two or more halogens, then the halogens may be same or different, and the phenyl group may optionally have one or more substituents selected from Group 5-2A, provided that when it has two or more substituents, then the substituents may be same or different;

the Group 5-2A consists of halogen, a C1-C6 alkyl group, and a C1-C6 alkoxy group;

in the Group 5-2A, the C1-C6 alkyl group and the C1-C6 alkoxy group may be optionally substituted with one or more halogens, provided that when they are substituted with two or more halogens, then the halogens may be same or different;

$G^{2A}$ represents a phenyl group having one or more substituents selected from Group $R^{4-2A}$ or a 5- or 6-membered heteroaryl group having one or more substituents selected from the Group $R^{4-2A}$;

wherein the substituents may be same or different when the phenyl group and 5- or 6-membered heteroaryl group have two or more substituents; and the phenyl group has two or more substituents when n is an integer of 0;

the Group $R^{4-2A}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a (C1-C6 alkyl)carbonyl group, a (C3-C6 cycloalkyl)carbonyl group, a (C1-C6 alkoxy) carbonyl group, a (C1-C6 alkylamino)carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4-2A}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-2A, provided that when they have two or more substituents, then the substituents may be same or different;

the Group 4-2A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 4-2A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and n is as defined above.

[32] The compound according to the above [31], wherein $R^{2-2A}$ is hydrogen, a C1-C6 alkyl group or a phenyl group wherein the C1-C6 alkyl group may be optionally substituted with one or more halogens, provided that when it is substituted with two or more halogens, then the halogens may be same or different, and the phenyl group may optionally have one or more halogens, provided that when, it has two or more halogens, then the halogens may be same or different;

$R^{5-2A}$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have one or more C1-C6 alkyl groups, provided that when it has two or more C1-C6 alkyl groups, then the C1-C6 alkyl groups may be same or different, and $G^{2A}$ is a phenyl group, a pyridyl group or a pyrazolyl group wherein the phenyl group, the pyridyl group, and the pyrazolyl group may optionally have one or more substituents selected from Group $R^{4-2A-1}$, provided that when they have two or more substituents, then the substituents may be same or different, and the phenyl group has two or more substituents when n is an integer of 0;

the Group $R^{4-2A-1}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-2A-1}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-2A-1, provided that when it has two or more substituents, then the substituents may be same or different;

the Group 4-2A-1 consists of halogen and a C1-C6 alkyl group;

in the Group 4-2A-1, the C1-C6 alkyl group may be optionally substituted with one or more halogens, provided that when it is substituted with two or more halogens, then the halogens may be same or different.

[33] The compound according to the above [31], wherein $R^{2-2A}$ is a methyl group, a 4-fluorophenyl group, or a trifluoromethyl group, $R^{3-2A}$ is a methyl group or a benzyl group, $R^{5-2A}$ is a methyl group or a 4-methylphenyl group, and $G^{2A}$ is a 2,4,6-triethylphenyl group, a 2-ethyl-5-(4-chlorophenyl) phenyl group or a 2,6-diethyl-4-methylphenyl group.

When $R^2$, $R^3$, $R^5$, and G are $R^{2-4A}$, $R^{3-4A}$, $R^{5-4A}$, and $G^{4A}$ as defined below, respectively:

[34] A compound of the formula (4A):

(4A)

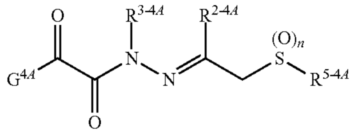

wherein the symbols in the formula (4A) are defined as follows:

$R^{2-4A}$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio) C1-C6 alkyl group, a (C1-C6 alkylsulfinyl)C1-C6 alkyl group, a (C1-C6 alkylsulfonyl)C1-C6 alkyl group, a phenyl group, or a 5- or 6-membered heteroaryl group;

wherein the C1-C6 alkyl group, the (C1-C6 alkoxy)C1-C6 alkyl group, the C2-C6 alkenyl group, the C2-C6 alkynyl group, the C3-C6 cycloalkyl group, the (C1-C6 alkylthio)C1-C6 alkyl group, the (C1-C6 alkylsulfinyl)C1-C6 alkyl group, and the (C1-C6 alkylsulfonyl)C1-C6 alkyl group may be optionally substituted with one or more halogens, provided that when they are substituted with two or more halogens, then the halogens may be same or different, the phenyl group and the 5- or 6-membered heteroaryl group may optionally have one or more substituents selected from Group 2-4A, provided that when they have two or more substituents, then the substituents may be same or different;

the Group 2-4A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 2-4A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

$R^{3-4A}$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio) C1-C6 alkyl group, a C1-C6 alkylsulfonyl group, a (C1-C6 alkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a phenyl group, a benzyl group, or a phenylsulfonyl group;

wherein the C1-C6 alkyl group, the (C1-C6 alkoxy)C1-C6 alkyl group, the C2-C6 alkenyl group, the C2-C6 alkynyl group, the C3-C6 cycloalkyl group, the (C1-C6 alkylthio)C1-C6 alkyl group, the C1-C6 alkylsulfonyl group, the (C1-C6 alkyl)carbonyl group, and the (C1-C6 alkoxy)carbonyl group may be optionally substituted with one or more halogens, provided that when they are substituted with two or more halogens, then the halogens may be same or different; and the phenyl group, the benzyl group, and the phenylsulfonyl group may optionally have one or more substituents selected from Group 3-4A, provided that when they have two or more substituents, then the substituents may be same or different;

the Group 3-4A consists of halogen, a C1-C6 alkyl group, a C1-C6 alkoxy group, and a (C1-C6 alkoxy)C1-C6 alkyl group;

in the Group 3-4A, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$R^{5-4A}$ represents a C1-C6 alkyl group or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 5-4A, provided that when it has two or more substituents, then the substituents may be same or different;

the Group 5-4A consists of halogen, a C1-C6 alkyl group, and a C1-C6 alkoxy group;

in the Group 5-4A, the C1-C6 alkyl group, and the C1-C6 alkoxy group may be optionally substituted with one or more halogens, provided that when they are substituted with two or more halogens, then the halogens may be same or different;

$G^{4A}$ represents a C6-C10 aryl group, a 5- or 6-membered heteroaryl group, or an 8- to 10-membered fused heteroaryl group;

wherein the C6-C10 aryl group, the 5- or 6-membered heteroaryl group, and the 8- to 10-membered fused heteroaryl group may optionally have one or more substituents selected from Group $R^{4-4A}$, provided that when they have two or more substituents, then the substituents may be same or different;

the Group $R^{4-4A}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4-4A}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more, halogens, then the halogens may be same or different; and the C6-C10 aryl group and the 5- or 6-membered heteroaryl group may optionally have one or more substituents selected from Group 4-4A, provided that when they have two or more substituents, then the substituents may be same or different;

the Group 4-4A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 4-4A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and n is as defined above.

[35] The compound according to the above [34], wherein $G^{4A}$ is a phenyl group wherein the phenyl group may optionally have one or more substituents selected from the Group $R^{4-4A}$, provided that when it has two or more substituents, then the substituents may be same or different.

[36] The compound according to the above [34] or [35], wherein the Group $R^{4-4A}$ is Group $R^{4-4A-1}$;

wherein the Group $R^{4-4A-1}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-4A-1}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-4A-1, provided that when it has two or more substituents, then the substituents may be same or different;

the Group 4-4A-1 consists of halogen and a C1-C6 alkyl group;

in the Group 4-4A-1, the C1-C6 alkyl group may be optionally substituted with one or more halogens, provided that when it is substituted with two or more halogens, then the halogens may be same or different.

[37] The compound according to the above [36], wherein $R^{2-4A}$ is hydrogen or a C1-C6 alkyl group wherein the C1-C6 alkyl group may be optionally substituted with one or more halogens, provided that when it is substituted with two or more halogens, then the halogens may be same or different;

$R^{3-4A}$ is hydrogen, a C1-C6 alkyl group, a (C1-C6 alkoxy) C1-C6 alkyl group, or a benzyl group wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and a C1-C6 alkoxy group, provided that when it has two or more substituents, then the substituents may be same or different;

$R^{5-4A}$ is a C1-C6 alkyl group or a phenyl group wherein the C1-C6 alkyl group may be optionally substituted with one or more halogens, provided that when it is substituted with two or more halogens, then the halogens may be same or different; and the phenyl group has one or more C1-C6 alkyl groups, provided that when it has two or more C1-C6 alkyl groups, then the C1-C6 alkyl groups may be same or different; and $G^{4A}$ is a phenyl group, a pyridyl group, an indolyl group or a pyrazolyl group wherein the phenyl group, the pyridyl group, the indolyl group and the pyrazolyl group may optionally have one or more substituents selected from Group $R^{4-4A-1}$, provided that when they have two or more substituents, then the substituents may be same or different.

[38] The compound according to the above [34], wherein $R^{2-4A}$ is a methyl group, a 4-fluorophenyl group or a trifluoromethyl group, $R^{3-4A}$ is a methyl group or a benzyl group, $R^{5-4A}$ is a methyl group or a 4-methylphenyl group, and $G^{4A}$ is a 2,4,6-triethylphenyl group, a 2-ethyl-5-(4-chlorophenyl) phenyl group, a 5-ethyl-3-(4-trifluoromethylphenyl)pyrazol-1-yl group, a 1-methylindol-3-yl group or a 2,6-diethyl-4-methylphenyl group.

When $R^2$, $R^3$, and $R^5$ are $R^{2-5A}$, $R^{3-5A}$, and $R^{5-5A}$ as defined below, respectively:

[39] A compound of the formula (5A):

(5A)

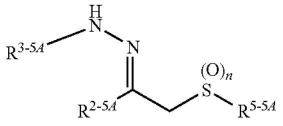

wherein the symbols in the formula (5A) are defined as follows:

$R^{2-5A}$ represents hydrogen, a C1-C6 alkyl group, a phenyl group, or a 5- or 6-membered heteroaryl group;

wherein the C1-C6 alkyl group may be optionally substituted with one or more halogens, provided that when it is substituted with two or more halogens, then the halogens may be same or different; and the phenyl group and the 5- or 6-membered heteroaryl group may optionally have one or more substituents selected from Group 2-5A, provided that when they have two or more substituents, then the substituents may be same or different;

the Group 2-5A consists of halogen and a C1-C6 alkyl group;

in the Group 2-5A, the C1-C6 alkyl group may be optionally substituted with one or more halogens, provided that when it is substituted with two or more halogens, then the halogens may be same or different;

$R^{3-5A}$ represents hydrogen, a C1-C6 alkyl group, a (C1-C6 alkoxy)C1-C6 alkyl group, or a benzyl group;

wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and a C1-C6 alkoxy group, provided that when it has two or more substituents, then the substituents may be same or different;

$R^{5-5A}$ represents a C1-C6 alkyl group;

wherein the C1-C6 alkyl group may be optionally substituted with one or more halogens, provided that when it is substituted with two or more halogens, then the halogens may be same or different; and n is as defined above.

[40] The compound according to the above [39], wherein $R^{2-5A}$ is a methyl group or a 4-fluorophenyl group, $R^{3-5A}$ is a methyl group or a benzyl group, and $R^{5-5A}$ is a methyl group.

When G and $X^1$ are $G^{6A}$ and $X^{1-6A}$ as defined below, respectively:

[41] A compound of the formula (6A):

(6A)

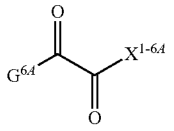

wherein the symbols in the formula (6A) are defined as follows:

$G^{6A}$ represents a 2,4,6-triethylphenyl group, a 2-ethyl-5-(4-chlorophenyl)phenyl group, a 5-ethyl-3-(4-trifluoromethylphenyl)pyrazol-1-yl group, a 1-methylindol-3-yl group or a 2,6-diethyl-4-methylphenyl group; and $X^{1-6A}$ represents chlorine.

When G is $G^{8A}$ as defined below, respectively:

[42] A compound of the formula (8A):

(8A)

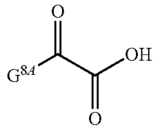

wherein $G^{8A}$ represents a 2,4,6-triethylphenyl group or a 2,6-diethyl-4-methylphenyl group.

When G and Y are $G^{9A}$ and $Y^{9A}$ as defined below, respectively:

[43] A compound of the formula (9A):

(9A)

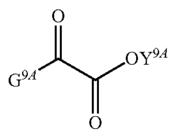

wherein the symbols in the formula (9A) are defined as follows:

$G^{9A}$ represents a 2,4,6-triethylphenyl group or a 2,6-diethyl-4-methylphenyl group; and $Y^{9A}$ represents a C1-C6 alkyl group;

wherein the C1-C6 alkyl group may be optionally substituted with one or more halogens, provided that when it is substituted with two or more halogens, then the halogens may be same or different.

[44] The compound according to the above [43], wherein $Y^{9A}$ is a methyl group or an ethyl group.

When $R^3$ and G are $R^{3\text{-}12A}$ and $G^{12A}$ as defined below, respectively:

[45] A compound of the formula (12A):

(12A)

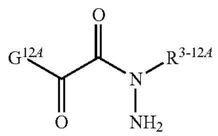

wherein the symbols in the formula (12A) are defined as follows:

$R^{3\text{-}12A}$ represents hydrogen, a C1-C6 alkyl group, or a (C1-C6 alkoxy)C1-C6 alkyl group;

wherein the C1-C6 alkyl group and the (C1-C6 alkoxy)C1-C6 alkyl group may be optionally substituted with one or more halogens, provided that when they are substituted with two or more halogens, then the halogens may be same or different, and $G^{12A}$ represents a phenyl group having a substituent selected from Group $R^{4\text{-}12A}$ at 2-position;

wherein the phenyl group may optionally further have one or more substituents selected from Group $R^{4\text{-}12A\text{-}a}$, the substituents may be same or different when the phenyl group has two or more substituents;

the Group $R^{4\text{-}12A}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a (C1-C6 alkyl)carbonyl group, a (C3-C6 cycloalkyl)carbonyl group, (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4\text{-}12A}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-12A, provided that when they have two or more substituents, then the substituents may be same or different;

the Group 4-12A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group;

in the Group 4-12A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

the Group $R^{4\text{-}12A\text{-}a}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a (C1-C6 alkyl)carbonyl group, a (C3-C6 cycloalkyl)carbonyl group, (C1-C6 alkoxy)carbonyl group, a tri(C1-C6 alkyl)silyl group, a C6-C10 aryl group, and a 5- or 6-membered heteroaryl group;

in the Group $R^{4\text{-}12A\text{-}a}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-12A-a, provided that when they have two or more substituents, then the substituents may be same or different;

the Group 4-12A-a consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)

amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group in the Group 4-12A-a, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different.

[46] The compound according to the above [45], wherein $G^{12A}$ is a phenyl group having a substituent selected from Group $R^{4-12A-1}$ at 2-position wherein the phenyl group may optionally further have one or more substituents selected from Group $R^{4-12A-a-1}$, the substituents may be same or different when the phenyl group has two or more substituents;

the Group $R^{4-12A-1}$ consists of halogen, a cyano group, a nitro group, a C1-C6 alkyl group, a C1-C6 alkoxy group, a C2-C6 alkynyl group, a C3-C6 cycloalkyl group, and a phenyl group;

in the Group $R^{4-12A-1}$, the C1-C6 alkyl group, the C1-C6 alkoxy group, the C2-C6 alkynyl group, and the C3-C6 cycloalkyl group may be optionally substituted with one or more halogens, provided that when they are substituted with two or more halogens, then the halogens may be same or different; and the phenyl group may optionally have one or more substituents selected from Group 4-12A-1, provided that when it has two or more substituents, then the substituents may be same or different;

the Group 4-12A-1 consists of halogen and a C1-C6 alkyl group;

in the Group 4-12A-1, the C1-C6 alkyl group may be optionally substituted with one or more halogens, provided that when it is substituted with two or more halogens, then the halogens may be same or different;

the Group $R^{4-12A-a-1}$ consists of halogen, a cyano group, a nitro group, a C1-C6 alkyl group, a C1-C6 alkoxy group, a C2-C6 alkynyl group, a C3-C6 cycloalkyl group, and a phenyl group;

in the Group $R^{4-12A-a-1}$, the C1-C6 alkyl group, the C1-C6 alkoxy group, the C2-C6 alkynyl group, and the C3-C6 cycloalkyl group may be optionally substituted with one or more halogens, provided that when they are substituted with two or more halogens, then the halogens may be same or different; and in the Group $R^{4-12A-a-1}$, the phenyl group may optionally have one or more substituents selected from Group 4-12A-a-1, provided that when it has two or more substituents, then the substituents may be same or different;

the Group 4-12A-a-1 consists of halogen and a C1-C6 alkyl group;

in the Group 4-12A-a-1, the C1-C6 alkyl group may be optionally substituted with one or more halogens, provided that when it is substituted with two or more halogens, then the halogens may be same or different.

[47] The compound according to the above [45] or [46], wherein $R^{3-12A}$ is a methyl group, and $G^{12A}$ is a 2,4,6-triethylphenyl group or a 2,6-diethyl-4-methylphenyl group.

[48] The method according to the above [7], wherein $R^1$ is hydrogen, a methyl group, an ethyl group, a n-butyl group or a phenyl group, $R^2$ is a methyl group, a 4-fluorophenyl group or a trifluoromethyl group, $R^3$ is a methyl group or a benzyl group, $R^5$ is a methyl group or a 4-methylphenyl group, and G is a 2,4,6-triethylphenyl group, a 2-ethyl-5-(4-chlorophenyl)phenyl group, a 1-methylindol-3-yl group or a 2,6-diethyl-4-methylphenyl group.

[49] The method according to above [13], wherein $R^1$ is hydrogen, a methyl group, an ethyl group, a n-butyl group or a phenyl group, $R^2$ is a methyl group or a 4-fluorophenyl group, $R^3$ is a methyl group or a benzyl group, $R^5$ is a methyl group or a 4-methylphenyl group, and G is a 2,4,6-triethylphenyl group, a 2-ethyl-5-(4-chlorophenyl)phenyl group, a 1-methylindol-3-yl group or a 2,6-diethyl-4-methylphenyl group.

[50] The method according to above [19], wherein $R^1$ is hydrogen, a methyl group, an ethyl group, a n-butyl group or a phenyl group, $R^2$ is a methyl group, or a trifluoromethyl group, $R^3$ is a methyl group or a benzyl group, $R^5$ is a methyl group or a 4-methylphenyl group, and G is a 2,4,6-triethylphenyl group or a 2,6-diethyl-4-methylphenyl group.

[51] A method for producing a compound of the formula (1B):

(1B)

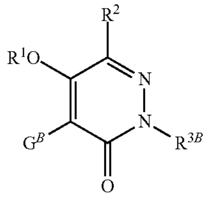

which comprises the steps of:

reacting a compound of the formula (12B):

(12B)

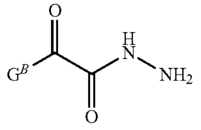

with a compound of the formula (20):

(20)

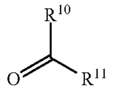

to obtain a compound of the formula (17):

(17)

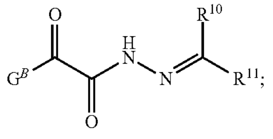

reacting the compound of the formula (17) with a compound of the formula (18):

$L-R^{3B}$ (18)

to obtain a compound of the formula (19):

(19)

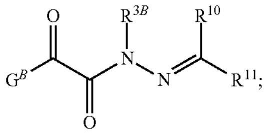

decomposing the compound of the formula (19) to obtain a compound of the formula (12C):

(12C)

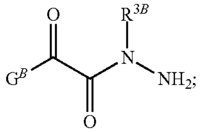

reacting the compound of the formula (12C) with a compound of the formula (7):

(7)

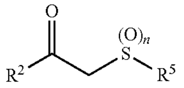

to obtain a compound of the formula (4B):

(4B)

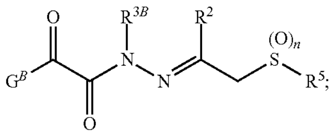

reacting the compound of the formula (4B) with a base to obtain a compound of the formula (2B):

(2B)

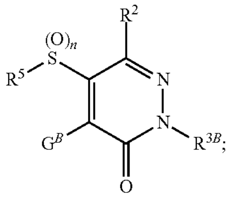

and reacting the compound of the formula (2B) with a compound of the formula (3):

$M(OR^1)_v$ (3).

[52] The method according to above [51], wherein $R^1$ is hydrogen, a methyl group, an ethyl group, a n-butyl group, a benzyl group or a phenyl group, $R^2$ is a methyl group, a trifluoromethyl group or a 4-fluorophenyl group, $R^5$ is a methyl group or a 4-methylphenyl group, $R^{3B}$ is a methyl group, $G^B$ is a 2,6-diethyl-4-methylphenyl group, $R^{10}$ is hydrogen or a methyl group, $R^{11}$ is hydrogen, a methyl group, an ethyl group, an isopropyl group or a phenyl group, and L is a methoxysulfonyloxy group.

[53] A method of for producing a compound of the formula (19):

(19)

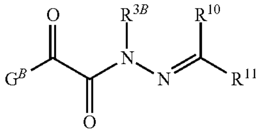

which comprises reacting a compound of the formula (17):

(17)

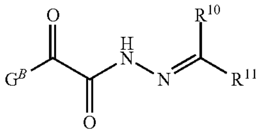

with a compound of the formula (18):

$L\text{-}R^{3B}$ (18).

[54] The method according to above [53], wherein $R^{3B}$ is a C1-C6 alkyl group, $G^B$ is a phenyl group wherein the phenyl group may optionally have one or more substituents selected from Group $R^{4-10}$, provided that when it has two or more substituents, then the substituents may be same or different;

the Group $R^{4-10}$ consists of a C1-C6 alkyl group and a phenyl group;

in the Group $R^{4-10}$, the phenyl group may be optionally substituted with one or more halogens, provided that when it is substituted with two or more halogens, then the halogens may be same or different;

$R^{10}$ is hydrogen or a C1-C6 alkyl group; and $R^{11}$ is hydrogen, a C1-C6 alkyl group or a phenyl group.

[55] The method according to above [53] wherein $R^{3B}$ is a methyl group, $G^B$ is a 2,6-diethyl-4-methylphenyl group, $R^{10}$ is hydrogen or a methyl group, $R^{11}$ is hydrogen, a methyl group, an ethyl group, an isopropyl group or a phenyl group, and L is a methoxysulfonyloxy group.

[56] A method for producing a compound of the formula (12C):

(12C)

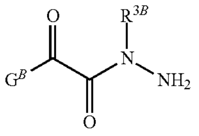

which comprises decomposing a compound of the formula (19):

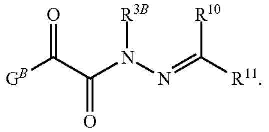

(19)

[57] The method according to above [56], wherein $R^{3B}$ is a C1-C6 alkyl group, $G^B$ is a phenyl group wherein the phenyl group may optionally have one or more substituents selected from Group $R^{4-11}$, provided that when it has two or more substituents, then the substituents may be same or different;

the Group $R^{4-11}$ consists of a C1-C6 alkyl group and a phenyl group;

in the Group $R^{4-11}$, the phenyl group may be optionally substituted with one or more halogens, provided that when it is substituted with two or more halogens, then the halogens may be same or different;

$R^{10}$ is hydrogen or a C1-C6 alkyl group, and $R^{11}$ is hydrogen, a C1-C6 alkyl group or a phenyl group.

[58] The method according to above [56] wherein $R^{3B}$ is a methyl group, $G^B$ is a 2,6-diethyl-4-methylphenyl group, $R^{10}$ is hydrogen or a methyl group, and $R^{11}$ is hydrogen, a methyl group, an ethyl group, an isopropyl group or a phenyl group.

[59] A compound of the formula (17A):

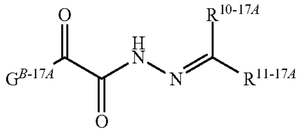

(17A)

wherein, $G^{B-17A}$ represents a phenyl group;

wherein the phenyl group may optionally have one or more substituents selected from Group $R^{4-17A}$, provided that when it has two or more substituents, then the substituents may be same or different;

the Group $R^{4-17A}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4-17A}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-17A, provided that when they have two or more substituents, then the substituents may be same or different;

the Group 4-17A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group;

in the Group 4-17A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and $R^{10-17A}$ and $R^{11-17A}$ may be same or different, and each represents hydrogen, a C1-C6 alkyl group, a C3-C6 cycloalkyl group or a phenyl group, or $R^{10-17A}$ and $R^{11-17A}$ may be combined to form 5- or 6-membered cyclic group with a carbon atom which is bonded with $R^{10-17A}$ and $R^{11-17A}$, wherein the C1-C6 alkyl group and the C3-C6 cycloalkyl group may be optionally substituted with one or more halogens, provided that when they are substituted with two or more halogens, then the halogens may be same or different; and the phenyl group may optionally have one or more substituents selected from Group 10-17A, provided that when it has two or more substituents, then the substituents may be same or different;

the Group 10-17A consists of halogen, a C1-C6 alkyl group and a C1-C6 alkoxy group.

[60] The compound according to above [59], wherein $G^{B-17A}$ is a phenyl group wherein the phenyl group may optionally have one or more substituents selected from Group $R^{4-17A-1}$, provided that when it has two or more substituents, then the substituents may be same or different;

the Group $R^{4-17A-1}$ consists of a C1-C6 alkyl group and a phenyl group;

in the Group $R^{4-17A-1}$, the phenyl group may be optionally substituted with one or more halogens, provided that when it is substituted with two or more halogens, then the halogens may be same or different;

$R^{10-17A}$ is hydrogen or a C1-C6 alkyl group, and $R^{11-17A}$ is hydrogen, a C1-C6 alkyl group or a phenyl group.

[61] The compound according to above [59] wherein $G^{B-17A}$ is a 2,6-diethyl-4-methylphenyl group, $R^{10-17A}$ is hydrogen or a methyl group, and $R^{11-17A}$ is hydrogen, a methyl group, an ethyl group, an isopropyl group or a phenyl group.

[62] A compound of the formula (19A):

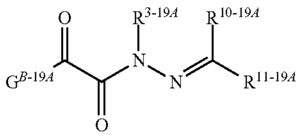

(19A)

wherein, $R^{3-19A}$ represents a C1-C6 alkyl group, a (C1-C6 alkoxy) C1-C6 alkyl group, a C2-C6 alkenyl group, a C2-C6 alkynyl group, a C3-C6 cycloalkyl group, a (C1-C6 alkylthio)C1-C6 alkyl group, a C1-C6 alkylsulfonyl group, a (C1-C6 alkyl) carbonyl group, a (C1-C6 alkoxy)carbonyl group, a (C1-C6 alkyl)aminocarbonyl group, a di(C1-C6 alkyl)aminocarbonyl group, a (C3-C6 cycloalkyl)aminocarbonyl group, a phenyl group, a benzyl group, or a phenylsulfonyl group;

wherein the C1-C6 alkyl group, the (C1-C6 alkoxy)C1-C6 alkyl group, the C2-C6 alkenyl group, the C2-C6 alkynyl group, the C3-C6 cycloalkyl group, the (C1-C6 alkylthio)C1-C6 alkyl group, the C1-C6 alkylsulfonyl group, the (C1-C6 alkyl)carbonyl group, and the (C1-C6 alkoxy)carbonyl group may be optionally substituted with one or more halogens, provided that when they are substituted with two or more halogens, then the halogens may be same or different; and the phenyl group, the benzyl group, and the phenylsulfonyl group may optionally have one or more substituents selected from Group 3-19A, provided that when they have two or more substituents, then the substituents may be same or different, the Group 3-19A consists of halogen, a C1-C6 alkyl group, a C1-C6 alkoxy group, and a (C1-C6 alkoxy)C1-C6 alkyl group;

in the Group 3-19A, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$G^{B-19A}$ represents a phenyl group;

wherein the phenyl group may optionally have one or more substituents selected from Group $R^{4-19A}$, provided that when it has two or more substituents, then the substituents may be same or different;

the Group $R^{4-19A}$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^{4-19A}$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl, group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4-19A, provided that when they have two or more substituents, then the substituents may be same or different;

the Group 4-19A consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl) carbonyl group, a (C3-C6 cycloalkyl)carbonyl group, a (C1-C6 alkoxy)carbonyl group, a (C1-C6 alkylamino) carbonyl group, a di(C1-C6 alkyl)aminocarbonyl group, a (C3-C6 cycloalkylamino)carbonyl group, and a tri(C1-C6 alkyl)silyl group;

in the Group 4-19A, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and $R^{10-19A}$ and $R^{11-19A}$ may be same or different, and each represents hydrogen, a C1-C6 alkyl group, a C3-C6 cycloalkyl group or a phenyl group, or $R^{10-19A}$ and $R^{11-19A}$ may be combined to form 5- or 6-membered cyclic group with a carbon atom which is bonded with $R^{10-17A}$ and $R^{11-17A}$, wherein the C1-C6 alkyl group and the C3-C6 cycloalkyl group may be optionally substituted with one or more halogens, provided that when they are substituted with two or more halogens, then the halogens may be same or different; and the phenyl group may optionally have one or more substituents selected from Group 10-19A, provided that when it has two or more substituents, then the substituents may be same or different;

the Group 10-19A consists of halogen, a C1-C6 alkyl group and a C1-C6 alkoxy group.

[63] The compound according to above [62], wherein $G^{B-19A}$ is a phenyl group wherein the phenyl group may optionally have one or more substituents selected from Group $R^{4-19A-1}$, provided that when it has two or more substituents, then the substituents may be same or different;

the Group $R^{4-19A-1}$ consists of a C1-C6 alkyl group and a phenyl group;

in the Group $R^{4-19A-1}$, the phenyl group may be optionally substituted with one or more halogens, provided that when it is substituted with two or more halogens, then the halogens may be same or different;

$R^{3-19A}$ is a C1-C6 alkyl group, $R^{10-19A}$ is hydrogen or a C1-C6 alkyl group, and $R^{11-19A}$ is hydrogen, a C1-C6 alkyl group or a phenyl group.

[64] The compound according to above [62] wherein $G^{B-19A}$ is a 2,6-diethyl-4-methylphenyl group, $R^{3-19A}$ is a C1-C6 alkyl group, $R^{10-19A}$ is hydrogen or a methyl group, and $R^{11-19A}$ is hydrogen, a methyl group, an ethyl group, an isopropyl group or a phenyl group.

DESCRIPTION OF EMBODIMENTS

Examples of each of the substituents described herein are shown below:

halogen: fluorine, chlorine, bromine and iodine;

C1-C6 alkyl group optionally substituted with one or more halogens: a methyl group, an ethyl group, a n-propyl group, an isopropyl group, a butyl group, an isobutyl group, a sec-butyl group, a tert-butyl group, a n-pentyl group, a n-hexyl group, a trifluoromethyl group, and a 2,2,2-trifluoroethyl group;

C1-C6 alkoxy group optionally substituted with one or more halogens: a methoxy group, a trifluoromethoxy group, an ethoxy group, a 2,2,2-trifluoroethoxy group, a propyloxy group, an isopropyloxy group, a butoxy group, an isobutyloxy group, a sec-butoxy group, a tert-butoxy group, a pentyloxy group, and a hexyloxy group;

(C1-C6 alkoxy)C1-C6 alkyl group optionally substituted with one or more halogens: a methoxymethyl group, a 2-methoxyethyl group, a 2-ethoxyethyl group, a 2-isopropyloxyethyl group, and a 2-trifluoromethoxyethyl group;

C2-C6 alkenyl group optionally substituted with one or more halogens: a ethenyl group, a 2-propenyl group, a 3-chloro-2-propenyl group, a 2-chloro-2-propenyl group, a 3,3-dichloro-2-propenyl group, a 2-butenyl group, a 3-butenyl group, a 2-methyl-2-propenyl group, a 3-methyl-2-butenyl group, a 2-pentenyl group, and a 1-hexenyl group;

C2-C6 alkynyl group optionally substituted with one or more halogens: a ethynyl group, a 2-propynyl group, a 3-chloro-2-propynyl group, a 3-bromo-2-propynyl group, a 2-butynyl group, a 3-butynyl group, a 2-pentynyl group, and a 2-hexynyl group;

C3-C6 cycloalkyl group optionally substituted with one or more halogens: a cyclopropyl group, a 2-chlorocyclopropyl group, a 2-bromocyclopropyl group, a cyclobutyl group, a cyclopentyl group, and a cyclohexyl group;

C1-C6 alkylthio group optionally substituted with one or more halogens: a methylthio group, a trifluoromethylthio group, an ethylthio group, a propylthio group, a butylthio group, a pentylthio group, and a hexylthio group;

C1-C6 alkylsulfinyl group optionally substituted with one or more halogens: a methylsulfinyl group, a trifluoromethylsulfinyl group, an ethylsulfinyl group, a propylsulfinyl group, a pentylsulfinyl group, and a hexylsulfinyl group;

C1-C6 alkylsulfonyl group optionally substituted with one or more halogens: a methylsulfonyl group, a trifluoromethylsulfonyl group, and an ethylsulfonyl group, a propylsulfonyl group, a pentylsulfonyl group, and a hexylsulfonyl group;

(C1-C6 alkylthio)C1-C6 alkyl group optionally substituted with one or more halogens: a methylthiomethyl group, a methylthioethyl group, a trifluoromethylthiomethyl group, and an ethylthiomethyl group;

(C1-C6 alkylsulfinyl)C1-C6 alkyl group optionally substituted with one or more halogens: a methylsulfinylmethyl group, a methylsulfinylethyl group, a trifluoromethylsulfinylmethyl group, and an ethylsulfinylmethyl group;

(C1-C6 alkylsulfonyl)C1-C6 alkyl group optionally substituted with one or more halogens: a methylsulfonylmethyl group, a methylsulfonylethyl group, a trifluoromethylsulfonylmethyl group, and an ethylsulfonylmethyl group;

C1-C6 alkylamino group: a methylamino group, an ethylamino group, a propylamino group, an isopropylamino group, a butylamino group, an isobutylamino group, a sec-butylamino group, a tert-butylamino group, a pentylamino group, and a hexylamino group;

di(C1-C6 alkyl)amino group: a dimethylamino group, a diethylamino group, an ethylmethylamino group, a dipropylamino group, a diisopropylamino group, a dibutylamino group, and a methylpropylamino group;

C3-C6 cycloalkylamino group: a cyclopropylamino group, a cyclobutylamino group, a cyclopentylamino group, and a cyclohexylamino group;

(C1-C6 alkyl)carbonyl group optionally substituted with one or more halogens: an acetyl group, a trifluoroacetyl group, a propionyl group, a pentafluoropropionyl group, an isobutyryl group, and a trimethylacetyl group;

(C3-C6 cycloalkyl)carbonyl group optionally substituted with one or more halogens: a cyclopropylcarbonyl group, a 2-chlorocyclopropylcarbonyl group, a 2-bromocyclopropylcarbonyl group, cyclobutylcarbonyl group, a cyclopentylcarbonyl group, and a cyclohexylcarbonyl group;

(C1-C6 alkoxy)carbonyl group optionally substituted with one or more halogens: a methoxycarbonyl group, an ethoxycarbonyl group, a 2,2,2-trifluoroethoxycarbonyl group, a propyloxycarbonyl group, an isopropyloxycarbonyl group, and a butoxycarbonyl group;

(C1-C6 alkylamino)carbonyl group: a methylaminocarbonyl group, an ethylaminocarbonyl group, a propylaminocarbonyl group, and an isopropylaminocarbonyl group;

di(C1-C6 alkyl)aminocarbonyl group: a dimethylaminocarbonyl group, a diethylaminocarbonyl group, an ethylmethylaminocarbonyl group, a dipropylaminocarbonyl group, a diisopropylaminocarbonyl group, a dibutylaminocarbonyl group, and a methylpropylaminocarbonyl group;

(C3-C6 cycloalkylamino)carbonyl group: a cyclopropylaminocarbonyl group, a cyclobutylaminocarbonyl group, cyclopentylaminocarbonyl group, and a cyclohexylaminocarbonyl group;

tri(C1-C6 alkyl)silyl group: a trimethylsilyl group, a triethylsilyl group, and a diethylisopropylsilyl group;

C6-C10 aryl group optionally having one or more substituents: a phenyl group, a 2-methylphenyl group, a 3-methylphenyl group, a 4-methylphenyl group, a 2,3-dimethylphenyl group, a 2,4-dimethylphenyl group, a 3,4-dimethylphenyl group, a 2,5-dimethylphenyl group, a 2,6-dimethylphenyl group, a 3,5-dimethylphenyl group, a 2,3,4-trimethylphenyl group, a 2,3,5-trimethylphenyl group, a 2,3,6-trimethylphenyl group, a 2,4,5-trimethylphenyl group, a 2,4,6-trimethylphenyl group, a 3,4,5-trimethylphenyl group, a 2-ethylphenyl group, a 3-ethylphenyl group, a 4-ethylphenyl group, a 2,3-diethylphenyl group, a 2,4-diethylphenyl group, a 3,4-diethylphenyl group, a 2,5-diethylphenyl group, a 2,6-diethylphenyl group, a 3,5-diethylphenyl group, a 2,3,4-triethylphenyl group, a 2,3,5-triethylphenyl group, a 2,3,6-triethylphenyl group, a 2,4,5-triethylphenyl group, a 2,4,6-triethylphenyl group, a 3,4,5-triethylphenyl group, a 2-fluorophenyl group, a 3-fluorophenyl group, a 4-fluorophenyl group, a 2,3-difluorophenyl group, a 2,4-difluorophenyl group, a 3,4-difluorophenyl group, a 2,5-difluorophenyl group, a 2,6-difluorophenyl group, a 3,5-difluorophenyl group, a 2,3,4-trifluorophenyl group, a 2,3,5-trifluorophenyl group, a 2,3,6-trifluorophenyl group, a 2,4,5-trifluorophenyl group, a 2,4,6-trifluorophenyl group, a 3,4,5-trifluorophenyl group, a 2-chlorophenyl group, a 3-chlorophenyl group, a 4-chlorophenyl group, a 2,3-dichlorophenyl group, a 2,4-dichlorophenyl group, a 3,4-dichlorophenyl group, a 2,5-dichlorophenyl group, a 2,6-dichlorophenyl group, a 3,5-dichlorophenyl group, a 2,3,4-trichlorophenyl group, a 2,3,5-trichlorophenyl group, a 2,3,6-trichlorophenyl group, a 2,4,5-trichlorophenyl group, a 2,4,6-trichlorophenyl group, a 3,4, 5-trichlorophenyl group, a 2-bromophenyl group, a 3-bromophenyl group, a 4-bromophenyl group, a 2,3-dibromophenyl group, a 2,4-dibromophenyl group, a 3,4-dibromophenyl group, a 2,5-dibromophenyl group, a 2,6-dibromophenyl group, a 3,5-dibromophenyl group, a 2,3,4-tribromophenyl group, a 2,3,5-tribromophenyl group, a 2,3,6-tribromophenyl group, a 2,4,5-tribromophenyl group, a 2,4,6-tribromophenyl group, a 3,4,5-tribromophenyl group, a 2-iodophenyl group, a 3-iodophenyl group, a 4-iodophenyl group, a 2,3-diiodophenyl group, a 2,4-diiodophenyl group, a 3,4-diiodophenyl group, a 2,5-diiodophenyl group, a 2,6-diiodophenyl group, a 3,5-diiodophenyl group, a 2,3,4-triiodophenyl group, a 2,3,5-triiodophenyl group, a 2,3,6-triiodophenyl group, a 2,4,5-triiodophenyl group, a 2,4,6-triiodophenyl group, a 3,4,5-triiodophenyl group, a 2-methoxyphenyl group, a 3-methoxyphenyl group, a 4-methoxyphenyl group, a 2,3-dimethoxyphenyl group, a 2,4-dimethoxyphenyl group, a 3,4-dimethoxyphenyl group, a 2,5-dimethoxyphenyl group, a 2,6-dimethoxyphenyl group, a 3,5-dimethoxyphenyl group, a 2,3,4-trimethoxyphenyl group, a 2,3,5-trimethoxyphenyl group, a 2,3,6-trimethoxyphenyl group, a 2,4,5-trimethoxyphenyl group, a 2,4,6-trimethoxyphenyl group, a 3,4,5-trimethoxyphenyl group, a 2-trifluoromethylphenyl group, a 3-trifluoromethylphenyl group, a 4-trifluoromethylphenyl group, a 2,3-bis(trifluoromethyl)phenyl group, a 2,4-bis(trifluoromethyl)phenyl group, a 3,4-bis(trifluoromethyl)phenyl group, a 2,5-bis(trifluoromethyl)phenyl group, a 2,6-bis(trifluoromethyl)phenyl group, a 3,5-bis(trifluoromethyl)phenyl group, a 2,3,4-tris(trifluoromethyl)phenyl group, a 2,3,5-tris(trifluoromethyl)phenyl group, a 2,3,6-tris(trifluoromethyl)phenyl group, a 2,4,5-tris(trifluoromethyl)phenyl group, a 2,4,6-tris(trifluoromethyl)phenyl group, a 3,4,5-tris(trifluoromethyl)phenyl group, a 2-ethyl-3-methylphenyl group, a 3-ethyl-2-methylphenyl group, a 2-ethyl-4-methylphenyl group, a 4-ethyl-2-methylphenyl group, a 3-ethyl-4-methylphenyl group, a 4-ethyl-3-methylphenyl group, a 5-ethyl-2-methylphenyl group, a 2-ethyl-5-methylphenyl group, a 2-ethyl-6-methylphenyl group, a 3-ethyl-5-methylphenyl group, a 2,3-diethyl-4-methylphenyl group, a 2,4-diethyl-3-methylphenyl group, a 3,4-diethyl-2-methylphenyl group, a 4-ethyl-2,3-dimethylphenyl group, a 3-ethyl-2,4-dimethylphenyl group, a 2-ethyl-3,4-dimethylphenyl group, a 3,5-diethyl-2-methylphenyl group, a 2,5-diethyl-3-methylphenyl group, a 2,3-diethyl-5-methylphenyl group, a 2-ethyl-3,5-dimethylphenyl group, a 3-ethyl-2,5-dimethylphenyl group, a 5-ethyl-2,3-dimethylphenyl group, a 2,3-diethyl-6-methylphenyl group, a 2,6-diethyl-3-methylphenyl group, a 3,6-diethyl-2-methylphenyl group, a 6-ethyl-2,3-dimethylphenyl group, a 3-ethyl-2,6-dimethylphenyl group, a 2-ethyl-3,6-dimethylphenyl group, a 2,4-diethyl-5-methylphenyl group, a 2,5-diethyl-4-methylphenyl group, a 4,5-diethyl-2-methylphenyl group, a 5-ethyl-2,4-dimethylphenyl group, a 4-ethyl-2,5-dimethylphenyl group, a 2-ethyl-4,5-dimethylphenyl group, a 2,4-diethyl-6-methylphenyl group, a 2,6-diethyl-4-methylphenyl group, a 6-ethyl-2,4-dimethylphenyl group, a 4-ethyl-2,6-dimethylphenyl group, a 3,4-diethyl-5-methylphenyl group, a 3,5-diethyl-4-methylphenyl group, a 5-ethyl-3,4-dimethylphenyl group, a 4-ethyl-3,5-dimethylphenyl group, a 2-fluoro-3-methylphenyl group, a 3-fluoro-2-methylphenyl group, a 2-fluoro-4-methylphenyl group, a 4-fluoro-2-methylphenyl group, a 3-fluoro-4-methylphenyl group, a 4-fluoro-3-methylphenyl group, a 5-fluoro-2-methylphenyl group, a 2-fluoro-5-methylphenyl group, a 2-fluoro-6-methylphenyl group, a 3-fluoro-5-methylphenyl group, a 2,3-difluoro-4-methylphenyl group, a 2,4-difluoro-3-methylphenyl group, a 3,4-difluoro-2-methylphenyl group, a 4-fluoro-2,3-dimethylphenyl group, a 3-fluoro-2,4-dimethylphenyl group, a 2-fluoro-3,4-dimethylphenyl group, a 3,5-difluoro-2-methylphenyl group, a 2,5-difluoro-3-methylphenyl group, a 2,3-difluoro-5-methylphenyl group, a 2-fluoro-3,5-dimethylphenyl group, a 3-fluoro-2,5-dimethylphenyl group, a 5-fluoro-2,3-dimethylphenyl group, a 2,3-difluoro-6-methylphenyl group, a 2,6-difluoro-3-methylphenyl group, a 3,6-difluoro-2-methylphenyl group, a 6-fluoro-2,3-dimethylphenyl group, a 3-fluoro-2,6-dimethylphenyl group, a 2-fluoro-3,6-dimethylphenyl group, a 2,4-difluoro-5-methylphenyl group, a 2,5-difluoro-4-methylphenyl group, a 4,5-difluoro-2-methylphenyl group, a 5-fluoro-2,4-dimethylphenyl group, a 4-fluoro-2,5-dimethylphenyl group, a 2-fluoro-4,5-dimethylphenyl group, a 2,4-difluoro-6-methylphenyl group, a 2,6-difluoro-4-methylphenyl group, a 6-fluoro-2,4-dimethylphenyl group, a 4-fluoro-2,6-dimethylphenyl group, a 3,4-difluoro-5-methylphenyl group, a 3,5-difluoro-4-methylphenyl group, a 5-fluoro-3,4-dimethylphenyl group, a 4-fluoro-3,5-dimethylphenyl group, a 2-chloro-3-methylphenyl group, a 3-chloro-2-methylphenyl group, a 2-chloro-4-methylphenyl group, a 4-chloro-2-methylphenyl group, a 3-chloro-4-methylphenyl group, a 4-chloro-3-methylphenyl group, a 5-chloro-2-methylphenyl group, a 2-chloro-5-methylphenyl group, a 2-chloro-6-methylphenyl group, a 3-chloro-5-methylphenyl group, a 2,3-dichloro-4-methylphenyl group, a 2,4-dichloro-3-methylphenyl group, a 3,4-dichloro-2-methylphenyl group, a 4-chloro-2,3-dimethylphenyl group, a 3-chloro-2,4-dimethylphenyl group, a 2-chloro-3,4-dimethyl-phenyl group, a 3,5-dichloro-2-methylphenyl group, a 2,5-dichloro-3-methylphenyl group, a 2,3-dichloro-5-methylphenyl group, a 2-chloro-3,5-dimethylphenyl group, a 3-chloro-2,5-dimethylphenyl group, a 5-chloro-2,3-dimethylphenyl group, a 2,3-dichloro-6-methylphenyl group, a 2,6-dichloro-3-methylphenyl group, a 3,6-dichloro-2-methylphenyl group, a 6-chloro-2,3-dimethylphenyl group, a 3-chloro-2,6-dimethylphenyl group, a 2-chloro-3,6-dimethylphenyl group, a 2,4-dichloro-5-methylphenyl group, a 2,5-dichloro-4-methylphenyl group, 4,5-dichloro-2-methylphenyl group, a 5-chloro-2,4-dimethylphenyl group, a 4-chloro-2,5-dimethylphenyl group, a 2-chloro-4,5-dimethylphenyl group, a 2,4-dichloro-6-methylphenyl group, a 2,6-dichloro-4-methylphenyl group, a 6-chloro-2,4-dimethylphenyl group, a 4-chloro-2,6-dimethylphenyl group, a 3,4-dichloro-5-methylphenyl group, a 3,5-dichloro-4-methylphenyl group, a 5-chloro-3,4-dimethylphenyl group, a 4-chloro-3,5-dimethylphenyl group, a 2-bromo-3-methylphenyl group, a 3-bromo-2-methylphenyl group, a 2-bromo-4-methylphenyl group, a 4-bromo-2-methylphenyl group, a 3-bromo-4-methylphenyl group, a 4-bromo-3-methylphenyl group, a 5-bromo-2-methylphenyl group, a 2-bromo-5-methylphenyl group, a 2-bromo-6-methylphenyl group, a 3-bromo-5-methylphenyl group, a 2,3-dibromo-4-methylphenyl group, a 2,4-dibromo-3-methylphenyl group, a 3,4-dibromo-2-methylphenyl group, a 4-bromo-2,3-dimethylphenyl group, a 3-bromo-2,4-dimethylphenyl group, a 2-bromo-3,4-dimethylphenyl group, a 3,5-dibromo-2-methylphenyl group, a 2,5-dibromo-3-methylphenyl group, a 2,3-dibromo-5-methylphenyl group, a 2-bromo-3,5-dimethylphenyl group, a 3-bromo-2,5-dimethylphenyl group, a 5-bromo-2,3-dimethylphenyl group, a 2,3-dibromo-methylphenyl group, a 2,6-dibromo-3-methylphenyl group, a 3,6-dibromo-2-methylphenyl group, a 6-bromo-2,3-dimethylphenyl group, a 3-bromo-2,6-dimethylphenyl group, 2-bromo-3,6-dimethylphenyl group, a 2,4-dibromo-5-methylphenyl group, a 2,5-dibromo-4-methylphenyl group, a 4,5-dibromo-2-methylphenyl group, a 5-bromo-2,4-dimethylphenyl group, a 4-bromo-2,5-dimethylphenyl group, a 2-bromo-4,5-dimethylphenyl group, a 2,4-dibromo-6-methylphenyl group, a 2,6-dibromo-4-methylphenyl group, a 6-bromo-2,4-dimethylphenyl group, a 4-bromo-2,6-dimethylphenyl group, a 3,4-dibromo-5-methylphenyl group, a 3,5-dibromo-4-methylphenyl group, a 5-bromo-3,4-dimethylphenyl group, a 4-bromo-3,5-dimethylphenyl group, a 2-ethyl-3-fluorophenyl group, a 3-ethyl-2-fluorophenyl group, a 2-ethyl-4-fluorophenyl group, a 4-ethyl-2-fluorophenyl group, a 3-ethyl-4-fluorophenyl group, a 4-ethyl-3-fluorophenyl group, a 5-ethyl-2-fluorophenyl group, a 2-ethyl-5-fluorophenyl group, a 2-ethyl-6-fluorophenyl group, a 3-ethyl-5-fluorophenyl group, a 2,3-diethyl-4-fluorophenyl group, a 2,4-diethyl-3-fluorophenyl group, a 3,4-diethyl-2-fluorophenyl group, a 4-ethyl-2,3-difluorophenyl group, a 3-ethyl-2,4-difluorophenyl group, a 2-ethyl-3,4-difluorophenyl group, a 3,5-diethyl-2-fluorophenyl group, a 2,5-diethyl-3-fluorophenyl group, a 2,3-diethyl-5-fluorophenyl group, a 2-ethyl-3,5-difluorophenyl group, a 3-ethyl-2,5-difluorophenyl group, a 5-ethyl-2,3-difluorophenyl group, a 2,3-diethyl-6-fluorophenyl group, a 2,6-diethyl-3-fluorophenyl group, a 3,6-diethyl-2-fluorophenyl group, a 6-ethyl-2,3-difluorophenyl group, a 3-ethyl-2,6-difluorophenyl group, a 2-ethyl-3,6-difluorophenyl group, a 2,4-diethyl-5-fluorophenyl group, a 2,5-diethyl-4-fluorophenyl group, a 4,5-diethyl-2-fluorophenyl group, a 5-ethyl-2,4-difluorophenyl group, a 4-ethyl-2,5-difluorophenyl group, a 2-ethyl-4,5-difluorophenyl group, a 2,4-diethyl-6-fluorophenyl group, a 2,6-diethyl-4-fluorophenyl group, a 6-ethyl-2,4-difluorophenyl group, a 4-ethyl-2,6-difluorophenyl group, a 3,4-diethyl-5-fluorophenyl group, a 3,5-diethyl-4-fluorophenyl group, a 5-ethyl-3,4-difluorophenyl group, a 4-ethyl-3,5-difluorophenyl group, a 2-chloro-3-ethylphenyl group, a 3-chloro-2-ethylphenyl group, a 2-chloro-4-ethylphenyl group, a 4-chloro-2-ethylphenyl group, a 3-chloro-4-ethylphenyl group, a 4-chloro-3-ethylphenyl group, a 5-chloro-2-ethylphenyl group, a 2-chloro-5-ethylphenyl group, a 2-chloro-6-ethylphenyl group, a 3-chloro-5-ethylphenyl group, a 2,3-dichloro-4-ethylphenyl group, a 2,4-dichloro-3-ethylphenyl group, a 3,4-dichloro-2-ethylphenyl group, a 4-chloro-2,3-diethylphenyl group, a 3-chloro-2,4-diethylphenyl group, a 2-chloro-3,4-diethylphenyl group, a 3,5-dichloro-2-ethylphenyl group, a 2,5-dichloro-3-ethylphenyl group, a 2,3-dichloro-5-ethylphenyl group, a 2-chloro-3,5-diethylphenyl group, a 3-chloro-2,5-diethylphenyl group, a 5-chloro-2,3-diethylphenyl group, a 2,3-dichloro-6-ethylphenyl group, a 2,6-dichloro-3-ethylphenyl group, a 3,6-dichloro-2-ethylphenyl group, a 6-chloro-2,3-diethylphenyl group, a 3-chloro-2,6-diethylphenyl group, a 2-chloro-3,6-diethylphenyl group, a 2,4-dichloro-5-ethylphenyl group, a 2,5-dichloro-4-ethylphenyl group, a 4,5-dichloro-2-ethylphenyl group, a 5-chloro-2,4-diethylphenyl group, a 4-chloro-2,5-diethylphenyl group, a 2-chloro-4,5-diethylphenyl group, a 2,4-dichloro-6-ethylphenyl group, a 2,6-dichloro-4-ethylphenyl group, a 6-chloro-2,4-diethylphenyl group, a 4-chloro-2,6-diethylphenyl group, a 3,4-dichloro-5-ethylphenyl group, a 3,5-dichloro-4-ethylphenyl group, a 5-chloro-3,4-diethylphenyl group, a 4-chloro-3,5-diethylphenyl group, a 2-bromo-3-ethylphenyl group, a 3-bromo-2-ethylphenyl group, a 2-bromo-4-ethylphenyl group, a 4-bromo-2-ethylphenyl group, a 3-bromo-4-ethylphenyl group, a 4-bromo-3-ethylphenyl group, a 5-bromo-2-ethylphenyl group, a 2-bromo-5-ethylphenyl group, a 2-bromo-6-ethylphenyl group, a 3-bromo-5-ethylphenyl group, a 2,3-dibromo-4-ethylphenyl group, a 2,4-dibromo-3-ethylphenyl group, a 3,4-dibromo-2-ethylphenyl group, a 4-bromo-2,3-diethylphenyl group, a 3-bromo-2,4-diethylphenyl group, a 2-bromo-3,4-diethylphenyl group, a 3,5-dibromo-2-ethylphenyl group, a 2,5-dibromo-3-ethylphenyl group, a 2,3-dibromo-5-ethylphenyl group, a 2-bromo-3,5-diethylphenyl group, a 3-bromo-2,5-diethylphenyl group, a 5-bromo-2,3-diethylphenyl group, a 2,3-dibromo-6-ethylphenyl group, a 2,6-dibromo-3-ethylphenyl group, a 3,6-dibromo-2-ethylphenyl group, a 6-bromo-2,3-diethylphenyl group, a 3-bromo-2,6-diethylphenyl group, a 2-bromo-3,6-diethylphenyl group, a 2,4-dibromo-ethylphenyl group, a 2,5-dibromo-4-ethylphenyl group, a 4,5-dibromo-2-ethylphenyl group, a 5-bromo-2,4-diethylphenyl group, a 4-bromo-2,5-diethylphenyl group, a 2-bromo-4,5-diethylphenyl group, a 2,4-dibromo-6-ethylphenyl group, a 2,6-dibromo-4-ethylphenyl group, a 6-bromo-2,4-diethylphenyl group, a 4-bromo-2,6-diethylphenyl group, a 3,4-dibromo-5-ethylphenyl group, a 3,5-dibromo-4-ethylphenyl group, a 5-bromo-3,4-diethylphenyl group, a 4-bromo-3,5-diethylphenyl group, a 2-chloro-3-fluorophenyl group, a 3-chloro-2-fluorophenyl group, a 2-chloro-4-fluorophenyl group, a 4-chloro-2-fluorophenyl group, a 3-chloro-4-fluorophenyl group, a 4-chloro-3-fluorophenyl group, a 5-chloro-2-fluorophenyl group, a 2-chloro-5-fluorophenyl group, a 2-chloro-6-fluorophenyl group, a 3-chloro-5-fluorophenyl group, a 2,3-dichloro-4-fluorophenyl group, a 2,4-dichloro-3-fluorophenyl group, a 3,4-dichloro-2-fluorophenyl group, a 4-chloro-2,3-difluorophenyl group, a 3-chloro-2,4-difluorophenyl group, a 2-chloro-3,4-difluorophenyl group, a 3,5-dichloro-2-fluorophenyl group, a 2,5-dichloro-3-fluorophenyl group, a 2,3-dichloro-5-fluorophenyl group, a 2-chloro-3,5-difluorophenyl group, a 3-chloro-2,5-difluorophenyl group, a 5-chloro-2,3-difluorophenyl group, a 2,3-dichloro-6-fluorophenyl group, a 2,6-dichloro-3-fluorophenyl group, a 3,6-dichloro-2-fluorophenyl group, a 6-chloro-2,3-difluorophenyl group, a 3-chloro-2,6-difluorophenyl group, a 2-chloro-3,6-difluorophenyl group, a 2,4-dichloro-5-fluorophenyl group, a 2,5-dichloro-4-fluorophenyl group, a 4,5-dichloro-2-fluorophenyl group, a 5-chloro-2,4-difluorophenyl group, a 4-chloro-2,5-difluorophenyl group, a 2-chloro-4,5-difluorophenyl group, a 2,4-dichloro-6-fluorophenyl group, a 2,6-dichloro-4-fluorophenyl group, a 6-chloro-2,4-difluorophenyl group, a 4-chloro-2,6-difluorophenyl group, a 3,4-dichloro-5-fluorophenyl group, a 3,5-dichloro-4-fluorophenyl group, a 5-chloro-3,4-difluorophenyl group, a 4-chloro-3,5-difluorophenyl group, a 2-bromo-3-chlorophenyl group, a 3-bromo-2-chlorophenyl group, a 2-bromo-4-chlorophenyl group, a 4-bromo-2-chlorophenyl group, a 3-bromo-4-chlorophenyl group, a 4-bromo-3-chlorophenyl group, a 5-bromo-2-chlorophenyl group, a 2-bromo-5-chlorophenyl group, a 2-bromo-6-chlorophenyl group, a 3-bromo-5-chlorophenyl group, a 2,3-dibromo-4-chlorophenyl group, a 2,4-dibromo-3-chlorophenyl group, a 3,4-dibromo-2-chlorophenyl group, a 4-bromo-2,3-dichlorophenyl group, a 3-bromo-2,4-dichlorophenyl group, a 2-bromo-3,4-dichlorophenyl group, a 3,5-dibromo-2-chlorophenyl group, a 2,5-dibromo-3-chlorophenyl group, a 2,3-dibromo-5-chlorophenyl group, a 2-bromo-3,5-dichlorophenyl group, a 3-bromo-2,5-dichlorophenyl group, a 5-bromo-2,3-dichlorophenyl group, a 2,3-dibromo-6-chlorophenyl group, a 2,6-dibromo-3-chlorophenyl group, a 3,6-dibromo-2-chlorophenyl group, a 6-bromo-2,3-dichlorophenyl group, a 3-bromo-2,6-dichlorophenyl group, a 2-bromo-3,6-dichlorophenyl group, a 2,4-dibromo-5-chlorophenyl group, a 2,5-dibromo-4-chlorophenyl group, a 4,5-dibromo-2-chlorophenyl group, a 5-bromo-2,4-dichlorophenyl group, a 4-bromo-2,5-dichlorophenyl group, a 2-bromo-4,5-dichlorophenyl group, a 2,4-dibromo-6-chlorophenyl group, a 2,6-dibromo-4-chlorophenyl group, a 6-bromo-2,4-dichlorophenyl group, a 4-bromo-2,6-dichlorophenyl group, a 3,4-dibromo-5-chlorophenyl group, a 3,5-dibromo-4-chlorophenyl group, a 5-bromo-3,4- dichlorophenyl group, a 4-bromo-3,5-dichlorophenyl group, a 2-cyano-3-methylphenyl group, a 3-cyano-2-methylphenyl group, a 2-cyano-4-methylphenyl group, a 4-cyano-2-methylphenyl group, a 3-cyano-4-methylphenyl group, a 4-cyano-3-methylphenyl group, a 5-cyano-2-methylphenyl group, a 2-cyano-5-methylphenyl group, a 2-cyano-6-methylphenyl group, a 3-cyano-5-methylphenyl group, a 4-cyano-2,3-dimethylphenyl group, a 3-cyano-2,4-dimethylphenyl group, a 2-cyano-3,4-dimethyl-phenyl group, a 2-cyano-3,5-dimethylphenyl group, a 3-cyano-2,5-dimethylphenyl group, a 5-cyano-2,3-dimethylphenyl group, a 6-cyano-2,3-dimethylphenyl group, a 3-cyano-2,6-dimethylphenyl group, a 2-cyano-3,6-dimethylphenyl group, a 5-cyano-2,4-dimethylphenyl group, a 4-cyano-2,5-dimethylphenyl group, a 2-cyano-4,5-dimethylphenyl group, a 6-cyano-2,4-dimethylphenyl group, a 4-cyano-2,6-dimethylphenyl group, a 5-cyano-3,4-dimethylphenyl group, a 4-cyano-3,5-dimethylphenyl group, a 2-methyl-3-trifluoromethylphenyl group, a 3-methyl-2-trifluoromethylphenyl group, a 2-methyl-4-trifluoromethylphenyl group, a 4-methyl-2-trifluoromethylphenyl group, a 3-methyl-4-trifluoromethylphenyl group, a 4-methyl-3-trifluoromethylphenyl group, a 5-methyl-2-trifluoromethylphenyl group, a 2-methyl-5-trifluoromethylphenyl group, a 2-methyl-6-trifluoromethylphenyl group, a 3-methyl-5-trifluoromethylphenyl group, a 2,3-dimethyl-4-trifluoromethylphenyl group, a 2,4-dimethyl-3-trifluoromethylphenyl group, a 3,4-dimethyl-2-trifluoromethylphenyl group, a 3,5-dimethyl-2-trifluoromethylphenyl group, a 2,5-dimethyl-3-trifluoromethylphenyl group, a 2,3-dimethyl-5-trifluoromethylphenyl group, a 2,3-dimethyl-6-trifluoromethylphenyl group, a 2,6-dimethyl-3-trifluoromethylphenyl group, a 3,6-dimethyl-2-trifluoromethylphenyl group, a 2,4-dimethyl-5-trifluoromethylphenyl group, a 2,5-dimethyl-4-trifluoromethylphenyl group, a 4,5-dimethyl-2-trifluoromethylphenyl group, a 2,4-dimethyl-6-trifluoromethylphenyl group, a 2,6-dimethyl-4-trifluoromethylphenyl group, a 3,4-dimethyl-5-trifluoromethylphenyl group, a 3,5-dimethyl-4-trifluoromethylphenyl group, a 2-cyclopropyl-3-methylphenyl group, a 3-cyclopropyl-2-methylphenyl group, a 2-cyclopropyl-4-methylphenyl group, a 4-cyclopropyl-2-methylphenyl group, a 3-cyclopropyl-4-methylphenyl group, a 4-cyclopropyl-3-methylphenyl group, a 5-cyclopropyl-2-methylphenyl group, a 2-cyclopropyl-5-methylphenyl group, a 2-cyclopropyl-6-methylphenyl group, a 3-cyclopropyl-5-methylphenyl group, a 4-cyclopropyl-2,3-dimethylphenyl group, a 3-cyclopropyl-2,4-dimethylphenyl group, a 2-cyclopropyl-3,4-dimethylphenyl group, a 2-cyclopropyl-3,5-dimethylphenyl group, a 3-cyclopropyl-2,5-dimethylphenyl group, a 5-cyclopropyl-2,3-dimethylphenyl group, a 6-cyclopropyl-2,3-dimethylphenyl group, a 3-cyclopropyl-2,6-dimethylphenyl group, a 2-cyclopropyl-3,6-dimethylphenyl group, a 5-cyclopropyl-2,4-dimethylphenyl group, a 4-cyclopropyl-2,5-dimethylphenyl group, a 2-cyclopropyl-4,5-dimethylphenyl group, a 6-cyclopropyl-2,4-dimethylphenyl group, a 4-cyclopropyl-2,6-dimethylphenyl group, a 5-cyclopropyl-3,4-dimethylphenyl group, a 4-cyclopropyl-3,5-dimethylphenyl group, a 2-ethinyl-3-methylphenyl group, a 3-ethinyl-2-methylphenyl group, a 2-ethinyl-4-methylphenyl group, a 4-ethinyl-2-methylphenyl group, a 3-ethinyl-4-methylphenyl group, a 4-ethinyl-3-methylphenyl group, a 5-ethinyl-2-methylphenyl group, a 2-ethinyl-5-methylphenyl group, a 2-ethinyl-6-methylphenyl group, a 3-ethinyl-5-methylphenyl group, a 4-ethinyl-2,3-dimethylphenyl group, a 3-ethinyl-2,4-dimethylphenyl group, a 2-ethinyl-3,4-dimethyl-phenyl group, a 2-ethinyl-3,5-dimethylphenyl group, a 3-ethinyl-2,5-dimethylphenyl group, a 5-ethinyl-2,3-dimethylphenyl group, a 6-ethinyl-2,3-dimethylphenyl group, a 3-ethinyl-2,6-dimethylphenyl group, a 2-ethinyl-3,6-dimethylphenyl group, a 5-ethinyl-2,4-dimethylphenyl group, a 4-ethinyl-2,5-dimethylphenyl group, a 2-ethinyl-4,5-dimethylphenyl group, a 6-ethinyl-2,4-dimethylphenyl group, a 4-ethinyl-2,6-dimethylphenyl group, a 5-ethinyl-3,4-dimethylphenyl group, a 4-ethinyl-3,5-dimethylphenyl group, a 2-methyl-3-nitrophenyl group, a 3-methyl-2-nitrophenyl group, a 2-methyl-4-nitrophenyl group, a 4-methyl-2-nitrophenyl group, a 3-methyl-4-nitrophenyl group, a 4-methyl-3-nitrophenyl group, a 5-methyl-2-nitrophenyl group, a 2-methyl-5-nitrophenyl group, a 2-methyl-6-nitrophenyl group, a 3-methyl-5-nitrophenyl group, a 2,3-dimethyl-4-nitrophenyl group, a 2,4-dimethyl-3-nitrophenyl group, a 3,4-dimethyl-2-nitrophenyl group, a 3,5-dimethyl-2-nitrophenyl group, a 2,5-dimethyl-3-nitrophenyl group, a 2,3-dimethyl-5-nitrophenyl group, a 2,3-dimethyl-6-nitrophenyl group, a 2,6-dimethyl-3-nitrophenyl group, a 3,6-dimethyl-2-nitrophenyl group, a 2,4-dimethyl-5-nitrophenyl group, a 2,5-dimethyl-4-nitrophenyl group, a 4,5-dimethyl-2-nitrophenyl group, a 2,4-dimethyl-6-nitrophenyl group, a 2,6-dimethyl-4-nitrophenyl group, a 3,4-dimethyl-5-nitrophenyl group, a 3,5-dimethyl-4-nitrophenyl group, a 2-methyl-3-methoxyphenyl group, a 3-methyl-2-methoxyphenyl group, a 2-methyl-4-methoxyphenyl group, a 4-methyl-2-methoxyphenyl group, a 3-methyl-4-methoxyphenyl group, a 4-methyl-3-methoxyphenyl group, a 5-methyl-2-methoxyphenyl group, a 2-methyl-5-methoxyphenyl group, a 2-methyl-6-methoxyphenyl group, a 3-methyl-5-methoxyphenyl group, a 2,3-dimethyl-4-methoxyphenyl group, a 2,4-dimethyl-3-methoxyphenyl group, a 3,4-dimethyl-2-methoxyphenyl group, a 3,5-dimethyl-2-methoxyphenyl group, a 2,5-dimethyl-3-methoxyphenyl group, a 2,3-dimethyl-5-methoxyphenyl group, a 2,3-dimethyl-6-methoxyphenyl group, a 2,6-dimethyl-3-methoxyphenyl group, a 3,6-dimethyl-2-methoxyphenyl group, a 2,4-dimethyl-5-methoxyphenyl group, a 2,5-dimethyl-4-methoxyphenyl group, a 4,5-dimethyl-2-methoxyphenyl group, a 2,4-dimethyl-6-methoxyphenyl group, a 2,6-dimethyl-4-methoxyphenyl group, a 3,4-dimethyl-5-methoxyphenyl group, a 3,5-dimethyl-4-methoxyphenyl group, a 2-cyano-3-ethylphenyl group, a 3-cyano-2-ethylphenyl group, a 2-cyano-4-ethylphenyl group, a 4-cyano-2-ethylphenyl group, a 3-cyano-4-ethylphenyl group, a 4-cyano-3-ethylphenyl group, a 5-cyano-2-ethylphenyl group, a 2-cyano-5-ethylphenyl group, a 2-cyano-6-ethylphenyl group, a 3-cyano-5-ethylphenyl group, a 4-cyano-2,3-diethylphenyl group, a 3-cyano-2,4-diethylphenyl group, a 2-cyano-3,4-diethylphenyl group, a 2-cyano-3,5-diethylphenyl group, a 3-cyano-2,5-diethylphenyl group, a 5-cyano-2,3-diethylphenyl group, a 6-cyano-2,3-diethylphenyl group, a 3-cyano-2,6-diethylphenyl group, a 2-cyano-3,6-diethylphenyl group, a 5-cyano-2,4-diethylphenyl group, a 4-cyano-2,5-diethylphenyl group, a 2-cyano-4,5-diethylphenyl group, a 6-cyano-2,4-diethylphenyl group, a 4-cyano-2,6-diethylphenyl group, a 5-cyano-3,4-diethylphenyl group, a 4-cyano-3,5-diethylphenyl group, a 2-ethyl-3-trifluoromethylphenyl group, a 3-ethyl-2-trifluoromethylphenyl group, a 2-ethyl-4-trifluoromethylphenyl group, a 4-ethyl-2-trifluoromethylphenyl group, a 3-ethyl-4-trifluoromethylphenyl group, a 4-ethyl-3-trifluoromethylphenyl group, a 5-ethyl-2-trifluoromethylphenyl group, a 2-ethyl-5-trifluoromethylphenyl group, a 2-ethyl-6-trifluoromethylphenyl group, a 3-ethyl-5-trifluoromethylphenyl group, a 2,3-diethyl-4-trifluoromethylphenyl group, a 2,4-diethyl-3-trifluoromethylphenyl group, a 3,4-diethyl-2-trifluoromethylphenyl group, a 3,5-diethyl-2-trifluoromethylphenyl group, a 2,5-diethyl-3-trifluoromethylphenyl group, a 2,3-diethyl-5-trifluoromethylphenyl group, a 2,3-diethyl-6-trifluoromethylphenyl group, a 2,6-diethyl-3- trifluoromethylphenyl group, a 3,6-diethyl-2-trifluoromethylphenyl group, a 2,4-diethyl-5-trifluoromethylphenyl group, a 2,5-diethyl-4-trifluoromethylphenyl group, a 4,5-diethyl-2-trifluoromethylphenyl group, a 2,4-diethyl-6-trifluoromethylphenyl group, a 2,6-diethyl-4-trifluoromethylphenyl group, a 3,4-diethyl-5-trifluoromethylphenyl group, a 3,5-diethyl-4-trifluoromethylphenyl group, a 2-cyclopropyl-3-ethylphenyl group, a 3-cyclopropyl-2-ethylphenyl group, a 2-cyclopropyl-4-ethylphenyl group, a 4-cyclopropyl-2-ethylphenyl group, a 3-cyclopropyl-4-ethylphenyl group, a 4-cyclopropyl-3-ethylphenyl group, a 5-cyclopropyl-2-ethylphenyl group, a 2-cyclopropyl-5-ethylphenyl group, a 2-cyclopropyl-6-ethylphenyl group, a 3-cyclopropyl-5-ethylphenyl group, a 4-cyclopropyl-2,3-diethylphenyl group, a 3-cyclopropyl-2,4-diethylphenyl group, a 2-cyclopropyl-3,4-diethylphenyl group, a 2-cyclopropyl-3,5-diethylphenyl group, a 3-cyclopropyl-2,5-diethylphenyl group, a 5-cyclopropyl-2,3-diethylphenyl group, a 6-cyclopropyl-2,3-diethylphenyl group, a 3-cyclopropyl-2,6-diethylphenyl group, a 2-cyclopropyl-3,6-diethylphenyl group, a 5-cyclopropyl-2,4-diethylphenyl group, a 4-cyclopropyl-2,5-diethylphenyl group, a 2-cyclopropyl-4,5-diethylphenyl group, a 6-cyclopropyl-2,4-diethylphenyl group, a 4-cyclopropyl-2,6-diethylphenyl group, a 5-cyclopropyl-3,4-diethylphenyl group, a 4-cyclopropyl-3,5-diethylphenyl group, a 2-ethyl-3-ethinylphenyl group, a 3-ethyl-2-ethinylphenyl group, a 2-ethyl-4-ethinylphenyl group, a 4-ethyl-2-ethinylphenyl group, a 3-ethyl-4-ethinylphenyl group, a 4-ethyl-3-ethinylphenyl group, a 5-ethyl-2-ethinylphenyl group, a 2-ethyl-5-ethinylphenyl group, a 2-ethyl-6-ethinylphenyl group, a 3-ethyl-5-ethinylphenyl group, a 2,3-diethyl-4-ethinylphenyl group, a 2,4-diethyl-3-ethinylphenyl group, a 3,4-diethyl-2-ethinylphenyl group, a 3,5-diethyl-2-ethinylphenyl group, a 2,5-diethyl-3-ethinylphenyl group, a 2,3-diethyl-5-ethinylphenyl group, a 2,3-diethyl-6-ethinylphenyl group, a 2,6-diethyl-3-ethinylphenyl group, a 3,6-diethyl-2-ethinylphenyl group, a 2,4-diethyl-5-ethinylphenyl group, a 2,5-diethyl-4-ethinylphenyl group, a 4,5-diethyl-2-ethinylphenyl group, a 2,4-diethyl-6-ethinylphenyl group, a 2,6-diethyl-4-ethinylphenyl group, a 3,4-diethyl-5-ethinylphenyl group, a 3,5-diethyl-4-ethinylphenyl group, a 2-ethyl-3-nitrophenyl group, a 3-ethyl-2-nitrophenyl group, a 2-ethyl-4-nitrophenyl group, a 4-ethyl-2-nitrophenyl group, a 3-ethyl-4-nitrophenyl group, a 4-ethyl-3-nitrophenyl group, a 5-ethyl-2-nitrophenyl group, a 2-ethyl-5-nitrophenyl group, a 2-ethyl-6-nitrophenyl group, a 3-ethyl-5-nitrophenyl group, a 2,3-diethyl-4-nitrophenyl group, a 2,4-diethyl-3-nitrophenyl group, a 3,4-diethyl-2-nitrophenyl group, a 3,5-diethyl-2-nitrophenyl group, a 2,5-diethyl-3-nitrophenyl group, a 2,3-diethyl-5-nitrophenyl group, 2,3-diethyl-6-nitrophenyl group, a 2,6-diethyl-3-nitrophenyl group, a 3,6-diethyl-2-nitrophenyl group, a 2,4-diethyl-5-nitrophenyl group, a 2,5-diethyl-4-nitrophenyl group, a 4,5-diethyl-2-nitrophenyl group, a 2,4-diethyl-6-nitrophenyl group, a 2,6-diethyl-4-nitrophenyl group, a 3,4-diethyl-5-nitrophenyl group, a 3,5-diethyl-4-nitrophenyl group, a 2-ethyl-3-methoxyphenyl group, a 3-ethyl-2-methoxyphenyl group, a 2-ethyl-4-methoxyphenyl group, a 4-ethyl-2-methoxyphenyl group, a 3-ethyl-4-methoxyphenyl group, a 4-ethyl-3-methoxyphenyl group, a 5-ethyl-2-methoxyphenyl group, a 2-ethyl-5-methoxyphenyl group, a 2-ethyl-6-methoxyphenyl group, a 3-ethyl-5-methoxyphenyl group, a 2,3-diethyl-4-methoxyphenyl group, a 2,4-diethyl-3-methoxyphenyl group, a 3,4-diethyl-2-methoxyphenyl group, a 3,5-diethyl-2-methoxyphenyl group, a 2,5-diethyl-3-methoxyphenyl group, a 2,3-diethyl-5-methoxyphenyl group, a 2,3-diethyl-6-methoxyphenyl group, a 2,6-diethyl-3-methoxyphenyl group, a 3,6-diethyl-2-methoxyphenyl group, a 2,4-diethyl-5-methoxyphenyl group, a 2,5-diethyl-4-methoxyphenyl group, a 4,5-diethyl-2-methoxyphenyl group, a 2,4-diethyl-6-methoxyphenyl group, a 2,6-diethyl-4-methoxyphenyl group, a 3,4-diethyl-5-methoxyphenyl group, a 3,5-diethyl-4-methoxyphenyl group, a 2-chloro-3-trifluoromethylphenyl group, a 3-chloro-2-trifluoromethylphenyl group, a 2-chloro-4-trifluoromethylphenyl group, a 4-chloro-2-trifluoromethylphenyl group, a 3-chloro-4-trifluoromethylphenyl group, a 4-chloro-3-trifluoromethylphenyl group, a 5-chloro-2-trifluoromethylphenyl group, a 2-chloro-5-trifluoromethylphenyl group, a 2-chloro-6-trifluoromethylphenyl group, a 3-chloro-5-trifluoromethylphenyl group, a 2,3-dichloro-4-trifluoromethylphenyl group, a 2,4-dichloro-3-trifluoromethylphenyl group, a 3,4-dichloro-2-trifluoromethylphenyl group, a 3,5-dichloro-2-trifluoromethylphenyl group, a 2,5-dichloro-3-trifluoromethylphenyl group, a 2,3-dichloro-5-trifluoromethylphenyl group, a 2,3-dichloro-6-trifluoromethylphenyl group, a 2,6-dichloro-3-trifluoromethylphenyl group, a 3,6-dichloro-2-trifluoromethylphenyl group, a 2,4-dichloro-5-trifluoromethylphenyl group, a 2,5-dichloro-4-trifluoromethylphenyl group, a 4,5-dichloro-2-trifluoromethylphenyl group, a 2,4-dichloro-6-trifluoromethylphenyl group, a 2,6-dichloro-4-trifluoromethylphenyl group, a 3,4-dichloro-5-trifluoromethylphenyl group, a 3,5-dichloro-4-trifluoromethylphenyl group, a 2-chloro-3-cyclopropylphenyl group, a 3-chloro-2-cyclopropylphenyl group, a 2-chloro-4-cyclopropylphenyl group, a 4-chloro-2-cyclopropylphenyl group, a 3-chloro-4-cyclopropylphenyl group, a 4-chloro-3-cyclopropylphenyl group, a 5-chloro-2-cyclopropylphenyl group, a 2-chloro-5-cyclopropylphenyl group, a 2-chloro-6-cyclopropylphenyl group, a 3-chloro-5-cyclopropylphenyl group, a 2,3-dichloro-4-cyclopropylphenyl group, a 2,4-dichloro-3-cyclopropylphenyl group, a 3,4-dichloro-2-cyclopropylphenyl group, a 3,5-dichloro-2-cyclopropylphenyl group, a 2,5-dichloro-3-cyclopropylphenyl group, a 2,3-dichloro-5-cyclopropylphenyl group, a 2,3-dichloro-6-cyclopropylphenyl group, a 2,6-dichloro-3-cyclopropylphenyl group, a 3,6-dichloro-2-cyclopropylphenyl group, a 2,4-dichloro-5-cyclopropylphenyl group, a 2,5-dichloro-4-cyclopropylphenyl group, a 4,5-dichloro-2-cyclopropylphenyl group, a 2,4-dichloro-6-cyclopropylphenyl group, a 2,6-dichloro-4-cyclopropylphenyl group, a 3,4-dichloro-5-cyclopropylphenyl group, a 3,5-dichloro-4-cyclopropylphenyl group, a 2-ethoxy-3-fluorophenyl group, a 3-ethoxy-2-fluorophenyl group, a 2-ethoxy-4-fluorophenyl group, a 4-ethoxy-2-fluorophenyl group, a 3-ethoxy-4-fluorophenyl group, a 4-ethoxy-3-fluorophenyl group, a 5-ethoxy-2-fluorophenyl group, a 2-ethoxy-5-fluorophenyl group, a 2-ethoxy-6-fluorophenyl group, a 3-ethoxy-5-fluorophenyl group, a 4-ethoxy-2,3-difluorophenyl group, a 3-ethoxy-2,4-difluorophenyl group, a 2-ethoxy-3,4-difluorophenyl group, a 2-ethoxy-3,5-difluorophenyl group, a 3-ethoxy-2,5-difluorophenyl group, a 5-ethoxy-2,3-difluorophenyl group, a 6-ethoxy-2,3-difluorophenyl group, a 3-ethoxy-2,6-difluorophenyl group, a 2-ethoxy-3,6-difluorophenyl group, a 5-ethoxy-2,4-difluorophenyl group, a 4-ethoxy-2,5-difluorophenyl group, a 2-ethoxy-4,5-difluorophenyl group, a 6-ethoxy-2,4-difluorophenyl group, a 4-ethoxy-2,6-difluorophenyl group, a 5-ethoxy-3,4-difluorophenyl group, a 4-ethoxy-3,5-difluorophenyl group, a 2-bromo-3-trifluoromethoxyphenyl group, a 3-bromo-2-trifluoromethoxyphenyl group, a 2-bromo-4-trifluoromethoxyphenyl group, a 4-bromo-2-trifluoromethoxyphenyl group, a 3-bromo-4-trifluoromethoxyphenyl group, a 4-bromo-3-trifluoromethoxyphenyl group, a 5-bromo-2-trifluoromethoxyphenyl group, a 2-bromo-5-trifluoromethoxyphenyl group, a 2-bromo-6-trifluoromethoxyphenyl group, a 3-bromo-5-trifluoromethoxyphenyl group, a 2,3-dibromo-4-trifluoromethoxyphenyl group, a 2,4-dibromo-3-trifluoromethoxyphenyl group, a 3,4-dibromo-2-trifluoromethoxyphenyl group, a 3,5-dibromo-2-trifluoromethoxyphenyl group, a 2,5-dibromo-3-trifluoromethoxyphenyl group, a 2,3-dibromo-5-trifluoromethoxyphenyl group, a 2,3-dibromo-6-trifluoromethoxyphenyl group, a 2,6-dibromo-3-trifluoromethoxyphenyl group, a 3,6-dibromo-2-trifluoromethoxyphenyl group, a 2,4-dibromo-5-trifluoromethoxyphenyl group, a 2,5-dibromo-4-trifluoromethoxyphenyl group, a 4,5-dibromo-2-trifluoromethoxyphenyl group, a 2,4-dibromo-6-trifluoromethoxyphenyl group, a 2,6-dibromo-4-trifluoromethoxyphenyl group, a 3,4-dibromo-5-trifluoromethoxyphenyl group, a 3,5-dibromo-4-trifluoromethoxyphenyl group, a 4-chloro-2,6-diethylphenyl group, a 2-bromo-4,6-dimethylphenyl group, a 4,6-dimethyl-2-methoxyphenyl group, a 2-bromo-4,6-dimethylphenyl group, a 4-bromo-2,6-diethylphenyl group, a 4-ethinyl-2,6-dimethylphenyl group, a 2,6-diethyl-4-methoxyphenyl group, a 2,6-diethyl-4-nitrophenyl group, a 2,6-diethyl-4-ethinylphenyl group, a 2-cyano-4,6-dimethylphenyl group, 2-cyano-4,6-diethylphenyl group, a 2-cyano-6-ethyl-4-methylphenyl group, a 2,4-dichloro-6-methylphenyl group, a 2-chloro-4,6-dimethylphenyl group, a 2-chloro-6-ethyl-4-methylphenyl group, a 2-chloro-6-ethyl-4-methoxyphenyl group, a 2,4-dichloro-6-ethylphenyl group, a 2-bromo-6-ethyl-4-methylphenyl group, a 2-ethyl-4-methyl-6-methoxyphenyl group, a 3-ethyl-5-ethinylbiphenyl-4-yl group, a 3-ethyl-5-methoxybiphenyl-4-yl group, a 2-cyclopropyl-6-ethyl-4-methylphenyl group, a 4-cyclopropyl-2,6-diethylphenyl group, a 2-chloro-6-fluoro-3-methylphenyl group, a 2-bromo-4-chloro-6-methylphenyl group, a 2-bromo-6-chloro-4-methylphenyl group, a 2-bromo-4-chloro-6-trifluoromethoxyphenyl group, a 2-chloro-6-cyclopropyl-4-methylphenyl group, a 4-bromo-2-chloro-6-trifluoromethoxyphenyl group, a 2-chloro-6-fluoro-3-methylphenyl group, a 3,5-diethylbiphenyl-4-yl group, a 4'-chloro-3,5-diethylbiphenyl-4-yl group, a 4'-methyl-3,5-diethylbiphenyl-4-yl group, a 4-methylbiphenyl-3-yl group, a 4-ethylbiphenyl-3-yl group, a 4-propylbiphenyl-3-yl group, a 4-cyclopropylbiphenyl-3-yl group, a 4-fluorobiphenyl-3-yl group, a 4-chlorobiphenyl-3-yl group, a 4-bromobiphenyl-3-yl group, a 4-iodobiphenyl-3-yl group, a 2'-fluoro-4-methylbiphenyl-3-yl group, a 4-ethyl-2'-fluorobiphenyl-3-yl group, a 2'-fluoro-4-propylbiphenyl-3-yl group, a 4-cyclopropyl-2'-fluorobiphenyl-3-yl group, a 4,2'-difluorobiphenyl-3-yl group, a 4-chloro-2'-fluorobiphenyl-3-yl group, a 4-bromo-2'-fluorobiphenyl-3-yl group, a 2'-fluoro-4-iodobiphenyl-3-yl group, a 2'-chloro-4-methylbiphenyl-3-yl group, a 2'-chloro-4-ethylbiphenyl-3-yl group, a 2'-chloro-4-propylbiphenyl-3-yl group, a 2'-chloro-4-cyclopropylbiphenyl-3-yl group, a 2'-chloro-4-fluorobiphenyl-3-yl group, a 4,2'-dichlorobiphenyl-3-yl group, a 4-bromo-2'-chlorobiphenyl-3-yl group, a 2'-chloro-4-iodobiphenyl-3-yl group, a 2'-bromo-4-methylbiphenyl-3-yl group, a 2'-bromo-4-ethylbiphenyl-3-yl group, a 2'-bromo-4-propylbiphenyl-3-yl group, a 2'-bromo-4-cyclopropylbiphenyl-3-yl group, a 2'-bromo-4-fluorobiphenyl-3-yl group, a 2'-bromo-4-chlorobiphenyl-3-yl group, a 4,2'-dibromobiphenyl-3-yl group, a 2'-bromo-4-iodobiphenyl-3-yl group, a 2'-iodo-4-methylbiphenyl-3-yl group, a 4-ethyl-2'-iodobiphenyl-3-yl group, a 2'-iodo-4-propylbiphenyl-3-yl group, a 4-cyclopropyl-2'-iodobiphenyl-3-yl group, a 4-fluoro-2'-iodobiphenyl-3-yl group, a 4-chloro-2'-iodobiphenyl-3-yl group, a 4-bromo-2'-iodobiphenyl-3-yl group, a 4,2'-diiodobiphenyl-3-yl group, a 4,2'-dimethylbiphenyl-3-yl group, a 4-ethyl-2'-methylbiphenyl-3-yl group, a 2'-methyl-4-propylbiphenyl-3-yl group, a 4-cyclopropyl-2'-methylbiphenyl-3-yl group, a 4-fluoro-2'-methylbiphenyl-3-yl group, a 4-chloro-2'-methylbiphenyl-3-yl group, a 4-bromo-2'-methylbiphenyl-3-yl group, a 4-iodo-2'-methylbiphenyl-3-yl group, a 2'-ethyl-4-methylbiphenyl-3-yl group, a 4,2'-diethylbiphenyl-3-yl group, a 2'-ethyl-4-propylbiphenyl-3-yl group, a 4-cyclopropyl-2'-ethylbiphenyl-3-yl group, a 2'-ethyl-4-fluorobiphenyl-3-yl group, a 4-chloro-2'-ethylbiphenyl-3-yl group, a 4-bromo-2'-ethylbiphenyl-3-yl group, a 2'-ethyl-4-iodobiphenyl-3-yl group, a 4-methyl-2'-trifluoromethylbiphenyl-3-yl group, a 4-ethyl-2'-trifluoromethylbiphenyl-3-yl group, a 4-propyl-2'-trifluoromethylbiphenyl-3-yl group, a 4-cyclopropyl-2'-trifluoromethylbiphenyl-3-yl group, a 4-fluoro-2'-trifluoromethylbiphenyl-3-yl group, a 4-chloro-2'-trifluoromethylbiphenyl-3-yl group, a 4-bromo-2'-trifluoromethylbiphenyl-3-yl group, a 4-iodo-2'-trifluoromethylbiphenyl-3-yl group, a 2'-methoxy-4-methylbiphenyl-3-yl group, a 4-ethyl-2'-methoxybiphenyl-3-yl group, a 2'-methoxy-4-propylbiphenyl-3-yl group, a 4-cyclopropyl-2'-methoxybiphenyl-3-yl group, a 4-fluoro-2'-methoxybiphenyl-3-yl group, a 4-chloro-2'-methoxybiphenyl-3-yl group, a 4-bromo-2'-methoxybiphenyl-3-yl group, a 4-iodo-2'-methoxybiphenyl-3-yl group, a 4-methyl-2'-trifluoromethoxybiphenyl-3-yl group, a 4-ethyl-2'-trifluoromethoxybiphenyl-3-yl group, a 4-propyl-2'-trifluoromethoxybiphenyl-3-yl group, a 4-cyclopropyl-2'-trifluoromethoxybiphenyl-3-yl group, a 4-fluoro-2'-trifluoromethoxybiphenyl-3-yl group, a 4-chloro-2'-trifluoromethoxybiphenyl-3-yl group, a 4-bromo-2'-trifluoromethoxybiphenyl-3-yl group, a 4-iodo-2'-trifluoromethoxybiphenyl-3-yl group, a 3'-fluoro-4-methylbiphenyl-3-yl group, a 4-ethyl-3'-fluorobiphenyl-3-yl group, a 3'-fluoro-4-propylbiphenyl-3-yl group, a 4-cyclopropyl-3'-fluorobiphenyl-3-yl group, a 4,3'-difluorobiphenyl-3-yl group, a 4-chloro-3'-fluorobiphenyl-3-yl group, a 4-bromo-3'-fluorobiphenyl-3-yl group, a 3'-fluoro-4-iodobiphenyl-3-yl group, a 3'-chloro-4-methylbiphenyl-3-yl group, a 3'-chloro-4-ethylbiphenyl-3-yl group, a 3'-chloro-4-propylbiphenyl-3-yl group, a 3'-chloro-4-cyclopropylbiphenyl-3-yl group, a 3'-chloro-4-fluorobiphenyl-3-yl group, a 4,3'-dichlorobiphenyl-3-yl group, a 4-bromo-3'-chlorobiphenyl-3-yl group, a 3'-chloro-4-iodobiphenyl-3-yl group, a 3'-bromo-4-methylbiphenyl-3-yl group, a 3'-bromo-4-ethylbiphenyl-3-yl group, a 3'-bromo-4-propylbiphenyl-3-yl group, a 3'-bromo-4-cyclopropylbiphenyl-3-yl group, a 3'-bromo-4-fluorobiphenyl-3-yl group, a 3'-bromo-4-chlorobiphenyl-3-yl group, a 4,3'-dibromobiphenyl-3-yl group, a 3'-bromo-4-iodobiphenyl-3-yl group, a 3'-iodo-4-methylbiphenyl-3-yl group, a 4-ethyl-3'-iodobiphenyl-3-yl group, a 3'-iodo-4-propylbiphenyl-3-yl group, a 4-cyclopropyl-3'-iodobiphenyl-3-yl group, a 4-fluoro-3'-iodobiphenyl-3-yl group, a 4-chloro-3'-iodobiphenyl-3-yl group, a 4-bromo-3'-iodobiphenyl-3-yl group, a 4,3'-diiodobiphenyl-3-yl group, a 4,3'-dimethylbiphenyl-3-yl group, a 4-ethyl-3'-methylbiphenyl-3-yl group, a 3'-methyl-4-propylbiphenyl-3-yl group, a 4-cyclopropyl-3'-methylbiphenyl-3-yl group, a 4-fluoro-3'-methylbiphenyl-3-yl group, a 4-chloro-3'-methylbiphenyl-3-yl group, a 4-bromo-3'-methylbiphenyl-3-yl group, a 4-iodo-3'-methylbiphenyl-3-yl group, a 3'-ethyl-4-methylbiphenyl-3-yl group, a 4,3'-diethylbiphenyl-3-yl group, a 3'-ethyl-4-propylbiphenyl-3-yl group, a 4-cyclopropyl-3'-ethylbiphenyl-3-yl group, a 3'-ethyl-4-fluorobiphenyl-3-yl group, a 4-chloro-3'-ethylbiphenyl-3-yl group, a 4-bromo-3'-ethylbiphenyl-3-yl group, a 3'-ethyl-4-iodobiphenyl-3-yl group, a 4-methyl-3'-trifluoromethylbiphenyl-3-yl group, a 4-ethyl-3'-trifluoromethylbiphenyl-3-yl group, a 4-propyl-3'-trifluoromethylbiphenyl-3-yl group, a 4-cyclopropyl-3'-trifluoromethylbiphenyl-3-yl group, a 4-fluoro-3'-trifluoromethylbiphenyl-3-yl group, a 4-chloro-3'-trifluoromethylbiphenyl-3-yl group, a 4-bromo-3'-trifluoromethylbiphenyl-3-yl group, a 4-iodo-3'-trifluoromethylbiphenyl-3-yl group, a 3'-methoxy-4-methylbiphenyl-3-yl group, a 4-ethyl-3'-methoxybiphenyl-3-yl group, a 3'-methoxy-4-propylbiphenyl-3-yl group, a 4-cyclopropyl-3'-methoxybiphenyl-3-yl group, a 4-fluoro-3'-methoxybiphenyl-3-yl group, a 4-chloro-3'-methoxybiphenyl-3-yl group, a 4-bromo-3'-methoxybiphenyl-3-yl group, a 4-iodo-3'-methoxybiphenyl-3-yl group, a 4-methyl-3'-trifluoromethoxybiphenyl-3-yl group, a 4-ethyl-3'-trifluoromethoxybiphenyl-3-yl group, a 4-propyl-3'-trifluoromethoxybiphenyl-3-yl group, a 4-cyclopropyl-3'-trifluoromethoxybiphenyl-3-yl group, a 4-fluoro-3'-trifluoromethoxybiphenyl-3-yl group, a 4-chloro-3'-trifluoromethoxybiphenyl-3-yl group, a 4-bromo-3'-trifluoromethoxybiphenyl-3-yl group, a 4-iodo-3'-trifluoromethoxybiphenyl-3-yl group, a 4-methylbiphenyl-3-yl group, a 4-ethylbiphenyl-3-yl group, a 4-propylbiphenyl-3-yl group, a 4-cyclopropylbiphenyl-3-yl group, a 4-fluorobiphenyl-3-yl group, a 4-chlorobiphenyl-3-yl group, a 4-bromobiphenyl-3-yl group, a 4-iodobiphenyl-3-yl group, a 4'-fluoro-4-methylbiphenyl-3-yl group, a 4-ethyl-4'-fluorobiphenyl-3-yl group, a 4'-fluoro-4-propylbiphenyl-3-yl group, a 4-cyclopropyl-4'-fluorobiphenyl-3-yl group, a 4,4'-difluorobiphenyl-3-yl group, a 4-chloro-4'-fluorobiphenyl-3-yl group, a 4-bromo-4'-fluorobiphenyl-3-yl group, a 4'-fluoro-4-iodobiphenyl-3-yl group, a 4'-chloro-4-methylbiphenyl-3-yl group, a 4'-chloro-4-ethylbiphenyl-3-yl group, a 4'-chloro-4-propylbiphenyl-3-yl group, a 4'-chloro-4-cyclopropylbiphenyl-3-yl group, a 4'-chloro-4-fluorobiphenyl-3-yl group, a 4,4'-dichlorobiphenyl-3-yl group, a 4-bromo-4'-chlorobiphenyl-3-yl group, a 4'-chloro-4-iodobiphenyl-3-yl group, a 4'-bromo-4-methylbiphenyl-3-yl group, a 4'-bromo-4-ethylbiphenyl-3-yl group, a 4'-bromo-4-propylbiphenyl-3-yl group, a 4'-bromo-4-cyclopropylbiphenyl-3-yl group, a 4'-bromo-4-fluorobiphenyl-3-yl group, a 4'-bromo-4-chlorobiphenyl-3-yl group, a 4,4'-dibromobiphenyl-3-yl group, a 4'-bromo-4-iodobiphenyl-3-yl group, a 4'-iodo-4-methylbiphenyl-3-yl group, a 4-ethyl-4'-iodobiphenyl-3-yl group, a 4'-iodo-4-propylbiphenyl-3-yl group, a 4-cyclopropyl-4'-iodobiphenyl-3-yl group, a 4-fluoro-4'-iodobiphenyl-3-yl group, chloro-4'-iodobiphenyl-3-yl group, a 4-bromo-4'-iodobiphenyl-3-yl group, a 4,4'-diiodobiphenyl-3-yl group, a 4,4'-dimethylbiphenyl-3-yl group, a 4-ethyl-4'-methylbiphenyl-3-yl group, a 4'-methyl-4-propylbiphenyl-3-yl group, a 4-cyclopropyl-4'-methylbiphenyl-3-yl group, a 4-fluoro-4'-methylbiphenyl-3-yl group, a 4-chloro-4'-methylbiphenyl-3-yl group, a 4-bromo-4'-methylbiphenyl-3-yl group, a 4-iodo-4'-methylbiphenyl-3-yl group, a 4'-ethyl-4-methylbiphenyl-3-yl group, a 4,4'-diethylbiphenyl-3-yl group, a 4'-ethyl-4-propylbiphenyl-3-yl group, a 4-cyclopropyl-4'-ethylbiphenyl-3-yl group, a 4'-ethyl-4-fluorobiphenyl-3-yl group, a 4-chloro-4'-ethylbiphenyl-3-yl group, a 4-bromo-4'-ethylbiphenyl-3-yl group, a 4'-ethyl-4-iodobiphenyl-3-yl group, a 4-methyl-4'-trifluoromethylbiphenyl-3-yl group, a 4-ethyl-4'-trifluoromethylbiphenyl-3-yl group, a 4-propyl-4'-trifluoromethylbiphenyl-3-yl group, a 4-cyclopropyl-4'-trifluoromethylbiphenyl-3-yl group, a 4-fluoro-4'-trifluoromethylbiphenyl-3-yl group, a 4-chloro-4'-trifluoromethylbiphenyl-3-yl group, a 4-bromo-4'-trifluoromethylbiphenyl-3-yl group, a 4-iodo-4'-trifluoromethylbiphenyl-3-yl group, a 4'-methoxy-4-methylbiphenyl-3-yl group, a 4-ethyl-4'-methoxybiphenyl-3-yl group, a 4'-methoxy-4-propylbiphenyl-3-yl group, a 4-cyclopropyl-4'-methoxybiphenyl-3-yl group, a 4-fluoro-4'-methoxybiphenyl-3-yl group, a 4-chloro-4'-methoxybiphenyl-3-yl group, a 4-bromo-4'-methoxybiphenyl-3-yl group, a 4-iodo-4'-methoxybiphenyl-3-yl group, a 4-methyl-4'-trifluoromethoxybiphenyl-3-yl group, a 4-ethyl-4'-trifluoromethoxybiphenyl-3-yl group, a 4-propyl-4'-trifluoromethoxybiphenyl-3-yl group, a 4-cyclopropyl-4'-trifluoromethoxybiphenyl-3-yl group, a 4-fluoro-4'-trifluoromethoxybiphenyl-3-yl group, a 4-chloro-4'-trifluoromethoxybiphenyl-3-yl group, a 4-bromo-4'-trifluoromethoxybiphenyl-3-yl group, a 4-iodo-4'-trifluoromethoxybiphenyl-3-yl group, a 2-methylnaphthalen-1-yl group, a 3-methylnaphthalen-1-yl group, an 8-methylnaphthalen-1-yl group, a 1-methylnaphthalen-2-yl group, a 3-methylnaphthalen-2-yl group, a 4-methylnaphthalen-2-yl group, a 2-ethylnaphthalen-1-yl group, a 3-ethylnaphthalen-1-yl group, an 8-ethylnaphthalen-1-yl group, a 1-ethylnaphthalen-2-yl group, a 3-ethylnaphthalen-2-yl group, a 4-ethylnaphthalen-2-yl group, a 2-fluoronaphthalen-1-yl group, a 3-fluoronaphthalen-1-yl group, an 8-fluoronaphthalen-1-yl group, a 1-fluoronaphthalen-2-yl group, a 3-fluoronaphthalen-2-yl group, a 4-fluoronaphthalen-2-yl group, a 2-chloronaphthalen-1-yl group, a 3-chloronaphthalen-1-yl group, an 8-chloronaphthalen-1-yl group, a 1-chloronaphthalen-2-yl group, a 3-chloronaphthalen-2-yl group, a 4-chloronaphthalen-2-yl group, a 2-bromonaphthalen-1-yl group, a 3-bromonaphthalen-1-yl group, an 8-bromonaphthalen-1-yl group, a 1-bromonaphthalen-2-yl group, a 3-bromonaphthalen-2-yl group, a 4-bromonaphthalen-2-yl group, a 2-iodonaphthalen-1-yl group, a 3-iodonaphthalen-1-yl group, an 8-iodonaphthalen-1-yl group, a 1-iodonaphthalen-2-yl group, a 3-iodonaphthalen-2-yl group, a 4-iodonaphthalen-2-yl group, a 2-trifluoromethylnaphthalen-1-yl group, a 3-trifluoromethylnaphthalen-1-yl group, an 8-trifluoromethylnaphthalen-1-yl group, a 1-trifluoromethylnaphthalen-2-yl group, a 3-trifluoromethylnaphthalen-2-yl group, a 4-trifluoromethylnaphthalen-2-yl group, a 2-methoxynaphthalen-1-yl group, a 3-methoxynaphthalen-1-yl group, an 8-methoxynaphthalen-1-yl group, a 1-methoxynaphthalen-2-yl group, a 3-methoxynaphthalen-2-yl group, a 4-methoxynaphthalen-2-yl group, a 2-cyclopropylnaphthalen-1-yl group, a 3-cyclopropylnaphthalen-1-yl group, an 8-cyclopropylnaphthalen-1-yl group, a 1-cyclopropylnaphthalen-2-yl group, a 3-cyclopropylnaphthalen-2-yl group, a 4-cyclopropylnaphthalen-2-yl group, a 2-ethinylnaphthalen-1-yl group, a 3-ethinylnaphthalen-1-yl group, an 8-ethinylnaphthalen-1-yl group, a 1-ethinylnaphthalen-2-yl group, a 3-ethinylnaphthalen-2-yl group, and a 4-ethinylnaphthalen-2-yl group;

5- or 6-membered heteroaryl group optionally having one or more substituents: a 1-pyrazolyl group, a 2-pyrazolyl group, a 3-pyrazolyl group, a 5-methyl-1-pyrazolyl group, a 5-ethyl-1-pyrazolyl group, a 3-phenyl-5-methyl-1-pyrazolyl group, a 3-phenyl-5-ethyl-1-pyrazolyl group, a 3-(4-chlorophenyl)-5-methyl-1-pyrazolyl group, a 3-(4-chlorophenyl)-5-ethyl-1-pyrazolyl group, a 3-(4-bromophenyl)-5-methyl-1-pyrazolyl group, a 3-(4-bromophenyl)-5-ethyl-1-pyrazolyl group, a 3-(4-trifluoromethylphenyl)-5-methyl-1-pyrazolyl group, a 3-(4-trifluoromethylphenyl)-5-ethyl-1-pyrazolyl group, a 1-imidazolyl group, a 2-methyl-1-imidazolyl group, a 2-ethyl-1-imidazolyl group, a 2-methyl-4-phenyl-1-imidazolyl group, a 2-ethyl-4-phenyl-1-imidazolyl group, a 2-methyl-4-(4-chlorophenyl)-1-imidazolyl group, a 2-ethyl-4-(4-chlorophenyl)-1-imidazolyl group, a 2-methyl-4-(4-bromophenyl)-1-imidazolyl group, a 2-ethyl-4-(4-bromophenyl)-1-imidazolyl group, a 2-methyl-4-(4-trifluoromethylphenyl)-1-imidazolyl group, a 2-ethyl-4-(4-trifluoromethylphenyl)-1-imidazolyl group, a 2-imidazolyl group, a 4-imidazolyl group, a 1-(1,2,4-triazolyl) group, a 3-(1,2,4-triazolyl) group, a 5-(1,2,4-triazolyl) group, a 1-tetrazolyl group, a 5-tetrazolyl group, a 2-oxazolyl group, a 4-oxazolyl group, a 5-oxazolyl group, a 3-isoxazolylzolyl group, a 4-isoxazolylzolyl group, a 5-isoxazolylzolyl group, a 3-(1,2,4-oxadiazolyl) group, a 5-(1,2,4-oxadiazolyl) group, a 2-(1,3,4-oxadiazolyl) group, a 2-thiazolyl group, a 4-thiazolyl group, a 5-thiazolyl group, a 3-isothiazolyl group, a 4-isothiazolyl group, a 5-isothiazolyl group, a 3-(1,2,4-thiadiazolyl) group, a 5-(1,2,4-thiadiazolyl) group, a 2-(1,3,4-thiadiazolyl) group, a 3-(1,2,5-thiadiazolyl) group, a 2-furyl group, a 3-furyl group, a 2-thienyl group, a 3-thienyl group, a 2-pyridyl group, a 3-pyridyl group, a 2-methyl-3-pyridyl group, a 2-ethyl-3-pyridyl group, a 2-methyl-5-phenyl-3-pyridyl group, a 2-ethyl-5-phenyl-3-pyridyl group, a 2-methyl-5-(4-chlorophenyl)-3-pyridyl group, a 2-ethyl-5-(4-chlorophenyl)-3-pyridyl group, a 2-methyl-5-(4-bromophenyl)-3-pyridyl group, a 2-ethyl-5-(4-bromophenyl)-3-pyridyl group, a 2-methyl-5-(4-trifluoromethylphenyl)-3-pyridyl group, a 2-ethyl-5-(4-trifluoromethylphenyl)-3-pyridyl group, a 4-pyridyl group, a 3-methyl-4-pyridyl group, a 3-ethyl-4-pyridyl group, a 2-phenyl-5-methyl-4-pyridyl group, a 2-phenyl-5-ethyl-4-pyridyl group, a 2-(4-chlorophenyl)-5-ethyl-4-pyridyl group, a 2-(4-bromophenyl)-5-methyl-4-pyridyl group, a 2-(4-bromophenyl)-5-ethyl-4-pyridyl group, a 2-(4-trifluoromethylphenyl)-5-methyl-4-pyridyl group, a 2-(4-trifluoromethylphenyl)-5-ethyl-4-pyridyl group, a 2-pyrimidyl group, a 4-pyrimidyl group, 5-pyrimidyl group, a 3-pyridazyl group, a 4-pyridazyl group, a 3-methyl-4-pyridazyl group, a 3-ethyl-4-pyridazyl group, a 3-methyl-6-phenyl-4-pyridazyl group, a 3-ethyl-6-phenyl-3-pyridazyl group, a 3-methyl-6-(4-chlorophenyl)-4-pyridazyl group, a 3-ethyl-6-(4-chlorophenyl)-4-pyridazyl group, a 3-methyl-6-(4-bromophenyl)-4-pyridazyl group, a 3-ethyl-6-(4-bromophenyl)-4-pyridazyl group, a 3-methyl-6-(4-trifluoromethylphenyl)-4-pyridazyl group, a 3-ethyl-6-(4-trifluoromethylphenyl)-4-pyridazyl group, a 2-pyrazyl group, a 3-methyl-2-pyrazyl group, a 3-ethyl-2-pyrazyl group, a 3-methyl-6-phenyl-2-pyrazyl group, a 3-ethyl-6-phenyl-2-pyrazyl group, a 3-methyl-6-(4-chlorophenyl)-2-pyrazyl group, a 3-ethyl-6-(4-chlorophenyl)-2-pyrazyl group, a 3-methyl-6-(4-bromophenyl)-2-pyrazyl group, a 3-ethyl-6-(4-bromophenyl)-2-pyrazyl group, a 3-methyl-6-(4-trifluoromethylphenyl)-2-pyrazyl group, a 3-ethyl-6-(4-trifluoromethylphenyl)-2-pyrazyl group, and a 2-(1,3,5-triazinyl) group;

8- to 10-membered fused heteroaryl group optionally having one or more substituents: an indol-1-yl group, an indol-2-yl group, an indol-3-yl group, an indol-4-yl group, an indol-5-yl group, an indol-6-yl group, an indol-7-yl group, a 1-methylindol-3-yl group, an indazol-1-yl group, an indazol-3-yl group, an indazol-4-yl group, an indazol-5-yl group, an indazol-6-yl group, an indazol-7-yl group, a benzotriazol-1-yl group, a benzotriazol-4-yl group, a benzotriazol-5-yl group, a benzotriazol-6-yl group, a benzotriazol-7-yl group, a benzofuran-2-yl group, a benzofuran-3-yl group, a benzofuran-4-yl group, a benzofuran-5-yl group, a benzofuran-6-yl group, a benzofuran-7-yl group, a benzothiophen-2-yl group, a benzothiophen-3-yl group, a benzothiophen-4-yl group, a benzothiophen-5-yl group, a benzothiophen-6-yl group, and a benzothiophen-7-yl group;

C1-C6 alkylsulfonyloxy group: a methylsulfonyloxy group, an ethylsulfonyloxy group, a propylsulfonyloxy group, and a hexylsulfonyloxy group;

C1-C6 alkoxysulfonyloxy group: a methoxysulfonyloxy group, an ethoxysulfonyloxy group, a propoxysulfonyloxy group, and a hexyloxysulfonyloxy group;

5- or 6-membered cyclic group formed with a carbon atom which is bonded to $R^{10}$ and $R^{11}$, $R^{10\text{-}17A}$ and $R^{11\text{-}17A}$, or $R^{10\text{-}19A}$ and $R^{11\text{-}19A}$: a cyclopentylidene group, and a cyclohexylidene group.

A compound of the formula (1-a) wherein R1 is a hydrogen atom can exist as tautomers of the formula (1-a') and the formula (1-a"). The compound of the formula (1-a) includes all of those tautomers and a mixture of two or more tautomers.

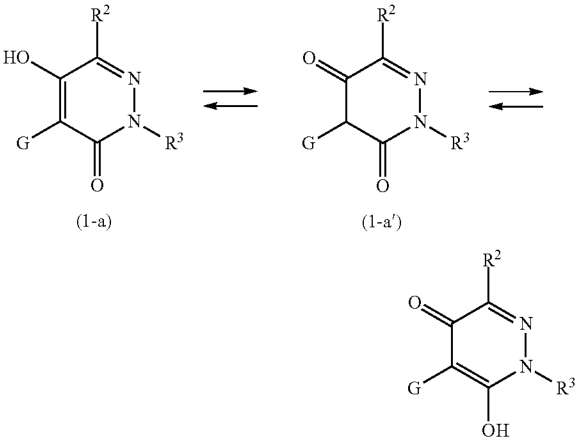

(1-a) (1-a') (1-a")

Each of the compounds of the formulae (4) and (5) can exist as isomers. The compounds of the formulae (4) and (5) include all of the isomers.

Then, a method of the production of the present invention will be illustrated.

Production Method 1:

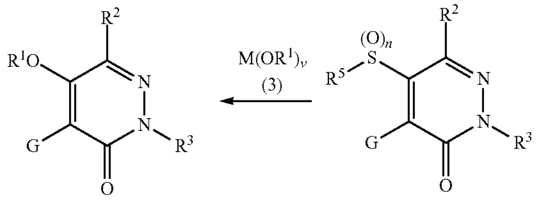

(1) (2)

wherein $R^1$, $R^2$, $R^3$, $R^5$, G, M, n, and V are as defined above.

A compound of the formula (1) (hereinafter referred to as Compound (1)) can be prepared by reacting a compound of the formula (2) (hereinafter referred to as Compound (2)) with a compound of the formula (3) (hereinafter referred to as Compound (3)).

The reaction is usually performed in the presence of a solvent. Examples of the solvent which can be used are water; an aromatic hydrocarbon solvent such as benzene, chlorobenzene, toluene, and xylene; a halogenated hydrocarbon solvent such as chloroform and dichloromethane; an alcohol solvent such as methanol, ethanol, isopropanol, n-butanol, and ethylene glycol; an ester solvent such as ethyl acetate; a ketone solvent such as acetone, methyl ethyl ketone, and methyl isobutyl ketone; an ether solvent such as 1,2-dimethoxyethane, diethylene glycol dimethyl ether, polyethyleneglycol, tetrahydrofuran, and dioxane; a nitrile solvent such as acetonitrile and propionitrile; an aromatic heterocycle solvent such as pyridine; a sulfoxide solvent such as dimethylsulfoxide; an amide solvent such as dimethylformamide, dimethylacetamide, and N-methylpyrrolidone; or a mixture thereof.

The amount of solvent is not limited, but usually 100 or less parts by weight to 1 part by weight of Compound (2) for an economic reason.

The reaction may be performed in the presence of a catalyst. Examples of the catalyst include a phase transfer catalyst such as a quaternary ammonium salt such as tetrabutyl ammonium chloride, tetrabutyl ammonium bromide, tetrabutyl ammonium iodide, benzyl tri-n-butylammonium bromide, benzyl trimethyl ammonium chloride, benzyl triethyl ammonium chloride, methyl tri-n-butyl ammonium chloride, tetraethyl ammonium chloride, tetra n-butyl ammonium chloride, benzyl trimethyl ammonium bromide, benzyl triethyl ammonium bromide, tetraethyl ammonium iodide, and benzyl trimethyl ammonium iodide; and a quaternary phosphonium salt such as n-heptyltriphenylphosphonium bromide and tetraphenylphosphonium bromide. The amount of catalyst may be catalytic amount, usually 0.01 to 10 moles to 1 mole of Compound (2).

Examples of Compound (3) include a metal hydroxide such as calcium hydroxide, lithium hydroxide, sodium hydroxide, and potassium hydroxide; a metal alkoxide such as sodium methoxide, potassium methoxide, lithium methoxide, sodium ethoxide, and sodium n-butoxide; and a metal phenoxide such as sodium phenoxide. They may be used as those which are commercially available or timely prepared or diluted with a solvent. The amount of Compound (3) may be one or more moles to 1 mole of Compound (2), though the upper limit is not limited, the amount is usually in the range of 1 to 10 moles.

The reaction temperature is usually not less than melting point of a solvent and not more than boiling point of the solvent, preferably from 50° C. to boiling point of the used solvent. A reaction mixture may be irradiated with microwave. The reaction time is, though it may be varied depending on the type and amount of Compound (3), the type and amount of solvent, the reaction temperature and the like, usually 0.1 to 100 hours, typically 0.1 to 60 hours.

In particular, the reaction can be performed by mixing a solution containing Compound (2) with Compound (3) or a solution containing Compound (3). The mixing may be performed by either a method which adds Compound (3) or a solution containing Compound (3) to a solution containing Compound (2), or a method which adds a solution containing Compound (2) to Compound (3) or a solution containing Compound (3), and each of the solvents used in those solutions may be same or different. When a catalyst is added, the catalyst may be added at any stage, and it may be added during the reaction in progress.

In order to monitor the progress of the reaction, conventional analysis techniques such as thin layer chromatography, gas chromatography, high-performance liquid chromatography, and NMR can be used.

The reaction mixture thus obtained usually contains Compound (1) as a main product. Compound (1) can be isolated by known procedures such as washing, filtration, concentration, and recrystallization. The isolated Compound (1) can be further purified by conventional techniques such as distillation, column chromatography, and recrystallization.

Production Method 2:

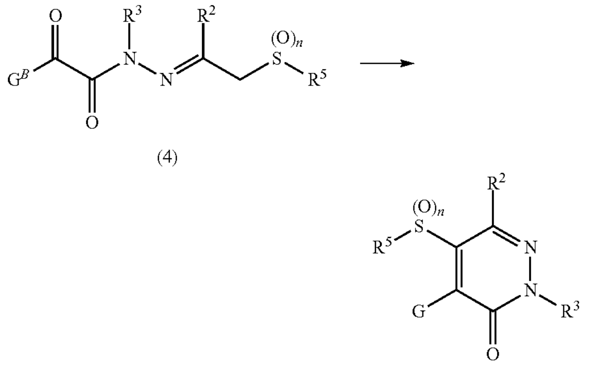

(4)

(2)

wherein $R^2$, $R^3$, $R^5$, G, and n are as defined above.

Compound (2) can be prepared by reacting a compound of the formula (4) (hereinafter referred to as Compound (4)) with a base.

The reaction is usually performed in the presence of a solvent.

Examples of the solvent which can be used are water; an aromatic hydrocarbon solvent such as benzene, chlorobenzene, toluene, and xylene; a halogenated hydrocarbon solvent such as chloroform and dichloromethane; a hydrocarbon solvent such as hexane and heptane; an alcohol solvent such as methanol, ethanol, isopropanol, n-butanol, and ethylene glycol; an ether solvent such as 1,2-dimethoxyethane, diethylene glycol dimethyl ether, tetrahydrofuran, and dioxane; an ester solvent such as ethyl acetate; a ketone solvent such as acetone, methyl ethyl ketone and methyl isobutyl ketone; a nitrile solvent such as acetonitrile and propionitrile; a sulfoxide solvent such as dimethylsulfoxide; an amide solvent such as dimethylformamide, dimethylacetamide, and N-methylpyrrolidone; or a mixture thereof.

The amount of solvent is not limited, but usually 100 or less parts by weight to 1 part by weight of Compound (4) for an economic reason.

The reaction may be performed in the presence of a catalyst. Examples of the catalyst which can be used are a phase transfer catalyst such as a quaternary ammonium salt such as tetrabutylammonium bromide, tetrabutylammonium iodide, and benzyl tri-n-butylammonium bromide; and a quaternary phosphonium salt such as n-heptyl triphenylphosphonium bromide and tetraphenylphosphonium bromide. The amount of catalyst may be catalytic amount, usually 0.01 to 10 moles to 1 mole of Compound (4).

Examples of the base which can be used are an organic base such as pyridine, 4-dimethylaminopyridine, triethylamine, ethyldiisopropylamine, and 1,8-diazabicyclo[5.4.0]-7-undecene; a metal amide base such as lithium diisopropylamide and sodium diisopropylamide; a metal disilazide base such as lithium hexamethyldisilazide and potassium hexamethyldisilazide; a metal hydroxide such as lithium hydroxide, sodium hydroxide, and potassium hydroxide; a metal hydride such as sodium hydride and potassium hydride; carbonates such as sodium carbonate, potassium carbonate, and sodium hydrogen carbonate; phosphates such as sodium phosphate, disodium hydrogen phosphate, and sodium dihydrogen phosphate; acetates such as sodium acetate; and a metal alkoxide such as sodium methoxide and lithium methoxide; among of them, carbonates and metal hydroxides are preferable.

The amount of base may be catalytic amount, usually 0.01 to 10 moles, preferably 0.1 to 5 moles, more preferably 0.1 to 2 moles to 1 mole of Compound (4).

The reaction temperature is usually not less than melting point of a solvent and not more than boiling point of the solvent, preferably from melting point the solvent to 70° C.

The reaction time is, though it may be varied depending on the type and amount of base, the type and amount of solvent, the reaction temperature and the like, usually 0.1 to 100 hours, typically 0.1 to 24 hours.

The reaction can be performed by mixing a solution containing Compound (4) with a base or a solution containing the base. The mixing may be performed by either a method which adds a base or a solution containing the base to a solution containing Compound (4), or a method which adds a solution containing Compound (4) to a base or a solution containing the base, and each of the solvents used in those solutions may be same or different.

In the reaction, a dihydropyridazinone compound of the formula (13):

(13)

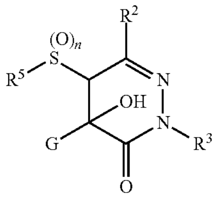

wherein $R^2$, $R^3$, $R^5$, G, and n are as defined above;

can be observed. The compound of the formula (13) is a reaction intermediate, and it may be subjected to dehydration after isolation and purification or without isolation.

In order to monitor the progress of the reaction, conventional analysis techniques such as thin layer chromatography, gas chromatography, high-performance liquid chromatography, and NMR can be used.

Compound (2) can be isolated by known procedures such as washing, filtration, concentration, and recrystallization. The isolated Compound (2) can be further purified by conventional techniques such as distillation, column chromatography, and recrystallization.

Also, Compound (2) wherein $R^3$ is not hydrogen can be prepared from a compound wherein $R^3$ is hydrogen.

(see Journal of American Chemical Society, 1945, 67, 60)

Also, Compound (2) wherein n is an integer 1 or 2 can be prepared from Compound (2) wherein n is an integer of 0.

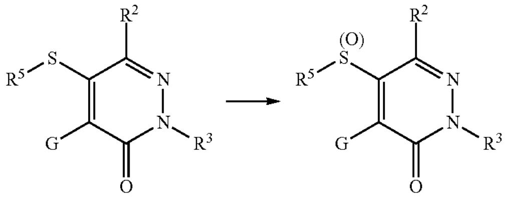

(2-O0) (2-O1)

OR

-continued

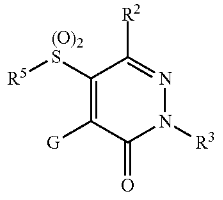

(2-O2)

wherein $R^2$, $R^3$, $R^5$, and G are as defined above.

A compound of the formula (2-O1) (hereinafter referred to as Compound (2-O1)) or a compound of the formula (2-O2) (hereinafter referred to as Compound (2-O2)) can be prepared by reacting a compound of the formula (2-O0) (hereinafter referred to as Compound (2-O0)) with an oxidizing agent.

The reaction is usually performed in the presence of a solvent.

Examples of the solvent which can be used are water; an aromatic hydrocarbon solvent such as benzene, chlorobenzene, toluene, and xylene; a halogenated hydrocarbon solvent such as chloroform and dichloromethane; a hydrocarbon solvent such as hexane and heptane; an alcohol solvent such as methanol, ethanol, isopropanol, n-butanol, and ethylene glycol; an ether solvent such as 1,2-dimethoxyethane, diethylene glycol dimethyl ether, tetrahydrofuran, and dioxane; an ester solvent such as ethyl acetate; a ketone solvent such as acetone, methyl ethyl ketone and methyl isobutyl ketone; a nitrile solvent such as acetonitrile and propionitrile; an amide solvent such as dimethylformamide, dimethylacetamide, and N-methylpyrrolidone; a carboxylic acid solvent such as formic acid and acetic acid; or a mixture thereof.

The amount of solvent is not limited, but usually 100 or less parts by weight to 1 part by weight of Compound (2-O0) for an economic reason.

The reaction may be performed in the presence of a catalyst. Examples of the catalyst which can be used are an oxide of heavy metal such as tungsten or vanadium. The amount of catalyst may be catalytic amount, usually 0.01 to 10 moles to 1 mole of Compound (2-O0).

Examples of the oxidizing agent which can be used are organic peroxide such as tert-butyl hydroperoxide (TBHP); inorganic peroxide such as hydrogen peroxide; and peracid such as meta-chloroperbenzoic acid (mCPBA) and peracetic acid; among of them, a meta-chloroperbenzoic acid and a hydrogen peroxide are preferable.

The amount of oxidizing agent may be, for Compound (2-O2) production, two or more moles to 1 mole, preferably 2 to 20 moles, and for Compound (2-O1) production, one or more moles, preferably 1.0 to 1.5 moles to 1 mole of Compound (2-O0).

The reaction temperature is usually not less than melting point of a solvent and not more than boiling point of the solvent, preferably from melting point of a solvent to 70° C.

The reaction time is, though it may be varied depending on the type and amount of oxidizing agent, the type and amount of solvent, the reaction temperature and the like, usually 0.1 to 100 hours, typically 0.1 to 24 hours.

The reaction can be performed by mixing a solution containing Compound (2-O0) with an oxidizing agent or a solution containing the oxidizing agent. The mixing may be performed by either a method which adds an oxidizing agent or a solution containing the oxidizing agent to a solution containing Compound (2-O0), or a method which adds a solution containing Compound (2-O0) to a oxidizing agent or a solution containing the oxidizing agent, and each of the solvents used in those solutions may be same or different. When a catalyst is used, the catalyst may be added at any stage, and it may be added during the reaction in progress.

In the reaction, for Compound (2-O2) production, Compound (2-O1) can be observed. Compound (2-O1) is a reaction intermediate, and it may be subjected to oxidation after isolation and purification or without isolation.

In order to monitor the progress of the reaction, conventional analysis techniques such as thin layer chromatography, gas chromatography, high-performance liquid chromatography, and NMR can be used.

Compound (2-O1) or Compound (2-O2) can be isolated by known procedures such as washing, filtration, concentration, and recrystallization. The isolated Compound (2-O1) or Compound (2-O2) can be further purified by conventional techniques such as distillation, column chromatography, and recrystallization.

Production Method 3:

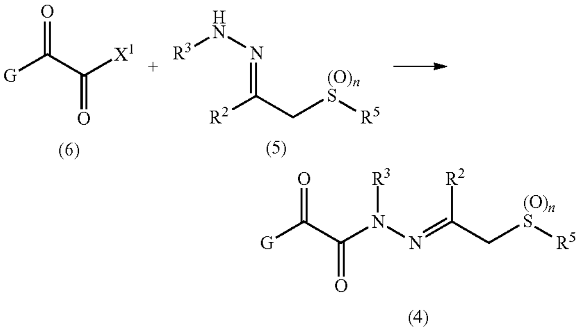

wherein $R^2$, $R^3$, $R^5$, G, n, and $X^1$ are as defined above.

Compound (4) can be prepared by reacting a compound of the formula (6) (hereinafter referred to as Compound (6)) with a compound of the formula (5) (hereinafter referred to as Compound (5)).

The reaction is usually performed in the presence of a solvent.

Examples of the solvent which can be used are an aromatic hydrocarbon solvent such as benzene, chlorobenzene, toluene, and Xylene; a halogenated hydrocarbon solvent such as dichloromethane and chloroform; an aromatic heterocycle solvent such as pyridine; a hydrocarbon solvent such as hexane and heptane; a nitrile solvent such as acetonitrile and propionitrile; an ether solvent such as 1,2-dimethoxyethane, diethylene glycol dimethyl ether, tetrahydrofuran, and dioxane; an ester solvent such as ethyl acetate; a ketone solvent such as acetone, methyl ethyl ketone and methyl isobutyl ketone; a sulfoxide solvent such as dimethylsulfoxide; an amide solvent such as dimethylformamide, dimethylacetamide, and N-methylpyrrolidone; or a mixture thereof; among of them, an aromatic hydrocarbon solvent and ether solvent are preferable.

The amount of solvent is not limited, but usually 100 or less parts by weight to 1 part by weight of Compound (6) for an economic reason.

The amount of Compound (5) may usually be one or more moles, preferably 1.0 to 3.0 moles to 1 mole of Compound (6).

The reaction may be performed in the presence of a base.

Examples of the base which can be used are an organic base such as pyridine, 4-dimethylaminopyridine, triethylamine, ethyldiisopropylamine, and 1,8-diazabicyclo[5.4.0]-7-undecene; a metal amide base such as lithium diisopropylamide and sodium diisopropylamide; a disilazide base such as lithium hexamethyldisilazide and potassium hexamethyldisilazide; a metal hydride such as sodium hydride and potassium hydride; a metal hydroxide such as sodium hydroxide and potassium hydroxide; carbonates such as sodium carbonate, potassium carbonate, and sodium hydrogen carbonate; phosphates such as sodium phosphate, disodium hydrogen phosphate, and sodium dihydrogen phosphate; acetates such as sodium acetate; and a metal alkoxide such as sodium methoxide and lithium methoxide; among of them, an organic base is preferable.

The amount of the base may usually be one or more moles, preferably 1 to 5 moles to 1 mole of Compound (6).

The reaction temperature is usually not less than melting point of a solvent and not more than boiling point of the solvent, preferably from −30° C. to 50° C.

The reaction time is, though it may be varied depending on the reaction temperature, the type and amount of base, the type and amount of solvent and the like, usually 0.1 to 100 hours, typically 0.1 to 24 hours.

The reaction is performed by mixing Compound (6) or a solution containing Compound (6) with a solution containing Compound (5). The mixing may be performed by either a method which adds Compound (6) or a solution containing Compound (6) to a solution containing Compound (5) at a favorable temperature, or a method which adds a solution containing Compound (5) to a solution containing Compound (6) at a favorable temperature, preferably a method which adds a solution containing Compound (6) to a solution containing Compound (5) at a favorable temperature. Each of the solvents used in those solutions may be same or different. When a base is used, though the base may be added at any stage, preferably, a base is added to a solution containing Compound (5), and then a solution containing Compound (6) is added at a favorable temperature.

In order to monitor the progress of the reaction, conventional analysis techniques such as thin layer chromatography, gas chromatography, high-performance liquid chromatography, and NMR can be used.

The reaction mixture thus obtained usually contains Compound (4) as a main product. Compound (4) can be isolated by known procedures such as filtration, concentration, and recrystallization. The isolated Compound (4) can be further purified by conventional techniques such as distillation, column chromatography, and recrystallization.

Production Method 4:

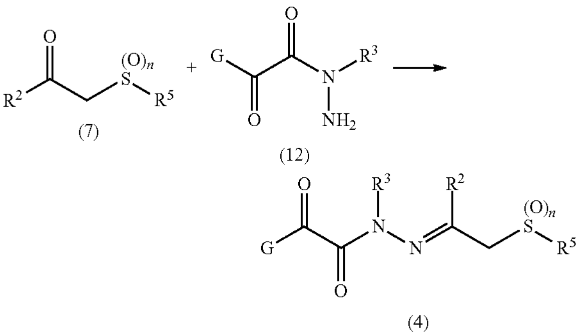

wherein $R^2$, $R^3$, $R^5$, G, and n are as defined above.

Compound (4) can be prepared by reacting a compound of the formula (7) (hereinafter referred to as Compound (7)) with a compound of the formula (12) (hereinafter referred to as Compound (12)).

The reaction is usually performed in the presence of a solvent.

Examples of the solvent which can be used are an aromatic hydrocarbon solvent such as benzene, chlorobenzene, toluene, and xylene; a halogenated hydrocarbon solvent such as dichloromethane and chloroform; a hydrocarbon solvent such as hexane and heptane; an alcohol solvent such as methanol, ethanol, isopropanol, n-butanol, and ethylene glycol; an ether solvent such as 1,2-dimethoxyethane, diethylene glycol dimethyl ether, tetrahydrofuran, and dioxane; a nitrile solvent such as acetonitrile and propionitrile; an ester solvent such as ethyl acetate; a sulfoxide solvent such as dimethylsulfoxide; an amide solvent such as dimethylformamide, dimethylacetamide, and N-methylpyrrolidone; or a mixture thereof; among of them, an alcohol solvent and an aromatic hydrocarbon solvent are preferable.

The amount of solvent is not limited, but usually 100 or less parts by weight to 1 part by weight of Compound (12) for an economic reason.

Compound (7) can usually be purchased or timely prepared. The method for producing Compound (7) is described, for example, in Organic Synthesis, 1977, 56, 72-74 or Heterocycles, 2007, 73 469-480.

The amount of Compound (7) may usually be one or more moles, preferably 1.0 to 3.0 moles to 1 mole of Compound (12).

The reaction may be performed in the presence of a dehydrating agent or an acid. Dehydration may also be achieved by azeotropic distillation.

Examples of the dehydrating agent which can be used are an inorganic dehydrating agent such as silica gel, molecular sieves, sodium sulfate, and magnesium sulfate.

The amount of dehydrating agent may usually be one or more parts by weight, preferably 1 to 5 parts by weight to 1 part by weight of Compound (12).

Examples of the acid include an organic acid such as methanesulfonic acid, p-toluenesulfonic acid, and acetic acid; and an inorganic acid such as hydrochloric acid, sulfuric acid, and phosphoric acid.

The amount of acid may usually be catalytic amount, for example, 0.01 to 10 moles to 1 mole of Compound (12).

The reaction temperature is usually not less than melting point of a solvent and not more than boiling point of the solvent, preferably from 0° C. to 150° C.

The reaction time is, though it may be varied depending on the reaction temperature, the type and amount of dehydrating agent or acid, the type and amount of solvent and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (4) as a main product. Compound (4) can be isolated by known procedures such as filtration, concentration, and recrystallization. The isolated Compound (4) can be further purified by conventional techniques such as distillation, column chromatography, and recrystallization.

Compound (4) wherein $R^3$ is not hydrogen can also be prepared from a compound wherein $R^3$ is hydrogen.

(see Journal of Organic Chemistry, 1998, 63, 8145-8149)

Production Method 5:

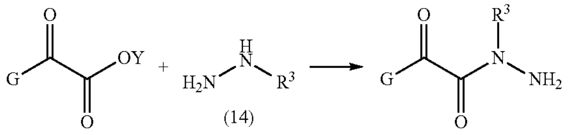

(9) (14) (12)

wherein $R^3$, G, and Y are as defined above.

Compound (12) can be prepared by reacting a compound of the formula (9) (hereinafter referred to as Compound (9)) with a compound of the formula (14) (hereinafter referred to as Compound (14)).

The reaction is usually performed in the presence of a solvent.

Examples of the solvent which can be used are water; an aromatic hydrocarbon solvent such as benzene, chlorobenzene, toluene, and xylene; a halogenated hydrocarbon solvent such as dichloromethane and chloroform; a hydrocarbon solvent such as hexane and heptane; an alcohol solvent such as methanol, ethanol, isopropanol, n-butanol, and ethylene glycol; an ether solvent such as 1,2-dimethoxyethane, diethylene glycol dimethyl ether, tetrahydrofuran, and dioxane; a nitrile solvent such as acetonitrile and propionitrile; an ester solvent such as ethyl acetate; a sulfoxide solvent such as dimethylsulfoxide; an amide solvent such as dimethylformamide, dimethylacetamide, and N-methylpyrrolidone; or a mixture thereof; among of them, an alcohol solvent is preferable.

The amount of solvent is not limited, but usually 100 or less parts by weight to 1 part by weight of Compound (9) for an economic reason.

The amount of Compound (14) may usually be one or more moles, preferably 1.0 to 3.0 moles to 1 mole of Compound (9).

Compound (14) may be purchased or timely prepared. The method for producing Compound (14) is described, for example, in Science of Synthesis, 40b, 1133-1210. Examples of the compound (14) are hydrazine, monomethylhydrazine, monoethylhydrazine, monomethoxycarbonylhydrazine, monobenzylhydrazine, hydrochloride or sulfate of those hydrazine compounds. Among of them, hydrazine and methylhydrazine are preferable.

The reaction may be performed in the presence of a base.

Examples of the base which can be used are an organic base such as pyridine, 4-dimethylaminopyridine, triethylamine, ethyldiisopropylamine, and 1,8-diazabicyclo[5.4.0]-7-undecene; a metal amide base such as lithium diisopropylamide and sodium diisopropylamide; a disilazide base such as lithium hexamethyldisilazide and potassium hexamethyldisilazide; a metal hydride such as sodium hydride and potassium hydride; a metal hydroxide such as sodium hydroxide and potassium hydroxide; acetates such as sodium acetate; and a metal alkoxide such as sodium methoxide and lithium methoxide; among of them, an organic base is preferable.

The amount of base may usually be catalytic amount, usually 0.1 to 5 moles to 1 mole of Compound (14).

The reaction temperature is usually not less than melting point of a solvent and not more than boiling point of the solvent, preferably from 0° C. to 50° C.

The reaction time is, though it may be varied depending on the reaction temperature, the type and amount of base, the type and amount of solvent and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (12), or the salt of Compound (12) when the salt of Compound (14) is used as a main product. A salt of Compound (12) can be converted to Compound (12) by basification with a base such as metal hydroxide (ex. sodium hydroxide, potassium hydroxide) and carbonate (ex. sodium carbonate, sodium hydrogen carbonate and potassium carbonate). Compound (12) can be isolated by known procedures such as filtration, concentration, and recrystallization. The isolated Compound (12) can be further purified by conventional techniques such as distillation, column chromatography, and recrystallization.

Production Method 6:

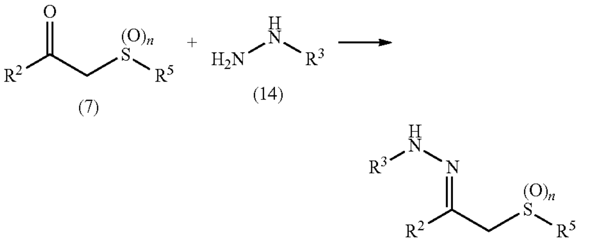

(7) (14) (5)

wherein $R^2$, $R^3$, $R^5$, and n are as defined above.

Compound (5) can be prepared by reacting a compound of the formula (7) (hereinafter referred to as Compound (7)) with a compound of the formula (14) (hereinafter referred to as Compound (14)).

The reaction is usually performed in the presence of a solvent.

Examples of the solvent which can be used are water; an aromatic hydrocarbon solvent such as benzene and chlorobenzene, toluene and xylene; a halogenated hydrocarbon solvent such as dichloromethane and chloroform; a hydrocarbon solvent such as hexane and heptane; an alcohol solvent such as methanol, ethanol, isopropanol, n-butanol, and ethylene glycol; an ether solvent such as 1,2-dimethoxyethane, diethylene glycol dimethyl ether, tetrahydrofuran, and dioxane; a nitrile solvent such as acetonitrile and propionitrile; an ester solvent such as ethyl acetate; a sulfoxide solvent such as dimethylsulfoxide; an amide solvent such as dimethylformamide, dimethylacetamide, and N-methylpyrrolidone; or a mixture thereof; among of them, an alcohol solvent, an aromatic hydrocarbon solvent, water, and mixed solvent of an aromatic hydrocarbon solvent and water are preferable.

The amount of solvent is not limited, but usually 100 or less parts by weight to 1 part by weight of Compound (7) for an economic reason.

Compound (14) may be purchased or timely prepared. The method for producing Compound (14) is described, for example, in Science of Synthesis, 40b 1133-1210. Examples of Compound (14) which can be used are hydrazine, monomethylhydrazine, monoethylhydrazine, and monomethoxycarbonylhydrazine, and a hydrate, hydrochloride or sulfate of those hydrazine compounds; among of them, hydrazine, hydrochloride of monobenzylhydrazine and methylhydrazine are preferable.

The amount of Compound (14) may usually be one or more moles, preferably 1.0 to 3.0 moles to 1 mole of Compound (7).

The reaction may be performed in the presence of a dehydrating agent or an acid. Dehydration may also be achieved by azeotropic distillation.

Examples of the dehydrating agent which can be used are an inorganic dehydrating agent such as silica gel, molecular sieve, sodium sulfate, and magnesium sulfate.

The amount of dehydrating agent may usually be one or more parts by weight, preferably 1 to 5 parts by weight, to 1 part by weight of Compound (7).

Examples of the acid which can be used are an organic acid such as methanesulfonic acid, p-toluenesulfonic acid, and acetic acid; and an inorganic acid such as hydrochloric acid, sulfuric acid, and phosphoric acid.

The amount of acid may usually be catalytic amount, usually 0.01 to 10 moles to 1 mole of Compound (7).

Compound (7) may usually be purchased or timely prepared. The method for producing Compound (7) is described, for example, in Organic Synthesis, 1977, 56, 72-74 or Heterocycles, 2007, 73 469-480.

The reaction temperature is usually not less than melting point of a solvent and not more than boiling point of the solvent, preferably from 0° C. to 50° C.

The reaction time is, though it may be varied depending on the reaction temperature, the type and amount of base, the type and amount of solvent and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (5), or salt of Compound (5) when salt of Compound (14) is used as a main product. A salt of Compound (5) can be converted to Compound (5) by basification with a base such as metal hydroxide (ex. sodium hydroxide, potassium hydroxide) and carbonate (ex. sodium carbonate, sodium hydrogen carbonate and potassium carbonate). Compound (5) can be isolated by known procedures such as filtration, concentration, and recrystallization. The isolated Compound (5) can be further purified by conventional techniques such as distillation, column chromatography, and recrystallization.

Production Method 7:

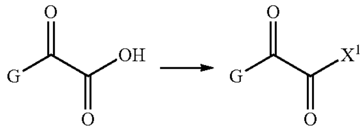

(8) (6)

wherein G and $X^1$ are as defined above.

Compound (6) can be prepared by halogenation of a compound of the formula (8) (hereinafter referred to as Compound (8)) with a halogenating agent.

A solvent may be used in the reaction.

Examples of the solvent which can be used are an aromatic hydrocarbon solvent such as benzene, chlorobenzene, toluene, and xylene; a halogenated hydrocarbon solvent such as dichloromethane and chloroform; a hydrocarbon solvent such as hexane and heptane; an ether solvent such as 1,2-dimethoxyethane, diethylene glycol dimethyl ether, tetrahydrofuran, and dioxane; or a mixture thereof; among of them, an aromatic hydrocarbon solvent is preferable.

The amount of solvent is not limited, but usually 100 or less parts by weight to 1 part by weight of Compound (8) for an economic reason.

Examples of the halogenating agent are thionyl chloride, thionyl brominde, phosphorous oxychloride, and oxalyl chloride; among of them, thionyl chloride is preferable.

The amount of halogenating agent may be one or more moles to 1 mole of Compound (8). Though the upper limit is not limited, the amount is usually in the range of 1 to 10 moles.

The reaction can be performed in the presence of a catalyst.

Example of the catalyst which can be used is an amide compound such as dimethylformamide, among of them, dimethylformamide is preferable.

The amount of the catalyst may be 0.01 or more moles to 1 mole of Compound (8). Though the upper limit is not limited, the amount is usually in the range of 0.01 to 0.5 moles.

The reaction temperature is usually not less than 35° C. and not more than boiling point of the solvent, preferably from 40° C. to 100° C.

The reaction time is, though it may be varied depending on the reaction temperature, the type and amount of halogenating agent, the type and amount of solvent, presence or absence of a catalyst and the like, usually 0.1 to 100 hours, typically 0.1 to 24 hours.

In order to monitor the progress of the reaction, conventional analysis techniques such as thin layer chromatography, gas chromatography, and NMR can be used. The reaction mixture thus obtained usually contains Compound (6) as a main product. Compound (6) can be isolated by known procedures such as washing, filtration, concentration, and recrystallization. The isolated Compound (6) can be further purified by conventional techniques such as distillation, column chromatography, and recrystallization.

Also, Compound (6) can be prepared by using Friedel-Crafts acylation as shown in the following scheme:

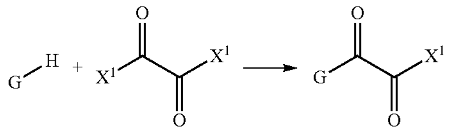

(6)

wherein G and $X^1$ are as defined above.

(see European J of Organic Chemistry, 2002, 14, 2298-2307)

Production Method 8:

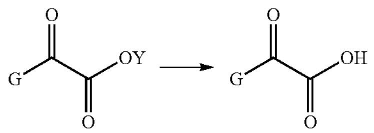

(9) (8)

wherein G, and Y are as defined above.

Compound (8) can be prepared by hydrolysis of a compound of the formula (9) (hereinafter referred to as Compound (9)).

The reaction is usually performed in the presence of a solvent.

Examples of the solvent which can be used are water; an aromatic hydrocarbon solvent such as benzene, chlorobenzene, toluene, and xylene; a halogenated hydrocarbon solvent such as dichloromethane and chloroform; an alcohol solvent such as methanol, ethanol, isopropanol, n-butanol, and ethylene glycol dimethyl ether; an ether solvent such as 1,2-dimethoxyethane, diethylene glycol, tetrahydrofuran, and dioxane; a nitrile solvent such as acetonitrile and propionitrile; a sulfoxide solvent such as dimethylsulfoxide; an amide solvent such as dimethylformamide, dimethylacetamide, and N-methylpyrrolidone; or a mixture thereof; among of them, water, an ether solvent such as tetrahydrofuran an alcohol solvent such as methanol or an aromatic hydrocarbon solvent such as toluene and xylene; or a mixture thereof are preferable.

The amount of solvent is not limited, but usually 100 or less parts by weight to 1 part by weight of Compound (9) for an economic reason.

The reaction can be performed in the presence of a base.

Examples of the base which can be used are a metal hydroxide such as sodium hydroxide, potassium hydroxide, and lithium hydroxide.

The amount of the base may be one or more moles to 1 mole of Compound (9). Though the upper limit is not limited, the amount is usually 1 to 10 moles.

The reaction can be performed in the presence of an acid in place of a base.

Examples of the acid which can be used are an inorganic acid such as hydrochloric acid, sulfuric acid, acetic acid, and phosphoric acid.

The amount of the acid may be a catalytic amount. Though the upper limit is not limited, the amount is usually in the range of 0.01 to 10 moles to 1 mole of Compound (9).

The reaction temperature is usually not less than melting point of a solvent and not more than boiling point of the solvent, preferably from room temperature to boiling point of a solvent.

The reaction time is, though it may be varied depending on the reaction temperature, the type and amount of a base or acid, the type and amount of solvent and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (8) or a salt of Compound (8), when a base was used, as a main product. A salt of Compound (8) can be converted to Compound (8) by acidification with an acid such as hydrochloric acid and sulfuric acid. Compound (8) can be isolated by known procedures such as washing, filtration, concentration, and recrystallization. The isolated Compound (8) can be further purified by conventional techniques such as distillation, recrystallization and column chromatography.

Production Method 9:

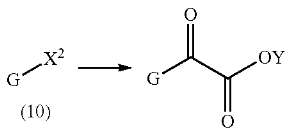

(10) (9)

wherein G, $X^2$, and Y are as defined above.

Compound (9) can be prepared by reacting a Grignard reagent which is prepared from a compound of the formula (10) (hereinafter referred to as Compound (10)) with a compound of the formula (15) (hereinafter referred to as Compound (15)):

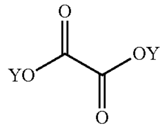

(15)

wherein Y is as defined above.

Examples of Compound (10) which can be used are a halogenated benzene such as bromobenzene, chlorobenzene, iodobenzene, 2-methylbromobenzene, 3-methylbromobenzene, 4-methylbromobenzene, 2,4-dimethylbromobenzene, 2,4,6-trimethylbromobenzene, 2,3,5-trimethylbromobenzene, 2,4,6-triethylbromobenzene, 2,4,6-tributylbromobenzene, 2-bromo-4-(4-chlorophenyl)-1-ethylbenzene, and 2,6-diethyl-4-methylbromobenzene; a halogenated naphthalene such as 1-bromonaphthalene and 2-bromonaphthalene; a halogenated furan such as 3-bromofuran; a halogenated pyridine such as 2-bromopyridine, 3-bromopyridine, and 4-bromopyridine; halogenated pyrimidine such as 2-bromopyrimidine and 4-bromopyrimidine; a halogenated quinoline such as 3-bromoquinoline, 4-bromoquinoline, 6-bromoquinoline, and 8-bromoquinoline; a halogenated thiophene such as 2-bromothiophene, 3-bromothiophene, and 4-bromothiophene; a halogenated thiazole such as 2-bromothiazole, 4-bromothiazole, and 5-bromothiazole; and a halogenated thianaphthalene such as 3-bromothianaphthalene; among of them, a halogenated benzene is preferable, and a brominated benzene and an iodinated benzene are more preferable. They may be purchased or timely prepared. The method for producing Compound (10) is described, for example, in Jikken Kagaku Kouza 19, Organic synthesis I, Hydrocarbon and Halide, fourth edition, 363-479, Maruzen Co., 1991.

The reaction comprises the first step of preparing Grignard reagent from Compound (10) and the second step of reacting Grignard reagent with Compound (15).

First Step:

The reaction is usually performed in the presence of a solvent.

Examples of the solvent which can be used are an aromatic hydrocarbon solvent such as benzene toluene, and xylene; a hydrocarbon solvent such as hexane and heptane; an ether solvent such as 1,2-dimethoxyethane, diethylene glycol dimethyl ether, tetrahydrofuran, and dioxane; or a mixture thereof; among of them, an ether solvent is preferable.

The amount of solvent is not limited, but usually 100 or less parts by weight to 1 part by weight of Compound (10) for an economic reason.

The type of magnesium used in the present invention is not limited, but cutting chip form is favorable for a safety and availability reason.

The amount of magnesium may be one or more moles to 1 mole of Compound (10). Though the upper limit is not limited, the amount is usually in the range of 1 to 2 moles. An activating agent such as dibromoethane and iodine may be added because commercial magnesium has usually oxide layer, thereby the reactivity is reduced.

The reaction temperature is usually not less than melting point of a solvent and not more than boiling point of the solvent, preferably from 0° C. to 50° C. The reaction time is, though it may be varied depending on the reaction temperature, the form and amount of magnesium, the type and amount of solvent, presence or absence of an activating agent ant the like, usually 0.1 to 100 hours, typically 0.1 to 24 hours.

Second Step:

The reaction is usually performed in the presence of a solvent.

Examples of the solvent which can be used are an aromatic hydrocarbon solvent such as benzene toluene, and xylene; a hydrocarbon solvent such as hexane and heptane; an ether solvent such as 1,2-dimethoxyethane, diethylene glycol dimethyl ether, tetrahydrofuran, and dioxane; or a mixture thereof; among of them, an ether solvent and an aromatic hydrocarbon solvent; or a mixture thereof are preferable.

The solvent may be same as or different from the solvent used in the first step.

The amount of solvent is not limited, but usually 100 or less parts by weight to 1 part by weight of Compound (10) for an economic reason.

Examples of Compound (15) which can be used are oxalates which the number of carbon in the ester moiety is 1-6 such as dimethyl oxalate, diethyl oxalate, dipropyl oxalate, dibutyl oxalate, dipentyl oxalate, and dihexyl oxalate; among of them, a diethyl oxalate is preferable.

The amount of Compound (15) may be one or more moles to 1 mole of Compound (10). Though the upper limit is not limited, the amount is usually in the range of 1 to 3 moles.

The reaction temperature is usually not less than melting point of a solvent and not more than boiling point of the solvent, preferably from 0° C. to 30° C.

The reaction time is, though it may be varied depending on the reaction temperature, the type and amount of Compound (15), the type and amount of solvent and the like, usually 0.1 to 100 hours, typically 0.1 to 24 hours.

The reaction is performed by mixing a solution from the first step with Compound (15) or a solution of Compound (15). The mixing may be performed by either a method wherein a solution from the first step at a favorable temperature, then a solution containing Compound (15) is added thereto; or a method wherein a solution from the first step is added dropwise to a solution containing Compound (15) at a favorable temperature.

In order to monitor the progress of the reaction, conventional analysis techniques such as thin layer chromatography, gas chromatography, high-performance liquid chromatography, and NMR can be used.

The reaction mixture thus obtained usually contains Compound (9) as a main product. Compound (9) can be isolated by known procedures such as washing, filtration, concentration, and recrystallization. The isolated Compound (9) can be further purified by conventional techniques such as distillation, and column chromatography.

(see Journal of Organic Chemistry., 1987, 52, 5026-5030)

Compound (9) can be prepared from Compound (16) by reacting a compound which is prepared by metalation reaction using an alkyl lithium base such as n-butyl lithium and tert-butyl lithium or a metal amide base such as lithium diisopropylamide with an oxalate diester as shown in the following scheme:

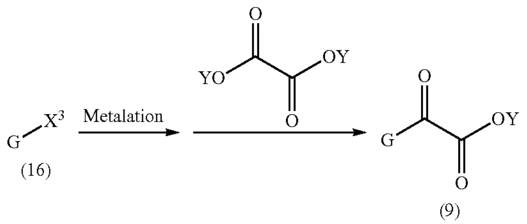

(16)

(9)

wherein $X^3$ represents a hydrogen atom, and G and Y are as defined above.

Production Method 10:

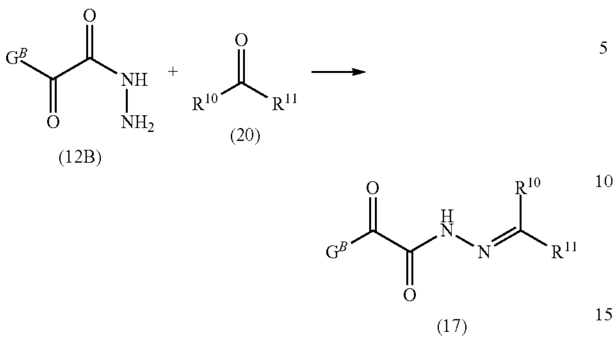

(12B) (20) (17)

wherein $R^{10}$, $R^{11}$ and $G^B$ are as defined above.

A compound of the formula (17) (hereinafter referred to as Compound (17)) can be prepared by reacting a compound of the formula (12B) (hereinafter referred to as Compound (12B)) with a compound of the formula (20) (hereinafter referred to as Compound (20))

The reaction is usually performed in the presence of a solvent.

Examples of the solvent which can be used are an aromatic hydrocarbon solvent such as benzene, chlorobenzene, toluene, and xylene; a halogenated hydrocarbon solvent such as dichloromethane and chloroform; a hydrocarbon solvent such as hexane and heptane; an alcohol solvent such as methanol, ethanol, isopropanol, n-butanol, and ethylene glycol dimethyl ether; an ether solvent such as 1,2-dimethoxyethane, diethylene glycol dimethyl ether, tetrahydrofuran, and dioxane; a nitrile solvent such as acetonitrile and propionitrile; a ester solvent such as ethyl acetate; a sulfoxide solvent such as dimethylsulfoxide; an amide solvent such as dimethylformamide, dimethylacetamide, and N-methylpyrrolidone; or a mixture thereof; among of them, an alcohol solvent and an aromatic hydrocarbon solvent are preferable.

The amount of solvent is not limited, but usually 100 or less parts by weight to 1 part by weight of Compound (12B) for an economic reason.

The compound (20) can be purchased. Examples of the compound (20) are formaldehyde, acetaldehyde, propanal, butanal, isobutanal, benzaldehyde, acetone, methyl ethyl ketone, methyl isobutyl ketone, acetophnone, cyclopentanone, and cyclohexanone.

The amount of the compound (20) may be one or more moles, preferably 1.0 to 3.0 moles to 1 mole of Compound (12B).

The reaction may be performed in the presence of a dehydrating agent or an acid. Dehydration may also be achieved by azeotropic distillation.

Examples of the dehydrating agent are inorganic dehydrating agent such as silica gel, molecular sieves, sodium sulfate and magnesium sulfate.

The amount of the dehydrating agent may be one or more parts by weight, preferably 1 to 5 parts by weight to 1 part by weight of Compound (12B).

Examples of the acid are an organic acid such as methanesulfonic acid, p-toluenesulfonic acid and acetic acid, and an inorganic acid such as hydrochloric acid, sulfuric acid and phosphoric acid.

The amount of the acid is 0.01 to 10 moles to 1 mole of Compound (12B). The reaction temperature is usually not less than melting point of a solvent and not more than boiling point of the solvent, preferably from 0° C. to 150° C.

The reaction time is, though it may be varied depending on the reaction temperature, the type and amount of the dehydrating agent or the acid, the type and amount of solvent and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (12) as a main product. Compound (17) can be isolated by known procedures such as filtration, concentration, and recrystallization. The isolated Compound (17) can be further purified by conventional techniques such as distillation, column chromatography, and recrystallization.

Production Method 11:

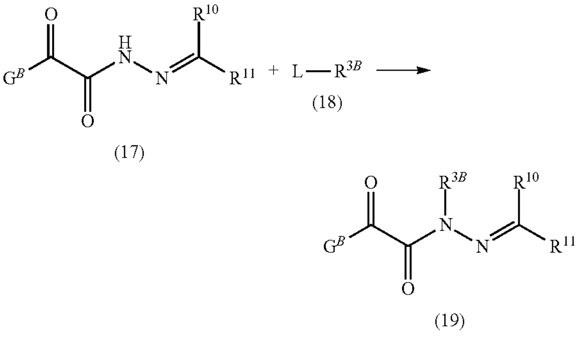

(17) (18) (19)

wherein $R^{3B}$, $R^{10}$, $R^{11}$, L and $G^B$ are as defined above.

A compound of the formula (19) (hereinafter referred to as Compound (19)) can be prepared by reacting Compound (17) with a compound of the formula (18) (hereinafter referred to as Compound (18)).

Examples of the compound (18) are methyl iodide, ethyl bromide, benzyl chloride, methyl methanesulfonate dimethylsulfate, and diethylsulfate. They may be purchased or timely prepared.

The reaction is usually performed in the presence of a solvent.

Examples of the solvent which can be used are water; an aromatic hydrocarbon solvent such as benzene, chlorobenzene, toluene, and xylene; a halogenated hydrocarbon solvent such as dichloromethane and chloroform; a hydrocarbon solvent such as hexane and heptane; a nitrile solvent such as acetonitrile and propionitrile; an ether solvent such as 1,2-dimethoxyethane, diethylene glycol dimethyl ether, tetrahydrofuran, and dioxane; an ester solvent such as ethyl acetate; a ketone solvent such as acetone, methyl ethyl ketone and methyl isobutyl ketone; a sulfoxide solvent such as dimethylsulfoxide; an amide solvent such as dimethylformamide, dimethylacetamide, and N-methylpyrrolidone; or a mixture thereof; among of them, a ketone solvent and an aromatic hydrocarbon solvent are preferable.

The amount of solvent is not limited, but usually 100 or less parts by weight to 1 part by weight of Compound (17) for an economic reason.

The amount of Compound (18) may usually be one or more moles, preferably 1.0 to 3.0 moles to 1 mole of Compound (17).

The reaction may be performed in the presence of a base.

Examples of the base which can be used are an organic base such as pyridine, 4-dimethylaminopyridine, triethylamine, ethyldiisopropylamine, and 1,8-diazabicyclo[5.4.0]-7-undecene; a metal hydride such as sodium hydride and potassium hydride; a metal hydroxide such as lithium hydroxide, sodium hydroxide and potassium hydroxide; a carbonate such as sodium carbonate, potassium carbonate and sodium hydrogen carbonate; a phosphate such as sodium phosphate, disodium hydrogen phosphate and sodium dihydrogen phosphate; an acetate such as sodium acetate; and a metal alkoxide such as sodium methoxide and lithium methoxide; among of them, a metal hydroxide and a carbonate are preferable.

The amount of base may be one or more moles, usually 1 to 5 moles to 1 mole of Compound (17).

The reaction may be performed in the presence of a catalyst.

Examples of the catalyst include a phase transfer catalyst such as a quaternary ammonium salt such as tetrabutyl ammonium bromide, tetrabutyl ammonium iodide and benzyl tri-n-butylammonium bromide, and a quaternary phosphonium salt such as n-heptyltriphenylphosphonium bromide and tetraphenylphosphonium bromide; and a hydrazine such as hydrazine hydrate, methyl hydrazine and N,N-dimethylhydrazine.

The amount of catalyst may be catalytic amount, usually 0.01 to 1 moles to 1 mole of Compound (17).

The reaction temperature is usually not less than melting point of a solvent and not more than boiling point of the solvent, preferably −30° C. to 50° C.

The reaction time is, though it may be varied depending on the reaction temperature, the type and amount of base, the type and amount of solvent, and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (19) as a main product. Compound (19) can be isolated by known procedures such as filtration, concentration, and recrystallization. The isolated Compound (19) can be further purified by conventional techniques such as distillation, column chromatography, and recrystallization.

Production Method 12:

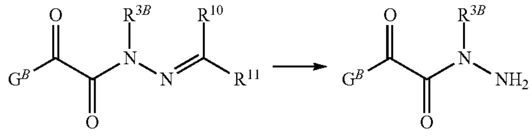

(19) (12C)

wherein $R^{3B}$, $R^{10}$, $R^{11}$ and $G^B$ are as defined above.

A compound of the formula (12C) (hereinafter referred to as Compound (12C)) can be prepared by decomposing Compound (19).

Examples of the method of the decomposition are hydrolysis and hydrogenation.

A hydrolysis reaction is usually performed in the presence of a solvent.

Examples of the solvent which can be used are water; an aromatic hydrocarbon solvent such as benzene, chlorobenzene, toluene, and xylene; a halogenated hydrocarbon solvent such as dichloromethane and chloroform; a hydrocarbon solvent such as hexane and heptane; an alcohol solvent such as methanol, ethanol, isopropanol, n-butanol and ethylene glycol; an ether solvent such as 1,2-dimethoxyethane, diethylene glycol dimethyl ether, tetrahydrofuran and dioxane; a nitrile solvent such as acetonitrile and propionitrile; a sulfoxide solvent such as dimethylsulfoxide; an amide solvent such as dimethylformamide, dimethylacetamide, and N-methylpyrrolidone; or a mixture thereof; among of them, water, an alcohol solvent, an ether solvent and a mixture thereof are preferable.

The amount of solvent is not limited, but usually 100 or less parts by weight to 1 part by weight of Compound (19) for an economic reason.

The reaction may be performed in the presence of an acid. Examples of the acid are an organic acid such as methanesulfonic acid, p-toluenesulfonic acid and acetic acid; and an inorganic acid such as hydrochloric acid, sulfuric acid and phosphoric acid.

The amount of the acid may be usually a catalytic amount, and 0.01 to 1 mole to 1 mole of Compound (19).

This reaction may be performed in the presence of a hydroxylamine; or a hydrochloride, a sulfate or a carbonate thereof.

The reaction temperature is usually not less than melting point of a solvent and not more than boiling point of the solvent, preferably 0° C. to 150° C.

The reaction time is, though it may be varied depending on the reaction temperature, the type and amount of acid, the type and amount of solvent, and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (12C) as a main product. Compound (12C) can be isolated by known procedures such as filtration, concentration, and recrystallization. The isolated Compound (12C) can be further purified by conventional techniques such as distillation, column chromatography, and recrystallization.

When at least one of $R^{10}$ and $R^{11}$ is a phenyl group, a hydrogenation reaction can be performed.

A hydrogenation reaction is usually performed in the presence of a solvent.

Examples of the solvent which can be used are water; an aromatic hydrocarbon solvent such as benzene, chlorobenzene, toluene, and xylene; a hydrocarbon solvent such as hexane and heptane; an alcohol solvent such as methanol, ethanol, isopropanol, n-butanol and ethylene glycol; an ether solvent such as 1,2-dimethoxyethane, diethylene glycol dimethyl ether, tetrahydrofuran and dioxane; an ester solvent such as ethyl acetate; or a mixture thereof; among of them, water, an alcohol solvent, an ether solvent and a mixture thereof are preferable.

The amount of solvent is not limited, but usually 100 or less parts by weight to 1 part by weight of Compound (19) for an economic reason.

The reaction may be usually performed in the presence of a catalyst.

Examples of the catalyst are those which metal such as palladium, platinum and rhodium is supported on activated carbon.

The rate of metal to activated carbon is not limited, but usually 0.1 to 10% by weight to 100% by weight activated carbon.

The amount of catalyst may be catalytic amount, and 0.001 to 0.1 part by weight to 1 part by weight of compound (19).

The reaction pressure is usually not less than atmospheric pressure and not more than 10 atm.

The reaction temperature is usually not less than melting point of a solvent and not more than boiling point of the solvent, preferably 0° C. to 80° C.

The reaction time is, though it may be varied depending on the reaction temperature, the type and amount of catalyst, the type and amount of solvent, and the like, usually 0.1 to 100 hours, typically 0.1 to 24 hours.

In order to monitor the progress of the reaction, conventional analysis techniques such as thin layer chromatography, gas chromatography, high-performance liquid chromatography, and NMR can be used.

The reaction mixture thus obtained usually contains Compound (12C) as a main product. Compound (12C) can be isolated by known procedures such as filtration, concentration, and recrystallization. The isolated Compound (12C) can be further purified by conventional techniques such as distillation, column chromatography, and recrystallization.

Examples of the compound which can be prepared by the method for producing of the present invention include as follows.

The combination of the symbols in the formula (1-1) to formula (1-31), formula (2-1) to formula (2-72), and formula (4-1) to formula (4-72) is shown in Tables 1-24. The combination of the symbols in the formula (1-101) to formula (1-115), formula (2-101) to formula (2-146), formula (4-101) to formula (4-145) is shown in Tables 25-26. The combination of the symbols in the formula (12-1) to formula (12-8) is shown in Tables 27-29, formula (1-201) and formula (1-301) is shown in Tables 30-31, and formula (2-201) to formula (2-203), formula (4-201) to formula (4-203), formula (2-301) to formula (2-303) and formula (4-301) to formula (4-303) is shown in Tables 32-37. The combination of the symbols in the formula (40-a) is shown in Table 38, the combination of symbols in the formula (40-b) is shown in Table 39, and the combination of the symbols in the formula (41-a) is shown in Table 40.

In the formulae and tables, "Me" means a methyl group, "Et" means an ethyl group, "n-Pr" means a n-propyl group, "i-Pr" means an isopropyl group, "c-Pr" means a cyclopropyl group, "n-Bu" means a n-butyl group, and "Ph" means a phenyl group.

(1-1)

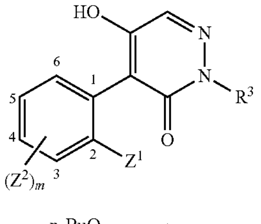

(1-2)

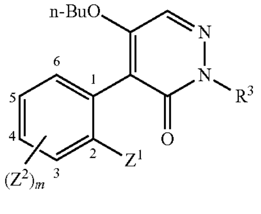

(1-3)

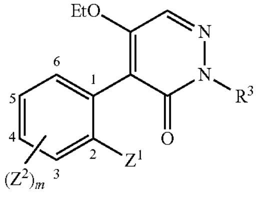

-continued (1-4)

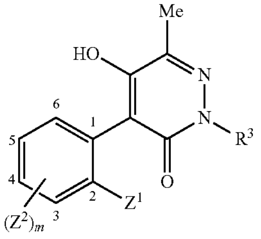

(1-5)

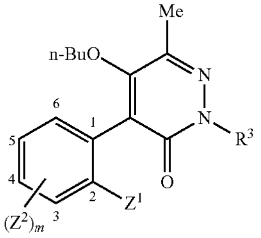

(1-6)

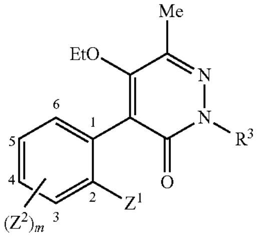

(1-7)

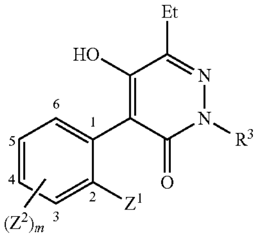

(1-8)

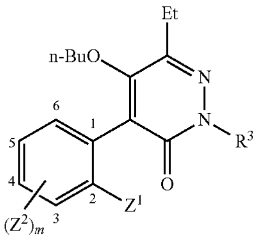

(1-9)

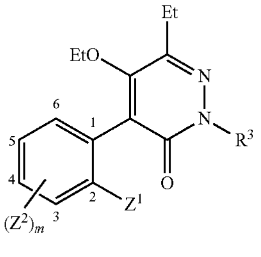

-continued
(1-10)
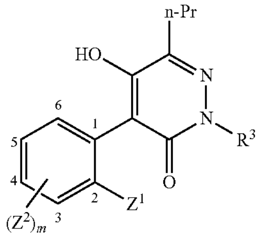
(1-11)
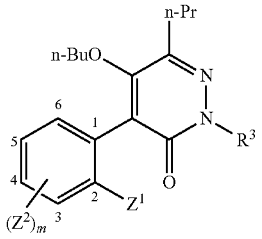
(1-12)
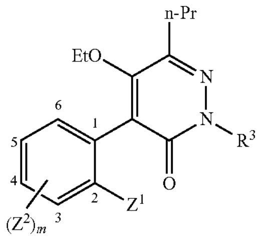
(1-13)
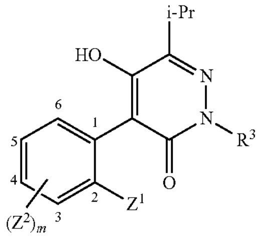
(1-14)
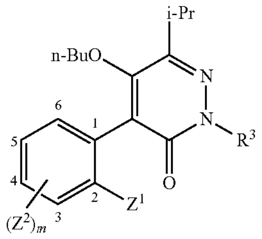
(1-15)
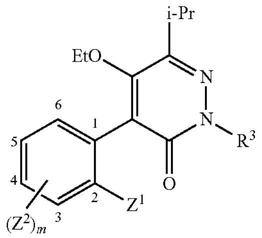
-continued
(1-16)
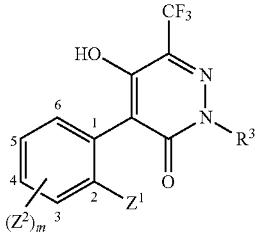
(1-17)
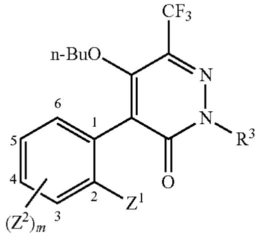
(1-18)
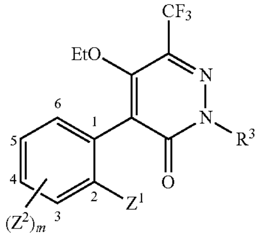
(1-19)
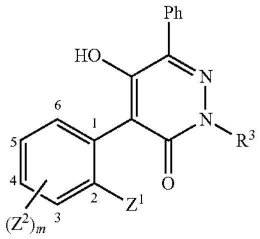
(1-20)
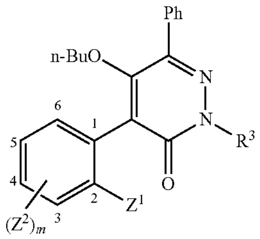
(1-21)
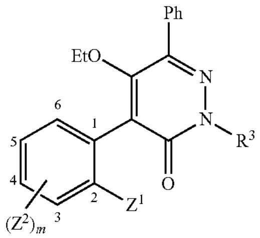

-continued
(1-22)
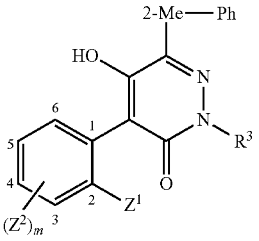
(1-23)
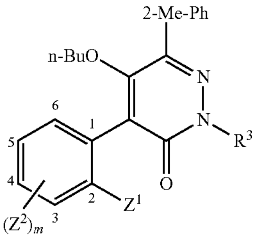
(1-24)
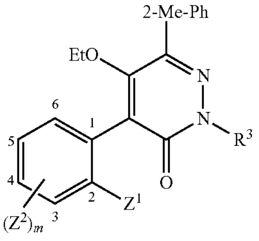
(1-25)
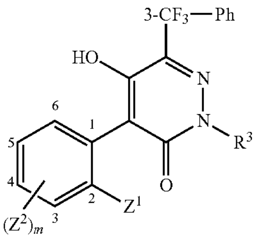
(1-26)
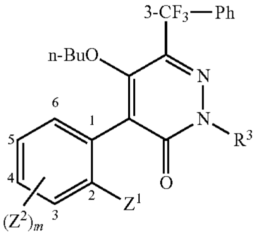
(1-27)
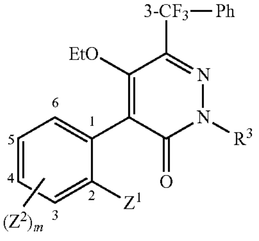
-continued
(1-28)
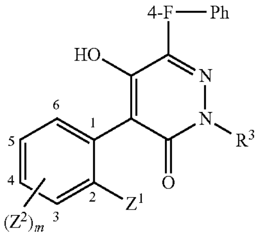
(1-29)
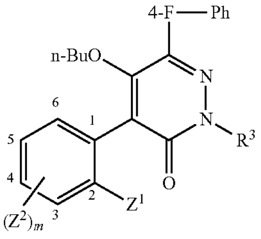
(1-30)
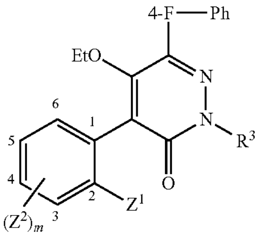
(1-31)
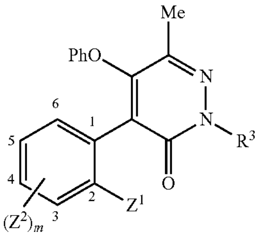
(2-1)
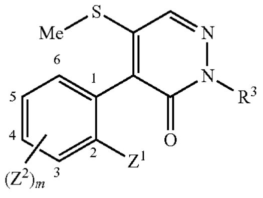
(2-2)
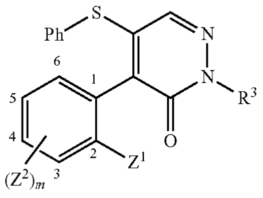
(2-3)
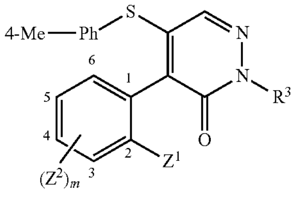

-continued
(2-4)
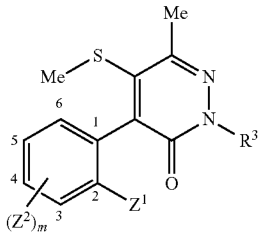
(2-5)
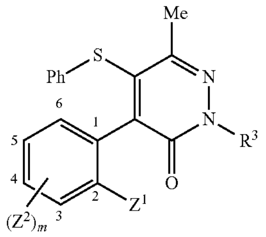
(2-6)
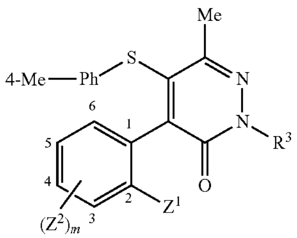
(2-7)
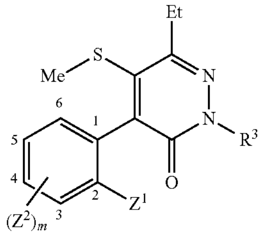
(2-8)
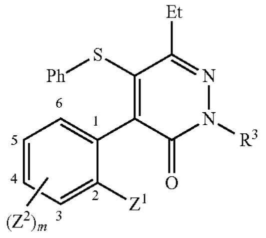
(2-9)
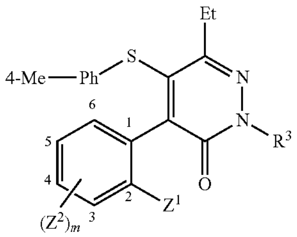
-continued
(2-10)
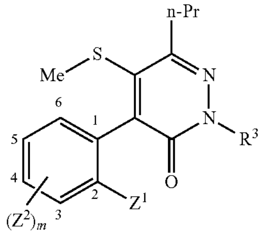
(2-11)
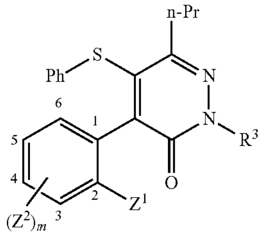
(2-12)
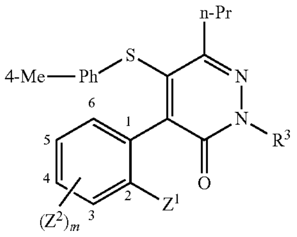
(2-13)
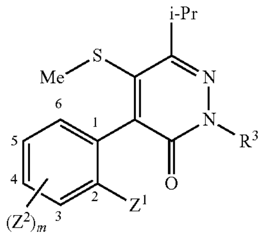
(2-14)
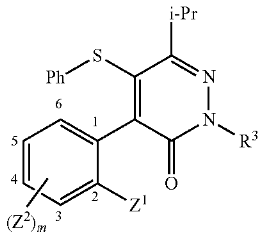
(2-15)
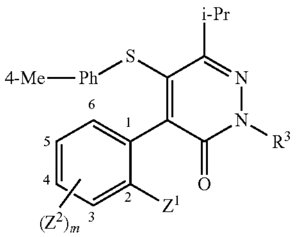

-continued
(2-16)
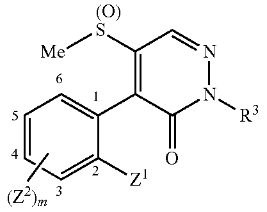
(2-17)
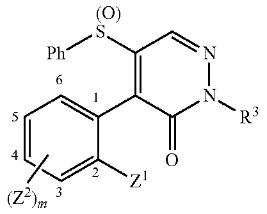
(2-18)
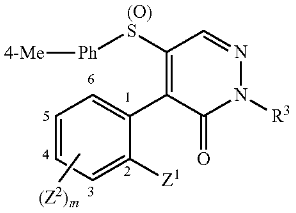
(2-19)
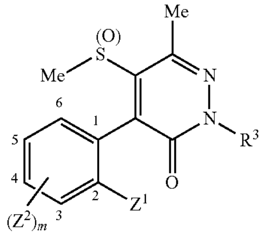
(2-20)
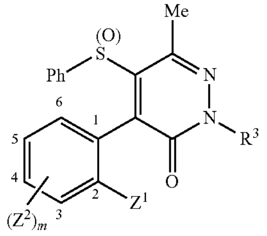
(2-21)
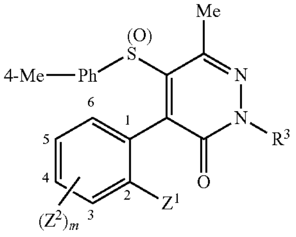
(2-22)
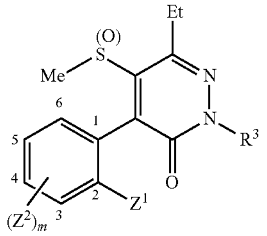
-continued
(2-23)
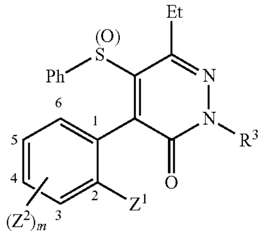
(2-24)
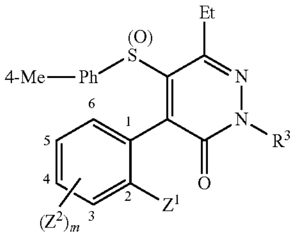
(2-25)
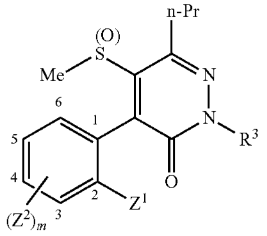
(2-26)
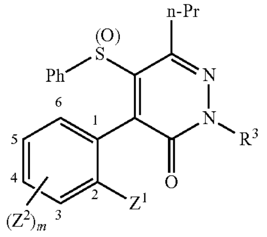
(2-27)
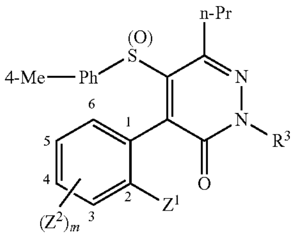
(2-28)
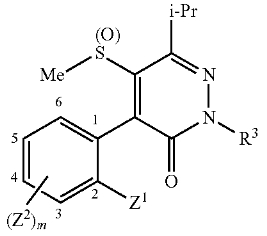

-continued
(2-29)
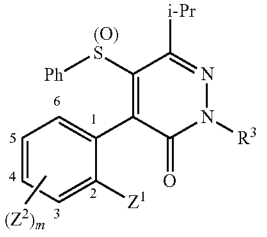
(2-30)
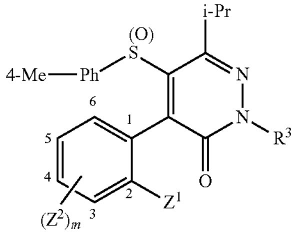
(2-31)
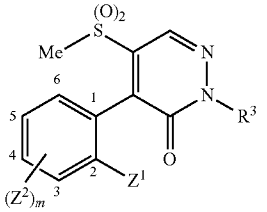
(2-32)
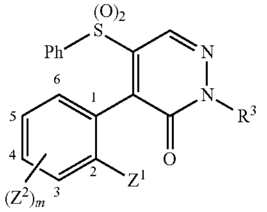
(2-33)
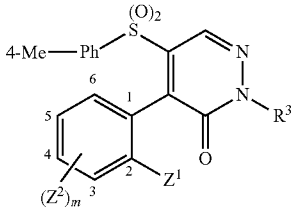
(2-34)
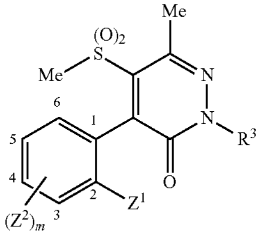
(2-35)
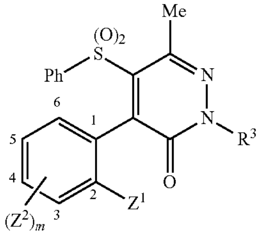
-continued
(2-36)
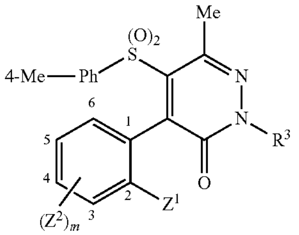
(2-37)
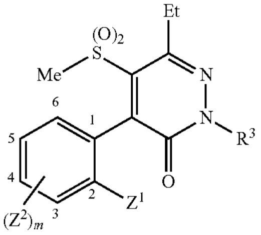
(2-38)
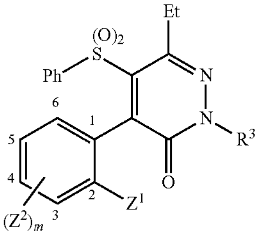
(2-39)
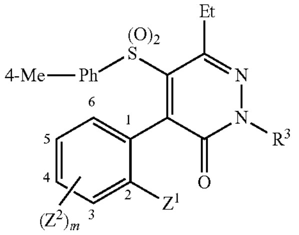
(2-40)
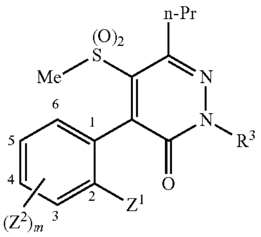
(2-41)
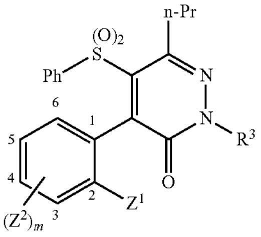

-continued
(2-42)
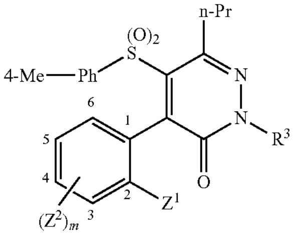
(2-43)
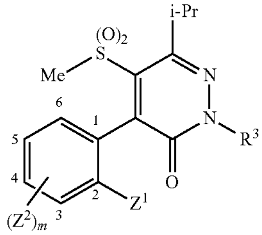
(2-44)
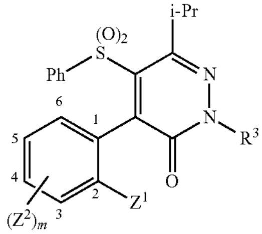
(2-45)
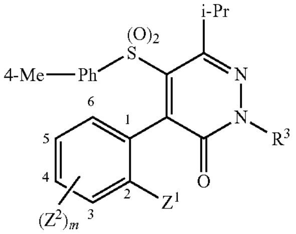
(2-46)
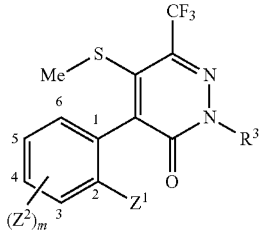
(2-47)
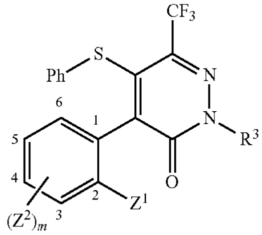
-continued
(2-48)
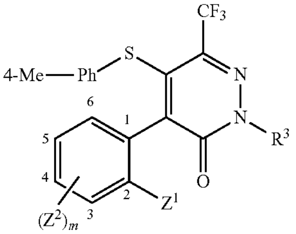
(2-49)
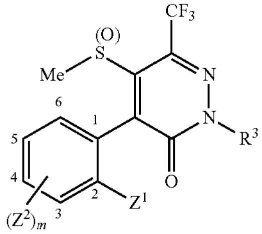
(2-50)
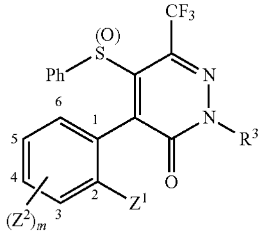
(2-51)
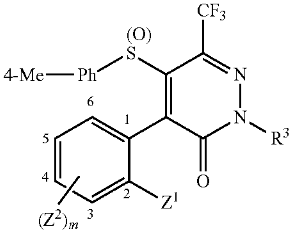
(2-52)
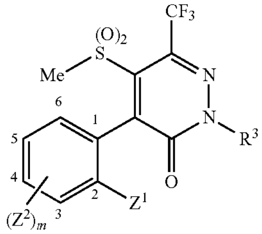
(2-53)
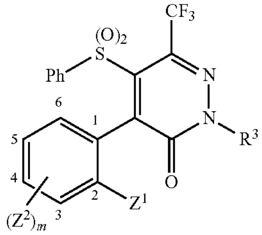

-continued
(2-54)
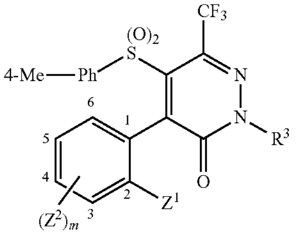
(2-55)
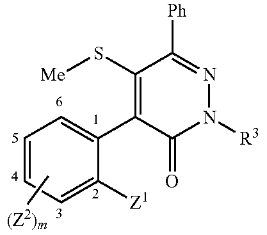
(2-56)
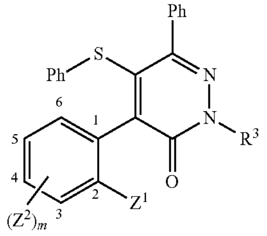
(2-57)
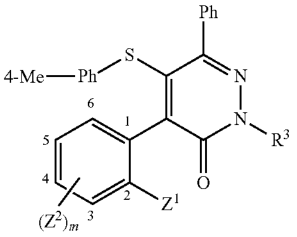
(2-58)
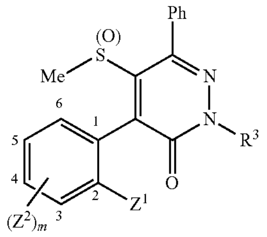
(2-59)
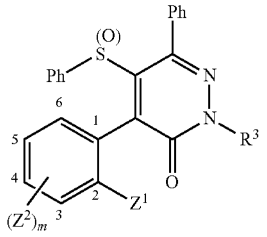
-continued
(2-60)
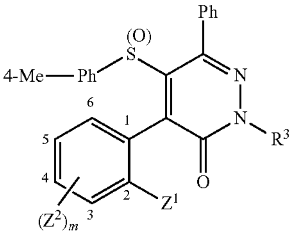
(2-61)
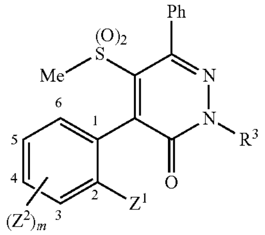
(2-62)
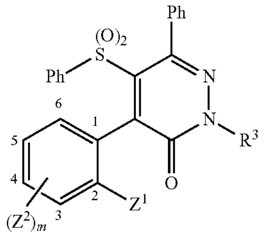
(2-63)
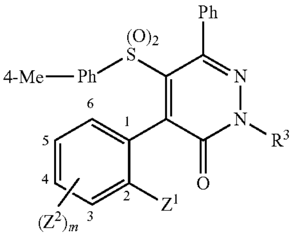
(2-64)
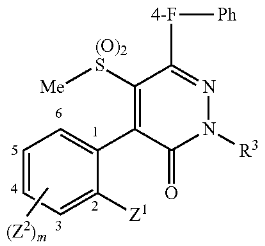
(2-65)
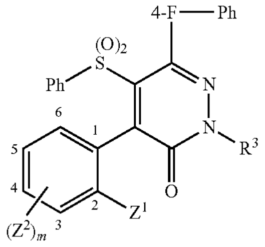

-continued
(2-66)
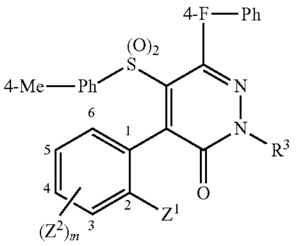
(2-67)
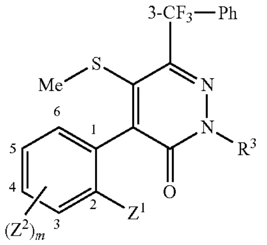
(2-68)
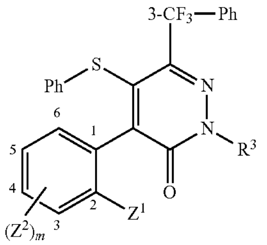
(2-69)
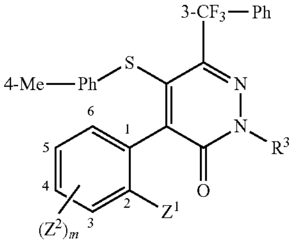
(2-70)
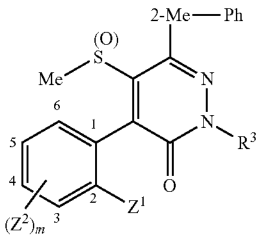
(2-71)
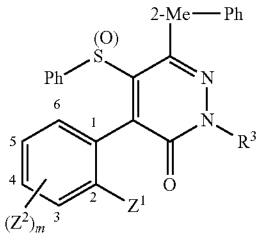
-continued
(2-72)
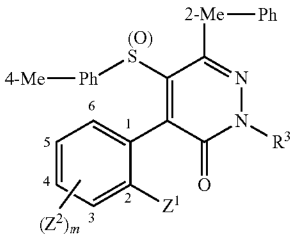
(4-1)
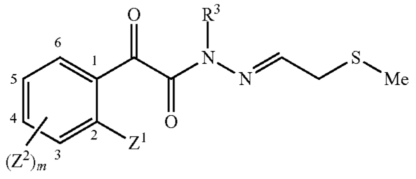
(4-2)
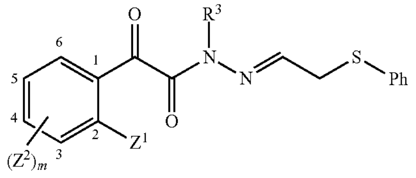
(4-3)
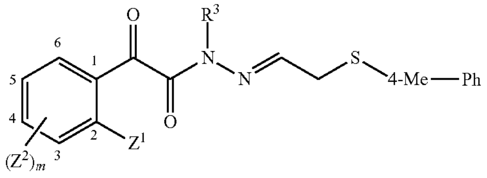
(4-4)
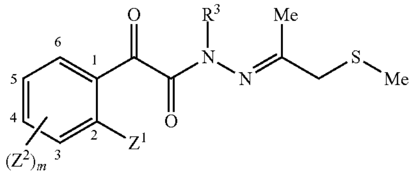
(4-5)
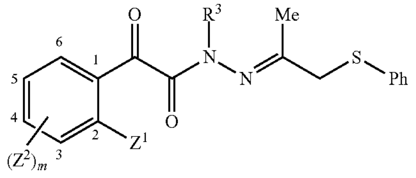
(4-6)
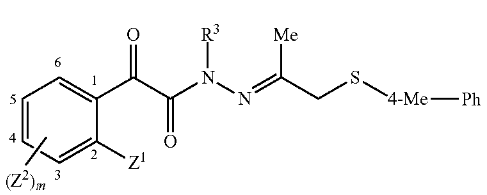
(4-7)
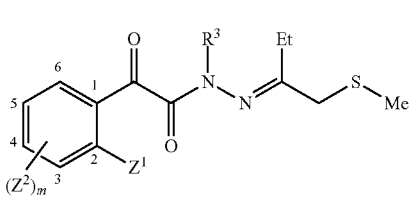

-continued
(4-8)
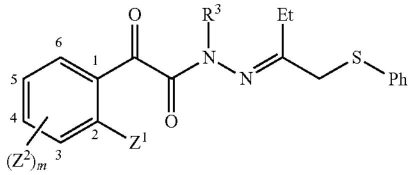
(4-9)
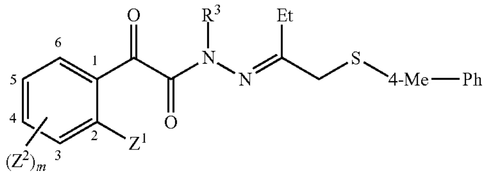
(4-10)
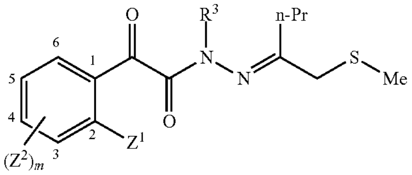
(4-11)
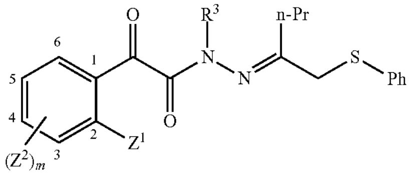
(4-12)
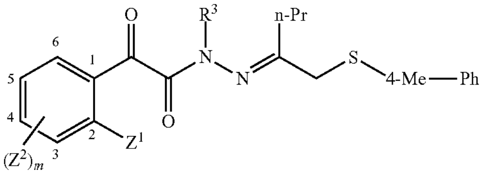
(4-13)
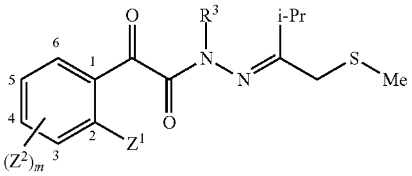
(4-14)
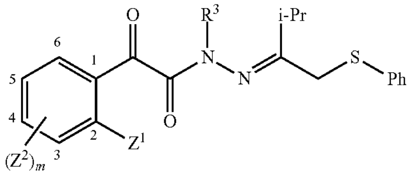
(4-15)
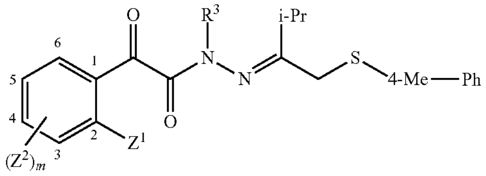
-continued
(4-16)
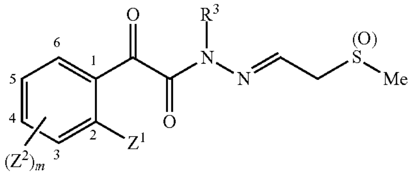
(4-17)
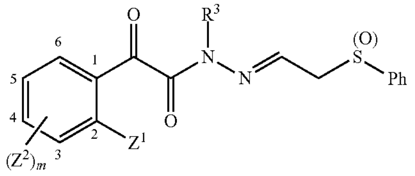
(4-18)
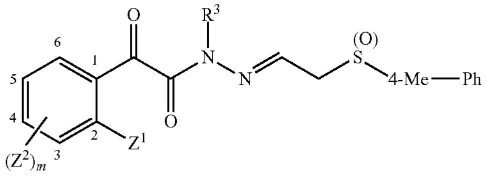
(4-19)
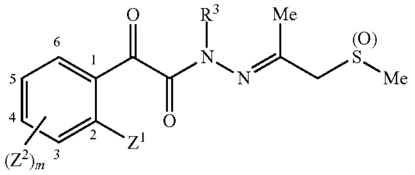
(4-20)
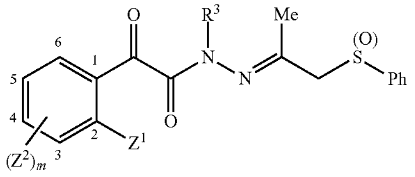
(4-21)
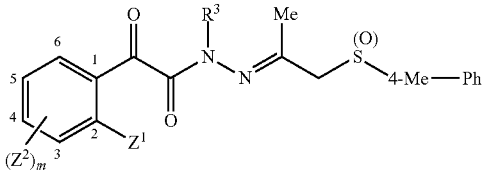
(4-22)
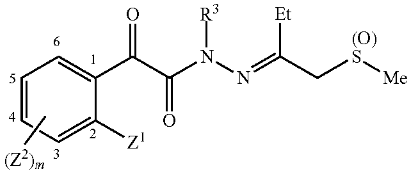
(4-23)
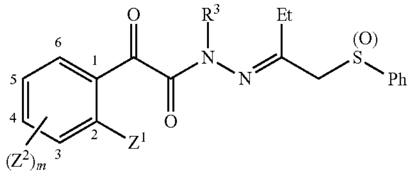

-continued
(4-24)
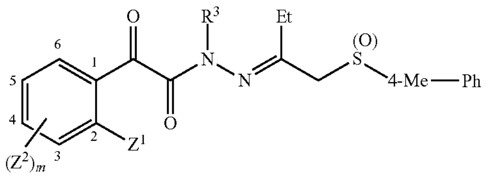
(4-25)
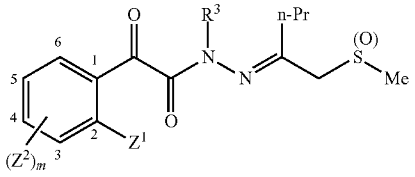
(4-26)
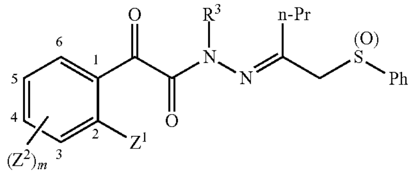
(4-27)
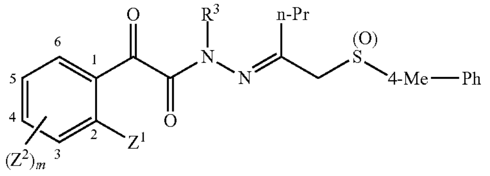
(4-28)
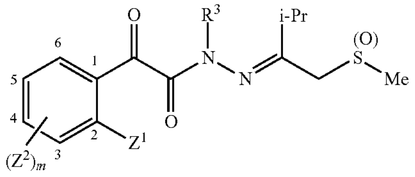
(4-29)
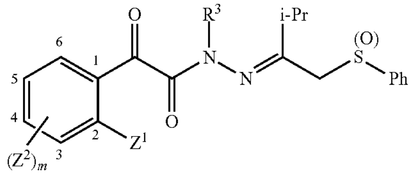
(4-30)
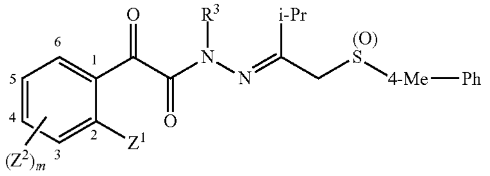
(4-31)
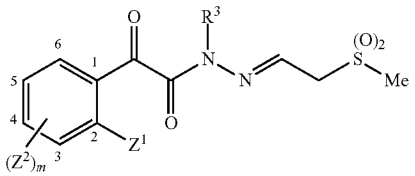
-continued
(4-32)
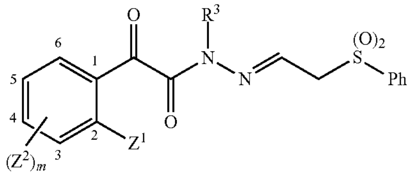
(4-33)
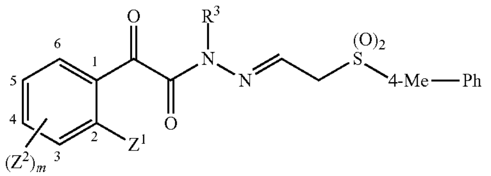
(4-34)
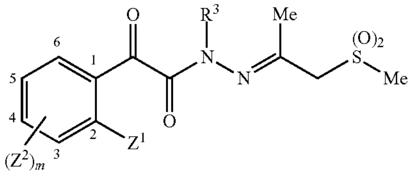
(4-35)
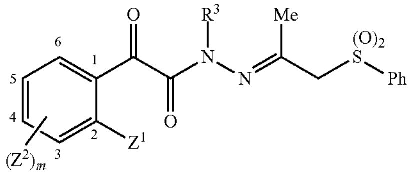
(4-36)
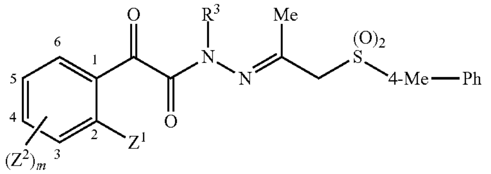
(4-37)
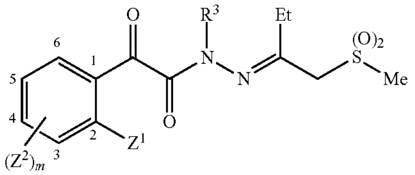
(4-38)
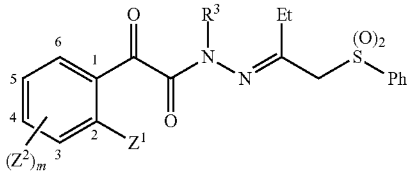
(4-39)
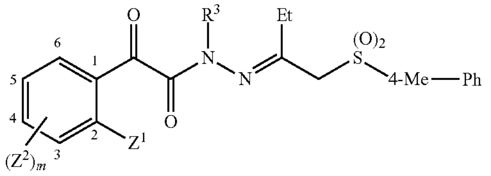

-continued
(4-40)
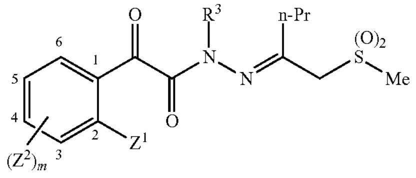
(4-41)
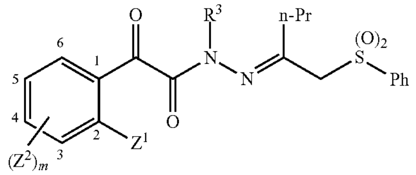
(4-42)
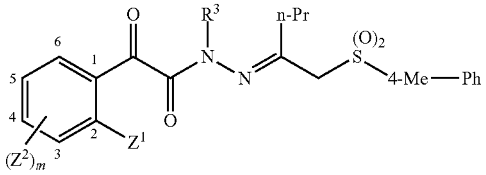
(4-43)
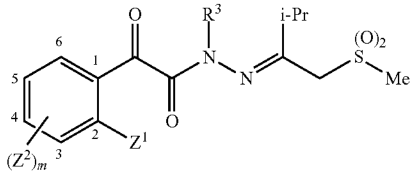
(4-44)
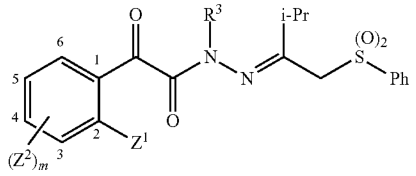
(4-45)
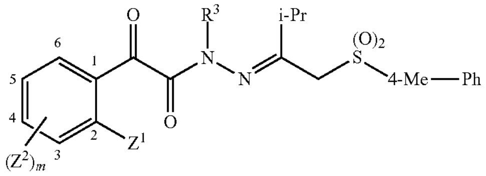
(4-46)
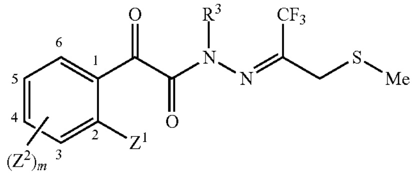
(4-47)
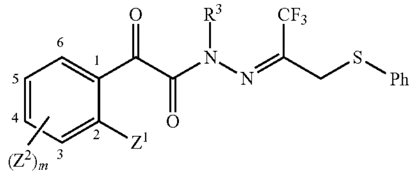
-continued
(4-48)
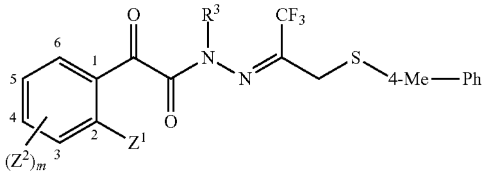
(4-49)
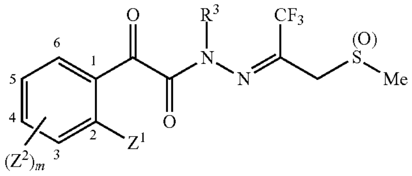
(4-50)
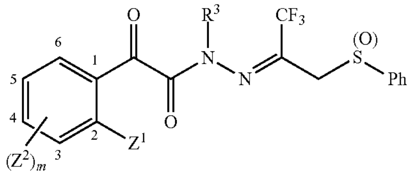
(4-51)
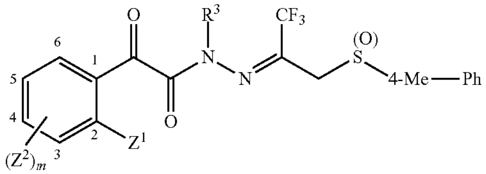
(4-52)
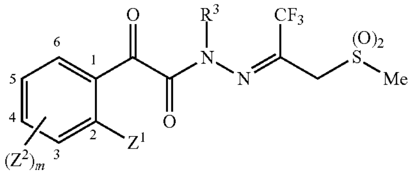
(4-53)
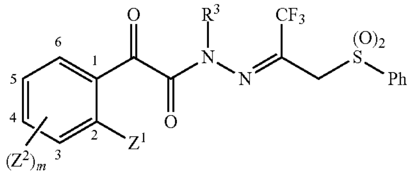
(4-54)
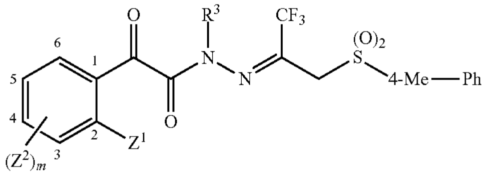
(4-55)
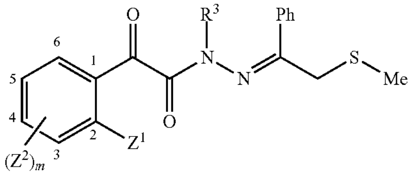

-continued
(4-56)
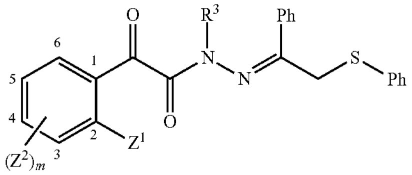
(4-57)
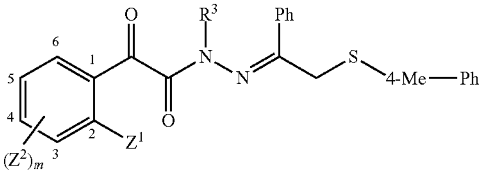
(4-58)
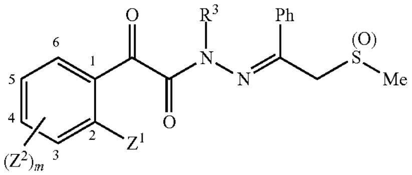
(4-59)
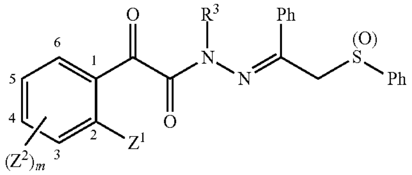
(4-60)
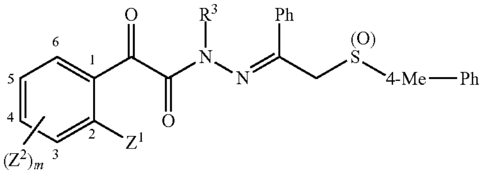
(4-61)
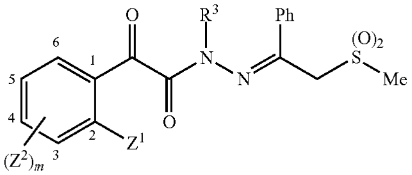
(4-62)
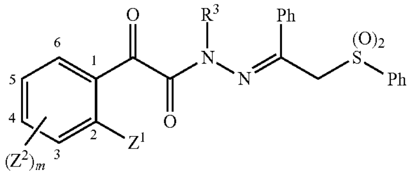
(4-63)
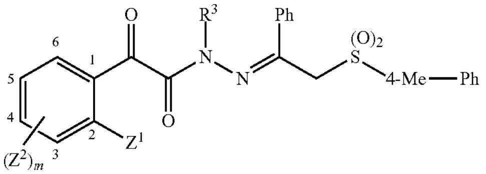
-continued
(4-64)
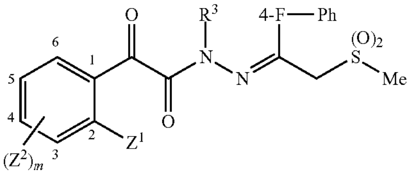
(4-65)
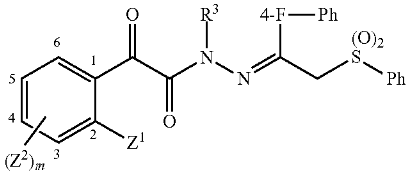
(4-66)
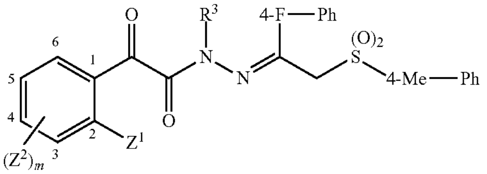
(4-67)
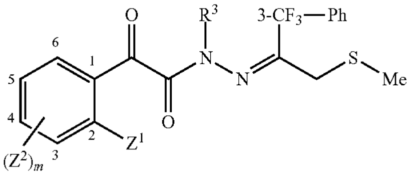
(4-68)
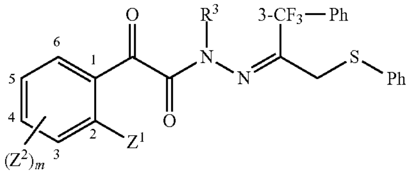
(4-69)
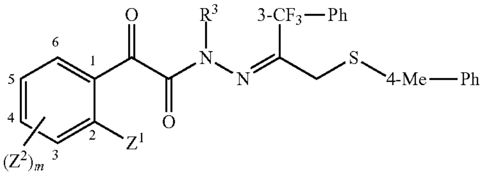
(4-70)
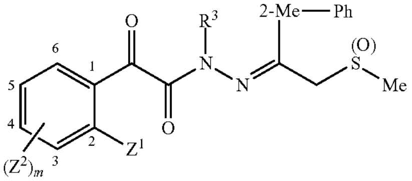
(4-71)
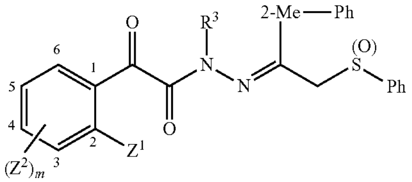

-continued (4-72)

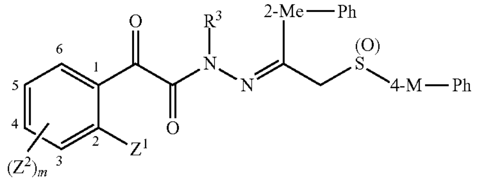

TABLE 1

| No. | R3 | Z1 | (Z2)m |
|---|---|---|---|
| (1)-1 | Me | Me | 4-Me |
| (1)-2 | Me | Me | 6-Me |
| (1)-3 | Me | Me | 4-Me, 6-Me |
| (1)-4 | Me | Me | 4-Me, 6-Cl |
| (1)-5 | Me | Me | 4-Cl |
| (1)-6 | Me | Me | 4-Cl, 6-Me |
| (1)-7 | Me | Me | 4-Cl, 6-Br |
| (1)-8 | Me | Me | 3-Br, 6-Me |
| (1)-9 | Me | Me | 4-Br, 6-Br |
| (1)-10 | Me | Me | 4-F, 6-F |
| (1)-11 | Me | Me | 3-(4-Cl—Ph) |
| (1)-12 | Me | Me | 5-Ph |
| (1)-13 | Me | Me | 5-(2-Cl—Ph) |
| (1)-14 | Me | Me | 5-(2-Br—Ph) |
| (1)-15 | Me | Me | 5-(2-F—Ph) |
| (1)-16 | Me | Me | 5-(2-OMe—Ph) |
| (1)-17 | Me | Me | 5-(2-Me—Ph) |
| (1)-18 | Me | Me | 5-(2-CF3—Ph) |
| (1)-19 | Me | Me | 5-(3-Cl—Ph) |
| (1)-20 | Me | Me | 5-(3-Br—Ph) |
| (1)-21 | Me | Me | 5-(3-F—Ph) |
| (1)-22 | Me | Me | 5-(3-OMe—Ph) |
| (1)-23 | Me | Me | 5-(3-Me—Ph) |
| (1)-24 | Me | Me | 5-(3-CF3—Ph) |
| (1)-25 | Me | Me | 5-(4-Cl—Ph) |
| (1)-26 | Me | Me | 5-(4-Br—Ph) |
| (1)-27 | Me | Me | 5-(4-F—Ph) |
| (1)-28 | Me | Me | 5-(4-OMe—Ph) |
| (1)-29 | Me | Me | 5-(4-Me—Ph) |
| (1)-30 | Me | Me | 5-(4-CF3—Ph) |
| (1)-31 | Me | CF3 | 5-CF3 |
| (1)-32 | Me | Et | — |
| (1)-33 | Me | Et | 4-Me |
| (1)-34 | Me | Et | 6-Me |
| (1)-35 | Me | Et | 4-Me, 6-Me |
| (1)-36 | Me | Et | 4-Me, 6-OMe |
| (1)-37 | Me | Et | 4-Et |
| (1)-38 | Me | Et | 6-Et |
| (1)-39 | Me | Et | 4-Me, 6-Et |
| (1)-40 | Me | Et | 4-Et, 6-Et |

TABLE 2

| No. | R3 | Z1 | (Z2)m |
|---|---|---|---|
| (1)-41 | Me | Et | 4-C≡CH, 6-Et |
| (1)-42 | Me | Et | 4-c-Pr, 6-Et |
| (1)-43 | Me | Et | 4-Ph, 6-Et |
| (1)-44 | Me | Et | 4-Ph, 6-C≡CH |
| (1)-45 | Me | Et | 4-Ph, 6-OMe |
| (1)-46 | Me | Et | 4-(4-Me—Ph), 6-Et |
| (1)-47 | Me | Et | 4-(4-Cl—Ph), 6-Et |
| (1)-48 | Me | Et | 4-CN, 6-Et |
| (1)-49 | Me | Et | 4-OMe, 6-Et |
| (1)-50 | Me | Et | 4-NO2, 6-Et |
| (1)-51 | Me | Et | 4-Cl, 6-Et |
| (1)-52 | Me | Et | 4-Br, 6-Et |
| (1)-53 | Me | Et | 4-F, 6-Et |
| (1)-54 | Me | Et | 5-Ph |
| (1)-55 | Me | Et | 5-(2-Cl—Ph) |
| (1)-56 | Me | Et | 5-(2-Br—Ph) |
| (1)-57 | Me | Et | 5-(2-F—Ph) |

TABLE 2-continued

| No. | R3 | Z1 | (Z2)m |
|---|---|---|---|
| (1)-58 | Me | Et | 5-(2-OMe—Ph) |
| (1)-59 | Me | Et | 5-(2-Me—Ph) |
| (1)-60 | Me | Et | 5-(2-CF3—Ph) |
| (1)-61 | Me | Et | 5-(3-Cl—Ph) |
| (1)-62 | Me | Et | 5-(3-Br—Ph) |
| (1)-63 | Me | Et | 5-(3-F—Ph) |
| (1)-64 | Me | Et | 5-(3-OMe—Ph) |
| (1)-65 | Me | Et | 5-(3-Me—Ph) |
| (1)-66 | Me | Et | 5-(3-CF3—Ph) |
| (1)-67 | Me | Et | 5-(4-Cl—Ph) |
| (1)-68 | Me | Et | 5-(4-Br—Ph) |
| (1)-69 | Me | Et | 5-(4-F—Ph) |
| (1)-70 | Me | Et | 5-(4-OMe—Ph) |
| (1)-71 | Me | Et | 5-(4-Me—Ph) |
| (1)-72 | Me | Et | 5-(4-CF3—Ph) |
| (1)-73 | Me | n-Pr | — |
| (1)-74 | Me | c-Pr | 4-Me, 6-Et |
| (1)-75 | Me | C≡CH | 4-Me, 6-Me |
| (1)-76 | Me | CN | 4-Me, 6-Me |
| (1)-77 | Me | CN | 4-Me, 6-Et |
| (1)-78 | Me | OMe | 4-Me, 6-Me |
| (1)-79 | Me | OEt | 3-F, 6-F |
| (1)-80 | Me | NO2 | — |

TABLE 3

| No. | R3 | Z1 | (Z2)m |
|---|---|---|---|
| (1)-81 | Me | F | 3-F |
| (1)-82 | Me | F | 5-F |
| (1)-83 | Me | F | 6-F |
| (1)-84 | Me | F | 3-Me, 6-F |
| (1)-85 | Me | F | 3-OMe, 6-F |
| (1)-86 | Me | F | 3-OEt, 6-F |
| (1)-87 | Me | F | 3-F, 5-Cl |
| (1)-88 | Me | F | 3-F, 6-F |
| (1)-89 | Me | Cl | — |
| (1)-90 | Me | Cl | 6-Me |
| (1)-91 | Me | Cl | 6-CF3 |
| (1)-92 | Me | Cl | 5-Ph |
| (1)-93 | Me | Cl | 3-Cl |
| (1)-94 | Me | Cl | 4-Cl |
| (1)-95 | Me | Cl | 6-Cl |
| (1)-96 | Me | Cl | 4-Br |
| (1)-97 | Me | Cl | 6-Br |
| (1)-98 | Me | Cl | 4-F |
| (1)-99 | Me | Cl | 6-F |
| (1)-100 | Me | Cl | 4-Me, 6-F |
| (1)-101 | Me | Cl | 4-Me, 6-Cl |
| (1)-102 | Me | Cl | 4-Me, 6-Br |
| (1)-103 | Me | Cl | 4-Me, 6-F |
| (1)-104 | Me | Cl | 4-Me, 6-OCF3 |
| (1)-105 | Me | Cl | 4-Me, 6-c-Pr |
| (1)-106 | Me | Cl | 4-OCF3, 6-Cl |
| (1)-107 | Me | Cl | 4-Cl, 6-Me |
| (1)-108 | Me | Cl | 4-Cl, 6-Et |
| (1)-109 | Me | Cl | 4-Cl, 6-c-Pr |
| (1)-110 | Me | Cl | 4-Cl, 6-OCF3 |
| (1)-111 | Me | Cl | 4-Cl, 6-Br |
| (1)-112 | Me | Cl | 4-Br, 6-Br |
| (1)-113 | Me | Cl | 4-Br, 6-OCF3 |
| (1)-114 | Me | Cl | 4-F, 6-F |
| (1)-115 | Me | Cl | 4-OMe, 6-Et |
| (1)-116 | Me | Br | 4-Me, 6-Me |
| (1)-117 | Me | Br | 4-Me, 6-Et |
| (1)-118 | Me | Br | 4-Me, 6-Br |
| (1)-119 | Me | Br | 4-Cl, 6-OCF3 |
| (1)-120 | Me | Br | 4-Br, 6-OCF3 |

TABLE 4

| No | R3 | Z1 | (Z2)m |
|---|---|---|---|
| (2)-1 | Et | Me | 4-Me |
| (2)-2 | Et | Me | 6-Me |
| (2)-3 | Et | Me | 4-Me, 6-Me |
| (2)-4 | Et | Me | 4-Me, 6-Cl |
| (2)-5 | Et | Me | 4-Cl |
| (2)-6 | Et | Me | 4-Cl, 6-Me |
| (2)-7 | Et | Me | 4-Cl, 6-Br |
| (2)-8 | Et | Me | 3-Br, 6-Me |
| (2)-9 | Et | Me | 4-Br, 6-Br |
| (2)-10 | Et | Me | 4-F, 6-F |
| (2)-11 | Et | Me | 3-(4-Cl—Ph) |
| (2)-12 | Et | Me | 5-Ph |
| (2)-13 | Et | Me | 5-(2-Cl—Ph) |
| (2)-14 | Et | Me | 5-(2-Br—Ph) |
| (2)-15 | Et | Me | 5-(2-F—Ph) |
| (2)-16 | Et | Me | 5-(2-OMe—Ph) |
| (2)-17 | Et | Me | 5-(2-Me—Ph) |
| (2)-18 | Et | Me | 5-(2-CF3—Ph) |
| (2)-19 | Et | Me | 5-(3-Cl—Ph) |
| (2)-20 | Et | Me | 5-(3-Br—Ph) |
| (2)-21 | Et | Me | 5-(3-F—Ph) |
| (2)-22 | Et | Me | 5-(3-OMe—Ph) |
| (2)-23 | Et | Me | 5-(3-Me—Ph) |
| (2)-24 | Et | Me | 5-(3-CF3—Ph) |
| (2)-25 | Et | Me | 5-(4-Cl—Ph) |
| (2)-26 | Et | Me | 5-(4-Br—Ph) |
| (2)-27 | Et | Me | 5-(4-F—Ph) |
| (2)-28 | Et | Me | 5-(4-OMe—Ph) |
| (2)-29 | Et | Me | 5-(4-Me—Ph) |
| (2)-30 | Et | Me | 5-(4-CF3—Ph) |
| (2)-31 | Et | CF3 | 5-CF3 |
| (2)-32 | Et | Et | — |
| (2)-33 | Et | Et | 4-Me |
| (2)-34 | Et | Et | 6-Me |
| (2)-35 | Et | Et | 4-Me, 6-Me |
| (2)-36 | Et | Et | 4-Me, 6-OMe |
| (2)-37 | Et | Et | 4-Et |
| (2)-38 | Et | Et | 6-Et |
| (2)-39 | Et | Et | 4-Me, 6-Et |
| (2)-40 | Et | Et | 4-Et, 6-Et |

TABLE 5

| No | R3 | Z1 | (Z2)m |
|---|---|---|---|
| (2)-41 | Et | Et | 4-C≡CH, 6-Et |
| (2)-42 | Et | Et | 4-c-Pr, 6-Et |
| (2)-43 | Et | Et | 4-Ph, 6-Et |
| (2)-44 | Et | Et | 4-Ph, 6-C≡CH |
| (2)-45 | Et | Et | 4-Ph, 6-OMe |
| (2)-46 | Et | Et | 4-(4-Me—Ph), 6-Et |
| (2)-47 | Et | Et | 4-(4-Cl—Ph), 6-Et |
| (2)-48 | Et | Et | 4-CN, 6-Et |
| (2)-49 | Et | Et | 4-OMe, 6-Et |
| (2)-50 | Et | Et | 4-NO2, 6-Et |
| (2)-51 | Et | Et | 4-Cl, 6-Et |
| (2)-52 | Et | Et | 4-Br, 6-Et |
| (2)-53 | Et | Et | 4-F, 6-Et |
| (2)-54 | Et | Et | 5-Ph |
| (2)-55 | Et | Et | 5-(2-Cl—Ph) |
| (2)-56 | Et | Et | 5-(2-Br—Ph) |
| (2)-57 | Et | Et | 5-(2-F—Ph) |
| (2)-58 | Et | Et | 5-(2-OMe—Ph) |
| (2)-59 | Et | Et | 5-(2-Me—Ph) |
| (2)-60 | Et | Et | 5-(2-CF3—Ph) |
| (2)-61 | Et | Et | 5-(3-Cl—Ph) |
| (2)-62 | Et | Et | 5-(3-Br—Ph) |
| (2)-63 | Et | Et | 5-(3-F—Ph) |
| (2)-64 | Et | Et | 5-(3-OMe—Ph) |
| (2)-65 | Et | Et | 5-(3-Me—Ph) |
| (2)-66 | Et | Et | 5-(3-CF3—Ph) |
| (2)-67 | Et | Et | 5-(4-Cl—Ph) |
| (2)-68 | Et | Et | 5-(4-Br—Ph) |
| (2)-69 | Et | Et | 5-(4-F—Ph) |
| (2)-70 | Et | Et | 5-(4-OMe—Ph) |

TABLE 5-continued

| No | R3 | Z1 | (Z2)m |
|---|---|---|---|
| (2)-71 | Et | Et | 5-(4-Me—Ph) |
| (2)-72 | Et | Et | 5-(4-CF3—Ph) |
| (2)-73 | Et | n-Pr | — |
| (2)-74 | Et | c-Pr | 4-Me, 6-Et |
| (2)-75 | Et | C≡CH | 4-Me, 6-Me |
| (2)-76 | Et | CN | 4-Me, 6-Me |
| (2)-77 | Et | CN | 4-Me, 6-Et |
| (2)-78 | Et | OMe | 4-Me, 6-Me |
| (2)-79 | Et | OEt | 3-F, 6-F |
| (2)-80 | Et | NO2 | — |

TABLE 6

| No | R3 | Z1 | (Z2)m |
|---|---|---|---|
| (2)-81 | Et | F | 3-F |
| (2)-82 | Et | F | 5-F |
| (2)-83 | Et | F | 6-F |
| (2)-84 | Et | F | 3-Me, 6-F |
| (2)-85 | Et | F | 3-OMe, 6-F |
| (2)-86 | Et | F | 3-OEt, 6-F |
| (2)-87 | Et | F | 3-F, 5-Cl |
| (2)-88 | Et | F | 3-F, 6-F |
| (2)-89 | Et | Cl | — |
| (2)-90 | Et | Cl | 6-Me |
| (2)-91 | Et | Cl | 6-CF3 |
| (2)-92 | Et | Cl | 5-Ph |
| (2)-93 | Et | Cl | 3-Cl |
| (2)-94 | Et | Cl | 4-Cl |
| (2)-95 | Et | Cl | 6-Cl |
| (2)-96 | Et | Cl | 4-Br |
| (2)-97 | Et | Cl | 6-Br |
| (2)-98 | Et | Cl | 4-F |
| (2)-99 | Et | Cl | 6-F |
| (2)-100 | Et | Cl | 4-Me, 6-F |
| (2)-101 | Et | Cl | 4-Me, 6-Cl |
| (2)-102 | Et | Cl | 4-Me, 6-Br |
| (2)-103 | Et | Cl | 4-Me, 6-F |
| (2)-104 | Et | Cl | 4-Me, 6-OCF3 |
| (2)-105 | Et | Cl | 4-Me, 6-c-Pr |
| (2)-106 | Et | Cl | 4-OCF3, 6-Cl |
| (2)-107 | Et | Cl | 4-Cl, 6-Me |
| (2)-108 | Et | Cl | 4-Cl, 6-Et |
| (2)-109 | Et | Cl | 4-Cl, 6-c-Pr |
| (2)-110 | Et | Cl | 4-Cl, 6-OCF3 |
| (2)-111 | Et | Cl | 4-Cl, 6-Br |
| (2)-112 | Et | Cl | 4-Br, 6-Br |
| (2)-113 | Et | Cl | 4-Br, 6-OCF3 |
| (2)-114 | Et | Cl | 4-F, 6-F |
| (2)-115 | Et | Cl | 4-OMe, 6-Et |
| (2)-116 | Et | Br | 4-Me, 6-Me |
| (2)-117 | Et | Br | 4-Me, 6-Et |
| (2)-118 | Et | Br | 4-Me, 6-Br |
| (2)-119 | Et | Br | 4-Cl, 6-OCF3 |
| (2)-120 | Et | Br | 4-Br, 6-OCF3 |

TABLE 7

| No | R3 | Z1 | (Z2)m |
|---|---|---|---|
| (3)-1 | n-Pr | Me | 4-Me |
| (3)-2 | n-Pr | Me | 6-Me |
| (3)-3 | n-Pr | Me | 4-Me, 6-Me |
| (3)-4 | n-Pr | Me | 4-Me, 6-Cl |
| (3)-5 | n-Pr | Me | 4-Cl |
| (3)-6 | n-Pr | Me | 4-Cl, 6-Me |
| (3)-7 | n-Pr | Me | 4-Cl, 6-Br |
| (3)-8 | n-Pr | Me | 3-Br, 6-Me |
| (3)-9 | n-Pr | Me | 4-Br, 6-Br |
| (3)-10 | n-Pr | Me | 4-F, 6-F |
| (3)-11 | n-Pr | Me | 3-(4-Cl—Ph) |
| (3)-12 | n-Pr | Me | 5-Ph |
| (3)-13 | n-Pr | Me | 5-(2-Cl—Ph) |

TABLE 7-continued

| No | R3 | Z1 | (Z2)m |
|---|---|---|---|
| (3)-14 | n-Pr | Me | 5-(2-Br—Ph) |
| (3)-15 | n-Pr | Me | 5-(2-F—Ph) |
| (3)-16 | n-Pr | Me | 5-(2-OMe—Ph) |
| (3)-17 | n-Pr | Me | 5-(2-Me—Ph) |
| (3)-18 | n-Pr | Me | 5-(2-CF3—Ph) |
| (3)-19 | n-Pr | Me | 5-(3-Cl—Ph) |
| (3)-20 | n-Pr | Me | 5-(3-Br—Ph) |
| (3)-21 | n-Pr | Me | 5-(3-F—Ph) |
| (3)-22 | n-Pr | Me | 5-(3-OMe—Ph) |
| (3)-23 | n-Pr | Me | 5-(3-Me—Ph) |
| (3)-24 | n-Pr | Me | 5-(3-CF3—Ph) |
| (3)-25 | n-Pr | Me | 5-(4-Cl—Ph) |
| (3)-26 | n-Pr | Me | 5-(4-Br—Ph) |
| (3)-27 | n-Pr | Me | 5-(4-F—Ph) |
| (3)-28 | n-Pr | Me | 5-(4-OMe—Ph) |
| (3)-29 | n-Pr | Me | 5-(4-Me—Ph) |
| (3)-30 | n-Pr | Me | 5-(4-CF3—Ph) |
| (3)-31 | n-Pr | CF3 | 5-CF3 |
| (3)-32 | n-Pr | Et | — |
| (3)-33 | n-Pr | Et | 4-Me |
| (3)-34 | n-Pr | Et | 6-Me |
| (3)-35 | n-Pr | Et | 4-Me, 6-Me |
| (3)-36 | n-Pr | Et | 4-Me, 6-OMe |
| (3)-37 | n-Pr | Et | 4-Et |
| (3)-38 | n-Pr | Et | 6-Et |
| (3)-39 | n-Pr | Et | 4-Me, 6-Et |
| (3)-40 | n-Pr | Et | 4-Et, 6-Et |

TABLE 8

| No | R3 | Z1 | (Z2)m |
|---|---|---|---|
| (3)-41 | n-Pr | Et | 4-C≡CH, 6-Et |
| (3)-42 | n-Pr | Et | 4-c-Pr, 6-Et |
| (3)-43 | n-Pr | Et | 4-Ph, 6-Et |
| (3)-44 | n-Pr | Et | 4-Ph, 6-C≡CH |
| (3)-45 | n-Pr | Et | 4-Ph, 6-OMe |
| (3)-46 | n-Pr | Et | 4-(4-Me—Ph), 6-Et |
| (3)-47 | n-Pr | Et | 4-(4-Cl—Ph), 6-Et |
| (3)-48 | n-Pr | Et | 4-CN, 6-Et |
| (3)-49 | n-Pr | Et | 4-OMe, 6-Et |
| (3)-50 | n-Pr | Et | 4-NO2, 6-Et |
| (3)-51 | n-Pr | Et | 4-Cl, 6-Et |
| (3)-52 | n-Pr | Et | 4-Br, 6-Et |
| (3)-53 | n-Pr | Et | 4-F, 6-Et |
| (3)-54 | n-Pr | Et | 5-Ph |
| (3)-55 | n-Pr | Et | 5-(2-Cl—Ph) |
| (3)-56 | n-Pr | Et | 5-(2-Br—Ph) |
| (3)-57 | n-Pr | Et | 5-(2-F—Ph) |
| (3)-58 | n-Pr | Et | 5-(2-OMe—Ph) |
| (3)-59 | n-Pr | Et | 5-(2-Me—Ph) |
| (3)-60 | n-Pr | Et | 5-(2-CF3—Ph) |
| (3)-61 | n-Pr | Et | 5-(3-Cl—Ph) |
| (3)-62 | n-Pr | Et | 5-(3-Br—Ph) |
| (3)-63 | n-Pr | Et | 5-(3-F—Ph) |
| (3)-64 | n-Pr | Et | 5-(3-OMe—Ph) |
| (3)-65 | n-Pr | Et | 5-(3-Me—Ph) |
| (3)-66 | n-Pr | Et | 5-(3-CF3—Ph) |
| (3)-67 | n-Pr | Et | 5-(4-Cl—Ph) |
| (3)-68 | n-Pr | Et | 5-(4-Br—Ph) |
| (3)-69 | n-Pr | Et | 5-(4-F—Ph) |
| (3)-70 | n-Pr | Et | 5-(4-OMe—Ph) |
| (3)-71 | n-Pr | Et | 5-(4-Me—Ph) |
| (3)-72 | n-Pr | Et | 5-(4-CF3—Ph) |
| (3)-73 | n-Pr | n-Pr | — |
| (3)-74 | n-Pr | c-Pr | 4-Me, 6-Et |
| (3)-75 | n-Pr | C≡CH | 4-Me, 6-Me |
| (3)-76 | n-Pr | CN | 4-Me, 6-Me |
| (3)-77 | n-Pr | CN | 4-Me, 6-Et |
| (3)-78 | n-Pr | OMe | 4-Me, 6-Me |
| (3)-79 | n-Pr | OEt | 3-F, 6-F |
| (3)-80 | n-Pr | NO2 | — |

TABLE 9

| No | R3 | Z1 | (Z2)m |
|---|---|---|---|
| (3)-81 | n-Pr | F | 3-F |
| (3)-82 | n-Pr | F | 5-F |
| (3)-83 | n-Pr | F | 6-F |
| (3)-84 | n-Pr | F | 3-Me, 6-F |
| (3)-85 | n-Pr | F | 3-OMe, 6-F |
| (3)-86 | n-Pr | F | 3-OEt, 6-F |
| (3)-87 | n-Pr | F | 3-F, 5-Cl |
| (3)-88 | n-Pr | F | 3-F, 6-F |
| (3)-89 | n-Pr | Cl | — |
| (3)-90 | n-Pr | Cl | 6-Me |
| (3)-91 | n-Pr | Cl | 6-CF3 |
| (3)-92 | n-Pr | Cl | 5-Ph |
| (3)-93 | n-Pr | Cl | 3-Cl |
| (3)-94 | n-Pr | Cl | 4-Cl |
| (3)-95 | n-Pr | Cl | 6-Cl |
| (3)-96 | n-Pr | Cl | 4-Br |
| (3)-97 | n-Pr | Cl | 6-Br |
| (3)-98 | n-Pr | Cl | 4-F |
| (3)-99 | n-Pr | Cl | 6-F |
| (3)-100 | n-Pr | Cl | 4-Me, 6-F |
| (3)-101 | n-Pr | Cl | 4-Me, 6-Cl |
| (3)-102 | n-Pr | Cl | 4-Me, 6-Br |
| (3)-103 | n-Pr | Cl | 4-Me, 6-F |
| (3)-104 | n-Pr | Cl | 4-Me, 6-OCF3 |
| (3)-105 | n-Pr | Cl | 4-Me, 6-c-Pr |
| (3)-106 | n-Pr | Cl | 4-OCF3, 6-Cl |
| (3)-107 | n-Pr | Cl | 4-Cl, 6-Me |
| (3)-108 | n-Pr | Cl | 4-Cl, 6-Et |
| (3)-109 | n-Pr | Cl | 4-Cl, 6-c-Pr |
| (3)-110 | n-Pr | Cl | 4-Cl, 6-OCF3 |
| (3)-111 | n-Pr | Cl | 4-Cl, 6-Br |
| (3)-112 | n-Pr | Cl | 4-Br, 6-Br |
| (3)-113 | n-Pr | Cl | 4-Br, 6-OCF3 |
| (3)-114 | n-Pr | Cl | 4-F, 6-F |
| (3)-115 | n-Pr | Cl | 4-OMe, 6-Et |
| (3)-116 | n-Pr | Br | 4-Me, 6-Me |
| (3)-117 | n-Pr | Br | 4-Me, 6-Et |
| (3)-118 | n-Pr | Br | 4-Me, 6-Br |
| (3)-119 | n-Pr | Br | 4-Cl, 6-OCF3 |
| (3)-120 | n-Pr | Br | 4-Br, 6-OCF3 |

TABLE 10

| No | R3 | Z1 | (Z2)m |
|---|---|---|---|
| (4)-1 | i-Pr | Me | 4-Me |
| (4)-2 | i-Pr | Me | 6-Me |
| (4)-3 | i-Pr | Me | 4-Me, 6-Me |
| (4)-4 | i-Pr | Me | 4-Me, 6-Cl |
| (4)-5 | i-Pr | Me | 4-Cl |
| (4)-6 | i-Pr | Me | 4-Cl, 6-Me |
| (4)-7 | i-Pr | Me | 4-Cl, 6-Br |
| (4)-8 | i-Pr | Me | 3-Br, 6-Me |
| (4)-9 | i-Pr | Me | 4-Br, 6-Br |
| (4)-10 | i-Pr | Me | 4-F, 6-F |
| (4)-11 | i-Pr | Me | 3-(4-Cl—Ph) |
| (4)-12 | i-Pr | Me | 5-Ph |
| (4)-13 | i-Pr | Me | 5-(2-Cl—Ph) |
| (4)-14 | i-Pr | Me | 5-(2-Br—Ph) |
| (4)-15 | i-Pr | Me | 5-(2-F—Ph) |
| (4)-16 | i-Pr | Me | 5-(2-OMe—Ph) |
| (4)-17 | i-Pr | Me | 5-(2-Me—Ph) |
| (4)-18 | i-Pr | Me | 5-(2-CF3—Ph) |
| (4)-19 | i-Pr | Me | 5-(3-Cl—Ph) |
| (4)-20 | i-Pr | Me | 5-(3-Br—Ph) |
| (4)-21 | i-Pr | Me | 5-(3-F—Ph) |
| (4)-22 | i-Pr | Me | 5-(3-OMe—Ph) |
| (4)-23 | i-Pr | Me | 5-(3-Me—Ph) |
| (4)-24 | i-Pr | Me | 5-(3-CF3—Ph) |
| (4)-25 | i-Pr | Me | 5-(4-Cl—Ph) |
| (4)-26 | i-Pr | Me | 5-(4-Br—Ph) |
| (4)-27 | i-Pr | Me | 5-(4-F—Ph) |
| (4)-28 | i-Pr | Me | 5-(4-OMe—Ph) |
| (4)-29 | i-Pr | Me | 5-(4-Me—Ph) |
| (4)-30 | i-Pr | Me | 5-(4-CF3—Ph) |

TABLE 10-continued

| No | R3 | Z1 | (Z2)m |
|---|---|---|---|
| (4)-31 | i-Pr | CF3 | 5-CF3 |
| (4)-32 | i-Pr | Et | — |
| (4)-33 | i-Pr | Et | 4-Me |
| (4)-34 | i-Pr | Et | 6-Me |
| (4)-35 | i-Pr | Et | 4-Me, 6-Me |
| (4)-36 | i-Pr | Et | 4-Me, 6-OMe |
| (4)-37 | i-Pr | Et | 4-Et |
| (4)-38 | i-Pr | Et | 6-Et |
| (4)-39 | i-Pr | Et | 4-Me, 6-Et |
| (4)-40 | i-Pr | Et | 4-Et, 6-Et |

TABLE 11

| No | R3 | Z1 | (Z2)m |
|---|---|---|---|
| (4)-41 | i-Pr | Et | 4-C≡CH, 6-Et |
| (4)-42 | i-Pr | Et | 4-c-Pr, 6-Et |
| (4)-43 | i-Pr | Et | 4-Ph, 6-Et |
| (4)-44 | i-Pr | Et | 4-Ph, 6-C≡CH |
| (4)-45 | i-Pr | Et | 4-Ph, 6-OMe |
| (4)-46 | i-Pr | Et | 4-(4-Me—Ph), 6-Et |
| (4)-47 | i-Pr | Et | 4-(4-Cl—Ph), 6-Et |
| (4)-48 | i-Pr | Et | 4-CN, 6-Et |
| (4)-49 | i-Pr | Et | 4-OMe, 6-Et |
| (4)-50 | i-Pr | Et | 4-NO2, 6-Et |
| (4)-51 | i-Pr | Et | 4-Cl, 6-Et |
| (4)-52 | i-Pr | Et | 4-Br, 6-Et |
| (4)-53 | i-Pr | Et | 4-F, 6-Et |
| (4)-54 | i-Pr | Et | 5-Ph |
| (4)-55 | i-Pr | Et | 5-(2-Cl—Ph) |
| (4)-56 | i-Pr | Et | 5-(2-Br—Ph) |
| (4)-57 | i-Pr | Et | 5-(2-F—Ph) |
| (4)-58 | i-Pr | Et | 5-(2-OMe—Ph) |
| (4)-59 | i-Pr | Et | 5-(2-Me—Ph) |
| (4)-60 | i-Pr | Et | 5-(2-CF3—Ph) |
| (4)-61 | i-Pr | Et | 5-(3-Cl—Ph) |
| (4)-62 | i-Pr | Et | 5-(3-Br—Ph) |
| (4)-63 | i-Pr | Et | 5-(3-F—Ph) |
| (4)-64 | i-Pr | Et | 5-(3-OMe—Ph) |
| (4)-65 | i-Pr | Et | 5-(3-Me—Ph) |
| (4)-66 | i-Pr | Et | 5-(3-CF3—Ph) |
| (4)-67 | i-Pr | Et | 5-(4-Cl—Ph) |
| (4)-68 | i-Pr | Et | 5-(4-Br—Ph) |
| (4)-69 | i-Pr | Et | 5-(4-F—Ph) |
| (4)-70 | i-Pr | Et | 5-(4-OMe—Ph) |
| (4)-71 | i-Pr | Et | 5-(4-Me—Ph) |
| (4)-72 | i-Pr | Et | 5-(4-CF3—Ph) |
| (4)-73 | i-Pr | n-Pr | — |
| (4)-74 | i-Pr | c-Pr | 4-Me, 6-Et |
| (4)-75 | i-Pr | C≡CH | 4-Me, 6-Me |
| (4)-76 | i-Pr | CN | 4-Me, 6-Me |
| (4)-77 | i-Pr | CN | 4-Me, 6-Et |
| (4)-78 | i-Pr | OMe | 4-Me, 6-Me |
| (4)-79 | i-Pr | OEt | 3-F, 6-F |
| (4)-80 | i-Pr | NO2 | — |

TABLE 12

| No | R3 | Z1 | (Z2)m |
|---|---|---|---|
| (4)-81 | i-Pr | F | 3-F |
| (4)-82 | i-Pr | F | 5-F |
| (4)-83 | i-Pr | F | 6-F |
| (4)-84 | i-Pr | F | 3-Me, 6-F |
| (4)-85 | i-Pr | F | 3-OMe, 6-F |
| (4)-86 | i-Pr | F | 3-OEt, 6-F |
| (4)-87 | i-Pr | F | 3-F, 5-Cl |
| (4)-88 | i-Pr | F | 3-F, 6-F |
| (4)-89 | i-Pr | Cl | — |
| (4)-90 | i-Pr | Cl | 6-Me |
| (4)-91 | i-Pr | Cl | 6-CF3 |
| (4)-92 | i-Pr | Cl | 5-Ph |
| (4)-93 | i-Pr | Cl | 3-Cl |

TABLE 12-continued

| No | R3 | Z1 | (Z2)m |
|---|---|---|---|
| (4)-94 | i-Pr | Cl | 4-Cl |
| (4)-95 | i-Pr | Cl | 6-Cl |
| (4)-96 | i-Pr | Cl | 4-Br |
| (4)-97 | i-Pr | Cl | 6-Br |
| (4)-98 | i-Pr | Cl | 4-F |
| (4)-99 | i-Pr | Cl | 6-F |
| (4)-100 | i-Pr | Cl | 4-Me, 6-F |
| (4)-101 | i-Pr | Cl | 4-Me, 6-Cl |
| (4)-102 | i-Pr | Cl | 4-Me, 6-Br |
| (4)-103 | i-Pr | Cl | 4-Me, 6-F |
| (4)-104 | i-Pr | Cl | 4-Me, 6-OCF3 |
| (4)-105 | i-Pr | Cl | 4-Me, 6-c-Pr |
| (4)-106 | i-Pr | Cl | 4-OCF3, 6-Cl |
| (4)-107 | i-Pr | Cl | 4-Cl, 6-Me |
| (4)-108 | i-Pr | Cl | 4-Cl, 6-Et |
| (4)-109 | i-Pr | Cl | 4-Cl, 6-c-Pr |
| (4)-110 | i-Pr | Cl | 4-Cl, 6-OCF3 |
| (4)-111 | i-Pr | Cl | 4-Cl, 6-Br |
| (4)-112 | i-Pr | Cl | 4-Br, 6-Br |
| (4)-113 | i-Pr | Cl | 4-Br, 6-OCF3 |
| (4)-114 | i-Pr | Cl | 4-F, 6-F |
| (4)-115 | i-Pr | Cl | 4-OMe, 6-Et |
| (4)-116 | i-Pr | Br | 4-Me, 6-Me |
| (4)-117 | i-Pr | Br | 4-Me, 6-Et |
| (4)-118 | i-Pr | Br | 4-Me, 6-Br |
| (4)-119 | i-Pr | Br | 4-Cl, 6-OCF3 |
| (4)-120 | i-Pr | Br | 4-Br, 6-OCF3 |

TABLE 13

| No | R3 | Z1 | (Z2)m |
|---|---|---|---|
| (5)-1 | CH2CH2OMe | Me | 4-Me |
| (5)-2 | CH2CH2OMe | Me | 6-Me |
| (5)-3 | CH2CH2OMe | Me | 4-Me, 6-Me |
| (5)-4 | CH2CH2OMe | Me | 4-Me, 6-Cl |
| (5)-5 | CH2CH2OMe | Me | 4-Cl |
| (5)-6 | CH2CH2OMe | Me | 4-Cl, 6-Me |
| (5)-7 | CH2CH2OMe | Me | 4-Cl, 6-Br |
| (5)-8 | CH2CH2OMe | Me | 3-Br, 6-Me |
| (5)-9 | CH2CH2OMe | Me | 4-Br, 6-Br |
| (5)-10 | CH2CH2OMe | Me | 4-F, 6-F |
| (5)-11 | CH2CH2OMe | Me | 3-(4-Cl—Ph) |
| (5)-12 | CH2CH2OMe | Me | 5-Ph |
| (5)-13 | CH2CH2OMe | Me | 5-(2-Cl—Ph) |
| (5)-14 | CH2CH2OMe | Me | 5-(2-Br—Ph) |
| (5)-15 | CH2CH2OMe | Me | 5-(2-F—Ph) |
| (5)-16 | CH2CH2OMe | Me | 5-(2-OMe—Ph) |
| (5)-17 | CH2CH2OMe | Me | 5-(2-Me—Ph) |
| (5)-18 | CH2CH2OMe | Me | 5-(2-CF3—Ph) |
| (5)-19 | CH2CH2OMe | Me | 5-(3-Cl—Ph) |
| (5)-20 | CH2CH2OMe | Me | 5-(3-Br—Ph) |
| (5)-21 | CH2CH2OMe | Me | 5-(3-F—Ph) |
| (5)-22 | CH2CH2OMe | Me | 5-(3-OMe—Ph) |
| (5)-23 | CH2CH2OMe | Me | 5-(3-Me—Ph) |
| (5)-24 | CH2CH2OMe | Me | 5-(3-CF3—Ph) |
| (5)-25 | CH2CH2OMe | Me | 5-(4-Cl—Ph) |
| (5)-26 | CH2CH2OMe | Me | 5-(4-Br—Ph) |
| (5)-27 | CH2CH2OMe | Me | 5-(4-F—Ph) |
| (5)-28 | CH2CH2OMe | Me | 5-(4-OMe—Ph) |
| (5)-29 | CH2CH2OMe | Me | 5-(4-Me—Ph) |
| (5)-30 | CH2CH2OMe | Me | 5-(4-CF3—Ph) |
| (5)-31 | CH2CH2OMe | CF3 | 5-CF3 |
| (5)-32 | CH2CH2OMe | Et | — |
| (5)-33 | CH2CH2OMe | Et | 4-Me |
| (5)-34 | CH2CH2OMe | Et | 6-Me |
| (5)-35 | CH2CH2OMe | Et | 4-Me, 6-Me |
| (5)-36 | CH2CH2OMe | Et | 4-Me, 6-OMe |
| (5)-37 | CH2CH2OMe | Et | 4-Et |
| (5)-38 | CH2CH2OMe | Et | 6-Et |
| (5)-39 | CH2CH2OMe | Et | 4-Me, 6-Et |
| (5)-40 | CH2CH2OMe | Et | 4-Et, 6-Et |

TABLE 14

| No | R3 | Z1 | (Z2)m |
|---|---|---|---|
| (5)-41 | CH2CH2OMe | Et | 4-C≡CH, 6-Et |
| (5)-42 | CH2CH2OMe | Et | 4-c-Pr, 6-Et |
| (5)-43 | CH2CH2OMe | Et | 4-Ph, 6-Et |
| (5)-44 | CH2CH2OMe | Et | 4-Ph, 6-C≡CH |
| (5)-45 | CH2CH2OMe | Et | 4-Ph, 6-OMe |
| (5)-46 | CH2CH2OMe | Et | 4-(4-Me—Ph), 6-Et |
| (5)-47 | CH2CH2OMe | Et | 4-(4-Cl—Ph), 6-Et |
| (5)-48 | CH2CH2OMe | Et | 4-CN, 6-Et |
| (5)-49 | CH2CH2OMe | Et | 4-OMe, 6-Et |
| (5)-50 | CH2CH2OMe | Et | 4-NO2, 6-Et |
| (5)-51 | CH2CH2OMe | Et | 4-Cl, 6-Et |
| (5)-52 | CH2CH2OMe | Et | 4-Br, 6-Et |
| (5)-53 | CH2CH2OMe | Et | 4-F, 6-Et |
| (5)-54 | CH2CH2OMe | Et | 5-Ph |
| (5)-55 | CH2CH2OMe | Et | 5-(2-Cl—Ph) |
| (5)-56 | CH2CH2OMe | Et | 5-(2-Br—Ph) |
| (5)-57 | CH2CH2OMe | Et | 5-(2-F—Ph) |
| (5)-58 | CH2CH2OMe | Et | 5-(2-OMe—Ph) |
| (5)-59 | CH2CH2OMe | Et | 5-(2-Me—Ph) |
| (5)-60 | CH2CH2OMe | Et | 5-(2-CF3—Ph) |
| (5)-61 | CH2CH2OMe | Et | 5-(3-Cl—Ph) |
| (5)-62 | CH2CH2OMe | Et | 5-(3-Br—Ph) |
| (5)-63 | CH2CH2OMe | Et | 5-(3-F—Ph) |
| (5)-64 | CH2CH2OMe | Et | 5-(3-OMe—Ph) |
| (5)-65 | CH2CH2OMe | Et | 5-(3-Me—Ph) |
| (5)-66 | CH2CH2OMe | Et | 5-(3-CF3—Ph) |
| (5)-67 | CH2CH2OMe | Et | 5-(4-Cl—Ph) |
| (5)-68 | CH2CH2OMe | Et | 5-(4-Br—Ph) |
| (5)-69 | CH2CH2OMe | Et | 5-(4-F—Ph) |
| (5)-70 | CH2CH2OMe | Et | 5-(4-OMe—Ph) |
| (5)-71 | CH2CH2OMe | Et | 5-(4-Me—Ph) |
| (5)-72 | CH2CH2OMe | Et | 5-(4-CF3—Ph) |
| (5)-73 | CH2CH2OMe | n-Pr | — |
| (5)-74 | CH2CH2OMe | c-Pr | 4-Me, 6-Et |
| (5)-75 | CH2CH2OMe | C≡CH | 4-Me, 6-Me |
| (5)-76 | CH2CH2OMe | CN | 4-Me, 6-Me |
| (5)-77 | CH2CH2OMe | CN | 4-Me, 6-Et |
| (5)-78 | CH2CH2OMe | OMe | 4-Me, 6-Me |
| (5)-79 | CH2CH2OMe | OEt | 3-F, 6-F |
| (5)-80 | CH2CH2OMe | NO2 | — |

TABLE 15

| No | R3 | Z1 | (Z2)m |
|---|---|---|---|
| (5)-81 | CH2CH2OMe | F | 3-F |
| (5)-82 | CH2CH2OMe | F | 5-F |
| (5)-83 | CH2CH2OMe | F | 6-F |
| (5)-84 | CH2CH2OMe | F | 3-Me, 6-F |
| (5)-85 | CH2CH2OMe | F | 3-OMe, 6-F |
| (5)-86 | CH2CH2OMe | F | 3-OEt, 6-F |
| (5)-87 | CH2CH2OMe | F | 3-F, 5-Cl |
| (5)-88 | CH2CH2OMe | F | 3-F, 6-F |
| (5)-89 | CH2CH2OMe | Cl | — |
| (5)-90 | CH2CH2OMe | Cl | 6-Me |
| (5)-91 | CH2CH2OMe | Cl | 6-CF3 |
| (5)-92 | CH2CH2OMe | Cl | 5-Ph |
| (5)-93 | CH2CH2OMe | Cl | 3-Cl |
| (5)-94 | CH2CH2OMe | Cl | 4-Cl |
| (5)-95 | CH2CH2OMe | Cl | 6-Cl |
| (5)-96 | CH2CH2OMe | Cl | 4-Br |
| (5)-97 | CH2CH2OMe | Cl | 6-Br |
| (5)-98 | CH2CH2OMe | Cl | 4-F |
| (5)-99 | CH2CH2OMe | Cl | 6-F |
| (5)-100 | CH2CH2OMe | Cl | 4-Me, 6-F |
| (5)-101 | CH2CH2OMe | Cl | 4-Me, 6-Cl |
| (5)-102 | CH2CH2OMe | Cl | 4-Me, 6-Br |
| (5)-103 | CH2CH2OMe | Cl | 4-Me, 6-F |
| (5)-104 | CH2CH2OMe | Cl | 4-Me, 6-OCF3 |
| (5)-105 | CH2CH2OMe | Cl | 4-Me, 6-c-Pr |
| (5)-106 | CH2CH2OMe | Cl | 4-OCF3, 6-Cl |
| (5)-107 | CH2CH2OMe | Cl | 4-Cl, 6-Me |
| (5)-108 | CH2CH2OMe | Cl | 4-Cl, 6-Et |
| (5)-109 | CH2CH2OMe | Cl | 4-Cl, 6-c-Pr |
| (5)-110 | CH2CH2OMe | Cl | 4-Cl, 6-OCF3 |

TABLE 15-continued

| No | R3 | Z1 | (Z2)m |
|---|---|---|---|
| (5)-111 | CH2CH2OMe | Cl | 4-Cl, 6-Br |
| (5)-112 | CH2CH2OMe | Cl | 4-Br, 6-Br |
| (5)-113 | CH2CH2OMe | Cl | 4-Br, 6-OCF3 |
| (5)-114 | CH2CH2OMe | Cl | 4-F, 6-F |
| (5)-115 | CH2CH2OMe | Cl | 4-OMe, 6-Et |
| (5)-116 | CH2CH2OMe | Br | 4-Me, 6-Me |
| (5)-117 | CH2CH2OMe | Br | 4-Me, 6-Et |
| (5)-118 | CH2CH2OMe | Br | 4-Me, 6-Br |
| (5)-119 | CH2CH2OMe | Br | 4-Cl, 6-OCF3 |
| (5)-120 | CH2CH2OMe | Br | 4-Br, 6-OCF3 |

TABLE 16

| No | R3 | Z1 | (Z2)m |
|---|---|---|---|
| (6)-1 | CH2CH2OEt | Me | 4-Me |
| (6)-2 | CH2CH2OEt | Me | 6-Me |
| (6)-3 | CH2CH2OEt | Me | 4-Me, 6-Me |
| (6)-4 | CH2CH2OEt | Me | 4-Me, 6-Cl |
| (6)-5 | CH2CH2OEt | Me | 4-Cl |
| (6)-6 | CH2CH2OEt | Me | 4-Cl, 6-Me |
| (6)-7 | CH2CH2OEt | Me | 4-Cl, 6-Br |
| (6)-8 | CH2CH2OEt | Me | 3-Br, 6-Me |
| (6)-9 | CH2CH2OEt | Me | 4-Br, 6-Br |
| (6)-10 | CH2CH2OEt | Me | 4-F, 6-F |
| (6)-11 | CH2CH2OEt | Me | 3-(4-Cl—Ph) |
| (6)-12 | CH2CH2OEt | Me | 5-Ph |
| (6)-13 | CH2CH2OEt | Me | 5-(2-Cl—Ph) |
| (6)-14 | CH2CH2OEt | Me | 5-(2-Br—Ph) |
| (6)-15 | CH2CH2OEt | Me | 5-(2-F—Ph) |
| (6)-16 | CH2CH2OEt | Me | 5-(2-OMe—Ph) |
| (6)-17 | CH2CH2OEt | Me | 5-(2-Me—Ph) |
| (6)-18 | CH2CH2OEt | Me | 5-(2-CF3—Ph) |
| (6)-19 | CH2CH2OEt | Me | 5-(3-Cl—Ph) |
| (6)-20 | CH2CH2OEt | Me | 5-(3-Br—Ph) |
| (6)-21 | CH2CH2OEt | Me | 5-(3-F—Ph) |
| (6)-22 | CH2CH2OEt | Me | 5-(3-OMe—Ph) |
| (6)-23 | CH2CH2OEt | Me | 5-(3-Me—Ph) |
| (6)-24 | CH2CH2OEt | Me | 5-(3-CF3—Ph) |
| (6)-25 | CH2CH2OEt | Me | 5-(4-Cl—Ph) |
| (6)-26 | CH2CH2OEt | Me | 5-(4-Br—Ph) |
| (6)-27 | CH2CH2OEt | Me | 5-(4-F—Ph) |
| (6)-28 | CH2CH2OEt | Me | 5-(4-OMe—Ph) |
| (6)-29 | CH2CH2OEt | Me | 5-(4-Me—Ph) |
| (6)-30 | CH2CH2OEt | Me | 5-(4-CF3—Ph) |
| (6)-31 | CH2CH2OEt | CF3 | 5-CF3 |
| (6)-32 | CH2CH2OEt | Et | — |
| (6)-33 | CH2CH2OEt | Et | 4-Me |
| (6)-34 | CH2CH2OEt | Et | 6-Me |
| (6)-35 | CH2CH2OEt | Et | 4-Me, 6-Me |
| (6)-36 | CH2CH2OEt | Et | 4-Me, 6-OMe |
| (6)-37 | CH2CH2OEt | Et | 4-Et |
| (6)-38 | CH2CH2OEt | Et | 6-Et |
| (6)-39 | CH2CH2OEt | Et | 4-Me, 6-Et |
| (6)-40 | CH2CH2OEt | Et | 4-Et, 6-Et |

TABLE 17

| No | R3 | Z1 | (Z2)m |
|---|---|---|---|
| (6)-41 | CH2CH2OEt | Et | 4-C≡CH, 6-Et |
| (6)-42 | CH2CH2OEt | Et | 4-c-Pr, 6-Et |
| (6)-43 | CH2CH2OEt | Et | 4-Ph, 6-Et |
| (6)-44 | CH2CH2OEt | Et | 4-Ph, 6-C≡CH |
| (6)-45 | CH2CH2OEt | Et | 4-Ph, 6-OMe |
| (6)-46 | CH2CH2OEt | Et | 4-(4-Me—Ph), 6-Et |
| (6)-47 | CH2CH2OEt | Et | 4-(4-Cl—Ph), 6-Et |
| (6)-48 | CH2CH2OEt | Et | 4-CN, 6-Et |
| (6)-49 | CH2CH2OEt | Et | 4-OMe, 6-Et |
| (6)-50 | CH2CH2OEt | Et | 4-NO2, 6-Et |
| (6)-51 | CH2CH2OEt | Et | 4-Cl, 6-Et |
| (6)-52 | CH2CH2OEt | Et | 4-Br, 6-Et |
| (6)-53 | CH2CH2OEt | Et | 4-F, 6-Et |

TABLE 17-continued

| No | R3 | Z1 | (Z2)m |
|---|---|---|---|
| (6)-54 | CH2CH2OEt | Et | 5-Ph |
| (6)-55 | CH2CH2OEt | Et | 5-(2-Cl—Ph) |
| (6)-56 | CH2CH2OEt | Et | 5-(2-Br—Ph) |
| (6)-57 | CH2CH2OEt | Et | 5-(2-F—Ph) |
| (6)-58 | CH2CH2OEt | Et | 5-(2-OMe—Ph) |
| (6)-59 | CH2CH2OEt | Et | 5-(2-Me—Ph) |
| (6)-60 | CH2CH2OEt | Et | 5-(2-CF3—Ph) |
| (6)-61 | CH2CH2OEt | Et | 5-(3-Cl—Ph) |
| (6)-62 | CH2CH2OEt | Et | 5-(3-Br—Ph) |
| (6)-63 | CH2CH2OEt | Et | 5-(3-F—Ph) |
| (6)-64 | CH2CH2OEt | Et | 5-(3-OMe—Ph) |
| (6)-65 | CH2CH2OEt | Et | 5-(3-Me—Ph) |
| (6)-66 | CH2CH2OEt | Et | 5-(3-CF3—Ph) |
| (6)-67 | CH2CH2OEt | Et | 5-(4-Cl—Ph) |
| (6)-68 | CH2CH2OEt | Et | 5-(4-Br—Ph) |
| (6)-69 | CH2CH2OEt | Et | 5-(4-F—Ph) |
| (6)-70 | CH2CH2OEt | Et | 5-(4-OMe—Ph) |
| (6)-71 | CH2CH2OEt | Et | 5-(4-Me—Ph) |
| (6)-72 | CH2CH2OEt | Et | 5-(4-CF3—Ph) |
| (6)-73 | CH2CH2OEt | n-Pr | — |
| (6)-74 | CH2CH2OEt | c-Pr | 4-Me, 6-Et |
| (6)-75 | CH2CH2OEt | C≡CH | 4-Me, 6-Me |
| (6)-76 | CH2CH2OEt | CN | 4-Me, 6-Me |
| (6)-77 | CH2CH2OEt | CN | 4-Me, 6-Et |
| (6)-78 | CH2CH2OEt | OMe | 4-Me, 6-Me |
| (6)-79 | CH2CH2OEt | OEt | 3-F, 6-F |
| (6)-80 | CH2CH2OEt | NO2 | — |

TABLE 18

| No | R3 | Z1 | (Z2)m |
|---|---|---|---|
| (6)-81 | CH2CH2OEt | F | 3-F |
| (6)-82 | CH2CH2OEt | F | 5-F |
| (6)-83 | CH2CH2OEt | F | 6-F |
| (6)-84 | CH2CH2OEt | F | 3-Me, 6-F |
| (6)-85 | CH2CH2OEt | F | 3-OMe, 6-F |
| (6)-86 | CH2CH2OEt | F | 3-OEt, 6-F |
| (6)-87 | CH2CH2OEt | F | 3-F, 5-Cl |
| (6)-88 | CH2CH2OEt | F | 3-F, 6-F |
| (6)-89 | CH2CH2OEt | Cl | — |
| (6)-90 | CH2CH2OEt | Cl | 6-Me |
| (6)-91 | CH2CH2OEt | Cl | 6-CF3 |
| (6)-92 | CH2CH2OEt | Cl | 5-Ph |
| (6)-93 | CH2CH2OEt | Cl | 3-Cl |
| (6)-94 | CH2CH2OEt | Cl | 4-Cl |
| (6)-95 | CH2CH2OEt | Cl | 6-Cl |
| (6)-96 | CH2CH2OEt | Cl | 4-Br |
| (6)-97 | CH2CH2OEt | Cl | 6-Br |
| (6)-98 | CH2CH2OEt | Cl | 4-F |
| (6)-99 | CH2CH2OEt | Cl | 6-F |
| (6)-100 | CH2CH2OEt | Cl | 4-Me, 6-F |
| (6)-101 | CH2CH2OEt | Cl | 4-Me, 6-Cl |
| (6)-102 | CH2CH2OEt | Cl | 4-Me, 6-Br |
| (6)-103 | CH2CH2OEt | Cl | 4-Me, 6-F |
| (6)-104 | CH2CH2OEt | Cl | 4-Me, 6-OCF3 |
| (6)-105 | CH2CH2OEt | Cl | 4-Me, 6-c-Pr |
| (6)-106 | CH2CH2OEt | Cl | 4-OCF3, 6-Cl |
| (6)-107 | CH2CH2OEt | Cl | 4-Cl, 6-Me |
| (6)-108 | CH2CH2OEt | Cl | 4-Cl, 6-Et |
| (6)-109 | CH2CH2OEt | Cl | 4-Cl, 6-c-Pr |
| (6)-110 | CH2CH2OEt | Cl | 4-Cl, 6-OCF3 |
| (6)-111 | CH2CH2OEt | Cl | 4-Cl, 6-Br |
| (6)-112 | CH2CH2OEt | Cl | 4-Br, 6-Br |
| (6)-113 | CH2CH2OEt | Cl | 4-Br, 6-OCF3 |
| (6)-114 | CH2CH2OEt | Cl | 4-F, 6-F |
| (6)-115 | CH2CH2OEt | Cl | 4-OMe, 6-Et |
| (6)-116 | CH2CH2OEt | Br | 4-Me, 6-Me |
| (6)-117 | CH2CH2OEt | Br | 4-Me, 6-Et |
| (6)-118 | CH2CH2OEt | Br | 4-Me, 6-Br |
| (6)-119 | CH2CH2OEt | Br | 4-Cl, 6-OCF3 |
| (6)-120 | CH2CH2OEt | Br | 4-Br, 6-OCF3 |

TABLE 19

| No | R3 | Z1 | (Z2)m |
|---|---|---|---|
| (7)-1 | CH2Ph | Me | 4-Me |
| (7)-2 | CH2Ph | Me | 6-Me |
| (7)-3 | CH2Ph | Me | 4-Me, 6-Me |
| (7)-4 | CH2Ph | Me | 4-Me, 6-Cl |
| (7)-5 | CH2Ph | Me | 4-Cl |
| (7)-6 | CH2Ph | Me | 4-Cl, 6-Me |
| (7)-7 | CH2Ph | Me | 4-Cl, 6-Br |
| (7)-8 | CH2Ph | Me | 3-Br, 6-Me |
| (7)-9 | CH2Ph | Me | 4-Br, 6-Br |
| (7)-10 | CH2Ph | Me | 4-F, 6-F |
| (7)-11 | CH2Ph | Me | 3-(4-Cl—Ph) |
| (7)-12 | CH2Ph | Me | 5-Ph |
| (7)-13 | CH2Ph | Me | 5-(2-Cl—Ph) |
| (7)-14 | CH2Ph | Me | 5-(2-Br—Ph) |
| (7)-15 | CH2Ph | Me | 5-(2-F—Ph) |
| (7)-16 | CH2Ph | Me | 5-(2-OMe—Ph) |
| (7)-17 | CH2Ph | Me | 5-(2-Me—Ph) |
| (7)-18 | CH2Ph | Me | 5-(2-CF3—Ph) |
| (7)-19 | CH2Ph | Me | 5-(3-Cl—Ph) |
| (7)-20 | CH2Ph | Me | 5-(3-Br—Ph) |
| (7)-21 | CH2Ph | Me | 5-(3-F—Ph) |
| (7)-22 | CH2Ph | Me | 5-(3-OMe—Ph) |
| (7)-23 | CH2Ph | Me | 5-(3-Me—Ph) |
| (7)-24 | CH2Ph | Me | 5-(3-CF3—Ph) |
| (7)-25 | CH2Ph | Me | 5-(4-Cl—Ph) |
| (7)-26 | CH2Ph | Me | 5-(4-Br—Ph) |
| (7)-27 | CH2Ph | Me | 5-(4-F—Ph) |
| (7)-28 | CH2Ph | Me | 5-(4-OMe—Ph) |
| (7)-29 | CH2Ph | Me | 5-(4-Me—Ph) |
| (7)-30 | CH2Ph | Me | 5-(4-CF3—Ph) |
| (7)-31 | CH2Ph | CF3 | 5-CF3 |
| (7)-32 | CH2Ph | Et | — |
| (7)-33 | CH2Ph | Et | 4-Me |
| (7)-34 | CH2Ph | Et | 6-Me |
| (7)-35 | CH2Ph | Et | 4-Me, 6-Me |
| (7)-36 | CH2Ph | Et | 4-Me, 6-OMe |
| (7)-37 | CH2Ph | Et | 4-Et |
| (7)-38 | CH2Ph | Et | 6-Et |
| (7)-39 | CH2Ph | Et | 4-Me, 6-Et |
| (7)-40 | CH2Ph | Et | 4-Et, 6-Et |

TABLE 20

| No | R3 | Z1 | (Z2)m |
|---|---|---|---|
| (7)-41 | CH2Ph | Et | 4-C≡CH, 6-Et |
| (7)-42 | CH2Ph | Et | 4-c-Pr, 6-Et |
| (7)-43 | CH2Ph | Et | 4-Ph, 6-Et |
| (7)-44 | CH2Ph | Et | 4-Ph, 6-C≡CH |
| (7)-45 | CH2Ph | Et | 4-Ph, 6-OMe |
| (7)-46 | CH2Ph | Et | 4-(4-Me—Ph), 6-Et |
| (7)-47 | CH2Ph | Et | 4-(4-Cl—Ph), 6-Et |
| (7)-48 | CH2Ph | Et | 4-CN, 6-Et |
| (7)-49 | CH2Ph | Et | 4-OMe, 6-Et |
| (7)-50 | CH2Ph | Et | 4-NO2, 6-Et |
| (7)-51 | CH2Ph | Et | 4-Cl, 6-Et |
| (7)-52 | CH2Ph | Et | 4-Br, 6-Et |
| (7)-53 | CH2Ph | Et | 4-F, 6-Et |
| (7)-54 | CH2Ph | Et | 5-Ph |
| (7)-55 | CH2Ph | Et | 5-(2-Cl—Ph) |
| (7)-56 | CH2Ph | Et | 5-(2-Br—Ph) |
| (7)-57 | CH2Ph | Et | 5-(2-F—Ph) |
| (7)-58 | CH2Ph | Et | 5-(2-OMe—Ph) |
| (7)-59 | CH2Ph | Et | 5-(2-Me—Ph) |
| (7)-60 | CH2Ph | Et | 5-(2-CF3—Ph) |
| (7)-61 | CH2Ph | Et | 5-(3-Cl—Ph) |
| (7)-62 | CH2Ph | Et | 5-(3-Br—Ph) |
| (7)-63 | CH2Ph | Et | 5-(3-F—Ph) |
| (7)-64 | CH2Ph | Et | 5-(3-OMe—Ph) |
| (7)-65 | CH2Ph | Et | 5-(3-Me—Ph) |
| (7)-66 | CH2Ph | Et | 5-(3-CF3—Ph) |
| (7)-67 | CH2Ph | Et | 5-(4-Cl—Ph) |
| (7)-68 | CH2Ph | Et | 5-(4-Br—Ph) |
| (7)-69 | CH2Ph | Et | 5-(4-F—Ph) |
| (7)-70 | CH2Ph | Et | 5-(4-OMe—Ph) |

TABLE 20-continued

| No | R3 | Z1 | (Z2)m |
|---|---|---|---|
| (7)-71 | CH2Ph | Et | 5-(4-Me—Ph) |
| (7)-72 | CH2Ph | Et | 5-(4-CF3—Ph) |
| (7)-73 | CH2Ph | n-Pr | — |
| (7)-74 | CH2Ph | c-Pr | 4-Me, 6-Et |
| (7)-75 | CH2Ph | C≡CH | 4-Me, 6-Me |
| (7)-76 | CH2Ph | CN | 4-Me, 6-Me |
| (7)-77 | CH2Ph | CN | 4-Me, 6-Et |
| (7)-78 | CH2Ph | OMe | 4-Me, 6-Me |
| (7)-79 | CH2Ph | OEt | 3-F, 6-F |
| (7)-80 | CH2Ph | NO2 | — |

TABLE 21

| No | R3 | Z1 | (Z2)m |
|---|---|---|---|
| (7)-81 | CH2Ph | F | 3-F |
| (7)-82 | CH2Ph | F | 5-F |
| (7)-83 | CH2Ph | F | 6-F |
| (7)-84 | CH2Ph | F | 3-Me, 6-F |
| (7)-85 | CH2Ph | F | 3-OMe, 6-F |
| (7)-86 | CH2Ph | F | 3-OEt, 6-F |
| (7)-87 | CH2Ph | F | 3-F, 5-Cl |
| (7)-88 | CH2Ph | F | 3-F, 6-F |
| (7)-89 | CH2Ph | Cl | — |
| (7)-90 | CH2Ph | Cl | 6-Me |
| (7)-91 | CH2Ph | Cl | 6-CF3 |
| (7)-92 | CH2Ph | Cl | 5-Ph |
| (7)-93 | CH2Ph | Cl | 3-Cl |
| (7)-94 | CH2Ph | Cl | 4-Cl |
| (7)-95 | CH2Ph | Cl | 6-Cl |
| (7)-96 | CH2Ph | Cl | 4-Br |
| (7)-97 | CH2Ph | Cl | 6-Br |
| (7)-98 | CH2Ph | Cl | 4-F |
| (7)-99 | CH2Ph | Cl | 6-F |
| (7)-100 | CH2Ph | Cl | 4-Me, 6-F |
| (7)-101 | CH2Ph | Cl | 4-Me, 6-Cl |
| (7)-102 | CH2Ph | Cl | 4-Me, 6-Br |
| (7)-103 | CH2Ph | Cl | 4-Me, 6-F |
| (7)-104 | CH2Ph | Cl | 4-Me, 6-OCF3 |
| (7)-105 | CH2Ph | Cl | 4-Me, 6-c-Pr |
| (7)-106 | CH2Ph | Cl | 4-OCF3, 6-Cl |
| (7)-107 | CH2Ph | Cl | 4-Cl, 6-Me |
| (7)-108 | CH2Ph | Cl | 4-Cl, 6-Et |
| (7)-109 | CH2Ph | Cl | 4-Cl, 6-c-Pr |
| (7)-110 | CH2Ph | Cl | 4-Cl, 6-OCF3 |
| (7)-111 | CH2Ph | Cl | 4-Cl, 6-Br |
| (7)-112 | CH2Ph | Cl | 4-Br, 6-Br |
| (7)-113 | CH2Ph | Cl | 4-Br, 6-OCF3 |
| (7)-114 | CH2Ph | Cl | 4-F, 6-F |
| (7)-115 | CH2Ph | Cl | 4-OMe, 6-Et |
| (7)-116 | CH2Ph | Br | 4-Me, 6-Me |
| (7)-117 | CH2Ph | Br | 4-Me, 6-Et |
| (7)-118 | CH2Ph | Br | 4-Me, 6-Br |
| (7)-119 | CH2Ph | Br | 4-Cl, 6-OCF3 |
| (7)-120 | CH2Ph | Br | 4-Br, 6-OCF3 |

TABLE 22

| No | R3 | Z1 | (Z2)m |
|---|---|---|---|
| (8)-1 | H | Me | 4-Me |
| (8)-2 | H | Me | 6-Me |
| (8)-3 | H | Me | 4-Me, 6-Me |
| (8)-4 | H | Me | 4-Me, 6-Cl |
| (8)-5 | H | Me | 4-Cl |
| (8)-6 | H | Me | 4-Cl, 6-Me |
| (8)-7 | H | Me | 4-Cl, 6-Br |
| (8)-8 | H | Me | 3-Br, 6-Me |
| (8)-9 | H | Me | 4-Br, 6-Br |
| (8)-10 | H | Me | 4-F, 6-F |
| (8)-11 | H | Me | 3-(4-Cl—Ph) |
| (8)-12 | H | Me | 5-Ph |
| (8)-13 | H | Me | 5-(2-Cl—Ph) |

TABLE 22-continued

| No | R3 | Z1 | (Z2)m |
|---|---|---|---|
| (8)-14 | H | Me | 5-(2-Br—Ph) |
| (8)-15 | H | Me | 5-(2-F—Ph) |
| (8)-16 | H | Me | 5-(2-OMe—Ph) |
| (8)-17 | H | Me | 5-(2-Me—Ph) |
| (8)-18 | H | Me | 5-(2-CF3—Ph) |
| (8)-19 | H | Me | 5-(3-Cl—Ph) |
| (8)-20 | H | Me | 5-(3-Br—Ph) |
| (8)-21 | H | Me | 5-(3-F—Ph) |
| (8)-22 | H | Me | 5-(3-OMe—Ph) |
| (8)-23 | H | Me | 5-(3-Me—Ph) |
| (8)-24 | H | Me | 5-(3-CF3—Ph) |
| (8)-25 | H | Me | 5-(4-Cl—Ph) |
| (8)-26 | H | Me | 5-(4-Br—Ph) |
| (8)-27 | H | Me | 5-(4-F—Ph) |
| (8)-28 | H | Me | 5-(4-OMe—Ph) |
| (8)-29 | H | Me | 5-(4-Me—Ph) |
| (8)-30 | H | Me | 5-(4-CF3—Ph) |
| (8)-31 | H | CF3 | 5-CF3 |
| (8)-32 | H | Et | — |
| (8)-33 | H | Et | 4-Me |
| (8)-34 | H | Et | 6-Me |
| (8)-35 | H | Et | 4-Me, 6-Me |
| (8)-36 | H | Et | 4-Me, 6-OMe |
| (8)-37 | H | Et | 4-Et |
| (8)-38 | H | Et | 6-Et |
| (8)-39 | H | Et | 4-Me, 6-Et |
| (8)-40 | H | Et | 4-Et, 6-Et |

TABLE 23

| No | R3 | Z1 | (Z2)m |
|---|---|---|---|
| (8)-41 | H | Et | 4-C≡CH, 6-Et |
| (8)-42 | H | Et | 4-c-Pr, 6-Et |
| (8)-43 | H | Et | 4-Ph, 6-Et |
| (8)-44 | H | Et | 4-Ph, 6-C≡CH |
| (8)-45 | H | Et | 4-Ph, 6-OMe |
| (8)-46 | H | Et | 4-(4-Me—Ph), 6-Et |
| (8)-47 | H | Et | 4-(4-Cl—Ph), 6-Et |
| (8)-48 | H | Et | 4-CN, 6-Et |
| (8)-49 | H | Et | 4-OMe, 6-Et |
| (8)-50 | H | Et | 4-NO2, 6-Et |
| (8)-51 | H | Et | 4-Cl, 6-Et |
| (8)-52 | H | Et | 4-Br, 6-Et |
| (8)-53 | H | Et | 4-F, 6-Et |
| (8)-54 | H | Et | 5-Ph |
| (8)-55 | H | Et | 5-(2-Cl—Ph) |
| (8)-56 | H | Et | 5-(2-Br—Ph) |
| (8)-57 | H | Et | 5-(2-F—Ph) |
| (8)-58 | H | Et | 5-(2-OMe—Ph) |
| (8)-59 | H | Et | 5-(2-Me—Ph) |
| (8)-60 | H | Et | 5-(2-CF3—Ph) |
| (8)-61 | H | Et | 5-(3-Cl—Ph) |
| (8)-62 | H | Et | 5-(3-Br—Ph) |
| (8)-63 | H | Et | 5-(3-F—Ph) |
| (8)-64 | H | Et | 5-(3-OMe—Ph) |
| (8)-65 | H | Et | 5-(3-Me—Ph) |
| (8)-66 | H | Et | 5-(3-CF3—Ph) |
| (8)-67 | H | Et | 5-(4-Cl—Ph) |
| (8)-68 | H | Et | 5-(4-Br—Ph) |
| (8)-69 | H | Et | 5-(4-F—Ph) |
| (8)-70 | H | Et | 5-(4-OMe—Ph) |
| (8)-71 | H | Et | 5-(4-Me—Ph) |
| (8)-72 | H | Et | 5-(4-CF3—Ph) |
| (8)-73 | H | n-Pr | — |
| (8)-74 | H | c-Pr | 4-Me, 6-Et |
| (8)-75 | H | C≡CH | 4-Me, 6-Me |
| (8)-76 | H | CN | 4-Me, 6-Me |
| (8)-77 | H | CN | 4-Me, 6-Et |
| (8)-78 | H | OMe | 4-Me, 6-Me |
| (8)-79 | H | OEt | 3-F, 6-F |
| (8)-80 | H | NO2 | — |

TABLE 24
| No | R3 | Z1 | (Z2)m |
|---|---|---|---|
| (8)-81 | H | F | 3-F |
| (8)-82 | H | F | 5-F |
| (8)-83 | H | F | 6-F |
| (8)-84 | H | F | 3-Me, 6-F |
| (8)-85 | H | F | 3-OMe, 6-F |
| (8)-86 | H | F | 3-OEt, 6-F |
| (8)-87 | H | F | 3-F, 5-Cl |
| (8)-88 | H | F | 3-F, 6-F |
| (8)-89 | H | Cl | — |
| (8)-90 | H | Cl | 6-Me |
| (8)-91 | H | Cl | 6-CF3 |
| (8)-92 | H | Cl | 5-Ph |
| (8)-93 | H | Cl | 3-Cl |
| (8)-94 | H | Cl | 4-Cl |
| (8)-95 | H | Cl | 6-Cl |
| (8)-96 | H | Cl | 4-Br |
| (8)-97 | H | Cl | 6-Br |
| (8)-98 | H | Cl | 4-F |
| (8)-99 | H | Cl | 6-F |
| (8)-100 | H | Cl | 4-Me, 6-F |
| (8)-101 | H | Cl | 4-Me, 6-Cl |
| (8)-102 | H | Cl | 4-Me, 6-Br |
| (8)-103 | H | Cl | 4-Me, 6-F |
| (8)-104 | H | Cl | 4-Me, 6-OCF3 |
| (8)-105 | H | Cl | 4-Me, 6-c-Pr |
| (8)-106 | H | Cl | 4-OCF3, 6-Cl |
| (8)-107 | H | Cl | 4-Cl, 6-Me |
| (8)-108 | H | Cl | 4-Cl, 6-Et |
| (8)-109 | H | Cl | 4-Cl, 6-c-Pr |
| (8)-110 | H | Cl | 4-Cl, 6-OCF3 |
| (8)-111 | H | Cl | 4-Cl, 6-Br |
| (8)-112 | H | Cl | 4-Br, 6-Br |
| (8)-113 | H | Cl | 4-Br, 6-OCF3 |
| (8)-114 | H | Cl | 4-F, 6-F |
| (8)-115 | H | Cl | 4-OMe, 6-Et |
| (8)-116 | H | Br | 4-Me, 6-Me |
| (8)-117 | H | Br | 4-Me, 6-Et |
| (8)-118 | H | Br | 4-Me, 6-Br |
| (8)-119 | H | Br | 4-Cl, 6-OCF3 |
| (8)-120 | H | Br | 4-Br, 6-OCF3 |
(1-101)
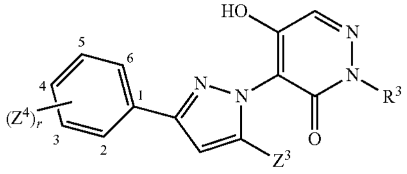
(1-102)
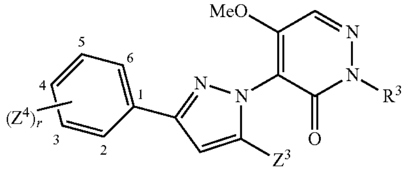
(1-103)
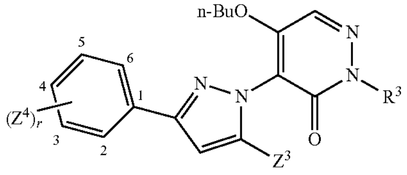
-continued
(1-104)
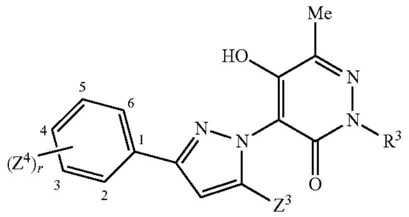
(1-105)
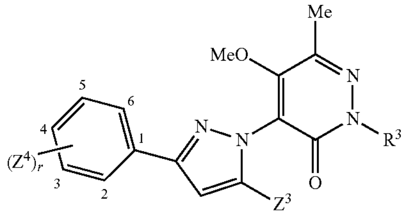
(1-106)
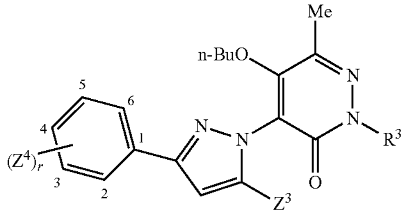
(1-107)
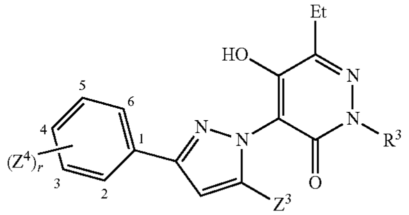
(1-108)
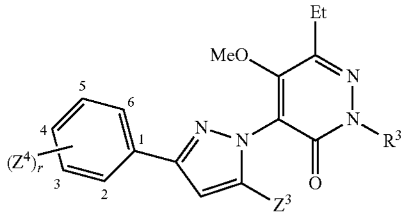
(1-109)
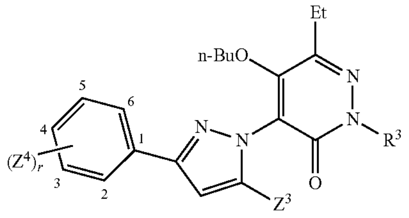
(1-110)
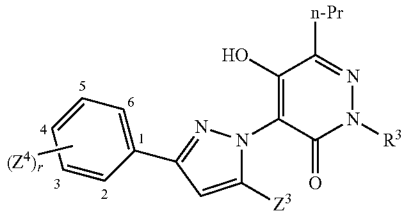

-continued
(1-111)
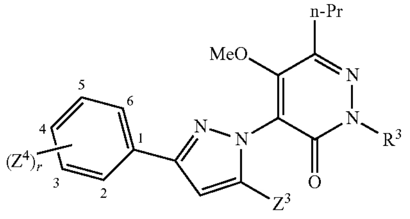
(1-112)
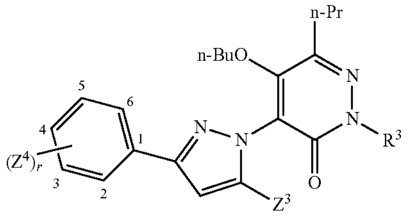
(1-113)
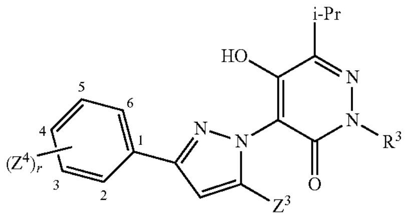
(1-114)
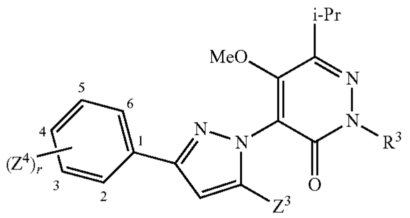
(1-115)
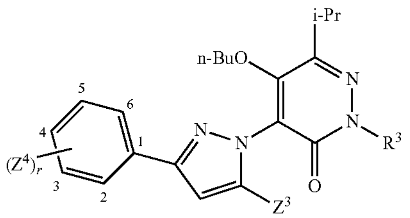
(2-101)
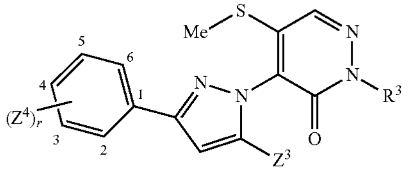
(2-102)
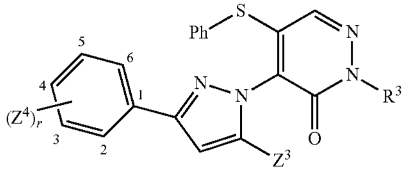
-continued
(2-103)
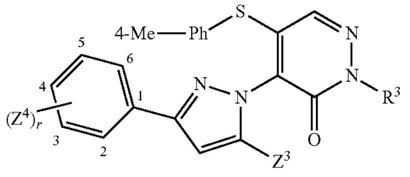
(2-104)
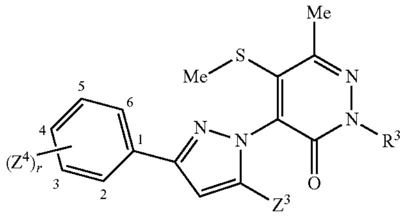
(2-105)
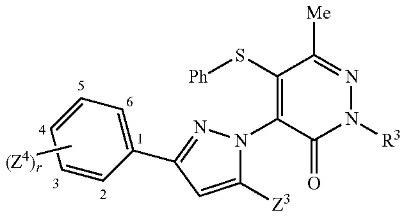
(2-106)
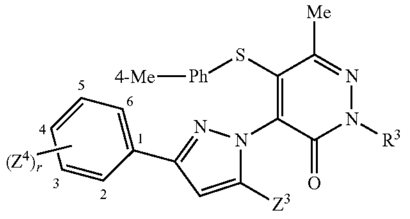
(2-107)
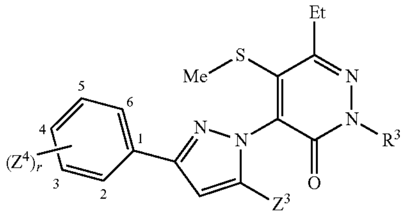
(2-108)
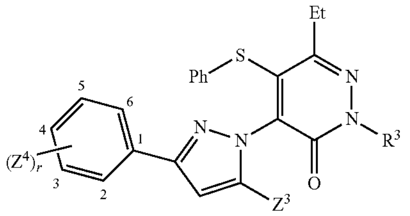
(2-109)
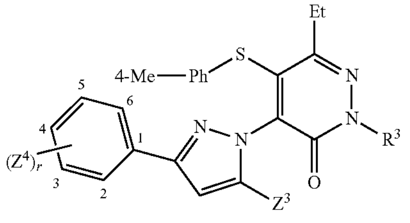

-continued
(2-110)
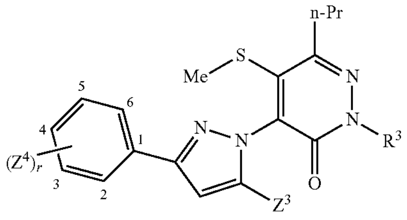
(2-111)
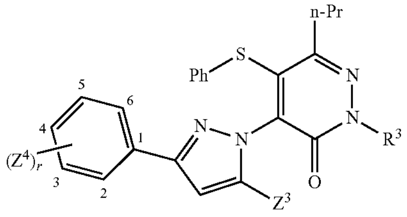
(2-112)
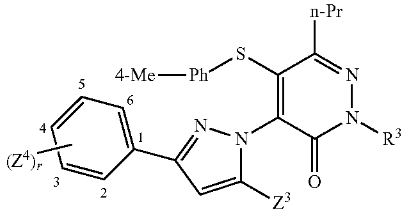
(2-113)
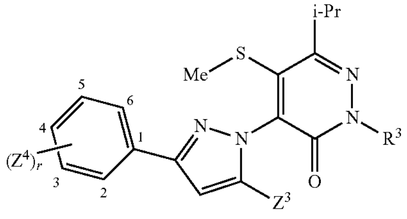
(2-114)
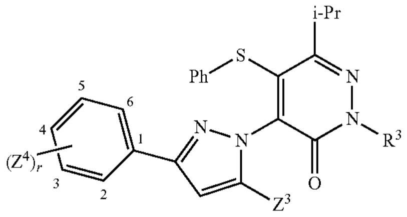
(2-115)
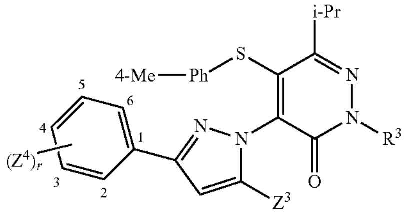
(2-116)
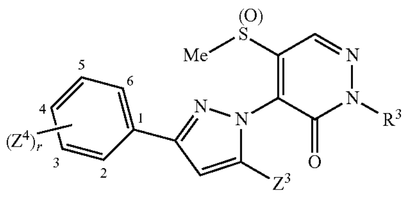
-continued
(2-117)
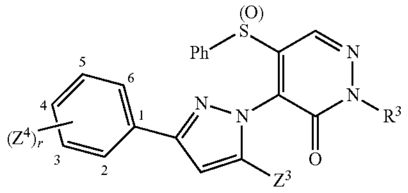
(2-118)
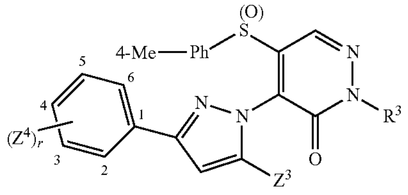
(2-119)
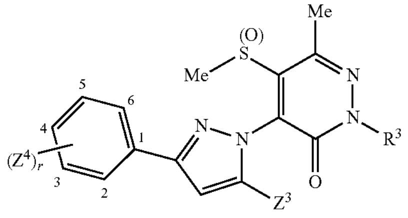
(2-120)
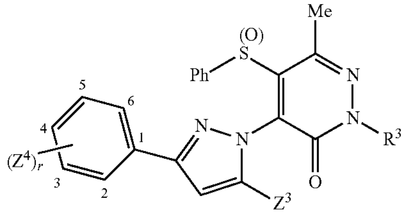
(2-121)
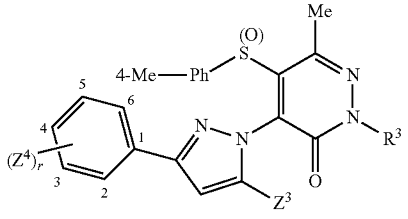
(2-123)
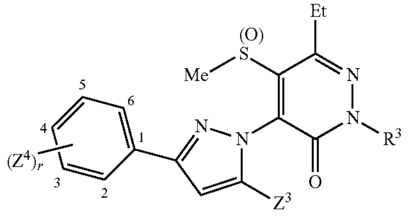
(2-124)
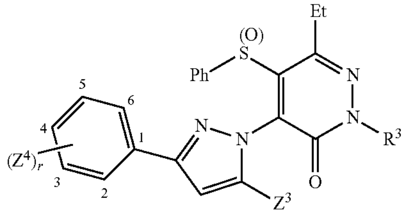

-continued
(2-125)
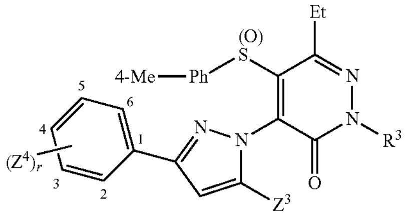
(2-126)
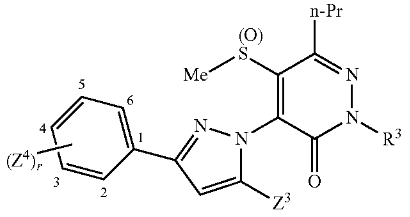
(2-127)
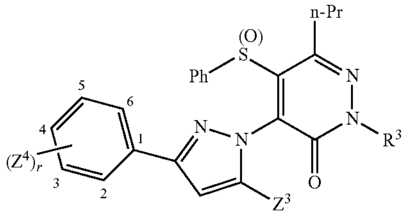
(2-128)
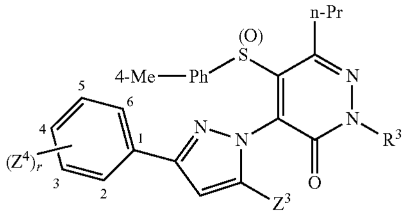
(2-129)
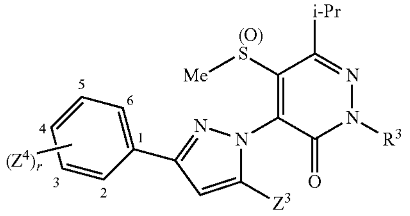
(2-130)
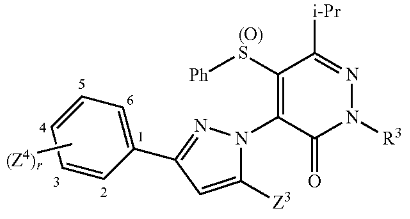
(2-131)
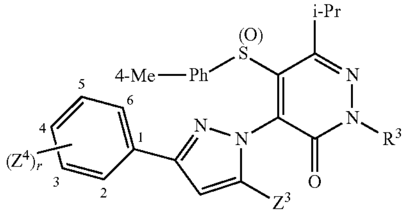
-continued
(2-132)
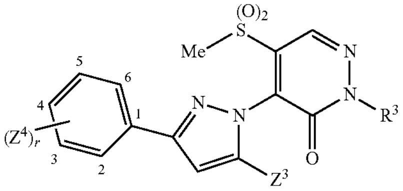
(2-133)
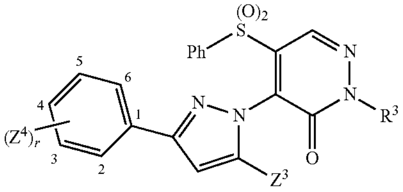
(2-134)
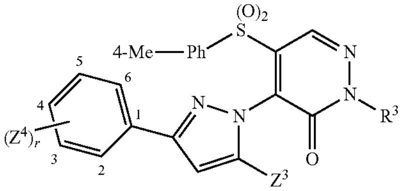
(2-135)
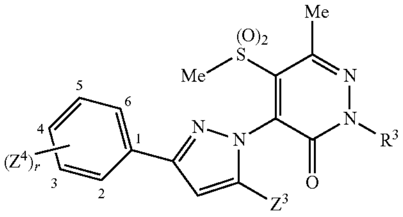
(2-136)
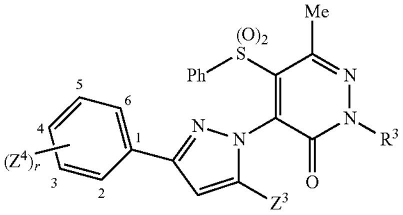
(2-137)
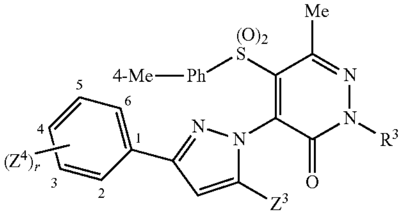
(2-138)
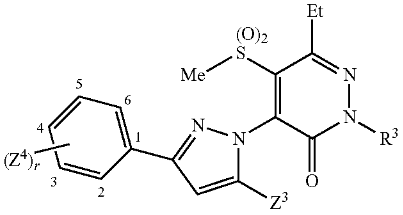

-continued
(2-139)
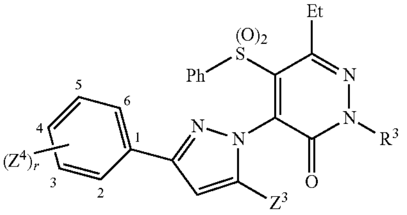
(2-140)
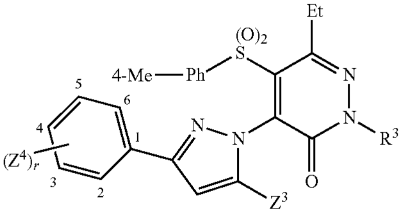
(2-141)
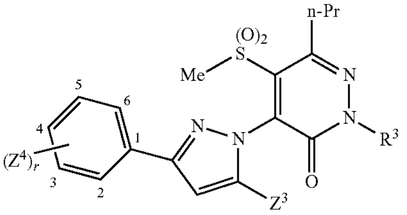
(2-142)
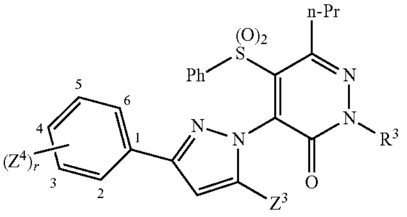
(2-143)
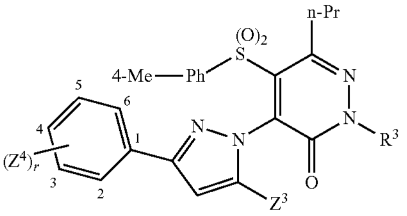
(2-144)
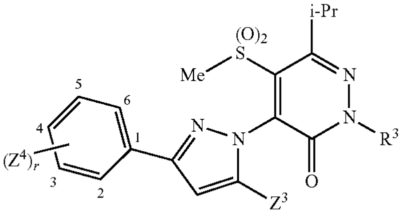
(2-145)
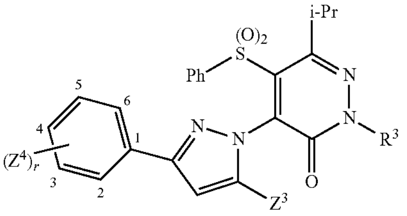
-continued
(2-146)
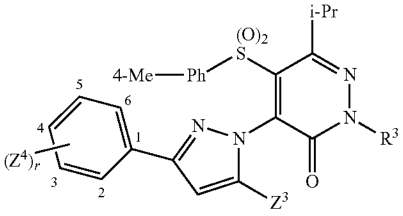
(4-101)
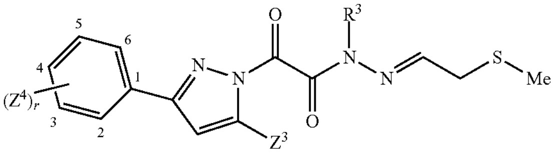
(4-102)
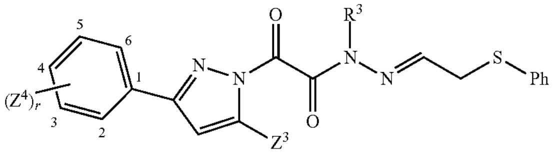
(4-103)
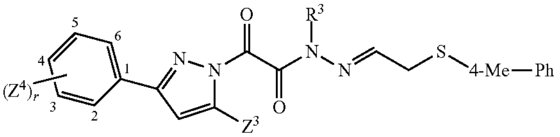
(4-104)
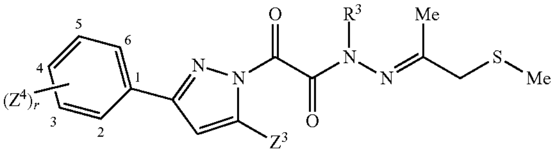
(4-105)
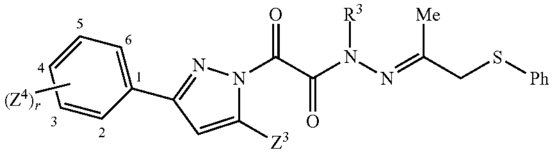
(4-106)
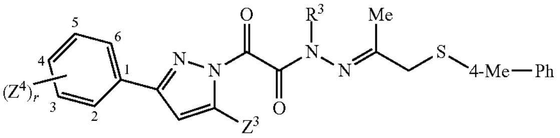
(4-107)
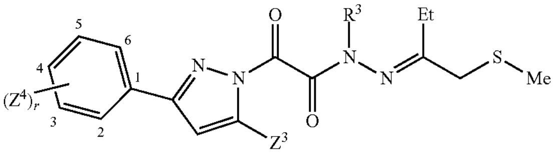

-continued
(4-108)
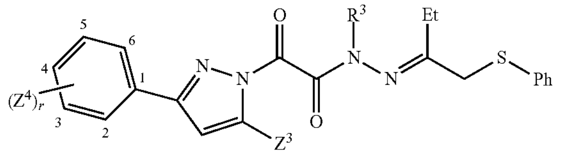
(4-109)
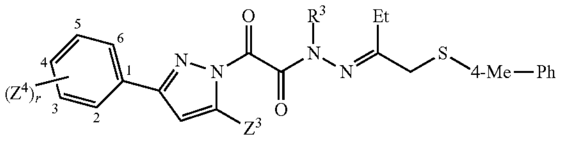
(4-110)
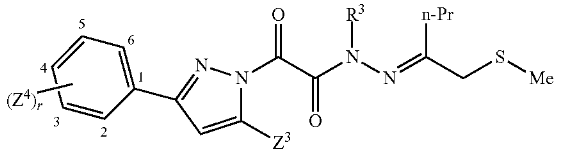
(4-111)
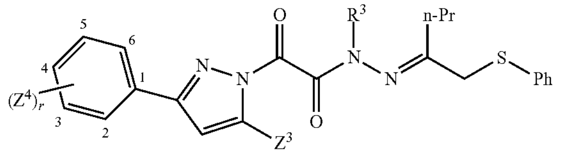
(4-112)
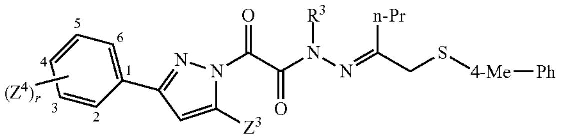
(4-113)
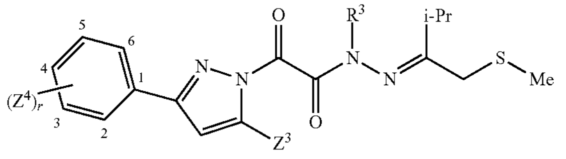
(4-114)
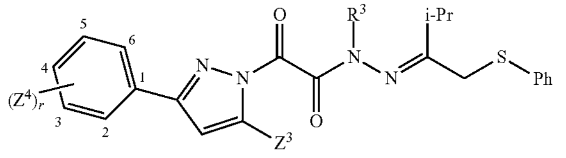
(4-115)
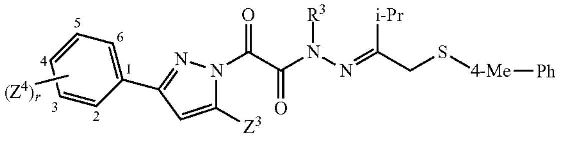
(4-116)
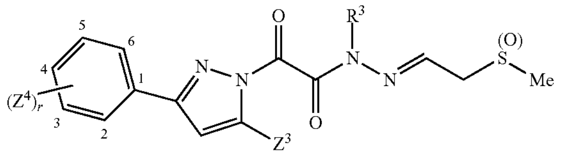
-continued
(4-117)
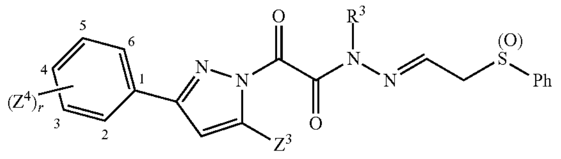
(4-118)
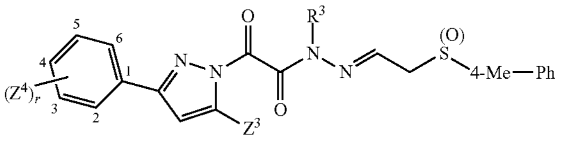
(4-119)
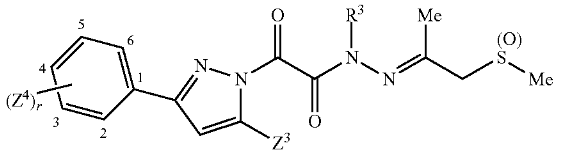
(4-120)
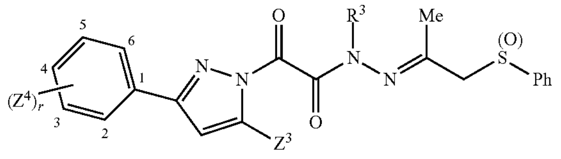
(4-121)
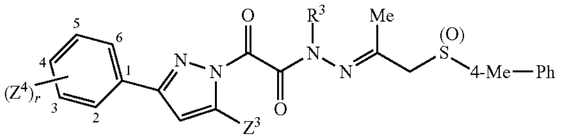
(4-122)
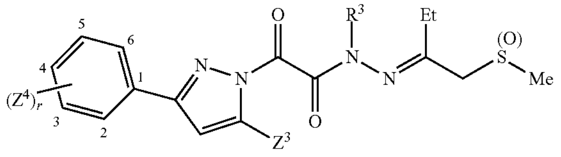
(4-123)
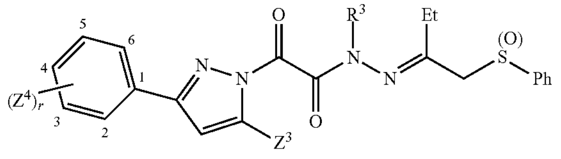
(4-124)
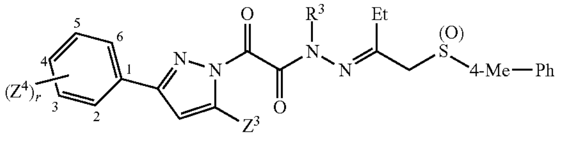
(4-125)
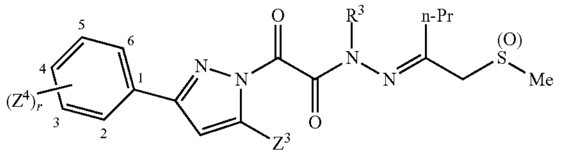

-continued
(4-126)
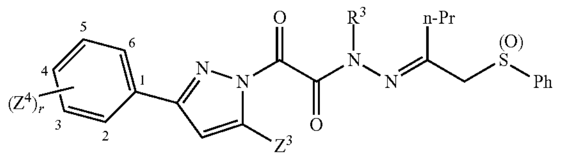
(4-127)
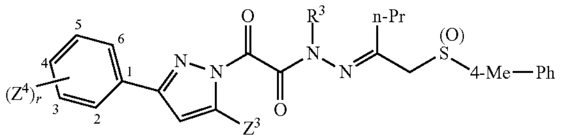
(4-128)
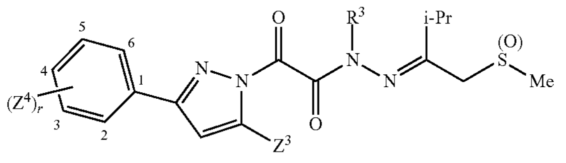
(4-129)
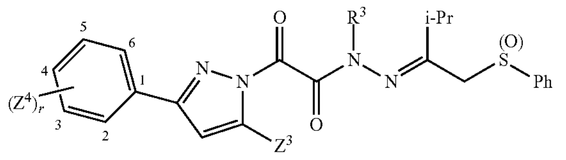
(4-130)
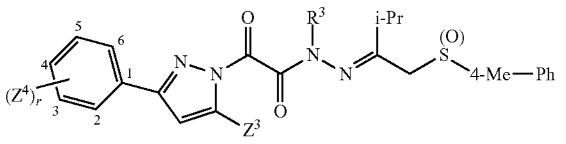
(4-131)
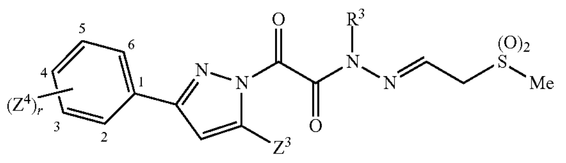
(4-132)
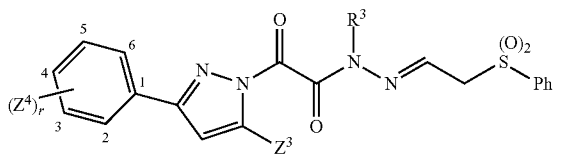
(4-133)
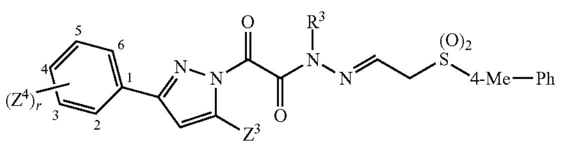
(4-134)
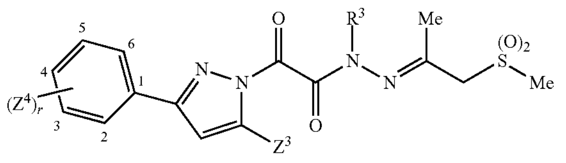
-continued
(4-135)
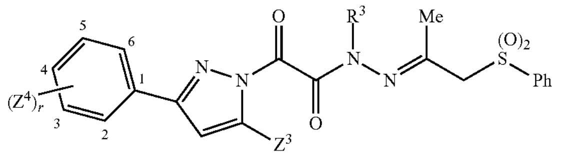
(4-136)
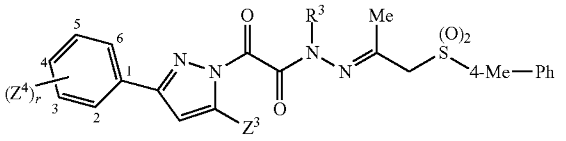
(4-137)
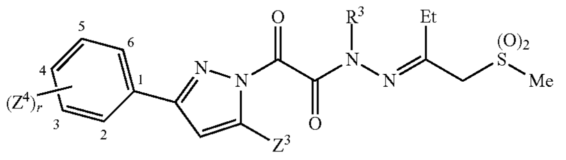
(4-138)
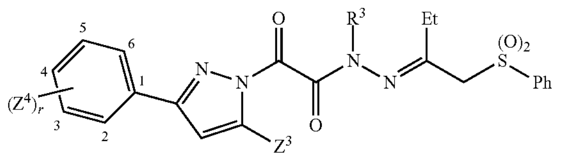
(4-139)
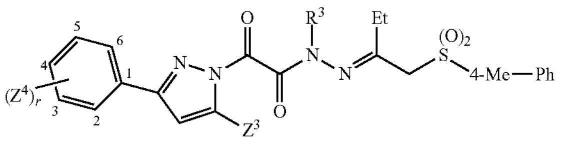
(4-140)
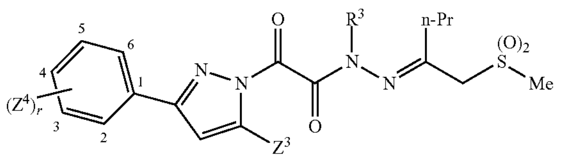
(4-141)
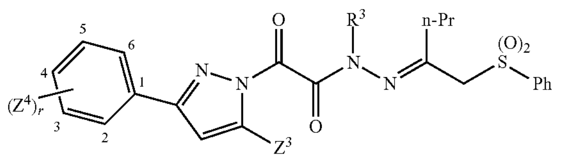
(4-142)
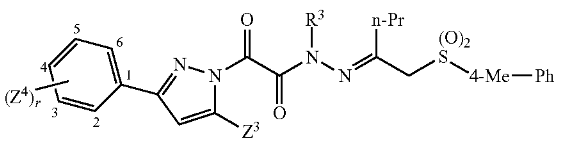
(4-143)
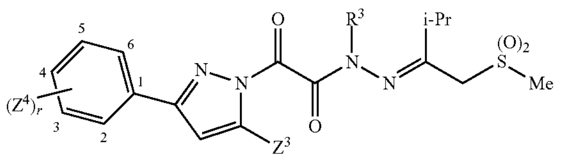

-continued (4-144)

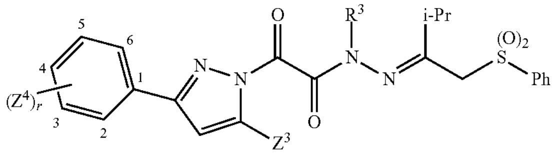

(4-145)

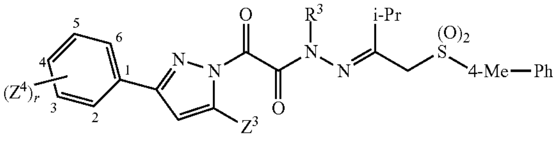

TABLE 25

| No. | R3 | $Z^3$ | $(Z^4)_r$ |
|---|---|---|---|
| (9)-1 | Me | Me | 4-CF3 |
| (9)-2 | Me | Me | 4-Cl |
| (9)-3 | Me | Me | 4-Br |
| (9)-4 | Me | Me | 4-F |
| (9)-5 | Me | Et | 4-CF3 |
| (9)-6 | Me | Et | 4-Cl |
| (9)-7 | Me | Et | 4-Br |
| (9)-8 | Me | Et | 4-F |
| (9)-9 | Et | Me | 4-CF3 |
| (9)-10 | Et | Me | 4-Cl |
| (9)-11 | Et | Me | 4-Br |
| (9)-12 | Et | Me | 4-F |
| (9)-13 | Et | Et | 4-CF3 |
| (9)-14 | Et | Et | 4-Cl |
| (9)-15 | Et | Et | 4-Br |
| (9)-16 | Et | Et | 4-F |
| (9)-17 | n-Pr | Me | 4-CF3 |
| (9)-18 | n-Pr | Me | 4-Cl |
| (9)-19 | n-Pr | Me | 4-Br |
| (9)-20 | n-Pr | Me | 4-F |
| (9)-21 | n-Pr | Et | 4-CF3 |
| (9)-22 | n-Pr | Et | 4-Cl |
| (9)-24 | n-Pr | Et | 4-Br |
| (9)-24 | n-Pr | Et | 4-F |
| (9)-25 | i-Pr | Me | 4-CF3 |
| (9)-26 | i-Pr | Me | 4-Cl |
| (9)-27 | i-Pr | Me | 4-Br |
| (9)-28 | i-Pr | Me | 4-F |
| (9)-29 | i-Pr | Et | 4-CF3 |
| (9)-30 | i-Pr | Et | 4-Cl |
| (9)-31 | i-Pr | Et | 4-Br |
| (9)-32 | i-Pr | Et | 4-F |
| (9)-33 | CH2CH2OMe | Me | 4-CF3 |
| (9)-34 | CH2CH2OMe | Me | 4-Cl |
| (9)-35 | CH2CH2OMe | Me | 4-Br |
| (9)-36 | CH2CH2OMe | Me | 4-F |
| (9)-37 | CH2CH2OMe | Et | 4-CF3 |
| (9)-38 | CH2CH2OMe | Et | 4-Cl |
| (9)-39 | CH2CH2OMe | Et | 4-Br |
| (9)-40 | CH2CH2OMe | Et | 4-F |

TABLE 26

| No. | R3 | $Z^3$ | $(Z^4)_r$ |
|---|---|---|---|
| (10)-1 | CH2CH2OEt | Me | 4-CF3 |
| (10)-2 | CH2CH2OEt | Me | 4-Cl |
| (10)-3 | CH2CH2OEt | Me | 4-Br |
| (10)-4 | CH2CH2OEt | Me | 4-F |
| (10)-5 | CH2CH2OEt | Et | 4-CF3 |
| (10)-6 | CH2CH2OEt | Et | 4-Cl |
| (10)-7 | CH2CH2OEt | Et | 4-Br |
| (10)-8 | CH2CH2OEt | Et | 4-F |
| (10)-9 | CH2Ph | Me | 4-CF3 |

TABLE 26-continued

| No. | R3 | $Z^3$ | $(Z^4)_r$ |
|---|---|---|---|
| (10)-10 | CH2Ph | Me | 4-Cl |
| (10)-11 | CH2Ph | Me | 4-Br |
| (10)-12 | CH2Ph | Me | 4-F |
| (10)-13 | CH2Ph | Et | 4-CF3 |
| (10)-14 | CH2Ph | Et | 4-Cl |
| (10)-15 | CH2Ph | Et | 4-Br |
| (10)-16 | CH2Ph | Et | 4-F |

(12-1)

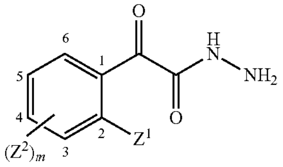

(12-2)

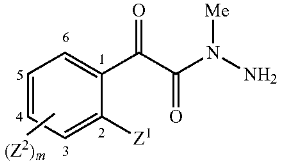

(12-3)

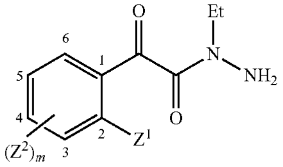

(12-4)

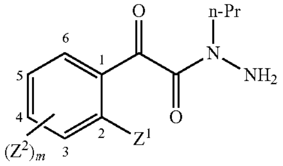

(12-5)

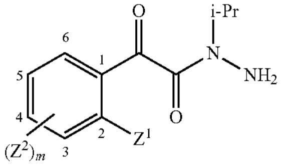

(12-6)

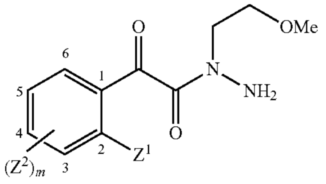

(12-7)

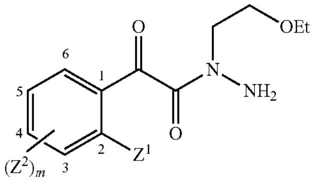

-continued (12-8)

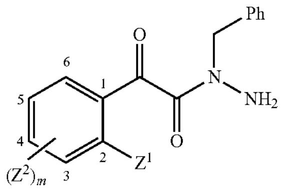

TABLE 27

| No | Z1 | (Z2)m |
|---|---|---|
| (11)-1 | Me | 4-Me |
| (11)-2 | Me | 6-Me |
| (11)-3 | Me | 4-Me, 6-Me |
| (11)-4 | Me | 4-Me, 6-Cl |
| (11)-5 | Me | 4-Cl |
| (11)-6 | Me | 4-Cl, 6-Me |
| (11)-7 | Me | 4-Cl, 6-Br |
| (11)-8 | Me | 3-Br, 6-Me |
| (11)-9 | Me | 4-Br, 6-Br |
| (11)-10 | Me | 4-F, 6-F |
| (11)-11 | Me | 3-(4-Cl—Ph) |
| (11)-12 | Me | 5-Ph |
| (11)-13 | Me | 5-(2-Cl—Ph) |
| (11)-14 | Me | 5-(2-Br—Ph) |
| (11)-15 | Me | 5-(2-F—Ph) |
| (11)-16 | Me | 5-(2-OMe—Ph) |
| (11)-17 | Me | 5-(2-Me—Ph) |
| (11)-18 | Me | 5-(2-CF3—Ph) |
| (11)-19 | Me | 5-(3-Cl—Ph) |
| (11)-20 | Me | 5-(3-Br—Ph) |
| (11)-21 | Me | 5-(3-F—Ph) |
| (11)-22 | Me | 5-(3-OMe—Ph) |
| (11)-23 | Me | 5-(3-Me—Ph) |
| (11)-24 | Me | 5-(3-CF3—Ph) |
| (11)-25 | Me | 5-(4-Cl—Ph) |
| (11)-26 | Me | 5-(4-Br—Ph) |
| (11)-27 | Me | 5-(4-F—Ph) |
| (11)-28 | Me | 5-(4-OMe—Ph) |
| (11)-29 | Me | 5-(4-Me—Ph) |
| (11)-30 | Me | 5-(4-CF3—Ph) |
| (11)-31 | CF3 | 5-CF3 |
| (11)-32 | Et | — |
| (11)-33 | Et | 4-Me |
| (11)-34 | Et | 6-Me |
| (11)-35 | Et | 4-Me, 6-Me |
| (11)-36 | Et | 4-Me, 6-OMe |
| (11)-37 | Et | 4-Et |
| (11)-38 | Et | 6-Et |
| (11)-39 | Et | 4-Me, 6-Et |
| (11)-40 | Et | 4-Et, 6-Et |

TABLE 28

| No | Z1 | (Z2)m |
|---|---|---|
| (11)-41 | Et | 4-C≡CH, 6-Et |
| (11)-42 | Et | 4-c-Pr, 6-Et |
| (11)-43 | Et | 4-Ph, 6-Et |
| (11)-44 | Et | 4-Ph, 6-C≡CH |
| (11)-45 | Et | 4-Ph, 6-OMe |
| (11)-46 | Et | 4-(4-Me—Ph), 6-Et |
| (11)-47 | Et | 4-(4-Cl—Ph), 6-Et |
| (11)-48 | Et | 4-CN, 6-Et |
| (11)-49 | Et | 4-OMe, 6-Et |
| (11)-50 | Et | 4-NO2, 6-Et |
| (11)-51 | Et | 4-Cl, 6-Et |
| (11)-52 | Et | 4-Br, 6-Et |
| (11)-53 | Et | 4-F, 6-Et |
| (11)-54 | Et | 5-Ph |
| (11)-55 | Et | 5-(2-Cl—Ph) |
| (11)-56 | Et | 5-(2-Br—Ph) |

TABLE 28-continued

| No | Z1 | (Z2)m |
|---|---|---|
| (11)-57 | Et | 5-(2-F—Ph) |
| (11)-58 | Et | 5-(2-OMe—Ph) |
| (11)-59 | Et | 5-(2-Me—Ph) |
| (11)-60 | Et | 5-(2-CF3—Ph) |
| (11)-61 | Et | 5-(3-Cl—Ph) |
| (11)-62 | Et | 5-(3-Br—Ph) |
| (11)-63 | Et | 5-(3-F—Ph) |
| (11)-64 | Et | 5-(3-OMe—Ph) |
| (11)-65 | Et | 5-(3-Me—Ph) |
| (11)-66 | Et | 5-(3-CF3—Ph) |
| (11)-67 | Et | 5-(4-Cl—Ph) |
| (11)-68 | Et | 5-(4-Br—Ph) |
| (11)-69 | Et | 5-(4-F—Ph) |
| (11)-70 | Et | 5-(4-OMe—Ph) |
| (11)-71 | Et | 5-(4-Me—Ph) |
| (11)-72 | Et | 5-(4-CF3—Ph) |
| (11)-73 | n-Pr | — |
| (11)-74 | c-Pr | 4-Me, 6-Et |
| (11)-75 | C≡CH | 4-Me, 6-Me |
| (11)-76 | CN | 4-Me, 6-Me |
| (11)-77 | CN | 4-Me, 6-Et |
| (11)-78 | OMe | 4-Me, 6-Me |
| (11)-79 | OEt | 3-F, 6-F |
| (11)-80 | NO2 | — |

TABLE 29

| No | Z1 | (Z2)m |
|---|---|---|
| (11)-81 | F | 3-F |
| (11)-82 | F | 5-F |
| (11)-83 | F | 6-F |
| (11)-84 | F | 3-Me, 6-F |
| (11)-85 | F | 3-OMe, 6-F |
| (11)-86 | F | 3-OEt, 6-F |
| (11)-87 | F | 3-F, 5-Cl |
| (11)-88 | F | 3-F, 6-F |
| (11)-89 | Cl | — |
| (11)-90 | Cl | 6-Me |
| (11)-91 | Cl | 6-CF3 |
| (11)-92 | Cl | 5-Ph |
| (11)-93 | Cl | 3-Cl |
| (11)-94 | Cl | 4-Cl |
| (11)-95 | Cl | 6-Cl |
| (11)-96 | Cl | 4-Br |
| (11)-97 | Cl | 6-Br |
| (11)-98 | Cl | 4-F |
| (11)-99 | Cl | 6-F |
| (11)-100 | Cl | 4-Me, 6-F |
| (11)-101 | Cl | 4-Me, 6-Cl |
| (11)-102 | Cl | 4-Me, 6-Br |
| (11)-103 | Cl | 4-Me, 6-F |
| (11)-104 | Cl | 4-Me, 6-OCF3 |
| (11)-105 | Cl | 4-Me, 6-c-Pr |
| (11)-106 | Cl | 4-OCF3, 6-Cl |
| (11)-107 | Cl | 4-Cl, 6-Me |
| (11)-108 | Cl | 4-Cl, 6-Et |
| (11)-109 | Cl | 4-Cl, 6-c-Pr |
| (11)-110 | Cl | 4-Cl, 6-OCF3 |
| (11)-111 | Cl | 4-Cl, 6-Br |
| (11)-112 | Cl | 4-Br, 6-Br |
| (11)-113 | Cl | 4-Br, 6-OCF3 |
| (11)-114 | Cl | 4-F, 6-F |
| (11)-115 | Cl | 4-OMe, 6-Et |
| (11)-116 | Br | 4-Me, 6-Me |
| (11)-117 | Br | 4-Me, 6-Et |
| (11)-118 | Br | 4-Me, 6-Br |
| (11)-119 | Br | 4-Cl, 6-OCF3 |
| (11)-120 | Br | 4-Br, 6-OCF3 |

(1-201)

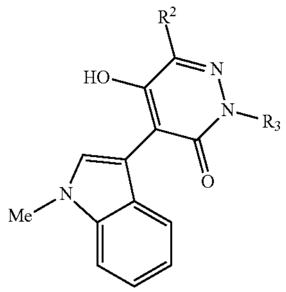

(1-301)

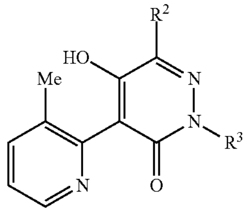

TABLE 30

| No | R2 | R3 |
|---|---|---|
| (12)-1 | H | H |
| (12)-2 | H | Me |
| (12)-3 | H | Et |
| (12)-4 | H | n-Pr |
| (12)-5 | H | i-Pr |
| (12)-6 | H | CH2CH2OMe |
| (12)-7 | H | CH2CH2OEt |
| (12)-8 | H | CH2Ph |
| (12)-9 | Me | H |
| (12)-10 | Me | Me |
| (12)-11 | Me | Et |
| (12)-12 | Me | n-Pr |
| (12)-13 | Me | i-Pr |
| (12)-14 | Me | CH2CH2OMe |
| (12)-15 | Me | CH2CH2OEt |
| (12)-16 | Me | CH2Ph |
| (12)-17 | Et | H |
| (12)-18 | Et | Me |
| (12)-19 | Et | Et |
| (12)-20 | Et | n-Pr |
| (12)-21 | Et | i-Pr |
| (12)-22 | Et | CH2CH2OMe |
| (12)-23 | Et | CH2CH2OEt |
| (12)-24 | Et | CH2Ph |
| (12)-25 | n-Pr | H |
| (12)-26 | n-Pr | Me |
| (12)-27 | n-Pr | Et |
| (12)-28 | n-Pr | n-Pr |
| (12)-29 | n-Pr | i-Pr |
| (12)-30 | n-Pr | CH2CH2OMe |
| (12)-31 | n-Pr | CH2CH2OEt |
| (12)-32 | n-Pr | CH2Ph |

TABLE 31

| No | R2 | R3 |
|---|---|---|
| (12)-33 | i-Pr | H |
| (12)-34 | i-Pr | Me |
| (12)-35 | i-Pr | Et |
| (12)-36 | i-Pr | n-Pr |
| (12)-37 | i-Pr | i-Pr |
| (12)-38 | i-Pr | CH2CH2OMe |
| (12)-39 | i-Pr | CH2CH2OEt |
| (12)-40 | i-Pr | CH2Ph |
| (12)-41 | Ph | H |

TABLE 31-continued

| No | R2 | R3 |
|---|---|---|
| (12)-42 | Ph | Me |
| (12)-43 | Ph | Et |
| (12)-44 | Ph | n-Pr |
| (12)-45 | Ph | i-Pr |
| (12)-46 | Ph | CH2CH2OMe |
| (12)-47 | Ph | CH2CH2OEt |
| (12)-48 | Ph | CH2Ph |
| (12)-49 | 4-F—Ph | H |
| (12)-50 | 4-F—Ph | Me |
| (12)-51 | 4-F—Ph | Et |
| (12)-52 | 4-F—Ph | n-Pr |
| (12)-53 | 4-F—Ph | i-Pr |
| (12)-54 | 4-F—Ph | CH2CH2OMe |
| (12)-55 | 4-F—Ph | CH2CH2OEt |
| (12)-56 | 4-F—Ph | CH2Ph |
| (12)-57 | 3-CF3—Ph | H |
| (12)-58 | 3-CF3—Ph | Me |
| (12)-59 | 3-CF3—Ph | Et |
| (12)-60 | 3-CF3—Ph | n-Pr |
| (12)-61 | 3-CF3—Ph | i-Pr |
| (12)-62 | 3-CF3—Ph | CH2CH2OMe |
| (12)-63 | 3-CF3—Ph | CH2CH2OEt |
| (12)-64 | 3-CF3—Ph | CH2Ph |
| (12)-65 | 2-Me—Ph | H |
| (12)-66 | 2-Me—Ph | Me |
| (12)-67 | 2-Me—Ph | Et |
| (12)-68 | 2-Me—Ph | n-Pr |
| (12)-69 | 2-Me—Ph | i-Pr |
| (12)-70 | 2-Me—Ph | CH2CH2OMe |
| (12)-71 | 2-Me—Ph | CH2CH2OEt |
| (12)-72 | 2-Me—Ph | CH2Ph |

(2-201)

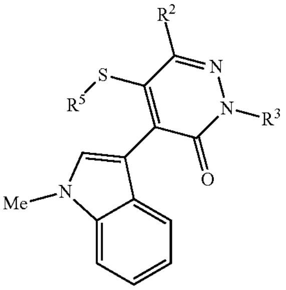

(2-202)

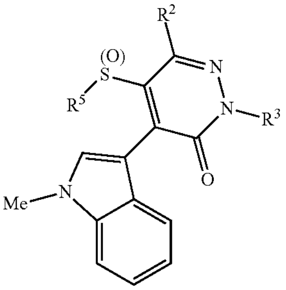

(4-201)

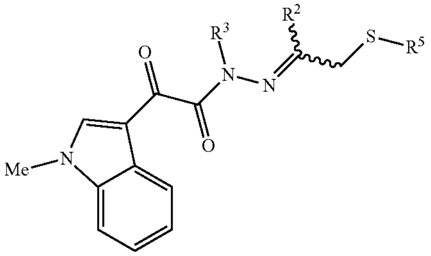

-continued (2-203)

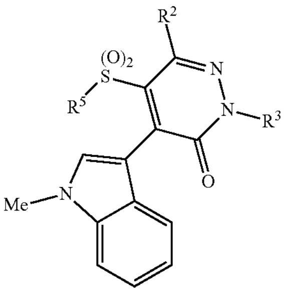

(4-202)

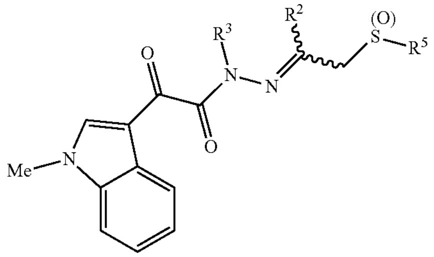

(4-203)

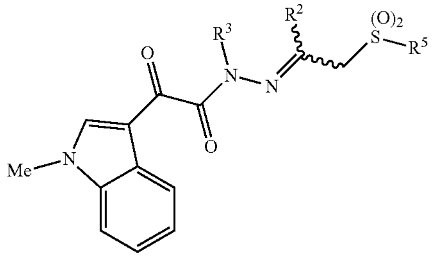

(2-301)

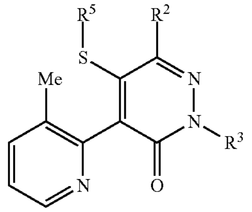

(2-302)

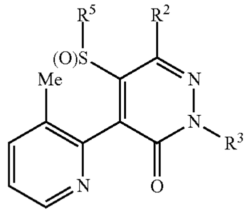

(4-301)

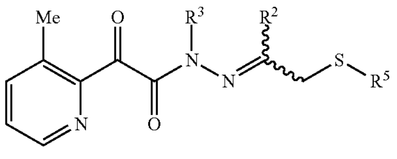

-continued (2-303)

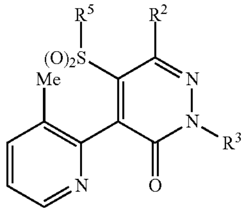

(4-302)

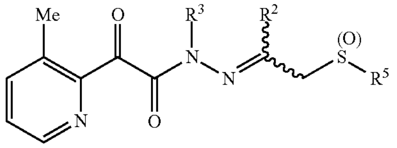

(4-303)

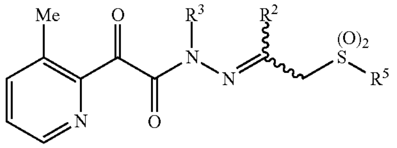

TABLE 32

| No. | R2 | R3 | R5 |
|---|---|---|---|
| (13)-1 | H | H | Me |
| (13)-2 | H | H | Ph |
| (13)-3 | H | H | 4-Me—Ph |
| (13)-4 | H | Me | Me |
| (13)-5 | H | Me | Ph |
| (13)-6 | H | Me | 4-Me—Ph |
| (13)-7 | H | Et | Me |
| (13)-8 | H | Et | Ph |
| (13)-9 | H | Et | 4-Me—Ph |
| (13)-10 | H | n-Pr | Me |
| (13)-11 | H | n-Pr | Ph |
| (13)-12 | H | n-Pr | 4-Me—Ph |
| (13)-13 | H | i-Pr | Me |
| (13)-14 | H | i-Pr | Ph |
| (13)-15 | H | i-Pr | 4-Me—Ph |
| (13)-16 | H | CH2CH2OMe | Me |
| (13)-17 | H | CH2CH2OMe | Ph |
| (13)-18 | H | CH2CH2OMe | 4-Me—Ph |
| (13)-19 | H | CH2CH2OEt | Me |
| (13)-20 | H | CH2CH2OEt | Ph |
| (13)-21 | H | CH2CH2OEt | 4-Me—Ph |
| (13)-22 | H | CH2Ph | Me |
| (13)-24 | H | CH2Ph | Ph |
| (13)-24 | H | CH2Ph | 4-Me—Ph |
| (13)-25 | Me | H | Me |
| (13)-26 | Me | H | Ph |
| (13)-27 | Me | H | 4-Me—Ph |
| (13)-28 | Me | Me | Me |
| (13)-29 | Me | Me | Ph |
| (13)-30 | Me | Me | 4-Me—Ph |
| (13)-31 | Me | Et | Me |
| (13)-32 | Me | Et | Ph |
| (13)-33 | Me | Et | 4-Me—Ph |
| (13)-34 | Me | n-Pr | Me |
| (13)-35 | Me | n-Pr | Ph |
| (13)-36 | Me | n-Pr | 4-Me—Ph |

TABLE 33

| No. | R2 | R3 | R5 |
|---|---|---|---|
| (13)-37 | Me | i-Pr | Me |
| (13)-38 | Me | i-Pr | Ph |
| (13)-39 | Me | i-Pr | 4-Me—Ph |
| (13)-40 | Me | CH2CH2OMe | Me |

TABLE 33-continued

| No. | R2 | R3 | R5 |
|---|---|---|---|
| (13)-41 | Me | CH2CH2OMe | Ph |
| (13)-42 | Me | CH2CH2OMe | 4-Me—Ph |
| (13)-43 | Me | CH2CH2OEt | Me |
| (13)-44 | Me | CH2CH2OEt | Ph |
| (13)-45 | Me | CH2CH2OEt | 4-Me—Ph |
| (13)-46 | Me | CH2Ph | Me |
| (13)-47 | Me | CH2Ph | Ph |
| (13)-48 | Me | CH2Ph | 4-Me—Ph |
| (13)-49 | Et | H | Me |
| (13)-50 | Et | H | Ph |
| (13)-51 | Et | H | 4-Me—Ph |
| (13)-52 | Et | Me | Me |
| (13)-53 | Et | Me | Ph |
| (13)-54 | Et | Me | 4-Me—Ph |
| (13)-55 | Et | Et | Me |
| (13)-56 | Et | Et | Ph |
| (13)-57 | Et | Et | 4-Me—Ph |
| (13)-58 | Et | n-Pr | Me |
| (13)-59 | Et | n-Pr | Ph |
| (13)-60 | Et | n-Pr | 4-Me—Ph |
| (13)-61 | Et | i-Pr | Me |
| (13)-62 | Et | i-Pr | Ph |
| (13)-63 | Et | i-Pr | 4-Me—Ph |
| (13)-64 | Et | CH2CH2OMe | Me |
| (13)-65 | Et | CH2CH2OMe | Ph |
| (13)-66 | Et | CH2CH2OMe | 4-Me—Ph |
| (13)-67 | Et | CH2CH2OEt | Me |
| (13)-68 | Et | CH2CH2OEt | Ph |
| (13)-69 | Et | CH2CH2OEt | 4-Me—Ph |
| (13)-70 | n-Pr | H | Me |
| (13)-71 | n-Pr | H | Ph |
| (13)-72 | n-Pr | H | 4-Me—Ph |
| (13)-73 | n-Pr | Me | Me |
| (13)-74 | n-Pr | Me | Ph |
| (13)-75 | n-Pr | Me | 4-Me—Ph |
| (13)-76 | n-Pr | Et | Me |
| (13)-77 | n-Pr | Et | Ph |
| (13)-78 | n-Pr | Et | 4-Me—Ph |

TABLE 34

| No. | R2 | R3 | R5 |
|---|---|---|---|
| (13)-79 | n-Pr | n-Pr | Me |
| (13)-80 | n-Pr | n-Pr | Ph |
| (13)-81 | n-Pr | n-Pr | 4-Me—Ph |
| (13)-82 | n-Pr | i-Pr | Me |
| (13)-83 | n-Pr | i-Pr | Ph |
| (13)-84 | n-Pr | i-Pr | 4-Me—Ph |
| (13)-85 | n-Pr | CH2CH2OMe | Me |
| (13)-86 | n-Pr | CH2CH2OMe | Ph |
| (13)-87 | n-Pr | CH2CH2OMe | 4-Me—Ph |
| (13)-88 | n-Pr | CH2CH2OEt | Me |
| (13)-89 | n-Pr | CH2CH2OEt | Ph |
| (13)-90 | n-Pr | CH2CH2OEt | 4-Me—Ph |
| (13)-91 | n-Pr | CH2Ph | Me |
| (13)-92 | n-Pr | CH2Ph | Ph |
| (13)-93 | n-Pr | CH2Ph | 4-Me—Ph |
| (13)-94 | i-Pr | H | Me |
| (13)-95 | i-Pr | H | Ph |
| (13)-96 | i-Pr | H | 4-Me—Ph |
| (13)-97 | i-Pr | Me | Me |
| (13)-98 | i-Pr | Me | Ph |
| (13)-99 | i-Pr | Me | 4-Me—Ph |
| (13)-100 | i-Pr | Et | Me |
| (13)-101 | i-Pr | Et | Ph |
| (13)-102 | i-Pr | Et | 4-Me—Ph |
| (13)-103 | i-Pr | n-Pr | Me |
| (13)-104 | i-Pr | n-Pr | Ph |
| (13)-105 | i-Pr | n-Pr | 4-Me—Ph |
| (13)-106 | i-Pr | i-Pr | Me |
| (13)-107 | i-Pr | i-Pr | Ph |
| (13)-108 | i-Pr | i-Pr | 4-Me—Ph |
| (13)-109 | i-Pr | CH2CH2OMe | Me |
| (13)-110 | i-Pr | CH2CH2OMe | Ph |

TABLE 34-continued

| No. | R2 | R3 | R5 |
|---|---|---|---|
| (13)-111 | i-Pr | CH2CH2OMe | 4-Me—Ph |
| (13)-112 | i-Pr | CH2CH2OEt | Me |
| (13)-113 | i-Pr | CH2CH2OEt | Ph |
| (13)-114 | i-Pr | CH2CH2OEt | 4-Me—Ph |
| (13)-115 | i-Pr | CH2Ph | Me |
| (13)-116 | i-Pr | CH2Ph | Ph |
| (13)-117 | i-Pr | CH2Ph | 4-Me—Ph |
| (13)-118 | Ph | H | Me |
| (13)-119 | Ph | H | Ph |
| (13)-120 | Ph | H | 4-Me—Ph |

TABLE 35

| No. | R2 | R3 | R5 |
|---|---|---|---|
| (13)-121 | Ph | Me | Me |
| (13)-122 | Ph | Me | Ph |
| (13)-123 | Ph | Me | 4-Me—Ph |
| (13)-124 | Ph | Et | Me |
| (13)-125 | Ph | Et | Ph |
| (13)-126 | Ph | Et | 4-Me—Ph |
| (13)-127 | Ph | n-Pr | Me |
| (13)-128 | Ph | n-Pr | Ph |
| (13)-129 | Ph | n-Pr | 4-Me—Ph |
| (13)-130 | Ph | i-Pr | Me |
| (13)-131 | Ph | i-Pr | Ph |
| (13)-132 | Ph | i-Pr | 4-Me—Ph |
| (13)-133 | Ph | CH2CH2OMe | Me |
| (13)-134 | Ph | CH2CH2OMe | Ph |
| (13)-135 | Ph | CH2CH2OMe | 4-Me—Ph |
| (13)-136 | Ph | CH2CH2OEt | Me |
| (13)-137 | Ph | CH2CH2OEt | Ph |
| (13)-138 | Ph | CH2CH2OEt | 4-Me—Ph |
| (13)-139 | Ph | CH2Ph | Me |
| (13)-140 | Ph | CH2Ph | Ph |
| (13)-141 | Ph | CH2Ph | 4-Me—Ph |
| (13)-142 | 4-F—Ph | H | Me |
| (13)-143 | 4-F—Ph | H | Ph |
| (13)-144 | 4-F—Ph | H | 4-Me—Ph |
| (13)-145 | 4-F—Ph | Me | Me |
| (13)-146 | 4-F—Ph | Me | Ph |
| (13)-147 | 4-F—Ph | Me | 4-Me—Ph |
| (13)-148 | 4-F—Ph | Et | Me |
| (13)-149 | 4-F—Ph | Et | Ph |
| (13)-150 | 4-F—Ph | Et | 4-Me—Ph |
| (13)-151 | 4-F—Ph | n-Pr | Me |
| (13)-152 | 4-F—Ph | n-Pr | Ph |
| (13)-153 | 4-F—Ph | n-Pr | 4-Me—Ph |
| (13)-154 | 4-F—Ph | i-Pr | Me |
| (13)-155 | 4-F—Ph | i-Pr | Ph |
| (13)-156 | 4-F—Ph | i-Pr | 4-Me—Ph |
| (13)-157 | 4-F—Ph | CH2CH2OMe | Me |
| (13)-158 | 4-F—Ph | CH2CH2OMe | Ph |
| (13)-159 | 4-F—Ph | CH2CH2OMe | 4-Me—Ph |
| (13)-160 | 4-F—Ph | CH2CH2OEt | Me |
| (13)-161 | 4-F—Ph | CH2CH2OEt | Ph |
| (13)-162 | 4-F—Ph | CH2CH2OEt | 4-Me—Ph |

TABLE 36

| No. | R2 | R3 | R5 |
|---|---|---|---|
| (13)-163 | 4-F—Ph | CH2Ph | Me |
| (13)-164 | 4-F—Ph | CH2Ph | Ph |
| (13)-165 | 4-F—Ph | CH2Ph | 4-Me—Ph |
| (13)-166 | 3-CF3—Ph | H | Me |
| (13)-167 | 3-CF3—Ph | H | Ph |
| (13)-168 | 3-CF3—Ph | H | 4-Me—Ph |
| (13)-169 | 3-CF3—Ph | Me | Me |
| (13)-170 | 3-CF3—Ph | Me | Ph |
| (13)-171 | 3-CF3—Ph | Me | 4-Me—Ph |
| (13)-172 | 3-CF3—Ph | Et | Me |
| (13)-173 | 3-CF3—Ph | Et | Ph |

TABLE 36-continued

| No. | R2 | R3 | R5 |
|---|---|---|---|
| (13)-174 | 3-CF3—Ph | Et | 4-Me—Ph |
| (13)-175 | 3-CF3—Ph | n-Pr | Me |
| (13)-176 | 3-CF3—Ph | n-Pr | Ph |
| (13)-177 | 3-CF3—Ph | n-Pr | 4-Me—Ph |
| (13)-178 | 3-CF3—Ph | i-Pr | Me |
| (13)-179 | 3-CF3—Ph | i-Pr | Ph |
| (13)-180 | 3-CF3—Ph | i-Pr | 4-Me—Ph |
| (13)-181 | 3-CF3—Ph | CH2CH2OMe | Me |
| (13)-182 | 3-CF3—Ph | CH2CH2OMe | Ph |
| (13)-183 | 3-CF3—Ph | CH2CH2OMe | 4-Me—Ph |
| (13)-184 | 3-CF3—Ph | CH2CH2OEt | Me |
| (13)-185 | 3-CF3—Ph | CH2CH2OEt | Ph |
| (13)-186 | 3-CF3—Ph | CH2CH2OEt | 4-Me—Ph |
| (13)-187 | 3-CF3—Ph | CH2Ph | Me |
| (13)-188 | 3-CF3—Ph | CH2Ph | Ph |
| (13)-189 | 3-CF3—Ph | CH2Ph | 4-Me—Ph |
| (13)-190 | 2-Me—Ph | H | Me |
| (13)-191 | 2-Me—Ph | H | Ph |
| (13)-192 | 2-Me—Ph | H | 4-Me—Ph |
| (13)-193 | 2-Me—Ph | Me | Me |
| (13)-194 | 2-Me—Ph | Me | Ph |
| (13)-195 | 2-Me—Ph | Me | 4-Me—Ph |
| (13)-196 | 2-Me—Ph | Et | Me |
| (13)-197 | 2-Me—Ph | Et | Ph |
| (13)-198 | 2-Me—Ph | Et | 4-Me—Ph |
| (13)-199 | 2-Me—Ph | n-Pr | Me |
| (13)-200 | 2-Me—Ph | n-Pr | Ph |
| (13)-201 | 2-Me—Ph | n-Pr | 4-Me—Ph |
| (13)-202 | 2-Me—Ph | i-Pr | Me |
| (13)-203 | 2-Me—Ph | i-Pr | Ph |
| (13)-204 | 2-Me—Ph | i-Pr | 4-Me—Ph |

TABLE 37

| No. | R2 | R3 | R5 |
|---|---|---|---|
| (13)-205 | 2-Me—Ph | CH2CH2OMe | Me |
| (13)-206 | 2-Me—Ph | CH2CH2OMe | Ph |
| (13)-207 | 2-Me—Ph | CH2CH2OMe | 4-Me—Ph |
| (13)-208 | 2-Me—Ph | CH2CH2OEt | Me |
| (13)-209 | 2-Me—Ph | CH2CH2OEt | Ph |
| (13)-210 | 2-Me—Ph | CH2CH2OEt | 4-Me—Ph |
| (13)-211 | 2-Me—Ph | CH2Ph | Me |
| (13)-212 | 2-Me—Ph | CH2Ph | Ph |
| (13)-213 | 2-Me—Ph | CH2Ph | 4-Me—Ph |

(40-a)

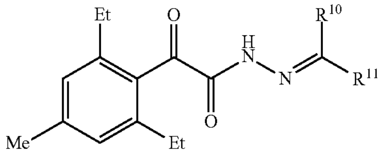

TABLE 38

| No. | R10 | R11 |
|---|---|---|
| (14)-1 | H | H |
| (14)-2 | H | Me |
| (14)-3 | H | Et |
| (14)-4 | H | i-Pr |
| (14)-5 | H | i-Bu |
| (14)-6 | H | Ph |
| (14)-7 | Me | Ph |
| (14)-8 | Me | i-Bu |
| (14)-9 | Me | Me |
| (14)-10 | Et | Ph |
| (14)-11 | —(CH2)5— | |
| (14)-12 | —(CH2)4— | |

(40-b)

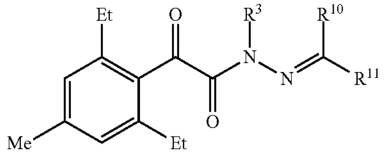

TABLE 39

| No. | R3 | R10 | R11 |
|---|---|---|---|
| (15)-1 | Me | H | H |
| (15)-2 | Me | H | Me |
| (15)-3 | Me | H | Et |
| (15)-4 | Me | H | i-Pr |
| (15)-5 | Me | H | Ph |
| (15)-6 | Me | Me | Ph |
| (15)-7 | Me | Me | Et |
| (15)-8 | Me | Me | i-Bu |
| (15)-9 | Me | —(CH2)5— | |
| (15)-10 | Et | H | H |
| (15)-11 | Et | H | Me |
| (15)-12 | Et | H | Et |
| (15)-13 | Et | H | i-Pr |
| (15)-14 | Et | H | Ph |
| (15)-15 | Et | Me | Ph |
| (15)-16 | Et | Me | Et |
| (15)-17 | Et | Me | i-Bu |
| (15)-18 | Et | —(CH2)5— | |
| (15)-19 | n-Pr | H | H |
| (15)-20 | n-Pr | H | Me |
| (15)-21 | n-Pr | H | Et |
| (15)-22 | n-Pr | H | i-Pr |
| (15)-23 | n-Pr | H | Ph |
| (15)-24 | n-Pr | Me | Ph |
| (15)-25 | n-Pr | Me | Et |
| (15)-26 | n-Pr | Me | i-Bu |
| (15)-27 | n-Pr | —(CH2)5— | |

(41-a)

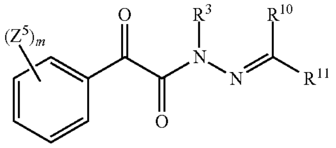

TABLE 40

| No. | (Z5)m | R3 | R10 | R11 |
|---|---|---|---|---|
| (16)-1 | 2-Et, 4-Et, 6-Et | H | H | H |
| (16)-2 | 2-Et, 4-Et, 6-Et | H | H | Ph |
| (16)-3 | 2-Et, 4-Et, 6-Et | H | Me | Ph |
| (16)-4 | 2-Et, 4-Et, 6-Et | H | Me | Et |
| (16)-5 | 2-Et, 4-Et, 6-Et | H | H | i-Pr |
| (16)-6 | 2-Et, 4-Et, 6-Et | Me | H | Ph |
| (16)-7 | 2-Et, 4-Et, 6-Et | Me | —(CH2)5— | |
| (16)-8 | 2-Et, 4-Et, 6-Et | Me | Me | Me |
| (16)-9 | 2-Et, 4-Et, 6-Et | Me | H | Et |
| (16)-10 | 2-Et, 4-Et, 6-Et | Me | Me | Ph |
| (16)-11 | 2-Et, 5-(4-Cl—Ph) | H | H | H |
| (16)-12 | 2-Et, 5-(4-Cl—Ph) | H | H | Ph |
| (16)-13 | 2-Et, 5-(4-Cl—Ph) | H | Me | Ph |
| (16)-14 | 2-Et, 5-(4-Cl—Ph) | H | | Me |
| (16)-15 | 2-Et, 5-(4-Cl—Ph) | H | H | i-Pr |
| (16)-16 | 2-Et, 5-(4-Cl—Ph) | Me | H | Ph |
| (16)-17 | 2-Et, 5-(4-Cl—Ph) | Me | —(CH2)4— | |
| (16)-18 | 2-Et, 5-(4-Cl—Ph) | Me | Me | Me |
| (16)-19 | 2-Et, 5-(4-Cl—Ph) | Me | H | Et |
| (16)-20 | 2-Et, 5-(4-Cl—Ph) | Me | Me | Ph |

EXAMPLES

Hereinafter, the present invention will be illustrated by following Examples in more detail, but not limited thereto.

In the Examples, room temperature means usually 10 to 30° C. In column chromatography, silica gel 60 (spheral, neutral, particle size: 63-210 nm, from KANTO CHEMICAL CO., INC.) was used. When a mixed solvent is used as a developing solvent, the mixture ratio by volume of each solvent is shown in parentheses. $^1$H NMR means proton nuclear magnetic resonance, and was measured with JEOL AL-400 (400 Hz) type and Bruker ADBANCE400 (400 Hz) type spectrometer using tetramethylsilan as an internal standard, and chemical shift (δ) was shown by ppm.

The abbreviations used in the Examples mean as follows: $CDCl_3$: chloroform-d, DMSO: dimethylsulfoxide, s: singlet, d: doublet, t: triplet, q: quartet, m: multiplet, br.: broad, J: coupling constant, Me: methyl group, Et: ethyl group, n-Pr: n-propyl group, i-Pr: isopropyl group, c-Pr: cyclopropyl group, and n-Bu: n-butyl group.

Example 1

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

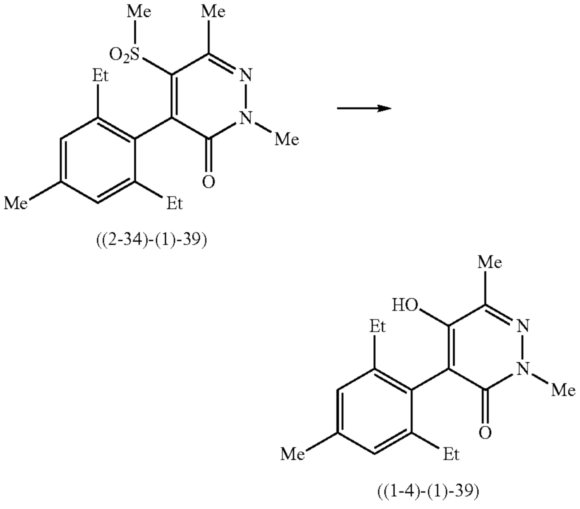

((2-34)-(1)-39)

((1-4)-(1)-39)

To a test tube (outside diameter: 21 mm ϕ×overall length: 160 mm), 4-(2,6-diethyl-4-methylphenyl)-2,6-dimethyl-5-methylsulfonyl-2,3-dihydropyridazine-3-one ((2-34)-(1)-39) (62.8 mg), dimethylsulfoxide (0.5 ml), and 3.8% by weight of aqueous sodium hydroxide solution (0.5 ml) were added under a nitrogen atmosphere at room temperature, and stirred at 70° C. for 4 hours. Then, to the reaction mixture was added 3.5% by weight of hydrochloric acid (4 ml) at room temperature, and extracted with tert-butyl methyl ether. The organic layer was concentrated under reduced pressure to give 37.5 mg of 4-(2,6-diethyl-4-methylphenyl)-5-hydroxy-2,6-dimethyl-2,3-dihydro-3-pyridazinone ((1-4)-(1)-39).

$^1$H NMR ($CDCl_3$)

δ ppm: 7.02 (2H, s), 5.28 (1H, br.), 3.75 (3H, s), 2.39-2.23 (10H, m), 1.06 (6H, t, J=7.6 Hz)

Example 2

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

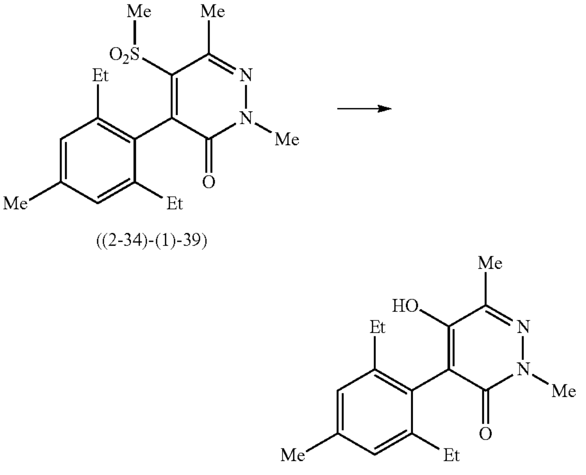

((2-34)-(1)-39)

((1-4)-(1)-39)

To a test tube (outside diameter: 21 mm ϕ×overall length: 160 mm), 4-(2,6-diethyl-4-methylphenyl)-2,6-dimethyl-5-methylsulfonyl-2,3-dihydropyridazin-3-one ((2-34)-(1)-39) (51.2 mg), toluene (0.47 ml), water (0.2 ml), tetra-n-butylammonium bromide (49.9 mg), and sodium hydroxide (54.3 m) were added under a nitrogen atmosphere at room temperature, and stirred at 120° C. for 4 hours. Then, the organic layer was removed. 3.5% by weight of hydrochloric acid (4 ml) was added to the mixture at room temperature, and extracted with tert-butyl methyl ether. Then, the organic layer was concentrated under reduced pressure to give 40.8 mg of 4-(2,6-diethyl-4-methylphenyl)-5-hydroxy-2,6-dimethyl-2,3-dihydro-3-pyridazinone ((1-4)-(1)-39).

Example 3

Production of 5-(n-butoxy)-4-(2,6-diethyl-4-methylphenyl)-2,6-dimethyl-2,3-dihydro-3-pyridazinone (a compound of the formula (1-5) and No. (1)-39 in Table 1)

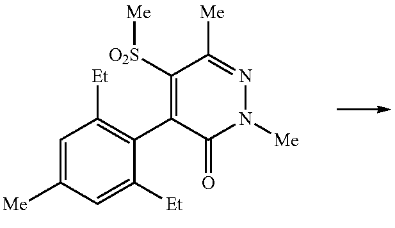

((2-34)-(1)-39)

-continued

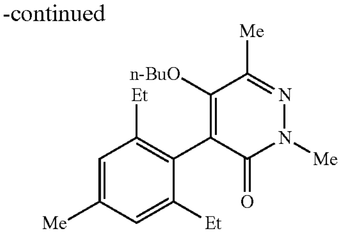

((1-5)-(1)-39)

To a test tube (outside diameter: 21 mm ϕ×overall length: 160 mm), 4-(2,6-diethyl-4-methylphenyl)-2,6-dimethyl-5-methylsulfonyl-2,3-dihydropyridazin-3-one ((2-34)-(1)-39) (0.21 g), 1-butanoll (4 ml), water (0.1 ml), and sodium hydroxide (0.20 g) were added under a nitrogen atmosphere at room temperature, and stirred at 120° C. for 8 hours. Then, to the reaction mixture was added water at room temperature, and extracted with tert-butyl methyl ether. The resulting organic layer was concentrated under reduced pressure to give 0.74 g of 5-(n-butoxy)-4-(2,6-diethyl-4-methylphenyl)-2,6-dimethyl-2,3-dihydro-3-pyridazinone ((1-5)-(1)-39).

$^1$H NMR ($CDCl_3$)

δ ppm: 6.94 (2H, s), 3.72 (3H, s), 3.39 (2H, t, J=6.2 Hz), 2.81 (3H, s), 2.47-2.31 (7H, m), 1.41 (2H, tt, J=8.0 Hz, 6.2 Hz), 1.23 (2H, qt, J=8.0 Hz, 7.3 Hz), 1.12 (6H, t, J=6.2 Hz), 0.78 (3H, t, J=7.3 Hz)

Example 4

Production of 5-ethoxy-4-(2,6-diethyl-4-methylphenyl)-2,6-dimethyl-2,3-dihydro-3-pyridazinone (a compound of the formula (1-6) and No. (1)-39 in Table 1)

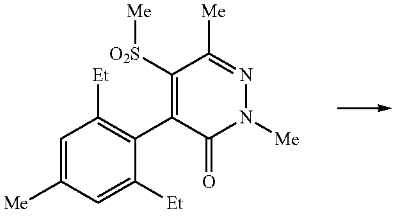

((2-34)-(1)-39)

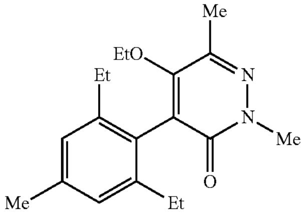

((1-6)-(1)-39)

To a test tube (outside diameter: 21 mm ϕ×overall length: 160 mm), 4-(2,6-diethyl-4-methylphenyl)-2,6-dimethyl-5-methylsulfonyl-2,3-dihydropyridazin-3-one ((2-34)-(1)-39) (52.2 mg), ethanol (674.3 mg), and sodium ethoxide (121.8 mg) were added under a nitrogen atmosphere at room temperature and stirred for 4 hours at 70° C. To the reaction mixture was added water (4 ml) at room temperature, and extracted with tert-butyl methyl ether. The organic layer was concentrated under reduced pressure to give 83.6 mg of 5-ethoxy-4-(2,6-diethyl-4-methylphenyl)-2,6-dimethyl-2,3-dihydro-3-pyridazinone ((1-6)-(1)-39).

$^1$H NMR ($CDCl_3$)

δ ppm: 6.94 (2H, s), 3.72 (3H, s), 3.45 (2H, q, J=7.0 Hz), 2.50-2.31 (7H, m), 2.28 (3H, s), 1.14-1.06 (9H, m)

Example 5

Production of 2-benzyl-4-(2,6-diethyl-4-methylphenyl)-5-hydroxy-6-methyl-2,3-dihydro-3-pyridazinone (a compound of the formula (1-4) and No. (7)-39 in Table 19)

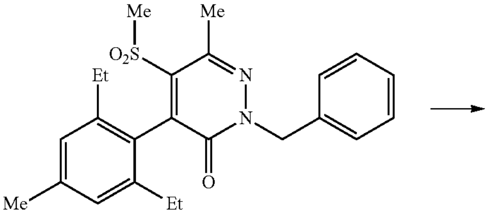

((2-34)-(7)-39)

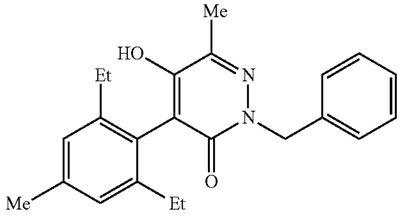

((1-4)-(7)-39)

To a 20 ml volume eggplant flask, 2-benzyl-4-(2,6-diethyl-4-methylphenyl)-6-methyl-5-methylsulfonyl-2,3-dihydro-3-pyridazinone ((2-34)-(7)-39) (67.5 mg), dimethylsulfoxide (0.9 ml), distilled water (0.2 ml), and sodium hydroxide (89.6 mg) were added under a nitrogen atmosphere, and stirred at 50° C. for 2 hours. Then, to the resulting mixture was added distilled water (5 ml) and tert-butyl methyl ether (5 ml) at room temperature to wash the aqueous layer. Then, the organic layer was removed, the aqueous layer was neutralized with concentrated sulfuric acid, followed by extracted with toluene. After the concentration of the extract, the residue was subjected to column chromatography (hexane:ethyl acetate=3:1) to gave 39.1 mg of 2-benzyl-4-(2,6-diethyl-4-methylphenyl)-5-hydroxy-6-methyl-2,3-dihydro-3-pyridazinone ((1-4)-(7)-39).

$^1$H NMR ($CDCl_3$)

δ ppm: 7.42 (2H, d, J=6.8 Hz), 7.32-2.26 (3H, m), 7.02 (2H, s), 5.32 (2H, s), 5.18 (1H, s) 2.36-2.25 (10H, m), 1.0 (6H, t, J=7.6 Hz)

Example 6

Production of ethyl 2-(2,6-diethyl-4-methylphenyl)-2-oxoacetate (a compound of the formula (9-a))

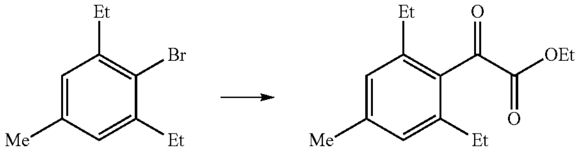

(10-a) (9-a)

To a 3 L volume four-necked flask, magnesium (cutting chip) (35.31 g) and tetrahydrofuran (anhydrous) (600 ml) were added under a nitrogen atmosphere at room temperature. Once starting to stir, the internal temperature was raised to about 30° C., dibromoethane (25.4 g) was added dropwise over 20 minutes to the mixture. After the resulting mixture was stirred for 30 minutes, the internal temperature was raised to about 50° C. To the mixture was added dropwise 2,6-diethyl-4-methylbromobenzene (10-a) (300.18 g) dissolved in tetrahydrofuran (150 ml) over 2 hours. The resulting mixture was stirred at 50° C. for 1 hour and cooled. To the mixture was added dropwise diethyl oxalate (192.5 g) at about 0° C. over 15 minutes. The resulting mixture was stirred at room temperature for 2 hours. Then, 3.5% by weight of hydrochloric acid (1000 ml) and concentrated hydrochloric acid (60 ml) were added with cooling. After the organic solvent was removed under reduced pressure, the aqueous layer was extracted with tert-butyl methyl ether. The organic layer was concentrated under reduced pressure to give 320.82 g of ethyl 2-(2,6-diethyl-4-methylphenyl)-2-oxoacetate (9-a).

$^1$H NMR ($CDCl_3$)

δ ppm: 6.92 (2H, s), 4.36 (2H, q, J=7.1 Hz), 2.52 (4H, q, J=7.6 Hz), 2.34 (3H, s), 1.36 (3H, t, J=7.1 Hz), 1.16 (6H, t, J=7.6 Hz)

Example 7

Production of 2-(2,6-diethyl-4-methylphenyl)-2-oxoacetohydrazide (a compound of the formula (12-1) and No. (11)-39 in Table 27)

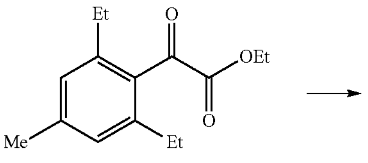

(9-a)

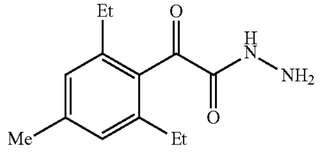

((12-1)-(11)-39)

To a 100 ml volume four-necked flask, methanol (22.91 g) and hydrazine hydrate (1.93 g) were added at room temperature, and cooled. Ethyl 2-(2,6-diethyl-4-methylphenyl)-2-oxoacetate (9-a) (5.01 g) diluted with methanol (10.02 g) was added dropwise at 1° C. over 5 minutes. The resulting mixture was stirred at 2° C. for 4 hours, then the mixture was filtered. The resulting filtrate was concentrated, added tert-butyl methyl ether (41 g), and washed with brine (14 g). The resulting organic layer was dried over sodium sulfate, and concentrated under reduced pressure. The residue was subjected to column chromatography (silica gel: 40 g, hexane:ethyl acetate=1:1) to gave 1.88 g of 2-(2,6-diethyl-4-methylphenyl)-2-oxoacetohydrazide ((12-1)-(11)-39).

$^1$H NMR ($CDCl_3$)

δ ppm: 8.13 (1H, br), 6.93 (2H, s), 4.11 (2H, br), 2.45 (4H, q, J=7.5 Hz), 2.34 (3H, s), 1.16 (6H, t, J=7.5 Hz)

Example 8

Production of 2-(2,6-diethyl-4-methylphenyl)-2-oxoacetic acid (a compound of the formula (8-a))

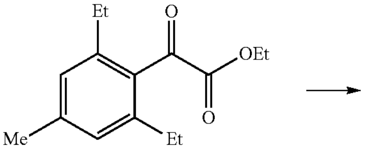

(9-a)

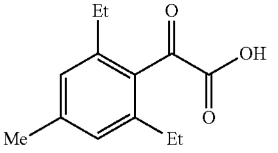

(8-a)

To a 3 L volume four-necked flask, ethyl 2-(2,6-diethyl-4-methylphenyl)-2-oxoacetate (9-a) (320.82 g) and tetrahydrofuran (600 ml) were added at room temperature and cooled. 10.7% by weight of aqueous sodium hydroxide solution (900 ml) was added dropwise at 10° C. over 2 hours. The resulting mixture was stirred at room temperature for 1 hour. After the organic solvent was removed under reduced pressure, tert-butyl methyl ether was added to the aqueous layer to wash. After the organic layer was removed, to the aqueous layer was added dropwise concentrated hydrochloric acid (180 ml), and extracted with tert-butyl methyl ether. The organic layer was concentrated under reduced pressure to give 166.55 g of 2-(2,6-diethyl-4-methylphenyl)-2-oxoacetic acid (8-a).

$^1$H NMR ($CDCl_3$)

δ ppm: 6.95 (2H, s), 2.49 (4H, q, J=7.5 Hz), 2.35 (3H, s), 1.16 (6H, t, J=7.5 Hz)

Example 9

Production of 2-(2,6-diethyl-4-methylphenyl)-2-oxoacetyl chloride (a compound of the formula (6-a))

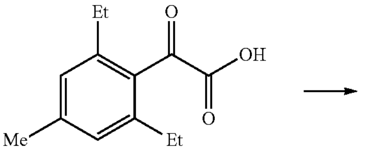

(8-a)

-continued

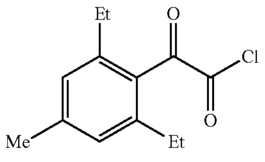

(6-a)

To a 50 ml volume four-necked flask, 2-(2,6-diethyl-4-methylphenyl)-2-oxoacetic acid (8-a) (0.94 g), toluene (anhydrous) (3.0 ml) and dimethylformamide (anhydrous) (0.2 ml) were added under a nitrogen atmosphere and the internal temperature was raised to about 50° C. Thionyl chloride (0.45 ml) was added thereto and the resulting mixture was stirred at 50° C. for 2 hours. The mixture was concentrated under reduced pressure, and azeotropically distilled with toluene to give 0.96 g of 2-(2,6-diethyl-4-methylphenyl)-2-oxoacetyl chloride (6-a).

$^1$H NMR ($CDCl_3$)

δ ppm: 6.96 (2H, s), 2.53 (4H, q, J=7.6 Hz), 2.38 (3H, s), 1.18 (6H, t, J=7.6 Hz)

Example 10

Production of 1-methyl-2-(1-methylsulfanyl-2-propylidene)hydrazine (a compound of the formula (5-0-1))

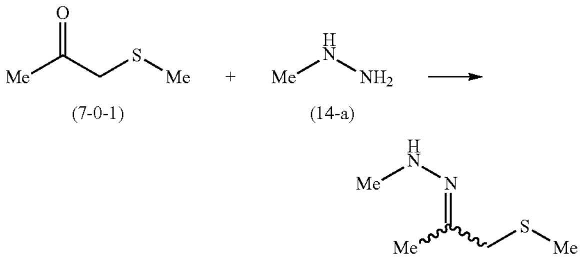

(7-0-1) (14-a)

(5-0-1)

To a 100 ml volume four-necked flask, 1-methylsulfanyl-2-propanone (7-0-1) (19.46 g) and ethanol (20 ml) were added under a nitrogen atmosphere at room temperature and cooled to about 0° C. To the mixture, monomethylhydrazine (14-a) (8.6 ml) was added dropwise and the resulting reaction mixture was stirred at room temperature for one day. The reaction mixture was concentrated under reduced pressure to give 16.91 g of 1-methyl-2-(1-methylsulfanyl-2-propylidene)hydrazine (5-0-1).

$^1$H NMR ($CDCl_3$)

δ ppm: 4.61 (1H, br), 3.20 (2H, s), 2.95 (3H, s), 2.01 (3H, s), 1.83 (3H, s)

Example 11

Production of 1-[2-(2,6-diethyl-4-methylphenyl)-2-oxoacetyl]-1-methyl-2-(1-methylsulfanyl-2-propylidene)hydrazine (a compound of the formula (4-4) and No. (1)-39 in Table 1)

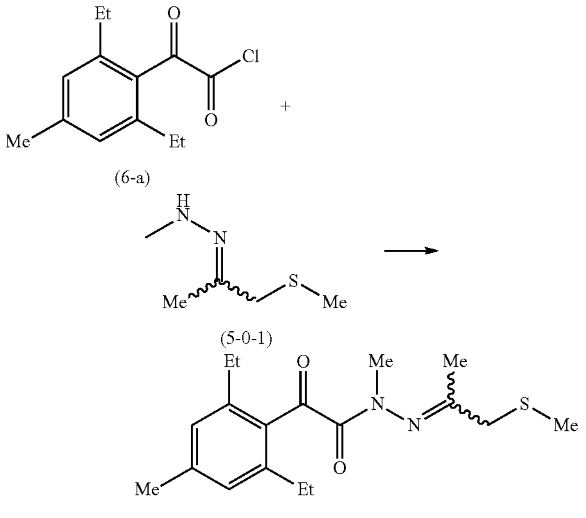

(6-a)

(5-0-1)

((4-4)-(1)-39)

To a 200 ml volume four-necked flask, 1-methyl-2-(1-methylsulfanyl-2-propylidene)hydrazine (5-0-1) (5.0 g), toluene (anhydrous) (9.6 g), and triethylamine (6.97 g) were added under a nitrogen atmosphere at room temperature. To the mixture, 2-(2,6-diethyl-4-methylphenyl)-2-oxoacetyl chloride (6-a) (9.57 g) dissolved in toluene (28.8 g) was added dropwise at 0° C. over 2 hours, and stirred at room temperature for 2 hours. To the reaction mixture was added water (30 ml) at room temperature, and extracted with tert-butyl methyl ether. The organic layer was concentrated under reduced pressure to give 10.96 g of 1-[2-(2,6-diethyl-4-methylphenyl)-2-oxoacetyl]-1-methyl-2-(1-methylsulfanyl-2-propylidene)hydrazine ((4-4)-(1)-39).

$^1$H NMR ($CDCl_3$)

δ ppm: 6.91 (1.0H, s), 6.89 (1.0H, s), 3.48 (1.5H, s), 3.31 (1H, s), 3.21 (1H, s), 3.19 (1.5H, s), 2.67-2.55 (4H, m), 2.32 (1.5H, s), 2.31 (1.5H, s), 2.18 (1.5H, s), 2.11 (1.5H, s), 2.05 (1.5H, s), 1.98 (1.5H, s), 1.23-1.16 (6H, m)

Example 12

Production of 1-[2-(2,6-diethyl-4-methylphenyl)-2-oxoacetyl]-1-methyl-2-(1-methylsulfanyl-2-propylidene)hydrazine (a compound of the formula (4-4) and No. (1)-39 in Table 1)

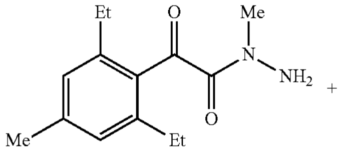

((12-2)-(11)-39)

-continued

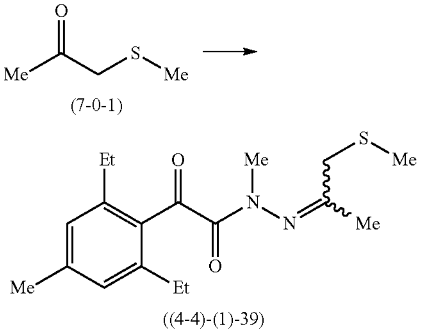

(7-0-1)

((4-4)-(1)-39)

To a 20 ml volume two-necked flask, 1-[2-(2,6-diethyl-4-methylphenyl)-2-oxoacetyl]-1-methylhydrazine ((12-2)-(11)-39) (0.50 g), tetrahydrofuran (anhydrous) (9 ml), and 1-methylsulfanyl-2-propanone (7-0-1) (0.23 g) were added and stirred at room temperature for 22 hours under a nitrogen atmosphere. Additional 1-methylsulfanyl-2-propanone (7-0-1) (0.12 g) was added thereto, and the mixture was further stirred at room temperature for 7 hours. Then, the reaction mixture was concentrated under reduced pressure. After the concentration, the residue was subjected to column chromatography (hexane:ethyl acetate=1:1) to gave 0.58 g of 1-[2-(2,6-diethyl-4-methylphenyl)-2-oxoacetyl]-1-methyl-2-(1-methylsulfanyl-2-propylidene)hydrazine ((4-4)-(1)-39).

Example 13

Production of 1-methyl-2-(1-methylsulfonyl-2-propylidene)hydrazine (a compound of the formula (5-2-1))

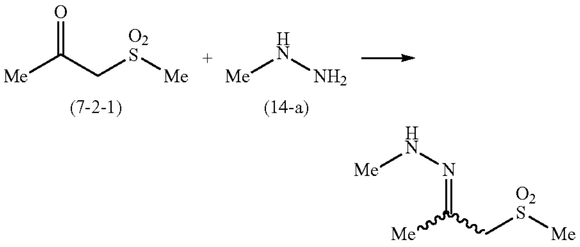

(7-2-1) (14-a)

(5-2-1)

To a 100 ml volume four-necked flask, 1-methylsulfonyl-2-propanone (7-2-1) (4.99 g) and toluene (36.0 g) were added under a nitrogen atmosphere, and added dropwise 40 wt % of aqueous monomethylhydrazine solution (14-a) (3.96 g) at room temperature. The resulting mixture was stirred at room temperature for 16 hours, and then added additional 40 wt % of aqueous monomethylhydrazine solution (0.35 g). The resulting mixture was stirred for 24 hours, and refluxed with Dean-Stark apparatus under reduced pressure at the internal temperature of 50° C. After refluxing, the resulting mixture was cooled to 0° C., and filtered to give 3.56 g of 1-methyl-2-(1-methylsulfonyl-2-propylidene)hydrazine (5-2-1).

$^1$H NMR ($CDCl_3$)

δ ppm: 3.83 (2H, s), 3.01 (3H, s), 2.90 (3H, s), 1.93 (3H, s)

Reference Production 1

Production of 1-methylsulfonyl-2-propanone (a compound of the formula (7-2-1))

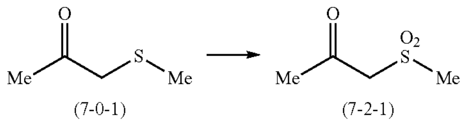 [SMILES: CSCC(C)=O ; CC(=O)CS(C)(=O)=O]

(7-0-1) (7-2-1)

To a 3000 ml volume four-necked flask, 1-methylsulfanyl-2-propanone (7-0-1) (100 g), methanol (900 g), and sodium tungstate (VI) dihydrate (31.66 g) were added at room temperature and the internal temperature was raised to 50° C. To the mixture, 30% of aqueous hydrogen peroxide solution (390 ml) was added dropwise over 3.5 hours. Then, the resulting mixture was stirred at room temperature for two days. Sodium thiosulfate (303.3 g) was added under ice-cooling, and extracted with tert-butyl methyl ether (1000 ml) 3 times then chloroform (1000 ml) 2 times. The organic layer was concentrated under reduced pressure to give 108.05 g of 1-methylsulfonyl-2-propanone.

$^1$H NMR ($CDCl_3$)

δ ppm: 4.05 (2H, s), 3.04 (3H, s), 2.44 (3H, s)

Reference Production 2

Production of 1-methylsulfonyl-2-propanone (a compound of the formula (7-2-1))

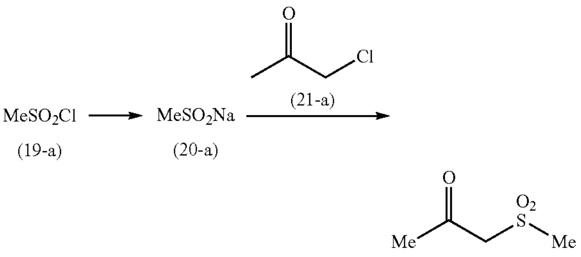

$MeSO_2Cl$ (19-a) $MeSO_2Na$ (20-a) (21-a)

(7-2-1)

To a 500 ml volume four-necked flask, sodium sulfite (57.56 g), water (149.35 g), and sodium hydrogen carbonate (43.56 g) were added under a nitrogen atmosphere at room temperature, and the internal temperature was raised to 50° C. To the mixture, methanesulfonyl chloride (19-a) (30.33 g) was added dropwise over 45 minutes. The resulting mixture was stirred at 50° C. for 5 hours, and added dropwise concentrated sulfuric acid (5.11 g). The resulting mixture was stirred at 50° C. for 1 hour. Then, the internal temperature was raised to 70° C., and chloroacetone (21-a) (22.55 g) was added dropwise over 10 minutes. The resulting mixture was stirred at 70° C. for 12 hours, extracted with ethyl acetate at 50° C., and concentrated under reduced pressure to give 29.59 g of 1-methylsulfonyl-2-propanone.

Example 14

Production of 1-[2-(2,6-diethyl-4-methylphenyl)-2-oxoacetyl]-1-methyl-2-(1-methylsulfonyl-2-propylidene) hydrazine (a compound of the formula (4-34) and No. (1)-39 in Table 1)

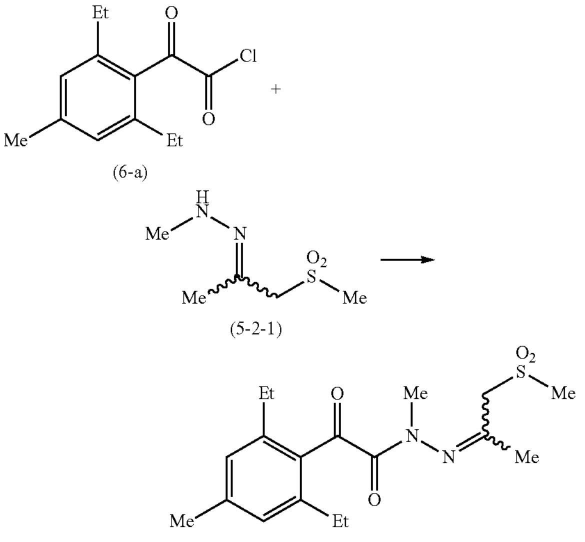

(6-a)

(5-2-1)

((4-34)-(1)-39)

To a 100 ml volume four-necked flask, 1-methyl-2-(1-methylsulfonyl-2-propylidene)hydrazine (5-2-1) (2.51 g), toluene (anhydrous) (10 ml), acetonitrile (anhydrous) (4.0 ml), and triethylamine (4.0 ml) were added under a nitrogen atmosphere and cooled to about 1° C. To the mixture, 2-(2,6-diethyl-4-methylphenyl)-2-oxoacetyl chloride (6-a) (3.44 g) dissolved in toluenel (5 ml) was added dropwise over 1 hour, followed by the mixture was stirred at 0° C. for 1.5 hours. Water (30 ml) was added thereto at room temperature, and then the mixture was extracted with tert-butyl methyl ether. The organic layer was concentrated under reduced pressure to give 5.09 g of 1-[2-(2,6-diethyl-4-methylphenyl)-2-oxoacetyl]-1-methyl-2-(1-methylsulfonyl-2-propylidene) hydrazine ((4-34)-(1)-39).

$^1$H NMR ($CDCl_3$)

δ ppm: 6.92 (1.2H, s), 6.91 (0.8H, s), 4.05 (1.2H, s), 3.95 (0.8H, s), 3.52 (1.8H, s), 3.27 (1.2H, s), 3.05 (1.8H, s), 2.96 (1.2H, s), 2.64-2.54 (4H, m), 2.34 (1.2H, s), 2.33 (3H, s), 2.11 (1.8H, s), 1.22-1.17 (6H, m)

Example 15

Production of 1-[2-(2,6-diethyl-4-methylphenyl)-2-oxoacetyl]-1-methyl-2-(1-methylethylidene)hydrazine (a compound of the formula (18-a))

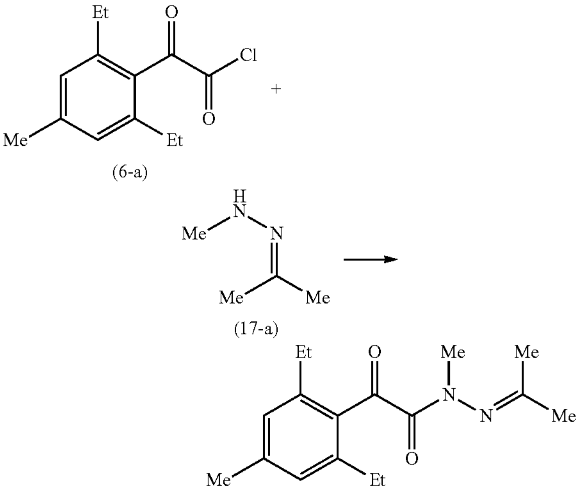

(6-a)

(17-a)

(18-a)

To a 1000 ml volume four-necked flask, 1-methyl-2-(2-propylidene)hydrazine (17-a) (9.61 g), acetonitrile (280 ml), and triethylamine (17 ml) were added under a nitrogen atmosphere and cooled to about 1° C. To the mixture, 2-(2,6-diethyl-4-methylphenyl)-2-oxoacetyl chloride (6-a) (27.12 g) dissolved in acetonitrile (77 ml) was added dropwise over 30 minutes.

After stirring at room temperature for 1 hour, the reaction mixture was concentrated under reduced pressure. Acetone (300 ml) was added, the precipitated crystal was filtered out, and the filtrate was concentrated under reduced pressure. The residue was subjected to column chromatography (hexane: acetone=3:1) to give 21.41 g of 1-[2-(2,6-diethyl-4-methylphenyl)-2-oxoacetyl]-1-methyl-2-(1-methylethylidene) hydrazine (18-a).

$^1$H NMR ($CDCl_3$)

δ ppm: 6.90 (1.2H, s), 6.88 (0.8H, s), 3.45 (1.2H, s), 3.14 (1.8H, s), 2.67-2.56 (4H, m), 2.32 (1.2H, s), 2.31 (1.8H, s), 2.14 (1.2H, s), 2.03 (1.8H, s), 2.02 (1.8H, s), 1.86 (1.2H, s), 1.23-1.17 (6H, m)

Example 16

Production of 1-[2-(2,6-diethyl-4-methylphenyl)-2-oxoacetyl]-1-methylhydrazine (a compound of the formula (12-2) and No. (11)-39 in Table 27)

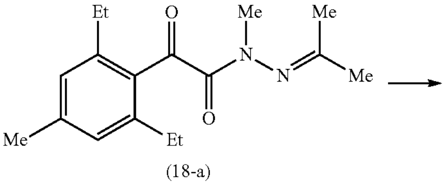

(18-a)

-continued

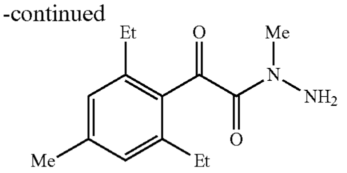

((12-2)-(11)-39)

To a 500 ml volume four-necked flask, 1-[(2,6-diethyl-4-methylphenyl)-2-oxoacetyl]-1-methyl-2-(1-methylethylidene)hydrazine (18-a) (21.41 g) and tetrahydrofuran (150 ml) were added under a nitrogen atmosphere at room temperature. To the mixture, 10% by weight of hydrochloric acid (29.23 g) was added dropwise over 5 minutes, and stirred at room temperature for 1 hour. Then, the reaction mixture was concentrated under reduced pressure. To the residue was added water (80 ml), and extracted with tert-butyl methyl ether. The organic layer was concentrated under reduced pressure, and added hexane (50 ml). The precipitated crystal was collected by filtration and dried to give 12.70 g of 1-[2-(2,6-diethyl-4-methylphenyl)-2-oxoacetyl]-1-methylhydrazine ((12-2)-(11)-39).

$^{1}$H NMR ($CDCl_3$)

δ ppm: 6.91 (2H, s), 4.60 (1.2H, s), 3.96 (0.8H, s), 3.44 (1.9H, s), 3.22 (1.1H, s), 2.66 (1.5H, q, J=7.6 Hz), 2.53 (2.5H, q, J=7.6 Hz), 2.32 (3H, s), 1.23-1.18 (6H, m)

Example 17

Production of 1-[2-(2,6-diethyl-4-methylphenyl)-2-oxoacetyl]-1-methyl-2-(1-methylsulfonyl-2-propylidene)hydrazine (a compound of the formula (4-34) and No. (1)-39 in Table 1)

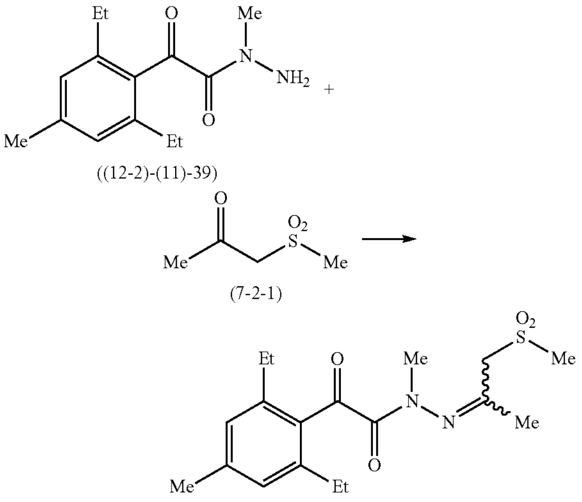

((12-2)-(11)-39)

(7-2-1)

((4-34)-(1)-39)

To a 20 ml volume two-necked flask, 1-[2-(2,6-diethyl-4-methylphenyl)-2-oxoacetyl]-1-methylhydrazine ((12-2)-(11)-39) (0.50 g), tetrahydrofuran (anhydrous) (9 ml), and 1-methylsulfonyl-2-propanone (7-2-1) (0.30 g) were added under a nitrogen atmosphere and stirred at room temperature for 22 hours. The reaction mixture was concentrated under reduced pressure. The residue was subjected to column chromatography (hexane:acetone=3:1) to give 0.25 g of 1-[2-(2,6-diethyl-4-methylphenyl)-2-oxoacetyl]-1-methyl-2-(1-methylsulfonyl-2-propylidene)hydrazine ((4-34-(1)-39).

Example 18

Production of (1-methylsulfonyl-2-propylidene)hydrazine (a compound of the formula (5-2-2))

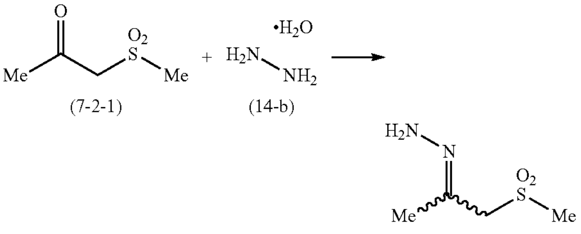

(7-2-1) (14-b)

(5-2-2)

To a 200 ml volume four-necked flask, 1-methylsulfonyl-2-propanone (7-2-1) (10.21 g) and ethanol (50 ml) were added under a nitrogen atmosphere and cooled to 0° C. Hydrazine monohydrate (14-b) (3.9 ml) was added dropwise. After stirring at room temperature for 23.5 hours, the mixture was concentrated under reduced pressure to give 10.69 g of (1-methylsulfonyl-2-propylidene)hydrazine (5-2-2).

$^{1}$H NMR ($CDCl_3$)

δ ppm: 5.37 (2H, br), 3.83 (2H, s), 2.90 (3H, s), 1.97 (3H, s)

Example 19

Production of 1-[2-(2,6-diethyl-4-methylphenyl)-2-oxoacetyl]-2-(1-methylsulfonyl-2-propylidene)hydrazine (a compound of the formula (4-34) and No. (8)-39 in Table 22)

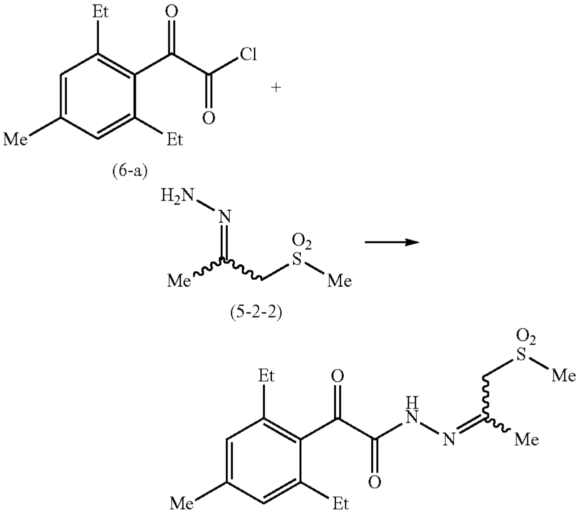

(6-a)

(5-2-2)

((4-34)-(8)-39)

To a test tube (outside diameter: 21 mm φ×overall length: 160 mm), 1-(1-methylsulfonyl-2-propylidene)hydrazine (5-2-2) (0.14 g), toluene (anhydrous) (0.9 ml), acetonitrile (anhydrous) (0.2 ml), and sodium hydrogen carbonate (0.14 g) were under a nitrogen atmosphere, and cooled on ice-bath. To the mixture, 2-(2,6-diethyl-4-methylphenyl)-2-oxoacetyl chloride (6-a) (0.2 g) dissolved in toluene (1.0 ml) was added dropwise.

After the addition, the mixture was stirred for 2 hours. 5.0 ml of water was added at room temperature, and extracted with tert-butyl methyl ether, and then the organic layer was concentrated under reduced pressure. The residue was subjected to column chromatography (chloroform:methanol=9:1) to give 0.06 g of 1-[2-(2,6-diethyl-4-methylphenyl)-2-oxoacetyl]-2-(1-methylsulfonyl-2-propylidene)hydrazine ((4-34)-(8)-39).

$^1$H NMR ($CDCl_3$)

δ ppm: 9.89 (1H, s), 6.95 (2H, s), 4.09 (2H, s), 3.01 (3H, s), 2.48 (4H, q, J=7.6 Hz), 2.35 (3H, s), 2.27 (3H, s), 1.17 (6H, t, J=7.6 Hz)

Example 20

Production of 1-[2-(2,6-diethyl-4-methylphenyl)-2-oxoacetyl]-2-(1-methylsulfanyl-2-propylidene)hydrazine (a compound of the formula (4-4) and No. (8)-39 in Table 22)

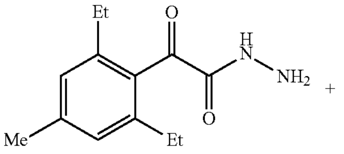

((12-1)-(11)-39)

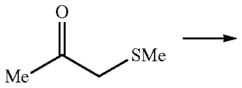

7-0-1

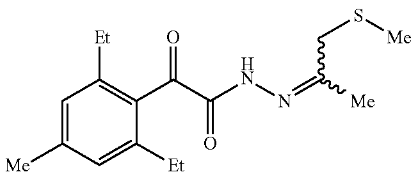

(4-4)-(8)-39)

To a 200 ml volume four-necked flask, 2-(2,6-diethyl-4-methylphenyl)-2-oxoacetohydrazine ((12-1)-(11)-39) (6.44 g), tetrahydrofuran (72 ml), and acetic acid (1.65 g) were added under a nitrogen atmosphere. 1-methylsulfanyl-2-propanone (7-0-1) (3.12 g) was added at room temperature, and the mixture was stirred at room temperature for 2 hours. To the reaction mixture was added water (30 ml), and extracted with tert-butyl methyl ether. The organic layer was concentrated under reduced pressure to give 7.17 g of 1-[2-(2,6-diethyl-4-methylphenyl)-2-oxoacetyl]-2-(1-methylsulfanyl-2-propylidene)hydrazine ((4-4)-(8)-39).

$^1$H NMR ($CDCl_3$)

δ ppm: 9.70 (1H, s), 6.93 (2H, s), 3.38 (2H, s), 2.48 (4H, q, J=7.6 Hz), 2.34 (3H, s), 2.14 (3H, s), 2.07 (3H, s), 1.16 (6H, t, J=7.5 Hz)

Example 21

Production of 1-benzyl-2-(1-methylsulfonyl-2-propylidene)hydrazine monohydrochloride (a compound of the formula (5-2-3))

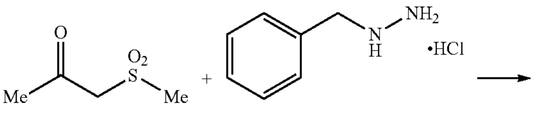

(7-2-1) (14-c)

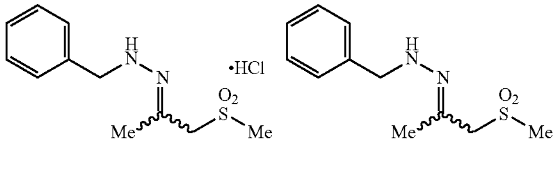

(5-2-3) (5-2-3')

To a 50 ml volume three-necked flask, 1-methylsulfonyl-2-propanone (7-2-1) (2.01 g), methanol (10 ml) and benzylhydrazine monohydrochloride (14-c) (2.56 g) were added under a nitrogen atmosphere at room temperature, then additional methanol (10 ml) was added. The resulting reaction mixture was stirred at room temperature for three days, and filtered to give the primary crystal. The filtrate was concentrated under reduced pressure, and filtered again to give the crystal. The crystal was combined with the primary crystal to give 4.2 g of 1-benzyl-2-(1-methylsulfonyl-2-propylidene) hydrazine monohydrochloride (5-2-3). Additionally, the hydrochloride (5-2-3) (0.28 g) was dissolved in saturated aqueous sodium hydrogen carbonate solution (5.0 ml), and extracted with tert-butyl methyl ether (5.0 ml) 2 times. Then, the organic layer was concentrated under reduced pressure to give 0.22 g of 1-benzyl-2-(1-methylsulfonyl-2-propylidene) hydrazine (5-2-3'). NMR data of Compound (5-2-3') is shown below.

$^1$H NMR ($CDCl_3$)

δ ppm: 7.34-7.23 (5H, m), 5.39 (1H, br), 4.39 (2H, d, J=4.8 Hz), 3.78 (2H, s), 2.67 (3H, s), 1.88 (3H, s)

Example 22

Production of 1-benzyl-1-[2-(2,6-diethyl-4-methylphenyl)-2-oxoacetyl]-2-(1-methylsulfonyl-2-propylidene)hydrazine (a compound of the formula (4-34) and No. (7)-39 in Table 19)

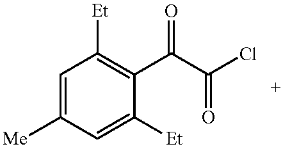

(6-a)

-continued

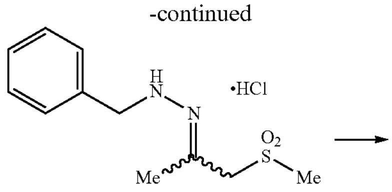

(5-2-3)

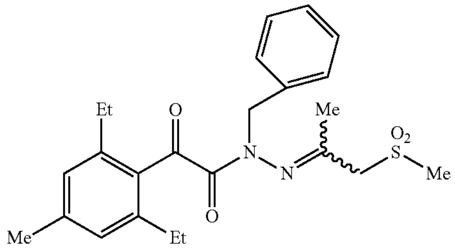

((4-34)-(7)-39)

To a 50 ml volume four-necked flask, 1-benzyl-2-(1-methylsulfonyl-2-propylidene)hydrazine monohydrochloride (5-2-3) (2.65 g), acetonitrile (9 ml), and triethylamine (2.5 ml) were added under a nitrogen atmosphere at room temperature, and cooled to about 0° C. To the mixture, 2-(2,6-diethyl-4-methylphenyl)-2-oxoacetyl chloride (6-a) (2.42 g) dissolved in toluene (6 ml) was added dropwise over 5 minutes.

The resulting mixture was stirred under ice-cooling for 2 hours. Then, the reaction mixture was poured into saturated aqueous sodium hydrogen carbonate solution (60 ml), and extracted with toluene (100 ml) 3 times. Then, the organic layer was washed with saturated aqueous ammonium chloride solution (100 ml), and concentrated under reduced pressure to give 3.90 g of crude 1-benzyl-1-[2-(2,6-diethyl-4-methylphenyl)-2-oxoacetyl]-2-(1-methylsulfonyl-2-propylidene)hydrazine ((4-34)-(7)-39). The crude product (1.08 g) was dissolved in ethyl acetate (3 ml) and added hexane (7 ml). The resulted precipitate was collected by filtration to give 0.33 g of 1-benzyl-1-[2-(2,6-diethyl-4-methylphenyl)-2-oxoacetyl]-2-(1-methylsulfonyl-2-propylidene) hydrazine ((4-34)-(7)-39) as a primary crystal. Further, the filtrate was concentrated under reduced pressure followed by a similar procedure to give 0.17 g of the second crystal.

$^{1}$H NMR ($CDCl_3$)

δ ppm: 7.49-7.47 (2H, m), 7.40-7.31 (3H, m), 6.94 (1.6H, s), 6.89 (0.4H, s), 5.06 (1.6H, s), 4.91 (0.4H, s), 3.91 (1.6H, s), 3.90 (0.4H, s), 2.79 (2.4H, s), 2.67-2.51 (4.6H, m), 2.34 (2.4H, s), 2.32 (0.6H, s), 2.20 (0.6H, s), 1.89 (2.4H, s), 1.26-1.11 (6H, m)

Example 23

Production of 4-(2,6-diethyl-4-methylphenyl)-2,6-dimethyl-5-methylsulfanyl-2,3-dihydro-3-pyridazinone (a compound of the formula (2-4) and No. (1)-39 in Table 1)

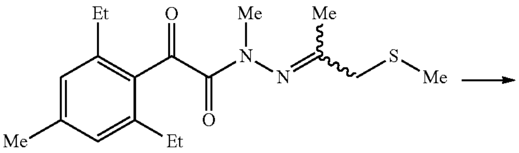

((4-4)-(1)-39)

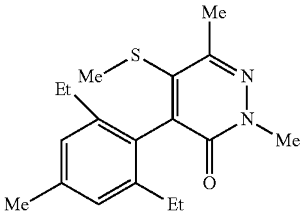

((2-4)-(1)-39)

To a 200 ml volume four-necked flask, tetrahydrofuran (anhydrous) (27.0 ml) and sodium hydride (1.90 g) were added under a nitrogen atmosphere at about 0° C., and stirred. Then, 1-[2-(2,6-diethyl-4-methylphenyl)-2-oxoacetyl]-1-methyl-2-(1-methylsulfanyl-2-propylidene)hydrazine ((4-4)-(1)-39) (14.2 g) dissolved in tetrahydrofuran (anhydrous) (45 ml) was added dropwise over 30 minutes, and then the mixture was stirred at 0° C. for 2 hours. Then, to the mixture was added water (100 ml) at room temperature, and extracted with tert-butyl methyl ether. The organic layer was concentrated under reduced pressure. The residue was subjected to column chromatography (hexane:ethyl acetate=4:1) to give 5.45 g of 4-(2,6-diethyl-4-methylphenyl)-2,6-dimethyl-5-methylsulfanyl-2,3-dihydro-3-pyridazinone.

$^{1}$H NMR ($CDCl_3$)

δ ppm: 6.95 (2H, s), 3.75 (3H, s), 2.44 (3H, s), 2.39-2.32 (7H, m), 1.85 (3H, s), 1.13 (6H, t, J=7.5 Hz)

Example 24

Production of 4-(2,6-diethyl-4-methylphenyl)-2,6-dimethyl-5-methylsulfonyl-2,3-dihydro-3-pyridazinone (a compound of the formula (2-34) and No. (1)-39 in Table 1)

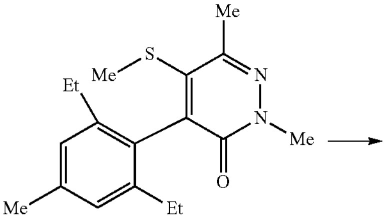

((2-4)-(1)-39)

-continued

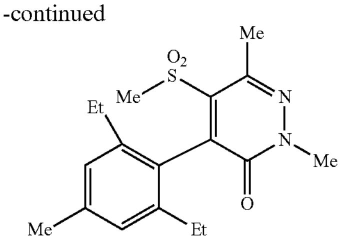

((2-34)-(1)-39)

To a 20 ml volume two-necked flask, 4-(2,6-diethyl-4-methylphenyl)-2,6-dimethyl-5-methylsulfanyl-2,3-dihydro-3-pyridazinone ((2-4)-(1)-39) (0.18 g), chloroform (1.0 ml), and sodium hydrogen carbonate (0.20 g) were added thereto under a nitrogen atmosphere. Meta-chloroperbenzoic acid (0.32 g) was added thereto at room temperature, and then the mixture was stirred for 4 hours. After stirring, to the reaction mixture was added saturated aqueous sodium sulfite solution, and extracted with tert-butyl methyl ether. Then, the organic layer was concentrated under reduced pressure. Then, the residue was subjected to column chromatography (silica gel 10 g, chloroform:ethyl acetate=15:1) to give 0.12 g of 4-(2,6-diethyl-4-methylphenyl)-2,6-dimethyl-5-methylsulfonyl-2,3-dihydro-3-pyridazinone ((2-34)-(1)-39).

$^1$H NMR ($CDCl_3$)

δ ppm: 7.02 (2H, s), 3.81 (3H, s), 2.73 (3H, s), 2.44 (3H, s), 2.39-2.31 (7H, m), 1.15 (6H, t, J=7.5 Hz)

Example 25

Production of 4-(2,6-diethyl-4-methylphenyl)-2,6-dimethyl-5-methylsulfonyl-2,3-dihydro-3-pyridazinone (a compound of the formula (2-34) and No. (1)-39 in Table 1)

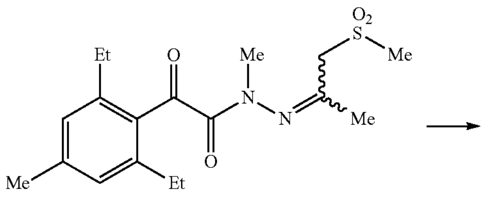

((4-34)-(1)-39)

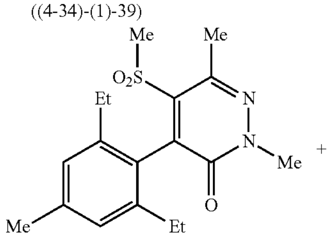

((2-34)-(1)-39)

-continued

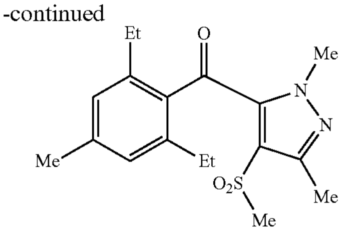

(22)

To a test tube (outside diameter: 21 mm ϕ×overall length: 160 mm), 1-[2-(2,6-diethyl-4-methylphenyl)-2-oxoacetyl]-1-methyl-2-(1-methylsulfonyl-2-propylidene)hydrazine ((4-34)-(1)-39) (104.0 mg), potassium carbonate (60.2 mg) and dimethylformamide (300 mg) were added at room temperature.

After stirring for 22 hours, to the mixture was added water at room temperature, and extracted with ethyl acetate. The organic layer was concentrated under reduced pressure to give 84.7 mg of a mixture of 4-(2,6-diethyl-4-methylphenyl)-2,6-dimethyl-5-methylsulfonyl-2,3-dihydro-3-pyridazinone ((2-34)-(1)-39), and 5-[(2,6-diethyl-4-methylphenyl)carbonyl]-1,3-dimethyl-4-methylsulfonyl-1H-pyrazole (22) (1H-NMR ratio: ((2-34)-(1)-39)/(22)=7/3).

1H NMR ($CDCl_3$)

4-(2,6-diethyl-4-methylphenyl)-2,6-dimethyl-5-methylsulfonyl-2,3-dihydro-3-pyridazinone ((2-34)-(1)-39)

δ ppm: 7.02 (2H, s), 3.81 (3H, s), 2.73 (3H, s), 2.44 (3H, s), 2.39-2.31 (7H, m), 1.15 (6H, t, J=7.5 Hz)

5-[(2,6-diethyl-4-methylphenyl)carbonyl]-1,3-dimethyl-4-methylsulfonyl-1H-pyrazole (22)

δ ppm: 6.97 (2H, s), 3.48 (3H, s), 3.18 (3H, s), 2.52-2.44 (7H, m), 2.36 (3H, s), 1.14 (6H, t, J=7.5 Hz)

Example 26

Production of 4-(2,6-diethyl-4-methylphenyl)-2,6-dimethyl-5-methylsulfonyl-2,3-dihydro-3-pyridazinone (a compound of the formula (2-34) and No. (1)-39 in Table 1)

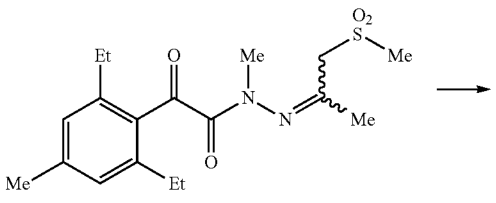

((4-34)-(1)-39)

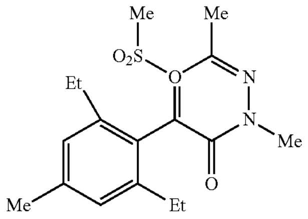

((2-34)-(1)-39)

To a test tube (outside diameter: 21 mm ϕ×overall length: 160 mm), 1-[2-(2,6-diethyl-4-methylphenyl)-2-oxoacetyl]-1-methyl-2-(1-methylsulfonyl-2-propylidene)hydrazine ((4-

34-(1)-39) (201.0 mg), potassium carbonate (115.1 mg), and methanol (757 μl) were added under ice-cooling.

The mixture was stirred under ice-cooling for 3 hours, then added water, and extracted with ethyl acetate. The organic layer was concentrated under reduced pressure to give 187.5 mg of 4-(2,6-diethyl-4-methylphenyl)-2,6-dimethyl-5-methylsulfonyl-2,3-dihydro-3-pyridazinone ((2-34)-(1)-39).

$^{1}$H NMR ($CDCl_3$)

δ ppm: 7.02 (2H, s), 3.81 (3H, s), 2.73 (3H, s), 2.44 (3H, s), 2.39-2.31 (7H, m), 1.15 (6H, t, J=7.5 Hz)

Example 27

Production of 2-benzyl-4-(2,6-diethyl-4-methylphenyl)-6-methyl-5-methylsulfonyl-2,3-dihydro-3-pyridazinone (a compound of the formula (2-34) and No. (7)-39 in Table 19)

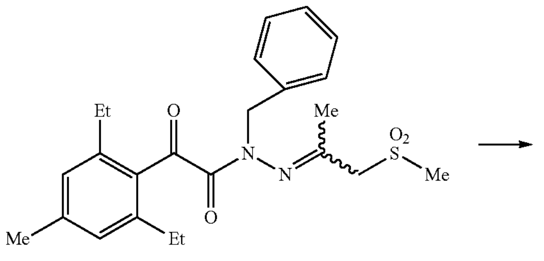

((4-34)-(7)-39)

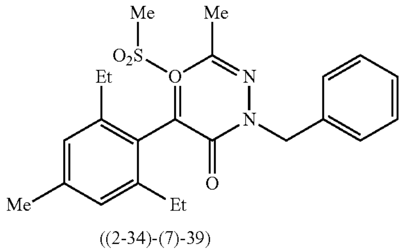

((2-34)-(7)-39)

To a 20 ml volume three-necked flask, 1-benzyl-1-[2-(2,6-diethyl-4-methylphenyl)-2-oxoacetyl]-2-(1-methylsulfonyl-2-propylidene)hydrazine ((4-34)-(7)-39) (340 mg), toluene (3.0 ml), and potassium carbonate (0.18 g) were added at room temperature, then additional toluene (0.5 ml) was added. The resulting mixture was stirred at room temperature for 15 hours, then at the internal temperature of about 50° C. for 18 hours. To the resulting mixture, water was added was extracted with tert-butyl methyl ether. The organic layer was concentrated under reduced pressure, purified by column chromatography (hexane:ethyl acetate=5:1), further recrystallized from ethyl acetate to give 67.5 mg of 2-benzyl-4-(2,6-diethyl-4-methylphenyl)-6-methyl-5-methylsulfonyl-2,3-dihydro-3-pyridazinone ((2-34)-(7)-39).

1H NMR ($CDCl_3$)

δ ppm: 7.43 (2H, d, J=3.7 Hz), 7.32-7.29 (3H, m), 6.99 (2H, s), 5.31 (2H, s), 2.73 (3H, s), 2.43 (3H, s), 2.36-2.21 (7H, m), 1.05 (6H, t, J=7.5 Hz)

Example 28

Production of 1-[2-(2,6-diethyl-4-methylphenyl)-2-oxoacetyl]-2-(1,1,1-trifluoro-3-methylsulfanyl-2-propylidene)-1-methylhydrazine (a compound of the formula (4-46) and No. (1)-39 in Table 1)

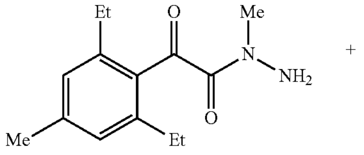

((12-2)-(11)-39)

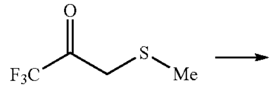

(7-0-2)

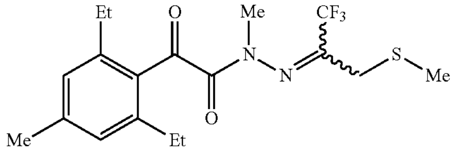

((4-46)-(1)-39)

To a 100 ml volume three-necked flask, 1-[2-(2,6-diethyl-4-methylphenyl)-2-oxoacetyl]-1-methylhydrazine ((12-2)-(11)-39) (3.04 g) was placed at room temperature, and added dropwise a solution of 1,1,1-trifluoro-3-methylsulfanyl-2-propanone (7-0-2) (2.29 g) in toluene (27 g). After para-toluenesulfonic acid monohydrate (0.028 g) was added, the resulting mixture was stirred under reflux for 45 minutes, and cooled to room temperature. The reaction mixture was poured into water (30 ml), and extracted with ethyl acetate (50 ml) 2 times. The resulting organic layer was dried over magnesium sulfate, concentrated under reduced pressure, and subjected to silica gel column chromatography (chloroform) to give 2.13 g of 1-[2-(2,6-diethyl-4-methylphenyl)-2-oxoacetyl]-2-(1,1,1-trifluoro-3-methylsulfanyl-2-propylidene)-1-methylhydrazine ((4-46)-(1)-39).

1H NMR ($CDCl_3$)

δ ppm: 6.92 (1.3H, s), 6.91 (0.7H, s), 3.64 (1H, s), 3.62 (2H, s), 3.57 (1.3H, s), 3.32 (0.7H, s), 2.67-2.50 (4H, m), 2.32 (3H, s), 2.20 (2H, s), 2.11 (1H, s), 1.27-1.11 (6H, m)

Example 29

Production of 4-(2,6-diethyl-4-methylphenyl)-2-methyl-5-methylsulfanyl-6-trifluoromethyl-2,3-dihydro-3-pyridazinone (a compound of the formula (2-46) and No. (1)-39 in Table 1)

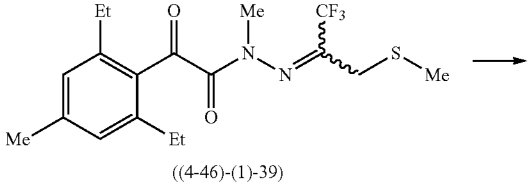

((4-46)-(1)-39)

-continued

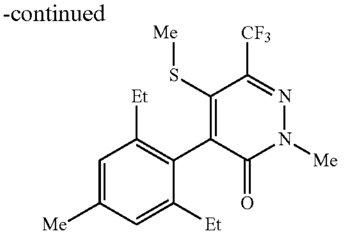

((2-46)-(1)-39)

To a 50 ml volume three-necked flask, tetrahydrofuran (anhydrous) (10 ml) and potassium t-butoxide (0.17 g) were added at room temperature. A solution of 1-[2-(2,6-diethyl-4-methylphenyl)-2-oxoacetyl]-2-(1,1,1-trifluoro-3-methylsulfanyl-2-propylidene)-1-methylhydrazine ((4-46)-(1)-39) (0.584 g) which was azeotropic-distilled with toluene one time in tetrahydrofuran (anhydrous) (15 ml) was added dropwise at room temperature over 8 minutes. The reaction mixture was stirred for 2 hours, and added additional potassium t-butoxide (0.166 g). Then, the resulting mixture was stirred for 2 hours. The reaction mixture was poured into water (70 ml), and extracted with ethyl acetate (50 ml) 2 times. The organic layer was washed with saturated brine (30 ml), dried over anhydrous magnesium sulfate, concentrated under reduced pressure, and subjected to silica gel column chromatography (hexane:ethyl acetate=30:1 to hexane:ethyl acetate=10:1 to hexane:ethyl acetate=5:1) to give 0.226 g of 4-(2,6-diethyl-4-methylphenyl)-2-methyl-5-methylsulfanyl-6-trifluoromethyl-2,3-dihydro-3-pyridazinone ((2-46)-(1)-39).

1H NMR ($CDCl_3$)

δ ppm: 7.00 (2H, s), 3.85 (3H, s), 3.37 (3H, s), 2.45-2.26 (4H, m), 1.86 (3H, s), 1.14 (6H, t, J=7.6 Hz)

Example 30

Production of 4-(2,6-diethyl-4-methylphenyl)-2-methyl-5-methylsulfinyl-6-trifluoromethyl-2,3-dihydro-3-pyridazinone (a compound of the formula (2-49) and No. (1)-39 in Table 1)

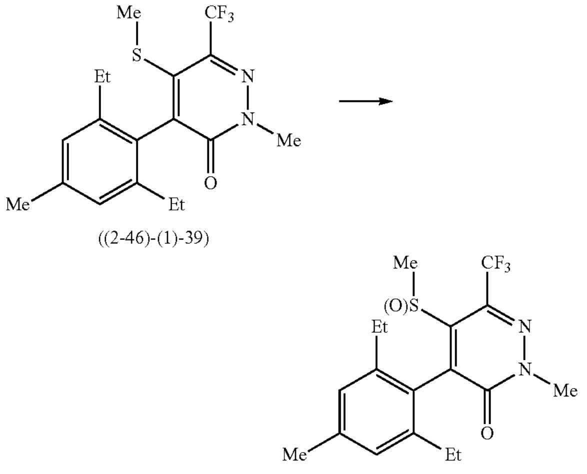

((2-46)-(1)-39)

((2-49)-(1)-39)

To a 50 ml volume three-necked flask, 4-(2,6-diethyl-4-methylphenyl)-2-methyl-5-methylsulfanyl-6-trifluoromethyl-2,3-dihydro-3-pyridazinone ((2-46)-(1)-39) (0.51 g) and chloroform (12.5 ml) were added at room temperature. Sodium hydrogen carbonate (0.46 g) and meta-chlorobenzoic acid (0.48 g) was added and the resulting mixture was stirred at room temperature for 3 hours. Then, the reaction mixture was poured into water (20 ml), added sodium sulfite (0.3 g), and extracted with t-butyl methyl ether (40 ml) 2 times. Then, the organic layer was washed with saturated brine, dried over anhydrous magnesium sulfate, concentrated under reduced pressure, and subjected to silica gel column chromatography (hexane:ethyl acetate=3:1 to hexane:ethyl acetate=1:1) to give 0.461 g of 4-(2,6-diethyl-4-methylphenyl)-2-methyl-5-methylsulfinyl-6-trifluoromethyl-2,3-dihydro-3-pyridazinone ((2-49)-(1)-39).

1H NMR ($CDCl_3$)

δ ppm: 7.02 (1H, s), 7.01 (1H, s), 3.92 (3H, s), 2.70 (3H, s), 2.37 (3H, s), 2.53-2.22 (3H, s), 2.17-2.04 (1H, m), 1.20-1.11 (6H, m)

Example 31

Production of 4-(2,6-diethyl-4-methylphenyl)-5-hydroxy-2-methyl-6-trifluoromethyl-2,3-dihydro-3-pyridazinone (a compound of the formula (1-16) and No. (1)-39 in Table 1)

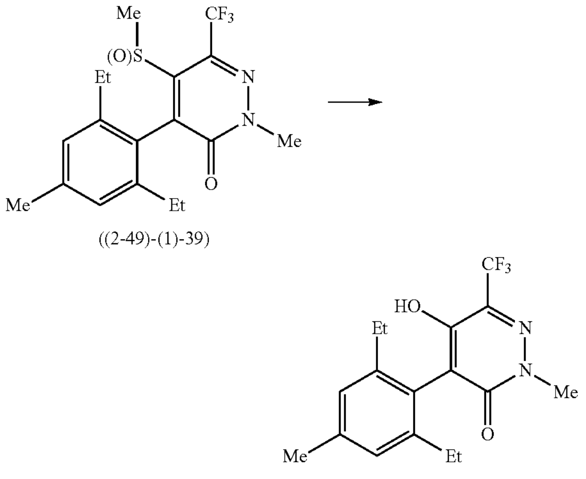

((2-49)-(1)-39)

((1-16)-(1)-39)

To a 30 ml volume three-necked flask, 4-(2,6-diethyl-4-methylphenyl)-2-methyl-5-methylsulfinyl-6-trifluoromethyl-2,3-dihydro-3-pyridazinone ((2-49)-(1)-39) (0.375 g), N-methylpyrrolidone (3.49 g), water (1.75 g), and sodium hydroxide (0.34 g) were added at room temperature. The resulting mixture was stirred at 50° C. for 4 hours. Then, the resulting mixture was cooled to room temperature, added 12N hydrochloric acid (1.5 ml) and water (15 ml), and extracted with ethyl acetate (30 ml). The organic layer was dried over anhydrous magnesium sulfate, concentrated under reduced pressure, and subjected to silica gel column chromatography (hexane:ethyl acetate=7:1 to hexane:ethyl acetate=5:1 to hexane:ethyl acetate=3:1) to give 0.147 g of 4-(2,6-diethyl-4-methylphenyl)-5-hydroxy-2-methyl-6-trifluoromethyl-2,3-dihydro-3-pyridazinone ((1-16)-(1)-39).

1H NMR ($CDCl_3$)

δ ppm: 7.06 (2H, s), 5.81 (1H, br), 3.86 (3H, s), 2.37 (3H, s), 2.42-2.24 (4H, s), 1.09 (6H, t, J=7.6 Hz)

Example 32

Production of 1-[2-(2,4,6-triethylphenyl)-2-oxoacetyl]-2-(1,1,1-trifluoro-3-methylsulfanyl-2-propylidene)-1-methylhydrazine (a compound of the formula (12-2) and No. (11)-40 in Table 27)

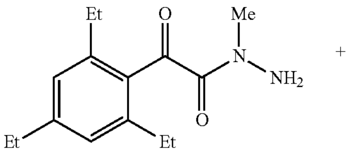

((12-2)-(11)-40)

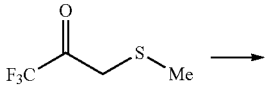

(7-0-2)

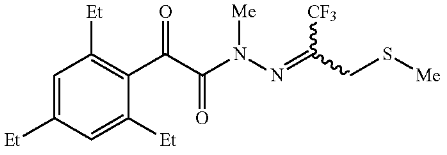

((4-46)-(1)-40)

To a 100 ml volume three-necked flask, 1-[2-(2,4,6-triethylphenyl)-2-oxoacetyl]-1-methylhydrazine ((12-2)-(11)-40) (3.01 g) was added, and to the mixture was added dropwise a solution of 1,1,1-trifluoro-3-methylsulfanyl-2-propanone (7-0-2) (2.10 g) in toluene (27 g), followed by the addition of para-toluenesulfonic acid monohydrate (0.030 g). The resulting mixture was stirred under reflux for 40 minutes. Then, the reaction mixture was cooled to room temperature, poured into water (30 ml), and extracted with ethyl acetate (50 ml) 3 times. The resulting organic layer was dried over magnesium sulfate, concentrated under reduced pressure, and subjected to silica gel column chromatography (chloroform) to give 2.31 g of 1-[2-(2,4,6-triethylphenyl)-2-oxoacetyl]-2-(1,1,1-trifluoro-3-methylsulfanyl-2-propylidene)-1-methylhydrazine ((4-46)-(1)-40).

1H NMR ($CDCl_3$)

δ ppm: 6.94 (0.7H, s), 6.92 (1.3H, s), 3.64 (1H, s), 3.62 (2H, s), 3.57 (1.3H, s), 3.32 (0.7H, s), 2.69-2.52 (6H, m), 2.19 (2H, s), 2.11 (1H, s), 1.27-1.14 (9H, m)

Example 33

Production of 4-(2,4,6-triethylphenyl)-2-methyl-5-methylsulfanyl-6-trifluoromethyl-2,3-dihydro-3-pyridazinone (a compound of the formula (2-46) and No. (1)-40 in Table 1)

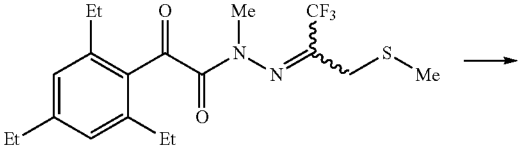

((4-46)-(1)-40)

-continued

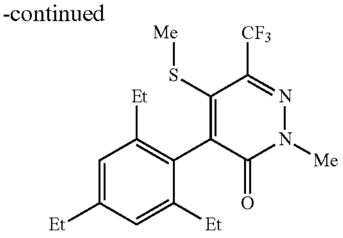

((2-46)-(1)-40)

To a 200 ml volume four-necked flask, tetrahydrofuran (anhydrous) (60 ml) and potassium t-butoxide (0.64 g) were added at room temperature. A solution of 1-[2-(2,4,6-triethylphenyl)-2-oxoacetyl]-2-(1,1,1-trifluoro-3-methylsulfanyl-2-propylidene)-1-methylhydrazine ((4-46)-(1)-40) (2.30 g) which was azeotropic-distilled with toluene one time in tetrahydrofuran (anhydrous) (60 ml) was added dropwise at room temperature over 23 minutes. The reaction mixture was stirred for 30 minutes, and then potassium t-butoxide (0.67 g) was added. The resulting reaction mixture was stirred for 30 minutes, poured into water (70 ml), and extracted with ethyl acetate (100 ml) 2 times. The organic layer was washed with saturated brine (30 ml), dried over anhydrous magnesium sulfate, concentrated under reduced pressure, purified by silica gel column chromatography (hexane:ethyl acetate=8:1 to hexane:ethyl acetate=3:1), recrystallized from hexane, to give 0.282 g of 4-(2,4,6-triethylphenyl)-2-methyl-5-methylsulfanyl-6-trifluoromethyl-2,3-dihydro-3-pyridazinone ((2-46)-(1)-40). Further, the filtrate was concentrated under reduced pressure, recrystallized from hexane again, and filtered to give 0.406 g of 4-(2,4,6-triethylphenyl)-2-methyl-5-methylsulfanyl-6-trifluoromethyl-2,3-dihydro-3-pyridazinone ((2-46)-(1)-40).

1H NMR ($CDCl_3$)

δ ppm: 7.02 (2H, s), 3.85 (3H, s), 2.67 (2H, q, J=7.6 Hz), 2.45-2.28 (4H, m), 1.84 (3H, s), 1.27 (3H, t, J=7.6 Hz), 1.15 (6H, t, J=7.6 Hz)

Example 34

Production of 4-(2,4,6-triethylphenyl)-2-methyl-5-methylsulfinyl-6-trifluoromethyl-2,3-dihydro-3-pyridazinone (a compound of the formula (2-49) and No. (1)-40 in Table 1)

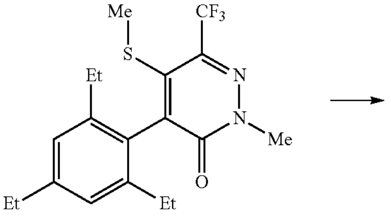

((2-46)-(1)-40)

-continued

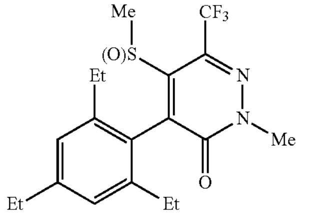

((2-49)-(1)-40)

To a 100 ml volume four-necked flask, 4-(2,4,6-triethylphenyl)-2-methyl-5-methylsulfanyl-6-trifluoromethyl-2,3-dihydro-3-pyridazinone ((2-46)-(1)-40) (0.683 g) and chloroform (24 ml) were added at room temperature, and stirred. Sodium hydrogen carbonate (0.597 g) and meta-chlorobenzoic acid (0.615 g) was added and the resulting mixture was stirred at room temperature for 4 hours. Then, the reaction mixture was poured into water (30 ml), added sodium sulfite (0.4 g), and extracted with t-butyl methyl ether (30 ml) 4 times. The combined organic layer was washed with saturated brine, dried over anhydrous magnesium sulfate, concentrated under reduced pressure, and subjected to silica gel column chromatography (hexane:ethyl acetate=5:1 to hexane:ethyl acetate=1:1) to give 0.692 g of 4-(2,4,6-triethylphenyl)-2-methyl-5-methylsulfinyl-6-trifluoromethyl-2,3-dihydro-3-pyridazinone ((2-49)-(1)-40).

1H NMR ($CDCl_3$)

δ ppm: 7.05 (1H, s), 7.02 (1H, s), 3.93 (3H, s), 2.70 (3H, s), 2.78-2.63 (2H, m), 2.53-2.04 (4H, m), 1.32-1.23 (3H, m), 1.22-1.11 (6H, m)

Example 35

Production of 4-(2,4,6-triethylphenyl)-5-hydroxy-2-methyl-6-trifluoromethyl-2,3-dihydro-3-pyridazinone (a compound of the formula (1-16) and No. (1)-40 in Table 1)

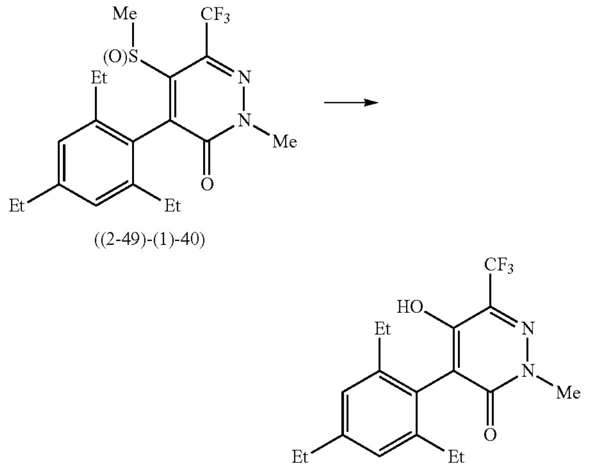

((2-49)-(1)-40)

((1-16)-(1)-40)

To a 50 ml volume three-necked flask, 4-(2,4,6-triethylphenyl)-2-methyl-5-methylsulfinyl-6-trifluoromethyl-2,3-dihydro-3-pyridazinone ((2-49)-(1)-40) (0.692 g), N-methylpyrrolidone (6.40 g), water (3.11 g), and sodium hydroxide (0.626 g) were added at room temperature. The resulting mixture was stirred at 50° C. for 4 hours. The reaction mixture was cooled to room temperature, added 12N hydrochloric acid (3 ml) and water (15 ml), and extracted with ethyl acetate (30 ml) 3 times. The combined organic layer was dried over anhydrous magnesium sulfate, concentrated under reduced pressure, and subjected to silica gel column chromatography (hexane:ethyl acetate=8:1 to hexane:ethyl acetate=5:1 to hexane:ethyl acetate=3:1). Then, the resulting fraction was concentrated under reduced pressure, recrystallized from hexane to give 0.331 g of 4-(2,4,6-triethylphenyl)-5-hydroxy-2-methyl-6-trifluoromethyl-2,3-dihydro-3-pyridazinone ((1-16)-(1)-40) on the filter paper.

1H NMR ($CDCl_3$)

δ ppm: 7.07 (2H, s), 5.99 (1H, br), 3.87 (3H, s), 2.67 (2H, q, J=7.6 Hz), 2.43-2.26 (4H, m), 1.27 (2H, t, J=7.6 Hz), 1.09 (6H, t, J=7.6 Hz)

Reference Production 3

Production of 1-methylsulfinyl-2-propanone (a compound of the formula (7-1-1))

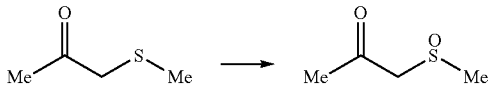

(7-0-1) (7-1-1)

To a 250 ml volume three-necked flask, 1-methylsulfanyl-2-propanone (7-0-1) (24.2 g) was added, and cooled on ice-bath. 33% of aqueous hydrogen peroxide solution (22.6 g) was added dropwise thereto. Then, the mixture was stirred below 5° C. for 3 hours. The resulting reaction mixture was subjected to silica gel column chromatography (ethyl acetate to acetonitrile) to give 24.9 g of 1-methylsulfinyl-2-propanone (7-1-1).

1H NMR ($CDCl_3$)

δ ppm: 3.70 (1H, d J=16 Hz), 3.86 (1H, d J=16 Hz), 2.69 (3H, s), 2.36 (3H, s)

Example 36

Production of 1-[2-(2,6-diethyl-4-methylphenyl)-2-oxoacetyl]-1-methyl-2-(1-methylsulfinyl-2-propylidene)hydrazine (a compound of the formula (4-19) and No. (1)-39 in Table 1)

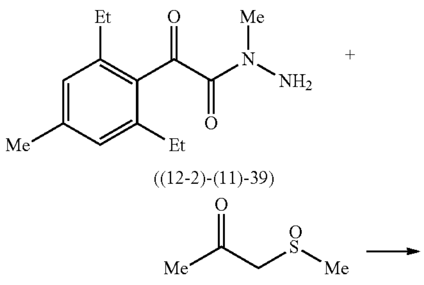

((12-2)-(11)-39)

(7-1-2)

-continued

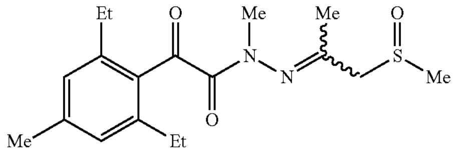

((4-19)-(1)-39)

To a 50 ml volume three-necked flask, 1-[2-(2,6-diethyl-4-methylphenyl)-2-oxoacetyl]-1-methylhydrazine ((12-2)-(11)-39) (2.0 g), tetrahydrofuran (anhydrous) (5 ml), and 1-methylsulfinyl-2-propanone (7-1-1) (1.65 g) were added under a nitrogen atmosphere, and stirred at room temperature for 48 hours. The reaction mixture was concentrated under reduced pressure at room temperature. The residue was subjected to silica gel column chromatography (ethyl acetate to chloroform) to give 0.48 g of 1-[2-(2,6-diethyl-4-methylphenyl)-2-oxoacetyl]-1-methyl-2-(1-methylsulfinyl-2-propylidene)hydrazine ((4-19)-(1)-39).

1H NMR ($CDCl_3$)

δ ppm: 6.92 (1.1H, s), 6.90 (0.9H, s), 3.87-3.64 (2.0H, m), 3.52 (1.7H, s), 3.23 (1.3H, s), 2.75-2.53 (7.0H, m), 2.32 (3.0H, s), 2.26 (1.3H, s), 2.00 (1.7H, s), 1.23-1.17 (6.0H, m)

Example 37

Production of 1-[2-(2,6-diethyl-4-methylphenyl)-2-oxoacetyl]-1-methyl-2-(1-methylsulfinyl-2-propylidene)hydrazine (a compound of the formula (4-19) and No. (1)-39 in Table 1)

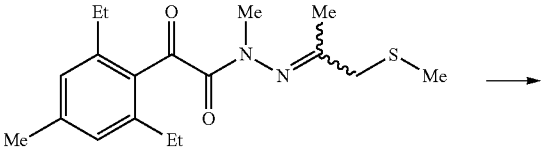

((4-4)-(1)-39)

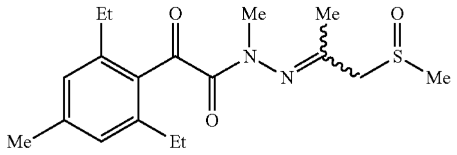

((4-19)-(1)-39)

To a 50 ml volume three-necked flask, 1-[2-(2,6-diethyl-4-methylphenyl)-2-oxoacetyl]-1-methyl-2-(1-methylsulfanyl-2-propylidene)hydrazine ((4-4)-(1)-39) (5.60 g) and methanol (14 ml) were added, and cooled on ice-bath. 33% of aqueous hydrogen peroxide solution (2.1 g) was added dropwise thereto. Then, the mixture was stirred at room temperature for 12 hours. The reaction mixture was concentrated under reduced pressure. The residue was subjected to silica gel column chromatography (ethyl acetate to chloroform) to give 1.95 g of 1-[2-(2,6-diethyl-4-methylphenyl)-2-oxoacetyl]-1-methyl-2-(1-methylsulfinyl-2-propylidene)hydrazine ((4-19)-(1)-39).

Example 38

Production of 4-(2,6-diethyl-4-methylphenyl)-2,6-dimethyl-5-methylsulfinyl-2,3-dihydro-3-pyridazinone (a compound of the formula (2-19) and No. (1)-39 in Table 1)

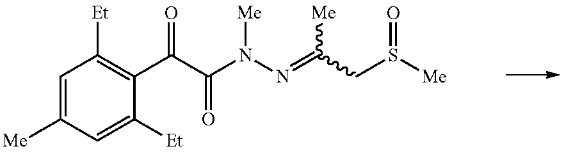

((4-19)-(1)-39)

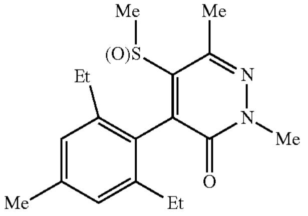

((2-19)-(1)-39)

To a 30 ml volume three-necked flask, 1-[2-(2,6-diethyl-4-methylphenyl)-2-oxoacetyl]-1-methyl-2-(1-methylsulfinyl-2-propylidene)hydrazine ((4-19)-(1)-39) (1.95 g), methanol (1.26 ml), and toluene (5.66 ml) were added, and cooled on ice-bath. Lithium hydroxide monohydrate (0.24 g) was added thereto, and the mixture was stirred for 8 hours.

The reaction mixture was added to water, extracted with ethyl acetate 3 times. The organic layer was washed with water, and dried over anhydrous magnesium sulfate. The organic layer was concentrated under reduced pressure. The residue was subjected to silica gel column chromatography (hexane:ethyl acetate=1:1) to give 1.3 g of 4-(2,6-diethyl-4-methylphenyl)-2,6-dimethyl-5-methylsulfinyl-2,3-dihydro-3-pyridazinone ((2-19)-(1)-39).

1H NMR ($CDCl_3$)

δ ppm: 7.01 (1.1H, s), 6.97 (0.9H, s), 3.82 (3.0H, s), 2.72 (3.0H, s), 2.70 (3.0H, s), 2.46-2.39 (2.0H, m), 2.37 (3.0H, s), 2.20-2.13 (2.0H, m), 1.18-1.13 (6.0H, m)

Example 39

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

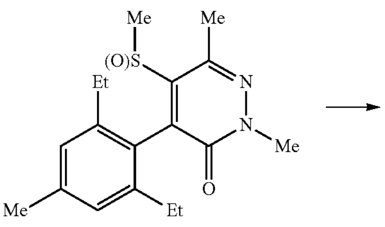

((2-19)-(1)-39)

-continued

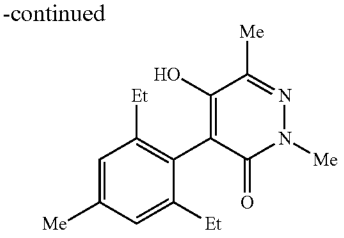

((1-4)-(1)-39)

To a 50 ml volume three-necked flask, 4-(2,6-diethyl-4-methylphenyl)-2,6-dimethyl-5-methylsulfinyl-2,3-dihydro-3-pyridazinone ((2-19)-(1)-39) (0.60 g), DMSO (2.73 ml), and 10% of aqueous tetra-n-butylammonium hydroxide solution (9.4 g) were added under a nitrogen atmosphere, and stirred at 90° C. for 2 hours. The reaction mixture was added to water and hydrochloric acid was added to adjust pH to less than 2. The resulting mixture was extracted with ethyl acetate. The organic layer was dried over anhydrous sodium sulfate and concentrated under reduced pressure. The residue was subjected to silica gel column chromatography (chloroform) to give 0.33 g of 4-(2,6-diethyl-4-methylphenyl)-5-hydroxy-2,6-dimethyl-2,3-dihydro-3-pyridazinone ((1-4)-(1)-39).

Example 40

Production of ethyl 2-(1,3,5-triethylphenyl)-2-oxoacetate (a compound of the formula (9-b))

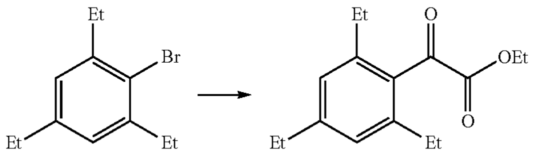

(10-b) (9-b)

To a 3 L volume four-necked flask, magnesium (cutting chip) (51.4 g) and tetrahydrofuran (anhydrous) (250 ml) were added under a nitrogen atmosphere. After the temperature of the mixture was raised to about 30° C., dibromoethane (17.3 g) was added dropwise. The resulting mixture was stirred for 30 minutes. To the mixture, 1,3,5-triethylbromobenzene (10-b) (443.5 g) dissolved in tetrahydrofuran (250 ml) was added dropwise over 2 hours. The mixture was stirred at 50° C. for 1 hour, and cooled to room temperature to give a solution of 1,3,5-triethylphenylmagnesium bromide in tetrahydrofuran.

On the other hand, to a 3 L volume four-necked flask, diethyl oxalate (295 g) and tetrahydrofuran (anhydrous) (350 ml) were added under a nitrogen atmosphere and cooled on ice-bath. The above mentioned solution of 1,3,5-triethylphenylmagnesium bromide in, tetrahydrofuran was added thereto with keeping the temperature below 10° C. The resulting mixture was stirred at room temperature for 2 hours. The pH of the mixture was adjusted to less than 2 with 20 w/w % of sulfuric acid under ice-cooling. The mixture was extracted with toluene. The organic layer was dried over anhydrous sodium sulfate, and concentrated under reduced pressure to give 495.3 g of ethyl 2-(1,3,5-triethylphenyl)-2-oxoacetate (9-b).

1H NMR ($CDCl_3$)

δ ppm: 6.94 (2H, s), 4.32-4.40 (2H, m), 2.47-2.79 (6H, m), 1.34-1.41 (3H, m), 1.13-1.28 (9H, m)

Example 41

Production of 2-(1,3,5-triethylphenyl)-2-oxoacetic acid (a compound of the formula (8-b))

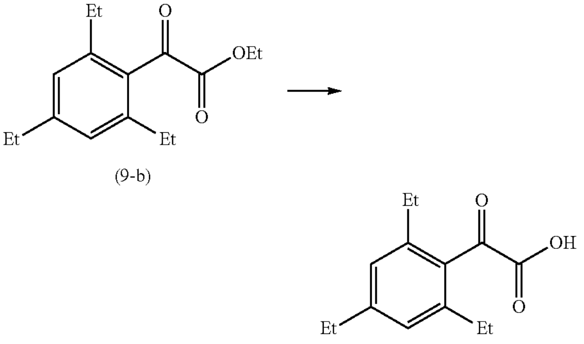

(9-b)

(8-b)

To a 3 L volume four-necked flask, tetrahydrofuran (750 ml) and ethyl 2-(1,3,5-triethylphenyl)-2-oxoacetate (9-b) (261.0 g) were added, and sodium hydroxide (88 g) dissolved in water (237 g) was added dropwise thereto at about 15-20° C. The resulting mixture was stirred at room temperature for 1 hour and 30 minutes. The solid was removed by decantation. The liquid part was concentrated under reduced pressure. The residue was extracted with toluene and water. After the organic layer was removed, the aqueous layer was washed with toluene. The pH of the aqueous layer was adjusted to 1 with dilute sulfuric acid under cooling, and then the aqueous layer was extracted with toluene. The organic layer was washed with water, dried over anhydrous magnesium sulfate, and filtered to remove the insolubles. The filtrate was concentrated under reduced pressure to give 214.8 g of 2-(1,3,5-triethylphenyl)-2-oxoacetic acid (8-b).

1H NMR ($CDCl_3$)

δ ppm: 6.97 (2H, s), 2.44-2.75 (6H, m), 1.13-1.28 (9H, m)

Example 42

Production of 2-(1,3,5-triethylphenyl)-2-oxoacetyl chloride (a compound of the formula (6-b))

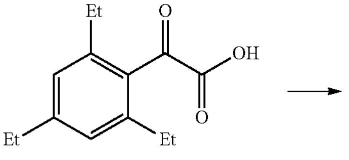

(8-b)

-continued

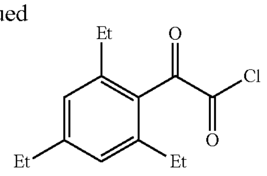

(6-b)

To a 3 L volume four-necked flask, 2-(1,3,5-triethylphenyl)-2-oxoacetic acid (8-b) (214.8 g), toluene (anhydrous) (740 ml), and dimethylformamide (anhydrous) (22.8 ml) were added under a nitrogen atmosphere. After the temperature was raised to about 50° C., thionyl chloride (131 g) was added. The resulting mixture was stirred at 50° C. for 2 hours, and concentrated under reduced pressure to give 204.5 g of 2-(1,3,5-triethylphenyl)-2-oxoacetyl chloride (6-b).

1H NMR ($CDCl_3$)

δ ppm: 6.98 (2H, s), 2.49-2.74 (6H, m), 1.14-1.29 (9H, m)

Example 43

Production of 1-[2-(1,3,5-triethylphenyl)-2-oxoacetyl]-1-methyl-2-(1-methylsulfonyl-2-propylidene)hydrazine (a compound of the formula (4-34) and No. (1)-40 in Table 1)

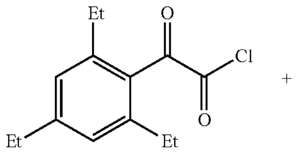

(6-b)

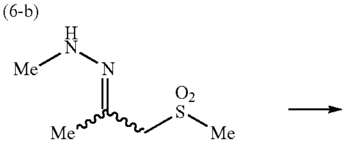

(5-2-1)

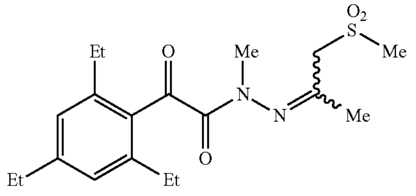

((4-34)-(1)-40)

To a 3 L volume four-necked flask, 1-methyl-2-(1-methylsulfonyl-2-propylidene)hydrazine (5-2-1) (116.0 g), tetrahydrofuran (anhydrous) (600 ml), and triethylamine (98.5 ml) were added under a nitrogen atmosphere, and cooled to about 1° C. To the mixture, 2-(1,3,5-triethylphenyl)-2-oxoacetyl chloride (6-b) (178.5 g) was added dropwise, and stirred at 0° C. for 1 hour. The reaction mixture was added dropwise to hexane (3 L) at room temperature, and stirred for 1 hour. The precipitated solids were collected by filtration, washed with hexane (0.5 L×2) and water (0.5 L×6), and dried under reduced pressure to give 200.9 g of 1-[2-(1,3,5-triethylphenyl)-2-oxoacetyl]-1-methyl-2-(1-methylsulfonyl-2-propylidene)hydrazine ((4-34)-(1)-40).

1H NMR ($CDCl_3$)

δ ppm: 6.94 (1.1H, s), 6.93 (0.9H, s), 4.05 (1.2H, s), 3.94 (0.8H, s), 3.52 (1.7H, s), 3.27 (1.3H, s), 3.06 (1.7H, s), 2.96 (1.3H, s), 2.65-2.55 (6.0H, m), 2.34 (1.3H, s), 2.11 (1.7H, s), 1.25-1.18 (9.0H, m)

Example 44

Production of 4-(1,3,5-triethylphenyl)-2,6-dimethyl-5-methylsulfonyl-2,3-dihydro-3-pyridazinone (a compound of the formula ((2-34) and No. (1)-40) in Table 1)

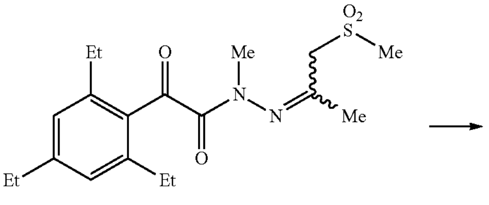

((4-34)-(1)-40)

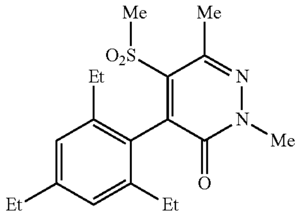

((2-34)-(1)-40)

To a 3 L volume four-necked flask, 1-[2-(1,3,5-triethylphenyl)-2-oxoacetyl]-1-methyl-2-(1-methylsulfonyl-2-propylidene)hydrazine ((4-34)-(1)-40) (137.9 g), methanol (87 ml), and toluene (400 ml) were added under a nitrogen atmosphere, and cooled on ice-bath. Lithium hydroxide monohydrate (15.2 g) was added thereto, and stirred at 0-5° C. for 6 hours.

Concentrated sulfuric acid (18.7 g) dissolved in water (75 ml) was added portionwise with keeping the solution temperature below 5° C. (pH 1). The mixture was extracted with toluene, and then the organic layer was washed with saturated brine, dried over anhydrous magnesium sulfate, and filtered to remove the insolubles. The filtrate was concentrated under reduced pressure. The resulting solid was washed with hot hexane, and dried under reduced pressure to give 101.0 g of 4-(1,3,5-triethylphenyl)-2,6-dimethyl-5-methylsulfonyl-2,3-dihydro-3-pyridazinone ((2-34)-(1)-40).

1H NMR ($CDCl_3$)

δ ppm: 7.03 (2H, s), 3.81 (3H, s), 2.73 (3H, s), 2.66 (2H, q, J=8 Hz), 2.40 (3H, s), 2.35 (4H, q, J=8 Hz), 1.25 (3H, t, J=8 Hz), 1.15 (6H, t, J=8 Hz)

Example 45

Production of 4-(1,3,5-triethylphenyl)-5-hydroxy-2,6-dimethyl-2,3-dihydro-3-pyridazinone (a compound of the formula (1-4) and No. (1)-40 in Table 1)

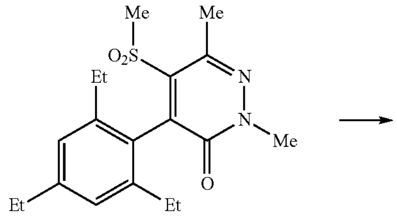

((2-34)-(1)-40)

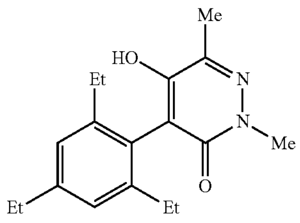

((1-4)-(1)-40)

To a 1 L volume four-necked flask, 4-(1,3,5-triethylphenyl)-2,6-dimethyl-5-methylsulfonyl-2,3-dihydro-3-pyridazinone ((2-34)-(1)-40) (98.5 g) and N-methyl-2-pyrrolidone (383 ml) were added at room temperature. Sodium hydroxide (43.5 g) dissolved in water (118 ml) and a container washing solution (39 ml of water×2) were added at room temperature. The mixture was heated to 70±2° C., and stirred for 6 hours. To the mixture, toluene (300 ml) and water (500 ml) were added. After the mixture was stirred vigorously, additional toluene (300 ml) was added. The organic layer was removed and ice-water (500 ml) was added to the aqueous layer. pH was adjusted to 1-2 with 20 w/w % of sulfuric acid below 20° C. The precipitated solids were collected by filtration and washed with water. After air-drying, the solids were dissolved in ethyl acetate, and dried over anhydrous sodium sulfate. The insolubles were removed by filtration. The filtrate was concentrated under reduced pressure. The resulting crude product was purified by recrystallization (ethyl acetate-hexane) to give 78.0 g of 4-(1,3,5-triethylphenyl)-5-hydroxy-2,6-dimethyl-2,3-dihydro-3-pyridazinone ((1-4)-(1)-40).

1H NMR ($CDCl_3$)

δ ppm: 7.05 (2H, s), 5.26 (1H, s), 3.77 (3H, s), 2.66 (2H, q, J=8 Hz), 2.43-2.26 (7H, m), 1.27 (3H, t, J=8 Hz), 1.07 (6H, t, J=8 Hz)

Reference Production 4

Production of 1-(4-fluorophenyl)-2-methylsulfonylethan-1-one (a compound of the formula (7-2-3))

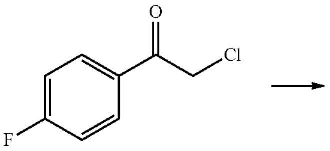

(21-b)

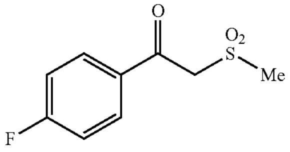

(7-2-3)

To a 1 L volume four-necked flask, sodium methanesulfinate (31.3 g), 4-fluorophenacyl chloride (21-b) (4.8.1 g), and ethanol (300 ml) were added under a nitrogen atmosphere, and heated to reflux for 1 hour. After the mixture was cooled to room temperature, water (500 ml) was added. The precipitated solids were collected by filtration, washed with water, and dried. The solids were dissolved in ethyl acetate, dried over anhydrous sodium sulfate, and concentrated under reduced pressure. The resulting residue was purified by recrystallization (hexane-ethyl acetate) to give 51.9 g of 1-(4-fluorophenyl)-2-methylsulfonylethan-1-one (7-2-3).

1H NMR ($CDCl_3$)

δ ppm: 8.07-8.03 (2H, m), 7.22-7.18 (2H, m), 4.59 (2H, s), 3.15 (3H, s)

Example 46

Production of 1-[1-(4-fluorophenyl)-2-methylsulfonylethylidene]-2-methylhydrazine (a compound of the formula (5-2-4))

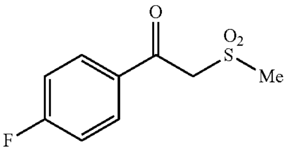

(7-2-3)

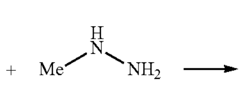

(14-a)

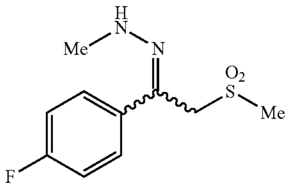

(5-2-4)

To a 50 ml volume three-necked flask, 1-(4-fluorophenyl)-2-methylsulfonylethan-1-one (7-2-3) (5.0 g), methylhydrazine (14-a) (1.2 g), and ethanol (17.1 ml) were added under a nitrogen atmosphere, and heated to reflux for 4 hours. After the mixture was cooled, the precipitated solid was removed by filtration. The filtrate was concentrated under reduced pressure. To the residue was added hot hexane to be dissolved. The mixture was left to cool. Then, the precipitated crystals were collected by filtration, washed, and dried under reduced pressure. The crystal was purified by recrystallization (methanol) to give 1.8 g of 1-[1-(4-fluorophenyl)-2-methylsulfonylethylidene]-2-methylhydrazine (5-2-4).

1H NMR ($CDCl_3$)

δ ppm: 7.69-7.66 (2H, m), 7.10-7.04 (2H, m), 6.65 (1H, s), 4.45 (2H, s), 3.12 (3H, s), 2.91 (3H, s)

Example 47

Production of 1-[2-(2,6-diethyl-4-methylphenyl)-2-oxoacetyl]-2-[1-(4-fluorophenyl)-2-methylsulfonylethylidene]-1-methylhydrazine (a compound of the formula (4-64) and No. (1)-39 in Table 1)

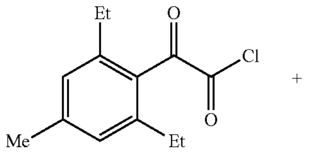

(6-a)

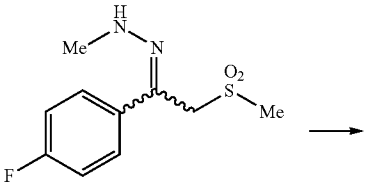

(5-2-4)

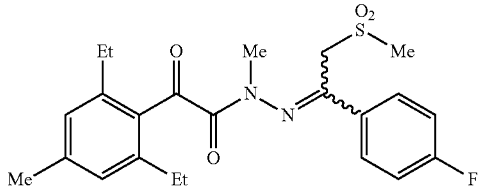

((4-64)-(1)-39)

To a 30 ml volume two-necked flask, 1-[1-(4-fluorophenyl)-2-methylsulfonylethylidene]-2-methylhydrazine (5-2-4) (0.90 g) and anhydrous tetrahydrofuran (5 ml) were added under a nitrogen atmosphere, and added triethylamine (0.37 g) under cooling. To the mixture, 2-(2,6-diethyl-4-methylphenyl)-2-oxoacetyl chloride (6-a) (0.88 g) was added dropwise below 0° C., and stirred under ice-cooling for 2 hours. The reaction mixture was added to water, and extracted with tert-butyl methyl ether. The organic layer was washed with saturated brine, dried over anhydrous sodium sulfate, and concentrated under reduced pressure. The residue was purified by silica gel column chromatography (tert-butyl methyl ether) to give 1.0 g of 1-[2-(2,6-diethyl-4-methylphenyl)-2-oxoacetyl]-2-[1-(4-fluorophenyl)-2-methylsulfonylethylidene]-1-methylhydrazine ((4-64)-(1)-39).

1H NMR ($CDCl_3$)

δ ppm: 7.61-7.57 (2H, m), 7.21-7.12 (2H, m), 6.96 (1.6H, s), 6.88 (0.4H, s), 4.41 (0.4H, s), 4.20 (1.6H, s), 2.99 (0.6H, s), 2.98 (2.4H, s), 2.93 (0.6H, s), 2.86 (2.4H, s), 2.70 (3.2H, q, J=7.5 Hz), 2.60 (0.8H, q, J=7.9 Hz), 2.34 (2.4H, s), 2.31 (0.6H, s), 1.25-1.21 (6.0H, m)

Example 48

Production of 4-(2,6-diethyl-4-methylphenyl)-6-(4-fluorophenyl)-2-methyl-5-methylsulfonyl-2,3-dihydro-3-pyridazinone (a compound of the formula (2-64) and No. (1)-39 in Table 1)

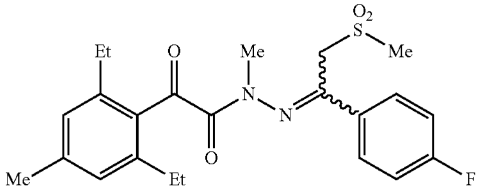

((4-64)-(1)-39)

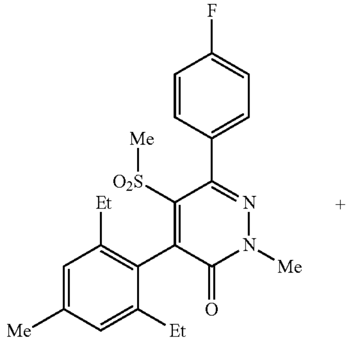

((2-64)-(1)-39)

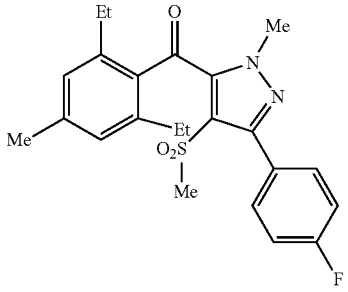

(22-b)

To a 10 ml volume two-necked flask, 1-[2-(2,6-diethyl-4-methylphenyl)-2-oxoacetyl]-2-[1-(4-fluorophenyl)-2-methylsulfonylethylidene]-1-methyl-2-oxoacetohydrazide ((4-64)-(1)-39) (0.66 g) and methanol (2.5 ml) were added under a nitrogen atmosphere. To the mixture, lithium hydroxide monohydrate (62 mg) was added under cooling on −5° C. bath, and stirred under ice-cooling for 4 hours. After cold dilute hydrochloric acid was added under ice-cooling, the mixture was added to cold water, and extracted with ethyl acetate 3 times. The organic layers were washed with saturated brine, dried over anhydrous sodium sulfate, and concentrated under reduced pressure. The residue was subjected to column chromatography (hexane:ethyl acetate=3:1) to give 0.31 g of 4-(2,6-diethyl-4-methylphenyl)-6-(4-fluorophenyl)-2-methyl-5-methylsulfonyl-2,3-dihydro-3-pyridazinone ((2-64)-(1)-39) and 0.12 mg of 5-[(2,6-diethyl-4-methylphenyl)carbonyl]-3-(4-fluorophenyl)-1-methyl-4-methylsulfonyl-1H-pyrazole (22-b).

4-(2,6-diethyl-4-methylphenyl)-6-(4-fluorophenyl)-2-methyl-5-methylsulfonyl-2,3-dihydro-3-pyridazinone ((2-64)-(1)-39)

1H NMR ($CDCl_3$)

δ ppm: 7.61-7.56 (2H, m), 7.19-7.14 (2H, m), 7.05 (2H, s), 3.89 (3H, s), 2.50-2.37 (7H, m), 2.33 (3H, s), 1.19 (6H, t, J=7 Hz)

5-[(2,6-diethyl-4-methylphenyl)carbonyl]-3-(4-fluorophenyl)-1-methyl-4-methylsulfonyl-1H-pyrazole (22-b)

1H NMR ($CDCl_3$)

δ ppm: 7.59-7.54 (2H, m), 7.15-7.09 (2H, m), 7.01 (2H, s), 3.64 (3H, s), 3.13 (3H, s), 2.59-2.51 (4H, m), 2.38 (3H, s), 1.17 (6H, t, J=7 Hz)

Example 49

Production of 4-(2,6-diethyl-4-methylphenyl)-6-(4-fluorophenyl)-5-hydroxy-2-methyl-2,3-dihydro-3-pyridazinone (a compound of the formula (1-28) and No. (1)-39 in Table 1)

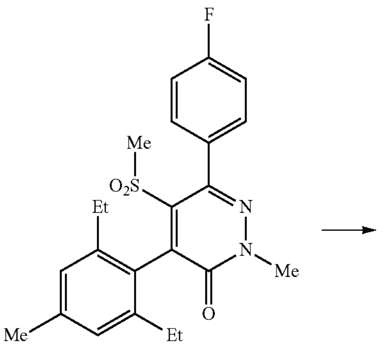

((2-64)-(1)-39)

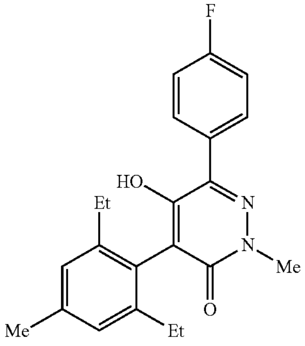

((1-28)-(1)-39)

To a 10 ml volume two-necked flask, 4-(2,6-diethyl-4-methylphenyl)-6-(4-fluorophenyl)-2-methyl-5-methylsulfonyl-2,3-dihydro-3-pyridazinone ((2-64)-(1)-39)) (0.28 g) and N-methyl-2-pyrrolidone (1.09 ml) were added under a nitrogen atmosphere. An aqueous solution of sodium hydroxide (0.11 g) in water (0.56 ml) was added and stirred at 70° C. for 3 hours.

After the mixture was cooling, the mixture was added to iced water, and added hydrochloric acid to adjust pH to 1. The mixture was extracted with ethyl acetate 3 times. The organic layer was washed with saturated brine, dried over anhydrous sodium sulfate, and concentrated under reduced pressure. The residue was subjected to column chromatography (chloroform) to give 0.10 g of 4-(2,6-diethyl-4-methylphenyl)-6-(4-fluorophenyl)-5-hydroxy-2-methyl-2,3-dihydro-3-pyridazinone ((1-28)-(1)-39).

1H NMR ($CDCl_3$)

δ ppm: δ: 7.87-7.81 (2H, m), 7.17-7.11 (2H, m), 7.07 (2H, s), 5.43 (1H, s), 3.89 (3H, s), 2.47-2.30 (7H, m), 1.11 (6H, t, J=8 Hz)

Example 50

Production of 1-[2-[5-ethyl-3-[4-(trifluoromethyl)phenyl]-1H-pyrazol-1-yl]-2-oxoacetyl]-1-methyl-2-(1-methylsulfonyl-2-propylidene)-hydrazine (a compound of the formula (4-134) and No. (9)-5 in Table 25)

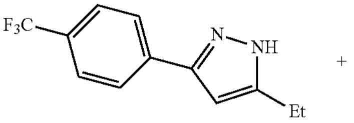

(24-a))

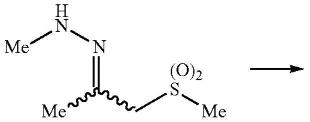

(5-2-1)

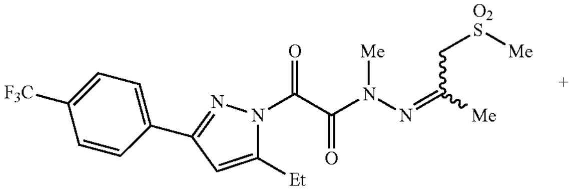

((4-134)-(9)-5)

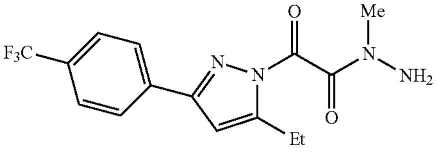

(12-9)

To a 10 ml volume two-necked flask, oxalyl chloride (0.3 g) and toluene (1 ml) were added under a nitrogen atmosphere, and added a solution of 5-ethyl-3-[4-(trifluoromethyl)phenyl]-1H-pyrazole (24-a) (0.5 g) and triethylamine (0.25 g) in toluene (1 ml) under cooling on ice-bath of −20° C. After the mixture was stirred under ice-cooling for 2 hours, a suspension of 1-methyl-2-(1-methylsulfonyl-2-propylidene)hydrazine (5-2-1) (0.66 g) and triethylamine (1.0 g) in toluene (2 ml) was added, and stirred for 3 hours.

The reaction mixture was added to water, and extracted with toluene 3 times. The organic layer was washed with saturated brine, and dried over anhydrous sodium sulfate. After the insolubles were removed by filtration, the filtrate was concentrated under reduced pressure. The residue was subjected to column chromatography (hexane:ethyl acetate=5:1 to 2:1) to give 0.27 g of 1-[2-[5-ethyl-3-[4-(trifluoromethyl)phenyl]-1H-pyrazol-1-yl]-2-oxoacetyl]-1-methyl-2-(1-methylsulfonyl-2-propylidene) hydrazine ((4-

134)-(9)-5) and 0.04 g of 1-[2-[5-ethyl-3-[4-(trifluoromethyl)phenyl]-1H-pyrazol-1-yl]-2-oxoacetyl-1-methylhydrazine (12-9).

1-[2-[5-ethyl-3-[4-(trifluoromethyl)phenyl]-1H-pyrazol-1-yl]-2-oxoacetyl]-1-methyl-2-(1-methylsulfonyl-2-propylidene)hydrazine ((4-134)-(9)-5)

1H NMR ($CDCl_3$)

δ ppm: 7.88 (2.0H, d, J=8 Hz), 7.70-7.65 (2.0H, m), 6.68 (0.4H, s), 6.61 (0.6H, s), 4.12 (0.8H, s), 3.75 (1.2H, s), 3.54 (1.7H, s), 3.28 (1.3H, s), 3.18-3.07 (3.3H, m), 2.57 (1.7H, s), 2.40 (1.3H, s), 2.34 (1.7H, s), 1.41-1.31 (3.0H, m).

1-[2-[5-ethyl-3-[4-(trifluoromethyl)phenyl]-1H-pyrazol-1-yl]-2-oxoacetyl]-1-methylhydrazine (12-9)

1H NMR ($CDCl_3$)

δ ppm: 7.92 (1.4H, d, J=8 Hz), 7.87 (0.6H, d, J=8 Hz), 7.69-7.63 (2.0H, m), 6.60 (0.7H, s), 6.44 (0.3H, s), 3.92 (1.0H, s), 3.33 (2.0H, s), 3.18-3.12 (1.6H, m), 2.74 (0.4H, q, J=8 Hz), 1.39-1.32 (3.0H, m).

Reference Production 5

Production of 2-(1-methyl-1H-indol-3-yl)-2-oxoacetyl chloride (a compound of the formula (26-a))

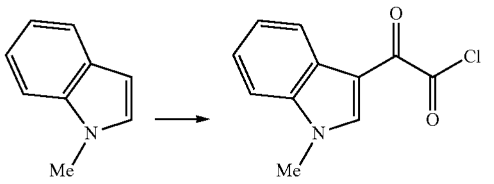

(25-a) (26-a)

To a 100 ml volume three-necked flask, N-methylindole (5.0 g) and diethylether (35 ml) were added under a nitrogen atmosphere, and added oxalyl chloride (9.7 g) at less than 5° C. The mixture was stirred under ice-cooling for 3 hours, and the precipitated solids were collected by suction filtration, washed with cold diethylether, and dried under reduced pressure to give 6.1 g of 2-(1-methyl-1H-indol-3-yl)-2-oxoacetyl chloride (26-a).

1H NMR ($CDCl_3$)

δ ppm: 8.40-8.38 (1H, m), 8.15 (1H, s), 7.43-7.40 (3H, m), 3.91 (3H, s)

Example 51

Production of 1-methyl-1-[2-(1-methyl-1H-indol-3-yl)-2-oxoacetyl]-2-(1-methylsulfonyl-2-propylidene) hydrazine (a compound of the formula (4-203) and No. (13)-28 in Table 32)

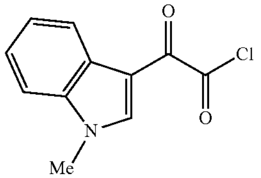

(26-a)

+

-continued

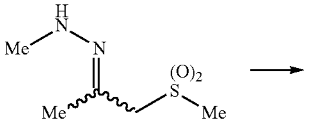

(5-2-1)

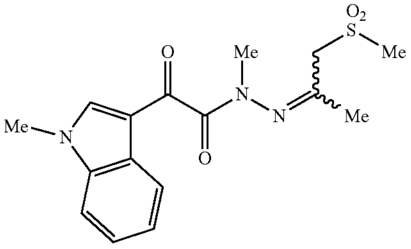

((4-203)-(13)-28)

To a 50 ml volume three-necked flask, 1-methyl-2-(1-methylsulfonyl-2-propylidene)hydrazine (5-2-1) (2.22 g) and tetrahydrofuran (anhydrous) (10 ml) were added under a nitrogen atmosphere. To the mixture, 2-(1-methyl-1H-indol-3-yl)-2-oxoacetyl chloride (26-a) (3.0 g) was added dropwise under ice-cooling, and stirred for 2 hours. The reaction mixture was added to iced water, and the precipitated solids were collected by filtration, washed with water and hexane, and dried under reduced pressure to give 3.4 g of 1-methyl-1-[2 (1-methyl-1H-indol-3-yl)-2-oxoacetyl]-2-(1-methylsulfonyl-2-propylidene)hydrazine ((4-203-(13)28).

1H NMR ($CDCl_3$)

δ ppm: 8.41-8.36 (0.6H, m), 8.22 (0.4H, d, J=7 Hz), 7.95 (0.6H, s), 7.84 (0.4H, s), 7.40-7.29 (3.0H, m), 4.10 (1.2H, s), 3.88-3.83 (3.8H, m), 3.38 (1.9H, s), 3.36 (1.1H, s), 3.16 (1.9H, s), 2.80 (1.1H, s), 2.31 (1.1H, s), 2.21 (1.9H, s)

Example 52

Production of 2,6-dimethyl-4-(1-methyl-1H-indol-3-yl)-5-methylsulfonyl-2,3-dihydro-3-pyridazinone (a compound of the formula (2-203) and No. (13)-28 in Table 32)

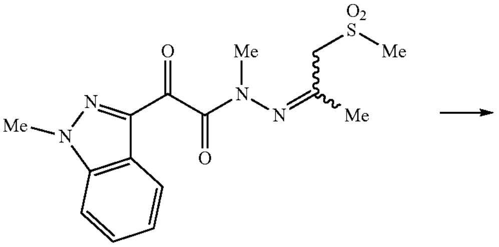

((4-203)-(13)-28)

-continued

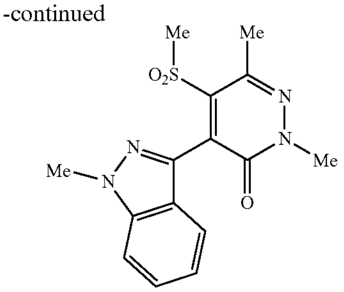

((2-203)-(13)-28)

To a 50 ml volume three-necked flask, 1-methyl-1-[2-(1-methyl-1H-indol-3-yl)-2-oxoacetyl]-2-(1-methylsulfonyl-2-propylidene)hydrazine ((4-203)-(13)-28) (2.0 g), methanol (7.59 ml), and toluene (2.31 ml) were added under a nitrogen atmosphere, then added lithium hydroxide monohydrate (0.24 g) under cooling on ice-bath of −5° C., and stirred for 2 hours. To the mixture, cold dilute hydrochloric acid was added under ice-cooling, and stirred for 5 minutes. Then, the mixture was added to ice water. The precipitated solids were collected by filtration, and dried under reduced pressure to give 1.7 g of 2,6-dimethyl-4-(1-methyl-1H-indol-3-yl)-5-methylsulfonyl-2,3-dihydro-3-pyridazinone ((2-203)-(13)-28).

1H NMR ($CDCl_3$)

δ ppm: 7.57-7.53 (2H, m), 7.39 (1H, d, J=8 Hz), 7.31 (1H, t, J=8 Hz), 7.23 (1H, t, J=7 Hz), 3.89 (3H, s), 3.82 (3H, s), 2.72 (3H, s), 2.51 (3H, s)

Example 53

Production of 5-hydroxy-2,6-dimethyl-4-(1-methyl-1H-indol-3-yl)-2,3-dihydro-3-pyridazinone (a compound of the formula (1-201) and No. (12)-10 in Table 30)

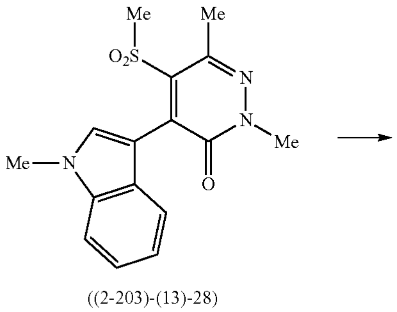

((2-203)-(13)-28)

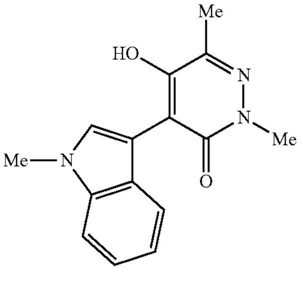

((1-201)-(12)-10)

To a 20 ml volume two-necked flask, 2,6-dimethyl-4-(1-methyl-1H-indol-3-yl)-5-methylsulfonyl-2,3-dihydro-3-pyridazinone ((2-203)-(13)-28) (0.30 g), N-methyl-2-pyrrolidone (1.17 ml), and an aqueous solution of sodium hydroxide (0.14 g) in water (0.6 ml) were added under a nitrogen atmosphere, and stirred at 70° C. for 2 hours. The reaction mixture was added to iced water, and washed with ethyl acetate. The pH of the resulting aqueous layer was adjusted to 5 with cold dilute hydrochloric acid under ice-cooling. The precipitated solids were collected by filtration, washed with water, and dried to give 0.18 g of 5-hydroxy-2,6-dimethyl-4-(1-methyl-1H-indol-3-yl)-2,3-dihydro-3-pyridazinone ((1-201)-(12)-10).

1H NMR ($CDCl_3$)

δ ppm: 7.63 (1H, s), 7.43-7.40 (2H, m), 7.32 (1H, t, J=7 Hz), 7.22 (1H, t, J=8 Hz), 5.95 (1H, s), 3.89 (3H, s), 3.78 (3H, s), 2.37 (3H, s)

Reference Production 6

Production of ethyl 2-(3-methylpyridin-2-yl)-2-oxoacetate (a compound of the formula (29-a))

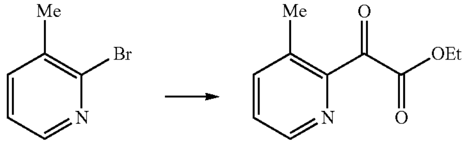

(28-a) (29-a)

To a 300 ml volume three-necked flask, 2-bromo-3-methylpyridine (28-a) (22.1 g) and diethylether (94 ml) were added under a nitrogen atmosphere, then added n-butyl lithium (2.5M in hexane) (54 ml) dropwise below −70° C., and stirred for 2 hours.

On the other hand, to a 500 ml volume three-necked flask, diethyl oxalate (39.4 g) and tetrahydrofuran (anhydrous) (66.3 g) were added under a nitrogen atmosphere, then added the above mentioned diethylether solution dropwise at less than −65° C., and stirred for 5 hours. To the mixture, water was added at less than −40° C., and extracted with methyl t-butyl ether 3 times. The organic layer was washed with saturated brine, dried over anhydrous sodium sulfate, and concentrated under reduced pressure. To the residue, methyl t-butyl ether was added under cooling, and then the precipitated crystals were collected by filtration, washed with cold methyl t-butyl ether, and dried. The residue was subjected to column chromatography (hexane:ethyl acetate=50:1 to 30:1 to 25:1 to 20:1 to 15:1) to give 11.5 g of ethyl 2-(3-methylpyridin-2-yl)-2-oxoacetate (29-a).

1H NMR ($CDCl_3$)

δ ppm: 8.58 (1H, d, J=5 Hz), 7.66 (1H, d, J=8 Hz), 7.41 (1H, dd, J=8, 5 Hz), 4.46 (2H, q, J=7 Hz), 2.67 (3H, s), 1.41 (3H, t, J=7 Hz)

Example 54

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

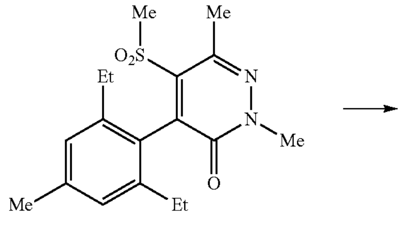

((2-34)-(1)-39)

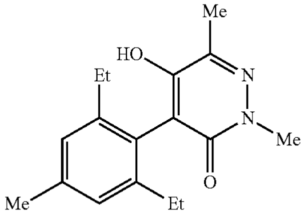

((1-4)-(1)-39)

To a 100 mL volume four-necked flask, 4-(2,6-diethyl-4-methylphenyl)-2,6-dimethyl-5-methylsulfonyl-2,3-dihydro-pyridazin-3-one ((2-34)-(1)-39) (6.57 g), toluene (16.7 g), benzyltrimethylammonium chloride (0.16 g), and sodium hydroxide (2.86 g) were added under a nitrogen atmosphere, and stirred at 120° C. for 38 hours. Then, water (24.2 g) was added at room temperature. The organic layer was removed, and the aqueous layer was mixed with 3.5 w/w % of hydrochloric acid (20 g) at the same temperature, and filtered. The residue was washed with water (12 g) and dried to give 4.8 g of 4-(2,6-diethyl-4-methylphenyl)-5-hydroxy-2,6-dimethyl-2,3-dihydro-3-pyridazinone ((1-4)-(1)-39).

Example 55

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

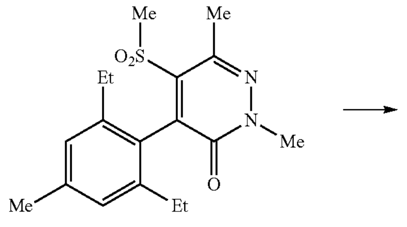

((2-34)-(1)-39)

-continued

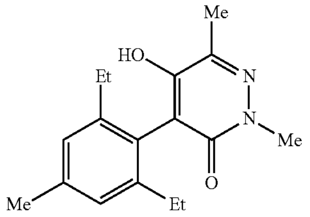

((1-4)-(1)-39)

To a 100 mL volume four-necked flask, 4-(2,6-diethyl-4-methylphenyl)-2,6-dimethyl-5-methylsulfonyl-2,3-dihydro-pyridazin-3-one ((2-34)-(1)-39) (6.57 g), toluene (16.7 g), diethylene glycol dimethylether (3.6 g), and sodium hydroxide (2.86 g) were added under a nitrogen atmosphere, and stirred at 120° C. for 15 hours. Then, water (24.2 g) was added at room temperature. The organic layer was removed, and then the aqueous layer was mixed with 3.5 w/w % of hydrochloric acid (25 g) at the same temperature, and filtered. The residue was washed with water (12 g) and dried to give 4.7 g of 4-(2,6-diethyl-4-methylphenyl)-5-hydroxy-2,6-dimethyl-2,3-dihydro-3-pyridazinone ((1-4)-(1)-39).

Example 56

Production of ethyl 2-(2,6-diethyl-4-methylphenyl)-2-oxoacetate (a compound of the formula (9-a))

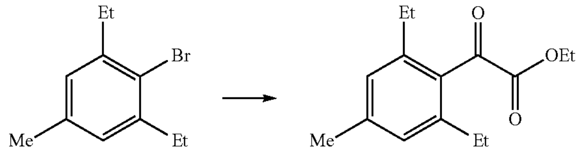

(10-a) (9-a)

To a 2 L volume four-necked flask, magnesium (cutting chip) (66.2 g), tetrahydrofuran (anhydrous) (494 g), and toluene (549 g) were added under a nitrogen atmosphere at room temperature. After starting to stir the mixture, dibromoethane (26.9 g) was added dropwise over 10 minutes at about 20° C., and then the internal temperature was raised to 33° C. The resulting mixture was stirred at 30° C. for 20 minutes. 2,6-diethyl-4-methylbromobenzene (10-a) (549.0 g) was added dropwise thereto at 40° C. over 1 hour. The resulting mixture was stirred at 50° C. for 51 hours, and diethyl oxalate (389.1 g) dissolved in toluene (550.1 g) was added dropwise thereto at about 0° C. over 1 hour. The resulting mixture was stirred at about 5° C. for 1 hour. Then, to the mixture, 3.5 w/w % of hydrochloric acid (832 g) was added dropwise at the same temperature. Then the mixture was warmed to room temperature, and the organic layer was separated. The aqueous layer was extracted with toluene (548.3 g). The organic layers were combined, washed with water (1098 g) and concentrated under reduced pressure to give 710.8 g of ethyl 2-(2,6-diethyl-4-methylphenyl)-2-oxoacetate (9-a).

Reference Production 7

Production of 1-(4-methylphenylsulfonyl)-2-propanone (a compound of the formula (7-2-4))

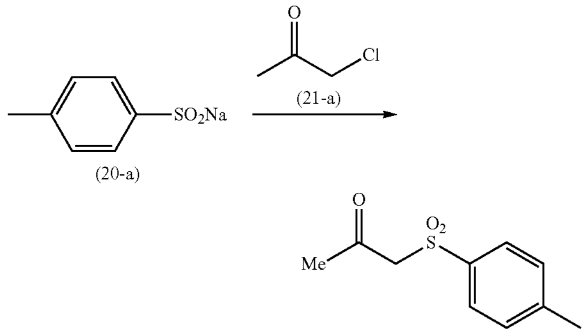

(20-a)

(21-a)

(7-2-4)

To a 100 ml volume three-necked flask, sodium p-toluenesulfinate (20-a) (9.25 g), tetrabutylammonium bromide (1.65 g), toluene (29 g), and chloroacetone (21-a) (5.0 g) were added, and stirred at 65° C. for 1.25 hours. To the mixture, water (10 g) was added, and stirred for 4 hours. After the mixture was cooled to room temperature, the organic layer was separated, and the aqueous layer was extracted with toluene 2 times. The organic layers were combined, washed with saturated brine, dried over anhydrous magnesium sulfate, and concentrated under reduced pressure. The residue was subjected to column chromatography (chloroform: ethyl acetate=20:1) to give 9.749 g of 1-(4-methylphenylsulfonyl)-2-propanone (7-2-4).

1H NMR ($CDCl_3$)

δ ppm: 7.76 (2H, d, J=8 Hz), 7.37 (2H, d, J=8 Hz), 4.14 (2H, s), 2.46 (3H, s), 2.41 (3H, s)

Example 57

Production of 1-[2-(2,6-diethyl-4-methylphenyl)-2-oxoacetyl]-1-methyl-2-[1-(4-methylphenylsulfonyl)-2-propylidene]hydrazine (a compound of the formula (4-36) and No. (1)-39 in Table 1)

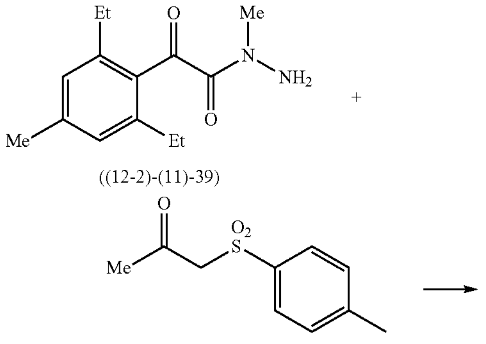

((12-2)-(11)-39)

+

(7-2-4)

-continued

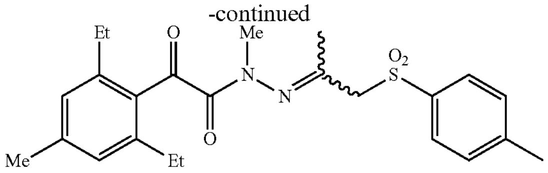

((4-36)-(1)-39)

To a 25 ml volume three-necked flask with Dean-Stark, 1-[2-(2,6-diethyl-4-methylphenyl)-2-oxoacetyl]-1-methylhydrazine ((12-2)-(11)-39) (500 mg), toluene (1.75 ml), and 1-(4-methylphenylsulfonyl)-2-propanone (7-2-4) (470 mg) were added. Water was removed by azeotropic distillation at 45-50° C. under 100 mmHg for 1.5 hours. To the mixture, toluene (1.75 ml) was added, and water was removed by azeotropic distillation at 60° C. under 120 mmHg for 6 hours. The reaction mixture was concentrated under reduced pressure to give 1.109 g of 1-[2-(2,6-diethyl-4-methylphenyl)-2-oxoacetyl]-1-methyl-2-[1-(4-methylphenylsulfonyl)-2-propylidene]hydrazine ((4-36)-(1)-39).

1H NMR ($CDCl_3$)

δ ppm: 7.84-7.70 (2.0H, m), 7.38-7.14 (2.0H, m), 6.90 (0.9H, s), 6.85 (1.1H, s), 4.13 (0.9H, s), 4.06 (1.1H, s), 3.25 (1.4H, s), 3.03 (1.6H, s), 2.55-2.24 (11.6H, m), 2.06 (1.4H, d, J=1 Hz), 1.17 (2.7H, t, J=8 Hz), 1.09 (3.3H, t, J=8 Hz)

Example 58

Production of 4-(2,6-diethyl-4-methylphenyl)-2,6-dimethyl-5-(4-methylphenylsulfonyl)-2,3-dihydro-3-pyridazinone (a compound of the formula (2-36) and No. (1)-39 in Table 1))

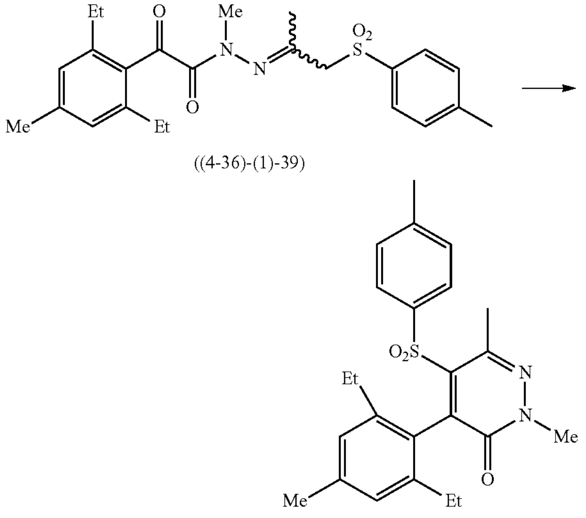

((4-36)-(1)-39)

((2-36)-(1)-39)

To a 10 ml volume two-necked flask, 1-[2-(2,6-diethyl-4-methylphenyl)-1-methyl-2-oxoacetyl]-2-[1-(4-methylphenylsulfonyl)-2-propylidene]hydrazine ((4-36)-(1)-39) (809 mg), toluene (2.3 ml), and methanol (0.5 ml) were added. To the mixture, lithium hydroxide monohydrate (77 mg) was added at 0° C., stirred for 4 hours, and left to stand at 5° C. for 16 hours. The pH of the mixture was adjusted to 1 with 20 w/w % of sulfuric acid. The organic layer was removed, and then the aqueous layer was extracted with toluene 2 times. The organic layers were combined, washed with saturated brine, dried over anhydrous magnesium sulfate, and concentrated under reduced pressure. The residue was subjected to column chromatography (hexane:ethyl acetate=3:1) to give 711 mg of 4-(2,6-diethyl-4-methylphenyl)-2,6-dimethyl-5-(4-methylphenylsulfonyl)-2,3-dihydro-3-pyridazinone ((2-36)-(1)-39).

1H NMR ($CDCl_3$)

δ ppm: 7.32 (2H, d, J=8 Hz), 7.07 (2H, d, J=9 Hz), 6.74 (2H, s), 3.77 (3H, s), 2.72 (3H, s), 2.38 (3H, s), 2.30 (3H, s), 2.13-2.05 (4H, m), 1.02 (6H, t, J=7 Hz).

Example 59

Production 4-(2,6-diethyl-4-methylphenyl)-5-hydroxy-2,6-dimethyl-2,3-dihydro-3-pyridazinone (a compound of the formula (1-4) and No. (1)-39 in Table 1)

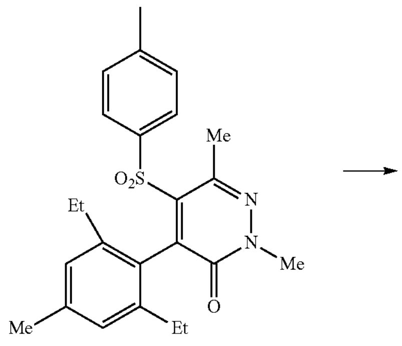

((2-36)-(1)-39)

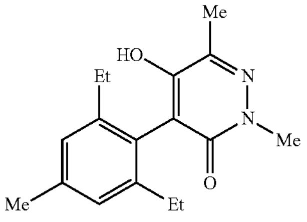

((1-4)-(1)-39)

TO a 10 ml volume two-necked flask with Dean-Stark, 4-(2,6-diethyl-4-methylphenyl)-2,6-dimethyl-5-(4-methylphenylsulfonyl)-2,3-dihydro-3-pyridazinone ((2-36)-(1)-39) (699 mg), toluene (2.45 ml), tetrabutylammonium bromide (27 mg), and 48 w/w % of aqueous sodium hydroxide solution (550 mg) were added. Water was removed by azeotropic distillation under reflux for 33 hours. After the mixture was cooled to room temperature, water was added, and the organic layer was removed. To the aqueous layer, 20 w/w % of sulfuric acid was added to adjust pH to 4, and extracted with toluene 2 times. The organic layers were combined, and concentrated under reduced pressure. The residue was subjected to column chromatography (hexane:ethyl acetate=5:1) to give 189 mg of 4-(2,6-diethyl-4-methylphenyl)-5-hydroxy-2,6-dimethyl-2,3-dihydro-3-pyridazinone ((1-4)-(1)-39).

Example 60

Production of 4-(2,6-diethyl-4-methylphenyl)-2,6-dimethyl-5-phenoxy-2,3-dihydro-3-pyridazinone (a compound of the formula (1-31) and No. (1)-39 in Table 1)

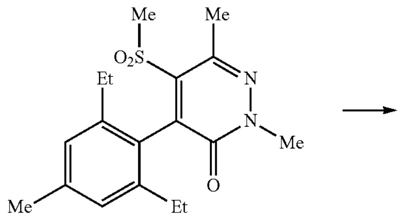

((2-34)-(1)-39)

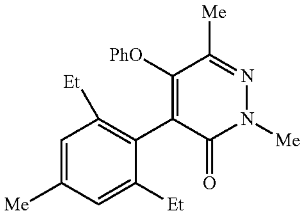

((1-31)-(1)-39)

To a test tube (outside diameter: 21 mm ϕ×overall length: 160 mm), phenol (108 mg), toluene (930 mg), and 60% of oily sodium hydride (44 mg) were added, and stirred at room temperature for 5 minutes. To the mixture, 4-(2,6-diethyl-4-methylphenyl)-2,6-dimethyl-5-methylsulfonyl-2,3-dihydro-pyridazin-3-one ((2-34)-(1)-39) (299 mg) was added, and stirred at room temperature for 1.5 hours and at 100° C. for 1.5 hours. To the mixture, benzyltriethylammonium chloride was added and stirred for 1.5 hours, and then DMSO (1.1 ml) was added and stirred for 2 hours. After the mixture was cooled to room temperature, water was added and extracted with toluene 3 times. The organic layers were combined, washed with 2N aqueous sodium hydroxide solution 3 times, and concentrated under reduced pressure. The residue was subjected to column chromatography (hexane: ethyl acetate=3:1) to give 91 mg of 4-(2,6-diethyl-4-methylphenyl)-2,6-dimethyl-5-phenoxy-2,3-dihydro-3-pyridazinone ((1-31)-(1)-39).

1H NMR ($CDCl_3$)

δ ppm: 7.10 (2H, dd, J=8, 8 Hz), 6.93 (1H, dd, J=8, 8 Hz), 6.79 (2H, s), 6.61 (2H, d, J=8 Hz), 3.82 (3H, s), 2.40-2.16 (10H, m), 1.06 (6H, t, J=7 Hz).

Example 61

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

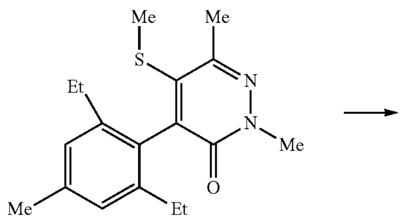

((2-4)-(1)-39)

-continued

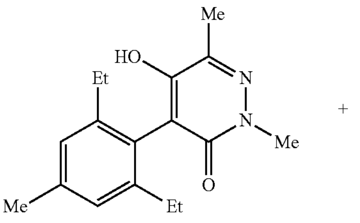

((1-4)-(1)-39)

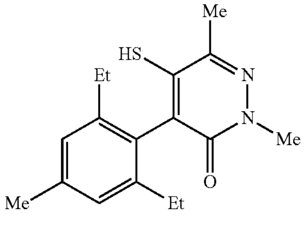

(30-a)

To a test-tube (outside diameter: 21 mm ϕ×overall length: 160 mm), 4-(2,6-diethyl-4-methylphenyl)-2,6-dimethyl-5-methylsulfanyl-2,3-dihydro-3-pyridazinone ((2-4)-(1)-39) (300 mg), N-methyl-2-pyrrolidone (875 mg), and sodium methoxide (410 mg) were added, and stirred at 90° C. for 16 hours. After the mixture was cooled to room temperature, water was added and washed with toluene. To the aqueous layer, 10 w/w % of hydrochloric acid was added to adjust pH to 1, and extracted with toluene 3 times. The organic layers were combined and concentrated under reduced pressure. The residue was subjected to column chromatography (hexane:ethyl acetate=3:1) to give 185 mg of 4-(2,6-diethyl-4-methylphenyl)-5-hydroxy-2,6-dimethyl-2,3-dihydro-3-pyridazinone ((1-4)-(1)-39) and 33 mg of 4-(2,6-diethyl-4-methylphenyl)-5-mercapto-2,6-dimethyl-2,3-dihydro-3-pyridazinone (30-a).

4-(2,6-diethyl-4-methylphenyl)-5-mercapto-2,6-dimethyl-2,3-dihydro-3-pyridazinone (30-a).

1H NMR ($CDCl_3$)

δ ppm: 7.02 (2H, s), 3.76 (3H, s), 3.42 (1H, s), 2.39-2.23 (10H, m), 1.11 (6H, t, J=8 Hz).

Example 62

Production of 1-[2-(2,4,6-triethylphenyl)-2-oxoacetyl]-1-methyl-2-(1-methylethylidene)hydrazine (a compound of the formula (18-b))

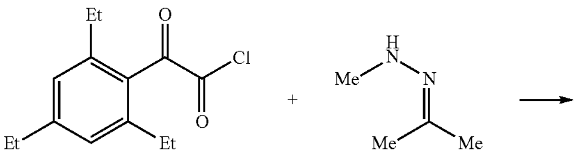

(6-b) (17-a)

-continued

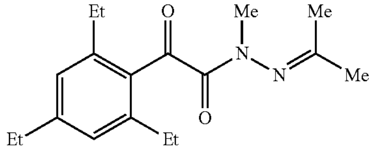

(18-b)

To a 500 ml volume four-necked flask, 1-methyl-2-(2-propylidene)hydrazine (17-a) (4.96 g) anhydrous acetonitrile (130 ml), and triethylamine (6.354 g) were added under a nitrogen atmosphere at room temperature. To the mixture, 2-(1,3,5-triethylphenyl)-2-oxoacetyl chloride (6-b) (15.13 g) dissolved in anhydrous acetonitrile (35 ml) was added dropwise over 12 minutes under ice-cooling. After the mixture was stirred at room temperature for 14 hours, water (200 ml) was added and extracted with ethyl acetate (100 ml×3). The organic layers were combined, and dried over anhydrous magnesium sulfate. After the inorganic salt was removed by filtration, the filtrate was concentrated under reduced pressure to give 14.34 g of 1-[2-(2,4,6-triethylphenyl)-2-oxoacetyl]-1-methyl-2-(1-methylethylidene)hydrazine (18-b).

$^1$H NMR ($CDCl_3$)

δ ppm: 6.92 (0.67H, s), 6.90 (1.33H, s), 3.45 (1H, s), 3.15 (2H, s), 2.77-2.48 (6H, m), 2.14 (1H, s), 2.03 (2H, s), 2.02 (1H, s), 1.87 (2H, s), 1.29-1.12 (9H, m)

Example 63

Production of 1-[2-(2,4,6-triethylphenyl)-2-oxoacetyl]-1-methylhydrazine (a compound of the formula (12-2) and No. (11)-40 in Table 27)

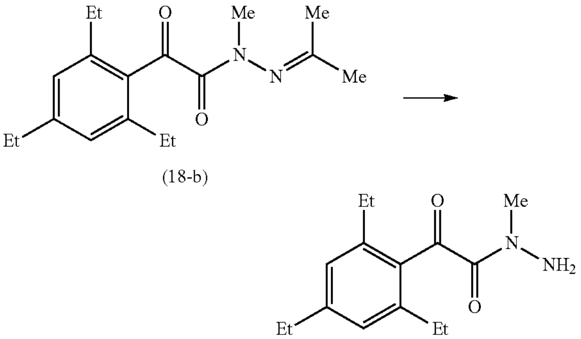

(18-b)

((12-2)-(11)-40)

To a 100 ml volume four-necked flask, 1-[2-(2,4,6-triethylphenyl)-2-oxoacetyl]-1-methyl-2-(1-methylethylidene) hydrazine (18-b) (21.41 g) and ethanol (35 ml) were added under a nitrogen atmosphere, 10 w/w % of hydrochloric acid (14.54 g) was added and stirred at room temperature for 2.5 hours. The reaction mixture was concentrated under reduced pressure. To the residue, saturated brine was added and extracted with chloroform (120 ml×1, 60 ml×2). The organic layers were combined, and dried over anhydrous magnesium sulfate. After the inorganic salt was removed by filtration, the filtrate was concentrated under reduced pressure to give 19.08 g of a crude product. The crude product was subjected to column chromatography (hexane:ethyl acetate=2:1 to 1:1) to give 3.008 g of 1-[2-(2,4,6-triethylphenyl)-2-oxoacetyl]-1-methylhydrazine ((12-2)-(11)-40).

$^1$H NMR ($CDCl_3$)

δ ppm: 6.93 (2H, s), 3.45 (2H, s), 3.24 (1H, s), 2.71-2.51 (6H, m), 1.26-1.16 (9H, m)

Example 64

Production of ethyl 2-[5-(4-chlorophenyl)-2-ethylphenyl]-2-oxoacetate (a compound of the formula (9-c))

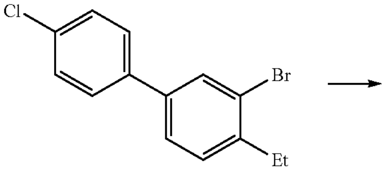

(10-c)

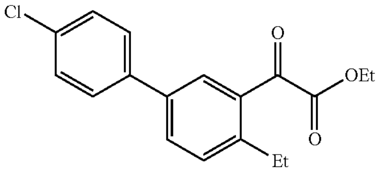

(9-c)

To a 50 ml volume three-necked flask, magnesium (cutting chip) (296 mg) and anhydrous tetrahydrofuran (6.75 ml) were added under a nitrogen atmosphere. Dibromoethane (95 mg) was added dropwise, and stirred at 50° C. for 30 minutes. To the mixture, 2-bromo-4-(4-chlorophenyl)-1-ethylbenzene (10-c) (3.0 g) dissolved in tetrahydrofuran (6.75 ml) was added dropwise over 10 minutes, stirred for 2.5 hours, and cooled to room temperature to give a solution of 5-(4-chlorophenyl)-2-ethylphenylmagnesium bromide in tetrahydrofuran.

On the other hand, to a 50 ml volume three-necked flask, diethyl oxalate (1.78 g) and tetrahydrofuran (anhydrous) (6.75 ml) were added under a nitrogen atmosphere To the mixture, the above mentioned solution was added dropwise under ice-cooling. After the resulting mixture was stirred at room temperature for 1 hour, diethyl oxalate (1.78 g) was added dropwise, and stirred at room temperature for 30 minutes. The pH of the mixture was adjusted to less than 2 with hydrochloric acid (10 w/w %) under ice-cooling, and the mixture was extracted with toluene 3 times. The organic layer was washed with dilute hydrochloric acid, water and brine, and concentrated under reduced pressure. The residue was subjected to column chromatography (hexane:ethyl acetate=20:1) to give ethyl 2-[5-(4-chlorophenyl)-2-ethylphenyl]-2-oxoacetate (9-c) (1.65 g).

1H NMR ($CDCl_3$)

δ ppm: 7.81 (1H, d, J=2 Hz), 7.70 (1H, dd, J=8, 2 Hz), 7.50-7.34 (5H, m), 4.45 (2H, q, J=7 Hz), 2.98 (2H, q, J=7 Hz), 1.42 (3H, t, J=7 Hz), 1.28 (3H, q, J=7 Hz)

Example 65

Production of 2-[5-(4-chlorophenyl)-2-ethylphenyl]-2-oxoacetic acid (a compound of the formula (8-c))

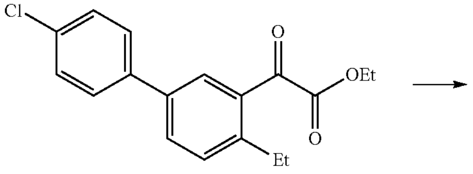

(9-c)

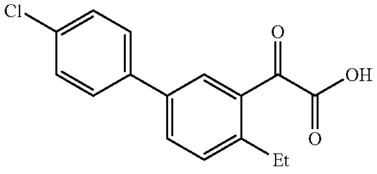

(8-c)

To a 50 ml volume three-necked flask, ethyl 2-[5-(4-chlorophenyl)-2-ethylphenyl]-2-oxoacetate (9-c) (1.43 g), methanol (1.9 ml), and potassium hydroxide (600 mg) dissolved in water (3 ml) were added at room temperature, then added methanol (7.6 ml) and water (3 ml), and stirred at 40° C. for 2 hours. To the mixture was added hexane and 2N aqueous potassium hydroxide solution (3 ml), and then the layers were separated. The aqueous layer was washed with hexane again. The organic layers were combined, and extracted with 2N potassium hydroxide. To the resulting aqueous layer, 10 w/w % of hydrochloric acid was added to adjust pH to less than 1, and extracted with ethyl acetate times. The organic layers were combined, washed with saturated brine, dried over anhydrous magnesium sulfate, and concentrated under reduced pressure to give 1.081 g of 2-[5-(4-chlorophenyl)-2-ethylphenyl]-2-oxoacetic acid (8-c).

1H NMR ($CDCl_3$)

δ ppm: 8.16 (1H, d, J=2 Hz), 7.73 (1H, dd, J=8, 2 Hz), 7.53-7.41 (4H, m), 7.18 (1H, d, J=8 Hz), 5.59 (1H, br s), 2.94 (2H, q, J=7 Hz), 1.27 (3H, t, J=7 Hz)

Example 66

Production of 2-[5-(4-chlorophenyl)-2-ethylphenyl]-2-oxoacetyl chloride (a compound of the formula (6-c))

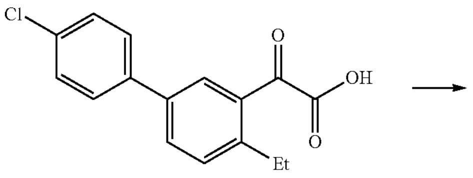

(8-c)

-continued

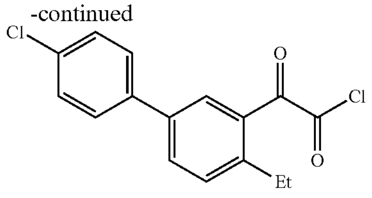

(6-c)

To a 20 ml volume three-necked flask, 2-[5-(4-chlorophenyl)-2-ethylphenyl]-2-oxoacetic acid (8-c) (1.01 g), toluene (3.5 ml), dimethylformamide (3 drops), and thionyl chloride (624 mg) were added under a nitrogen atmosphere, and stirred at 50° C. for 3 hours. The mixture was concentrated under reduced pressure, and azeotropic-distilled with toluene 3 times to give 937 mg of 2-[5-(4-chlorophenyl)-2-ethylphenyl]-2-oxoacetyl chloride (6-c).

1H NMR ($CDCl_3$)

δ ppm: 7.80 (1H, d, J=2 Hz), 7.77 (1H, dd, J=8, 2 Hz), 7.51-7.43 (5H, m), 3.03 (2H, q, J=7 Hz), 1.29 (3H, t, J=7 Hz).

Example 67

Production of 1-[2-[5-(4-chlorophenyl)-2-ethylphenyl]-2-oxoacetyl]-1-methyl-2-(1-methylsulfonyl-2-propylidene)hydrazine (a compound of the formula (4-34) and No. (1)-67 in Table 2)

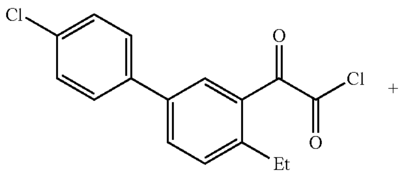

(6-c)

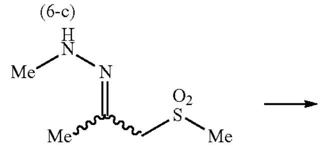

(5-2-1)

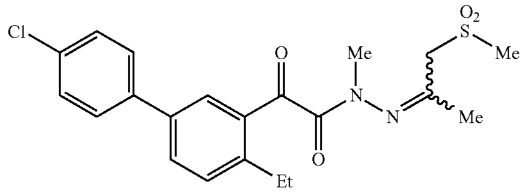

((4-34)-(1)-67)

To a 25 ml volume three-necked flask, 1-methyl-2-(1-methylsulfonyl-2-propylidene)hydrazine (5-2-1) (670 mg), tetrahydrofuran (anhydrous) (2.25 ml), and triethylamine (390 mg) were added under a nitrogen atmosphere. To the mixture, 2-[5-(4-chlorophenyl)-2-ethylphenyl]-2-oxoacetyl chloride (6-c) (937 mg) was added dropwise at 0° C. and stirred for 2 hours. To hexane (15 ml) in a 50 ml volume three-necked flask, the reaction mixture was added dropwise, stirred for 10 minutes, and filtered. The residue was dried under reduced pressure, dissolved in ethyl acetate, and filtered again. The filtrate was concentrated under reduced pressure to give 853 mg of 1-[2-[5-(4-chlorophenyl)-2-ethylphenyl]-2-oxoacetyl]-1-methyl-2-(1-methylsulfonyl-2-propylidene) hydrazine ((4-34)-(1)-67). The filtrate from the first filtration was concentrated under reduced pressure, the residue was subjected to column chromatography (hexane:ethyl acetate=1.5:1) to give 240 mg of additional 1-[2-[5-(4-chlorophenyl)-2-ethylphenyl]-2-oxoacetyl]-1-methyl-2-(1-methylsulfonyl-2-propylidene)hydrazine ((4-34)-(1)-67).

1H NMR ($CDCl_3$)

δ ppm: 7.84-7.76 (1.0H, m), 7.73-7.64 (1.0H, m), 7.50-7.40 (5.0H, m), 4.10 (0.5H, s), 4.05 (0.5H, s), 3.82 (0.3H, s), 3.76 (0.7H, s), 3.47 (1.3H, s), 3.30 (0.9H, s), 3.29 (0.8H, s), 3.12-3.00 (3.7H, m), 2.62 (1.2H, s), 2.44 (0.8H, s), 2.32 (1.3H, s), 2.23 (1.0H, s), 1.32-1.25 (3.0H, m)

Example 68

Production of 4-[5-(4-chlorophenyl)-2-ethylphenyl]-2,6-dimethyl-5-methylsulfonyl-2,3-dihydro-3-pyridazinone (a compound of the formula (2-34) and No. (1)-67 in Table 2)

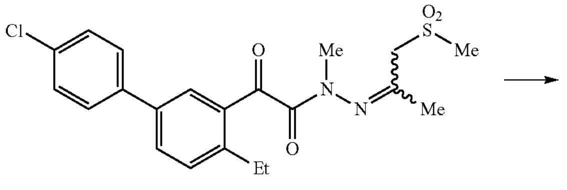

((4-34)-(1)-67)

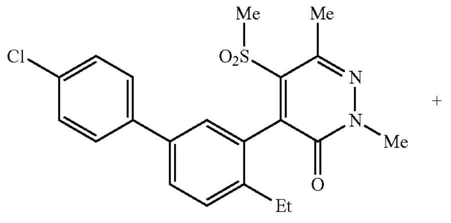

((2-34)-(1)-67)

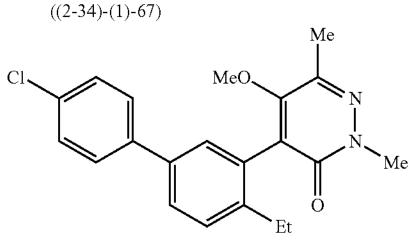

(31-a)

To a 25 ml volume three-necked flask, 1-[2-[5-(4-chlorophenyl)-2-ethylphenyl]-2-oxoacetyl]-1-methyl-2-(1-methylsulfonyl-2-propylidene)hydrazine ((4-34)-(1)-67) (853 mg), toluene (1.75 ml), and methanol (1.85 ml) were added under a nitrogen atmosphere, then added lithium hydroxide monohydrate (83 mg) at 0° C. After the mixture was stirred at 0° C. for 3 hours, 10 w/w % of hydrochloric acid was added to adjust pH to less than 1, and extracted with toluene 3 times. The organic layers were combined, and concentrated under reduced pressure. The residue was subjected to column chromatography (hexane:ethyl acetate=3:1) to give 349 mg of 4-[5-(4-chlorophenyl)-2-ethylphenyl]-2,6-dimethyl-5-methylsulfonyl-2,3-dihydro-3-pyridazinone ((2-34)-(1)-67) and 66 mg of 4-[5-(4-chlorophenyl)-2-ethylphenyl]-5-methoxy-2,6-dimethyl-2,3-dihydro-3-pyridazinone (31-a).

1H NMR ($CDCl_3$)

4-[5-(4-chlorophenyl)-2-ethylphenyl]-2,6-dimethyl-5-methylsulfonyl-2,3-dihydro-3-pyridazinone ((2-34)-(1)-67)

δ ppm: 7.63 (1H, dd, J=8, 2 Hz), 7.51-7.45 (3H, m), 7.39-7.36 (2H, m), 7.27 (1H, d, J=2 Hz), 3.83 (3H, s), 2.73 (3H, s), 2.63 (3H, s), 2.61-2.45 (2H, m), 1.27 (3H, t, J=7 Hz).

4-[5-(4-chlorophenyl)-2-ethylphenyl]-5-methoxy-2,6-dimethyl-2,3-dihydro-3-pyridazinone (31-a)

δ ppm: 7.58-7.48 (3H, m), 7.43-7.33 (4H, m), 3.75 (3H, s), 3.40 (3H, s), 2.64-2.45 (2H, m), 2.29 (3H, s), 1.21 (3H, t, J=8 Hz)

Example 69

Production of 4-[5-(4-chlorophenyl)-2-ethylphenyl]-5-hydroxy-2,6-dimethyl-2,3-dihydro-3-pyridazinone (a compound of the formula (1-4) and No. (1)-67 in Table 2)

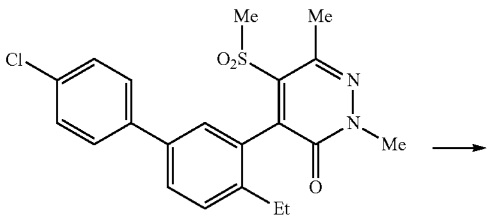

((2-34)-(1)-67)

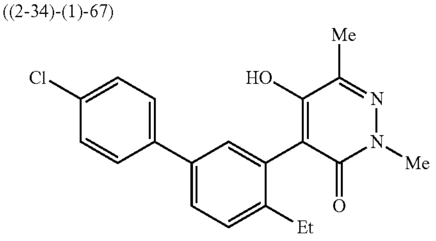

((1-4)-(1)-67)

To a 25 ml volume three-necked flask, 4-[5-(4-chlorophenyl)-2-ethylphenyl]-2,6-dimethyl-5-methylsulfonyl-2,3-dihydro-3-pyridazinone ((2-34)-(1)-67) (290 mg), N-methyl-2-pyrrolidone (890 mg), and aqueous sodium hydroxide solution (410 mg) were added under a nitrogen atmosphere, and stirred at 70° C. for 3 hours. After the reaction mixture was cooled to room temperature, toluene was added and washed. The organic layer was removed. To the resulting aqueous layer, 10 wt % of hydrochloric acid was added to adjust pH to less than 1, and extracted with ethyl acetate times. The organic layers were combined, washed with saturated brine, dried over anhydrous magnesium sulfate, and concentrated under reduced pressure. The residue was subjected to column chromatography (hexane:ethyl acetate=2:1) to give 157 mg of 4-[5-(4-chlorophenyl)-2-ethylphenyl]-5-hydroxy-2,6-dimethyl-2,3-dihydro-3-pyridazinone ((1-4)-(1)-67).

1H NMR ($CDCl_3$)

δ ppm: 7.60 (1H, dd, J=8.2 Hz), 7.49 (3H, d, J=8.0 Hz), 7.38 (2H, d, J=8.0 Hz), 7.32 (1H, d, J=2.0 Hz), 5.43 (1H, s), 3.77 (3H, s), 2.61-2.43 (2H, m), 2.34 (3H, s), 1.15 (3H, t, J=8.0 Hz)

Example 70

Production of 1-[2-(2,6-diethyl-4-methylphenyl)-2-oxoacetyl]-1-methyl-2-(1-methylsulfonyl-2-propylidene)hydrazine (a compound of the formula (4-34) and No. (1)-39 in Table 1)

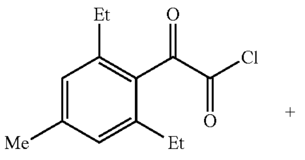

(6-a)

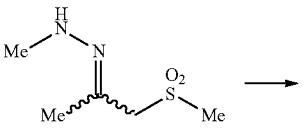

(5-2-1)

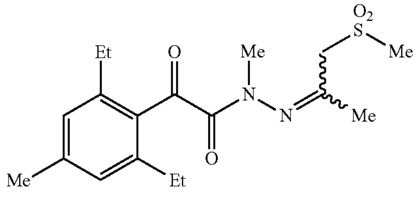

((4-34)-(1)-39)

To a 25 mL volume three-necked flask, 1-methyl-2-(1-methylsulfonyl-2-propylidene)hydrazine (5-2-1) (1.36 g), tetrahydrofuran (anhydrous) (4.50 ml), and triethylamine (1.22 ml) were added under a nitrogen atmosphere, and cooled on ice-bath. To the mixture, 2-(2,6-diethyl-4-methylphenyl)-2-oxoacetyl chloride (6-a) (2.0 g) was added dropwise, and stirred for 2 hours.

On the other hand, to a 50 ml volume three-necked flask, heptane (15 ml) was added. The above mentioned reaction mixture was added dropwise with stirring under ice-cooling. The precipitated crystals were collected by filtration, washed with heptane 2 times, washed with water 2 times, and dried under reduced pressure to give 2.44 g of 1-[2-(2,6-diethyl-4-methylphenyl)-2-oxoacetyl]-1-methyl-2-(1-methylsulfonyl-2-propylidene)hydrazine ((4-34)-(1)-39).

Example 71

Production of 4-(2,6-diethyl-4-methylphenyl)-2,6-dimethyl-5-methylsulfonyl-2,3-dihydro-3-pyridazinone (a compound of the formula (2-34) and No. (1)-39 in Table 1)

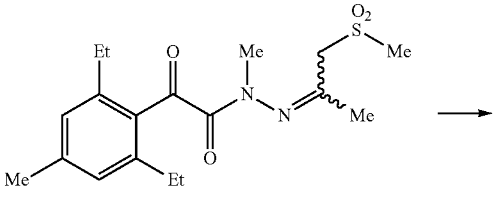

((4-34)-(1)-39)

-continued

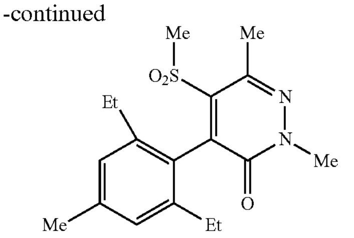

((2-34)-(1)-39)

To a 25 mL volume three-necked flask, 1-[2-(2,6-diethyl-4-methylphenyl)-2-oxoacetyl]-1-methyl-2-(1-methylsulfonyl-2-propylidene)hydrazine ((4-34)-(1)-39) (1.95 g), toluene (4.85 ml), and methanol (1.05 ml) were added under a nitrogen atmosphere, then added lithium hydroxide monohydrate (169 mg) at 0° C. After the mixture was stirred at 0° C. for 4 hours, 10 w/w % of hydrochloric acid was added to adjust to pH to less than 1, and extracted with toluene 3 times. The organic layers were combined and concentrated under reduced pressure. The residue was subjected to column chromatography (hexane:ethyl acetate=3:1) to give 1.077 g of 4-(2,6-diethyl-4-methylphenyl)-2,6-dimethyl-5-methylsulfonyl-2,3-dihydro-3-pyridazinone ((2-34)-(1)-39).

Example 72

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

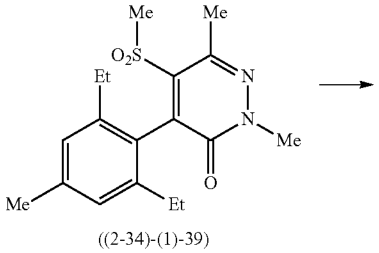

((2-34)-(1)-39)

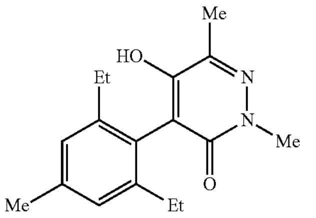

((1-4)-(1)-39)

To a 25 mL volume three-necked flask, 4-(2,6-diethyl-4-methylphenyl)-2,6-dimethyl-5-methylsulfonyl-2,3-dihydro-3-pyridazinone ((2-34)-(1)-39) (1.71 g), N-methyl-2-pyrrolidone (3.1 ml), and 27 w/w % of aqueous sodium hydroxide solution (2.99 g) were added, and stirred at 70° C. for 6 hours. To the mixture was added water (4.0 ml) and toluene (4.6 ml), and then the organic layer was removed. To the resulting aqueous layer, 35 w/w % of hydrochloric acid was added to adjust to pH to less than 1. The precipitated crystals were collected by filtration, washed with water, and dried under reduced pressure to give 1.23 g of 4-(2,6-diethyl-4-methylphenyl)-5-hydroxy-2,6-dimethyl-2,3-dihydro-3-pyridazinone ((1-4)-(1)-39).

Example 73

Production of 4-(2,6-diethyl-4-methylphenyl)-2,6-dimethyl-5-methylsulfonyl-2,3-dihydro-3-pyridazinone (a compound of the formula (2-34) and No. (1)-39 in Table 1)

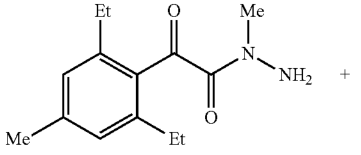

((12-2)-(11)-39)

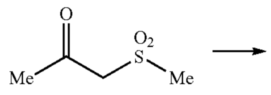

(7-2-1)

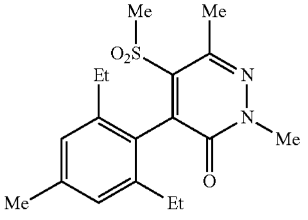

((2-34)-(1)-39)

To a 25 mL volume three-necked flask with Dean-Stark, 1-[2-(2,6-diethyl-4-methylphenyl)-2-oxoacetyl]-1-methylhydrazine ((12-2)-(11)-39) (1.01 g), 1-methylsulfonyl-2-propanone (7-2-1) (613 mg), and toluene (2.9 ml) were added under a nitrogen atmosphere. Water was removed by azeotropic distillation at 60° C. under 100 mmHg for 4 hours. The mixture was concentrated under reduced pressure. To the residue, toluene (1.73 g) and methanol (1.90 ml) were added, then lithium hydroxide monohydrate (80 mg) was added at 0° C. After the mixture was stirred at 0° C. for 4 hours and at 5° C. for 20 hours, 20 w/w % of sulfuric acid was added to adjust pH to less than 1. To the mixture was added toluene and water, and then the organic layer was removed. The aqueous layer was extracted with toluene 2 times. The organic layers were combined, and concentrated under reduced pressure to give 1.28 g of 4-(2,6-diethyl-4-methylphenyl)-2,6-dimethyl-5-methylsulfonyl-2,3-dihydro-3-pyridazinone ((2-34)-(1)-39).

Example 74

Production of 4-(2,6-diethyl-4-methylphenyl)-5-hydroxy-2,6-dimethyl-2,3-dihydro-3-pyridazinone (a compound of the formula (1-4) and No. (1)-39 in Table 1)

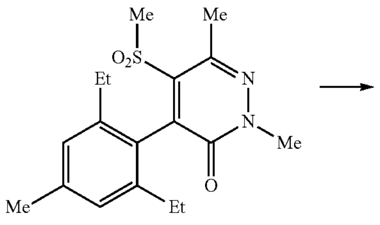

((2-34)-(1)-39)

-continued

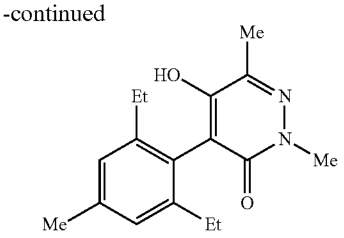

((1-4)-(1)-39)

To a 25 mL volume three-necked flask with Dean-Stark, 4-(2,6-diethyl-4-methylphenyl)-2,6-dimethyl-5-methylsulfonyl-2,3-dihydro-3-pyridazinone ((2-34)-(1)-39) (1.31 g), toluene (4.55 ml), tetrabutylammonium bromide (61 mg), and 48 w/w % of aqueous sodium hydroxide solution (1.25 g) were added under a nitrogen atmosphere. Water was removed by azeotropic distillation under atmospheric pressure for 22 hours. The reaction mixture was cooled to room temperature, added water, and washed with toluene. To the resulting aqueous layer, 10 w/w % of hydrochloric acid was added to adjust pH to less than 3. The precipitated crystals were collected by filtration, washed with water and dried under reduced pressure to give 0.949 g of 4-(2,6-diethyl-4-methylphenyl)-5-hydroxy-2,6-dimethyl-2,3-dihydro-3-pyridazinone ((1-4)-(1)-39).

Example 75

Production of 4-(2,6-diethyl-4-methylphenyl)-5-methoxy-2,6-dimethyl-2,3-dihydro-3-pyridazinone (a compound of the formula (31-b))

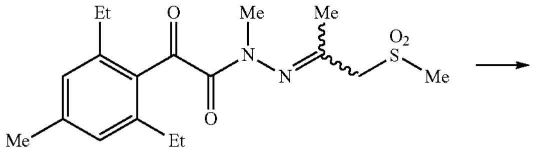

((4-34)-(1)-39)

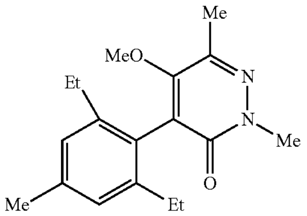

(31-b)

To a 25 mL volume three-necked flask, 1-[2-(2,6-diethyl-4-methylphenyl)-2-oxoacetyl]-1-methyl-2-(1-methylsulfonyl-2-propylidene)hydrazine ((4-34)-(1)-39) (1.00 g) and methanol (3.8 ml) were added under a nitrogen atmosphere, and cooled to 0° C. To the mixture was added toluene (1.15 g) and lithium hydroxide monohydrate (56 mg). After the mixture was stirred at 0° C. for 4 hours and at 5 for 16 hours, 48 w/w % of aqueous sodium hydroxide solution (445 mg) was added at 5° C., and stirred at room temperature for 1.5 hours and at 60° C. for 3 hours. To the mixture, water and toluene were added, then 20 w/w % of sulfuric acid was added to adjust pH to less than 1. After the organic layer was removed, the aqueous layer was extracted with toluene 2 times. The organic layers were combined, washed with saturated brine, and concentrated under reduced pressure to give 746 mg of 4-(2,6-diethyl-4-methylphenyl)-5-methoxy-2,6-dimethyl-2,3-dihydro-3-pyridazinone (31-b).

1H NMR ($CDCl_3$)

δ ppm: 6.95 (2H, s), 3.72 (3H, s), 3.33 (3H, s), 2.47-2.32 (7H, m), 2.27 (3H, s), 1.13 (6H, t, J=8 Hz).

Example 76

Production of 2-(2,6-diethyl-4-methylphenyl)-2-oxoacetohydrazide (a compound of the formula (12-1) and No. (11)-39 in Table 27)

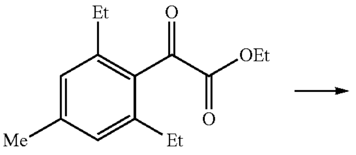

(9-a)

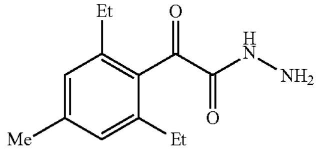

((12-1)-(11)-39)

To a 100 mL volume three-necked flask, ethyl 2-(2,6-diethyl-4-methylphenyl)-2-oxoacetate ((9-a) (10.0 g)) and toluene (35 ml) were added. Hydrazine hydrate (2.13 ml) was added dropwise thereto at 60° C. and the obtained mixture was stirred at 70° C. for 7 hours. The reaction mixture was cooled to room temperature, water was added thereto and the organic layer was removed. The aqueous layer was extracted with toluene. The organic layers were combined and concentrated under reduced pressure to give 9.40 g of 2-(2,6-diethyl-4-methylphenyl)-2-oxoacetohydrazide ((12-1)-(11)-39).

Example 77

Production of 1-[2-(2,6-diethyl-4-methylphenyl)-2-oxoacetyl]-2-(1-phenyl-1-ethylidene)hydrazine (a compound of the formula (40-a) and No. (14)-7 in Table 38)

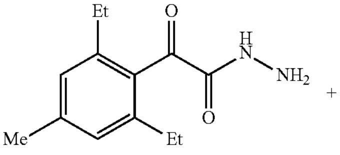

((12-1)-(11)-39)

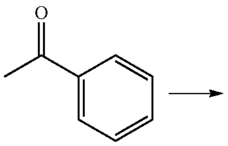

(20-a)

-continued

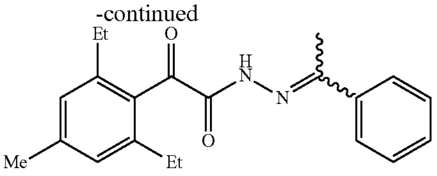

((40-a)-(14)-7)

To a 50 mL volume two-necked flask, 3.0 g of 2-(2,6-diethyl-4-methylphenyl)-2-oxoacetohydrazide ((12-1)-(11)-39), 20 ml of THF (anhydrous), 1.73 g of acetophenone and 780 mg of acetic acid were added under a nitrogen atmosphere, and the mixture was stirred for 6 hours under reflux. The reaction mixture was cooled to room temperature and concentrated under reduced pressure. Water was added to the residue and the resultant was extracted with t-butyl methyl ether. The organic layer was concentrated under reduced pressure and hexane was added thereto. The precipitated crystals were collected by filtration and dried to give 3.77 g of 1-[2-(2,6-diethyl-4-methylphenyl)-2-oxoacetyl]-2-(1-phenyl-1-ethylidene)hydrazine ((40-a)-(14)-7).

1H NMR ($CDCl_3$)

δ ppm: 9.95 (1H, s), 7.89 (2H, m), 7.41 (3H, m), 6.95 (2H, s), 2.49 (4H, q, J=8 Hz), 2.41 (3H, s), 2.35 (3H, s), 1.18 (6H, t, J=8 Hz).

Example 78

Production of 1-[2-(2,6-diethyl-4-methylphenyl)-2-oxoacetyl]-1-methyl-2-(1-phenyl-1-ethylidene)hydrazine (a compound of the formula (40-b) and No. (15)-6 in Table 39)

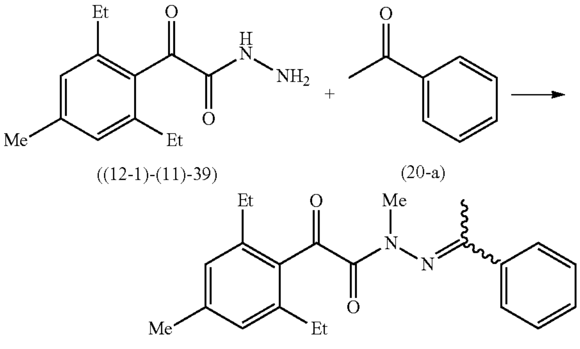

((12-1)-(11)-39) (20-a)

((40-b)-(15)-6)

To a 20 mL volume two-necked flask, 0.50 g of 1-[2-(2,6-diethyl-4-methylphenyl)-2-oxoacetyl]-1-methylhydrazine ((12-2)-(11)-39), 10 ml of tetrahydrofuran (anhydrous), 0.27 g of acetophenone and 130 mg of acetic acid were added under a nitrogen atmosphere, and the mixture was stirred for 6 hours under reflux. The reaction mixture was cooled to room temperature and concentrated under reduced pressure. Water (60 ml) was added to the residue and the resultant was extracted with t-butyl methyl ether. The organic layer was concentrated under reduced pressure and subjected to silica gel column, chromatography (ethyl acetate:chloroform=3:1) to give 0.32 g of 1-[2-(2,6-diethyl-4-methylphenyl)-2-oxoacetyl]-1-methyl-2-(1-phenyl-1-ethylidene)hydrazine ((40-b)-(15)-6).

1H NMR ($CDCl_3$)

δ ppm: 7.84 (0.6H, d, J=6.6 Hz), 7.89 (1.4H, d, J=7.1 Hz), 7.41 (3H, m), 6.91 (0.7H, s), 6.87 (1.3H, s), 3.59 (1H, s), 3.27 (2H, s), 2.65 (4H, m), 2.41 (2H, s), 2.32 (1H, s), 2.30 (2H, s), 2.24 (1H, s), 1.23 (2H, t, J=7.5 Hz), 1.19 (4H, t, J=7.5 Hz)

Example 79

Production of 1-[2-(2,6-diethyl-4-methylphenyl)-2-oxoacetyl]-2-(phenylmethylidene)hydrazine (a compound of the formula (40-a) and No. (14)-6 in Table 38)

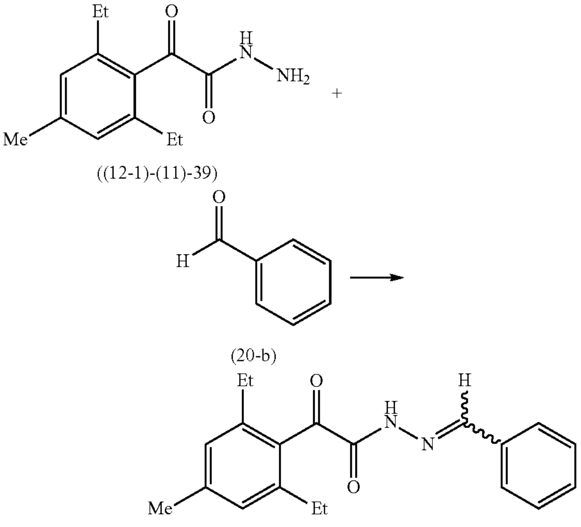

((12-1)-(11)-39)

(20-b)

((40-a)-(14)-6)

To a 100 mL volume three-necked flask with Dean-Stark, 9.38 g of 2-(2,6-diethyl-4-methylphenyl)-2-oxoacetohydrazide ((12-1)-(11)-39), 32 ml of toluene and 4.51 g of benzaldehyde were added under a nitrogen atmosphere, and the mixture was subjected to azeotropic dehydration under 100 mmHg at 50° C. for 2 hours. The reaction mixture was concentrated under reduced pressure to give 12.51 g of 1-[2-(2,6-diethyl-4-methylphenyl)-2-oxoacetyl]-2-(phenylmethylidene)hydrazine ((40-a)-(14)-6).

1H NMR ($CDCl_3$)

δ ppm: 9.99 (1H, s), 8.40 (1H, d, J=10 Hz), 7.81-7.77 (2H, m), 7.45-7.40 (3H, m), 6.94 (2H, s), 2.50 (4H, q, J=7 Hz), 2.35 (3H, s), 1.17 (6H, t, J=7 Hz).

Example 80

Production of 1-[2-(2,6-diethyl-4-methylphenyl)-2-oxoacetyl]-1-methyl-2-(phenylmethylidene)hydrazine (a compound of the formula (40-b) and No. (15)-5 in Table 39)

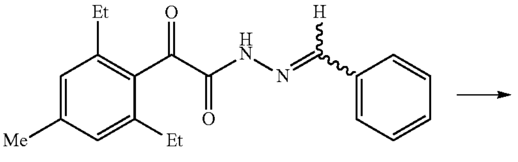

((40-a)-(14)-6)

-continued

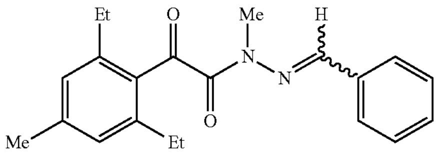

((40-b)-(15)-5)

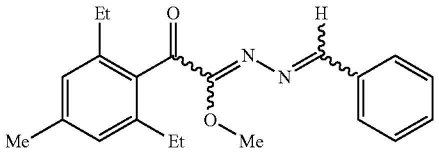

(x-1)

To a 25 mL volume three-necked flask, 300 mg of 1-[2-(2,6-diethyl-4-methylphenyl)-2-oxoacetyl]-2-(phenylmethylidene)hydrazine ((40-a)-(14)-6), 1.9 ml of acetone, 386 mg of potassium carbonate and 152 mg of dimethyl sulfate were added under a nitrogen atmosphere, and the mixture was stirred at room temperature for 1.5 hours. Water was added to the reaction mixture and the resultant was extracted with ethyl acetate three times. The organic layers were combined and dried over anhydrous magnesium sulfate and concentrated under reduced pressure. The residue was subjected to column chromatography (hexane:ethyl acetate=10:1) to give 261 mg of 1-[2-(2,6-diethyl-4-methylphenyl)-2-oxoacetyl]-1-methyl-2-(phenylmethylidene)hydrazine ((40-b)-(15)-5) and 28 mg of methyl 2-(2,6-diethyl-4-methylphenyl)-2-oxo-N-(phenylmethylidene)ethanehydrazonate (compound (x-1)).

1-[2-(2,6-diethyl-4-methylphenyl)-2-oxoacetyl]-1-methyl-2-(phenylmethylidene)hydrazine ((40-b)-(15)-5)

1H NMR ($CDCl_3$)

δ ppm: 7.81 (1H, s), 7.54-7.51 (2H, m), 7.38-7.33 (3H, m), 6.94 (2H, s), 3.47 (3H, s), 2.71 (4H, q, J=7 Hz), 2.33 (3H, s), 1.20 (6H, t, J=7 Hz).

Methyl 2-(2,6-diethyl-4-methylphenyl)-2-oxo-N-(phenylmethylidene)ethanehydrazonate 1H NMR ($CDCl_3$)

δ ppm: 8.67 (1H, s), 7.87-7.83 (2H, m), 7.48-7.45 (3H, m), 6.93 (2H, s), 3.90 (3H, s), 2.51 (4H, q, J=7 Hz), 2.34 (3H, s), 1.16 (6H, t, J=7 Hz).

Example 81

Production of 1-[2-(2,6-diethyl-4-methylphenyl)-2-oxoacetyl]-1-methyl-2-(phenylmethylidene)hydrazine (a compound of the formula (40-b) and No. (15)-5 in Table 39)

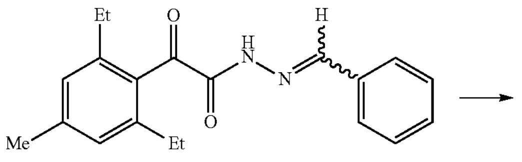

((40-a)-(14)-6)

-continued

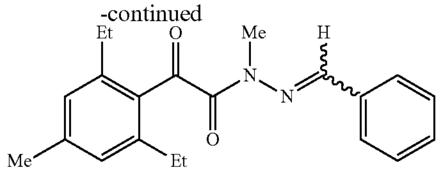

((40-b)-(15)-5)

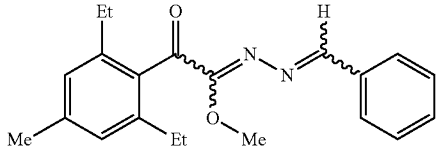

(x-1)

To a 100 mL volume three-necked flask, 5.0 g of 1-[2-(2,6-diethyl-4-methylphenyl)-2-oxoacetyl]-2-(phenylmethylidene)hydrazine ((40-a)-(14)-6), 31 ml of methyl isobutyl ketone, 6.43 g of potassium carbonate and 1.75 ml of dimethyl sulfate were added and the mixture was stirred at room temperature for 7.5 hours. Water was added to the reaction mixture, the organic layer was removed and then the aqueous layer was extracted with 31 ml of methyl isobutyl ketone. The organic layers were combined, dried over anhydrous magnesium sulfate and concentrated under reduced pressure to give 0.324 g of 1-[2-(2,6-diethyl-4-methylphenyl)-2-oxoacetyl]-1-methyl-2-(phenylmethylidene)hydrazine ((40-b)-(15)-5)) and 0.324 g of methyl 2-(2,6-diethyl-4-methylphenyl)-2-oxo-N-(phenylmethylidene)ethanehydrazonate (X-1).

Example 82

Production of 1-[2-(2,6-diethyl-4-methylphenyl)-2-oxoacetyl]-1-methyl-2-(phenylmethylidene)hydrazine (a compound of the formula (40-b) and No. (15)-5 in Table 39)

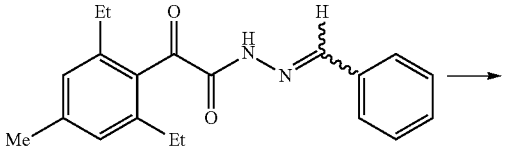

((40-a)-(14)-6)

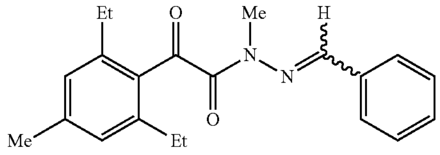

((40-b)-(15)-5)

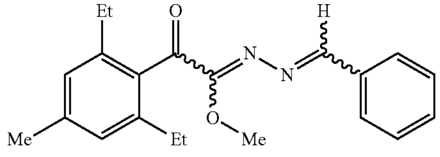

(x-1)

To a 50 mL volume three-necked flask, 7.6 mg of hydrazine hydrate, 2.3 ml of toluene, 629 mg of potassium carbonate and 574 mg of dimethyl sulfate were added and the mixture was stirred at room temperature for 1 hour. The reaction mixture was cooled to 5° C. and 1.6 g of 1-[2-(2,6-diethyl-4-methylphenyl)-2-oxoacetyl]-2-(phenylmethylidene)hydrazine ((40-a)-(14)-6) solved in 2.3 g of toluene was added thereto. The reaction mixture was stirred at 5° C. for 31.5 hours. 5 mL of water was added and the resultant was neutralized to pH 7 with 20 wt % of sulfuric acid. The organic layer was removed and the aqueous layer was extracted with toluene two times. The organic layers were combined and concentrated under reduced pressure to give 1.22 g of a mixture (22:1 (GC area %)) of 1-[2-(2,6-diethyl-4-methylphenyl)-2-oxoacetyl]-1-methyl-2-(phenylmethylidene)hydrazine ((40-b)-(15)-5) and methyl 2-(2,6-diethyl-4-methylphenyl)-2-oxo-N-(phenylmethylidene) ethanehydrazonate (x-1).

Example 83

Production of 1-[2-(2,6-diethyl-4-methylphenyl)-2-oxoacetyl]-1-methyl-2-(phenylmethylidene)hydrazine (a compound of the formula (40-b) and No. (15)-5 in Table 39)

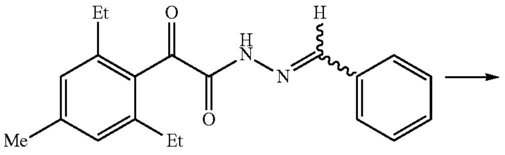

((40-a)-(14)-6)

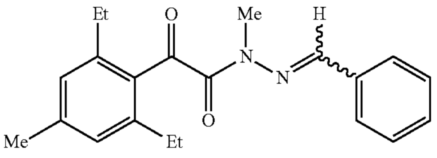

((40-b)-(15)-5)

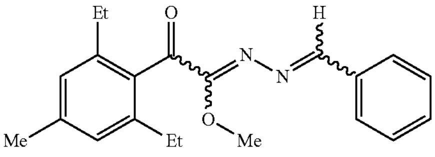

(x-1)

To a 50 mL volume three-necked flask, 1.0 g of 1-[2-(2,6-diethyl-4-methylphenyl)-2-oxoacetyl]-2-(phenylmethylidene)hydrazine ((40-a)-(14)-6), 3.5 ml of toluene and 629 mg of potassium carbonate were added and then, 9.1 mg of N,N-dimethylhydrazine solved in 2.3 ml of toluene and 577 mg of dimethyl sulfate were added thereto at 5° C. The mixture was stirred at 5° C. for 24 hours, 3 g of water was added thereto and the organic layer was removed. The aqueous layer was extracted with 3.5 ml of toluene two times. The organic layers were combined and concentrated under reduced pressure to give 1.037 g of a mixture (19:1 (GC area %)) of 1-[2-(2,6-diethyl-4-methylphenyl)-2-oxoacetyl]-1-methyl-2-(phenylmethylidene)hydrazine ((40-b)-(15)-5) and methyl 2-(2,6-diethyl-4-methylphenyl)-2-oxo-N-(phenylmethylidene)ethanehydrazonate (x-1).

Example 84

Production of 1-[2-(2,6-diethyl-4-methylphenyl)-2-oxoacetyl]-1-methyl-2-(phenylmethylidene)hydrazine (a compound of the formula (40-b) and No. (15)-5 in Table 39)

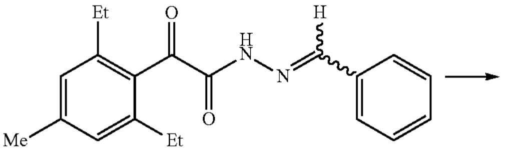

((40-a)-(14)-6)

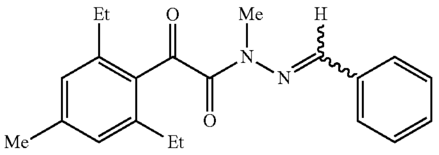

((40-b)-(15)-5)

To a 25 mL volume two-necked flask, 500 mg of 1-[2-(2,6-diethyl-4-methylphenyl)-2-oxoacetyl]-2-(phenylmethylidene)hydrazine ((40-a)-(14)-6), 2.3 ml of toluene, 345 mg of dimethyl sulfate and 315 mg of potassium carbonate were added and the mixture was stirred at 5° C. for 24 hours. To the reaction mixture, 2 ml of water and 2.3 ml of toluene were added and the resultant was extracted. Further, the aqueous layer was extracted with 2.5 ml of toluene two times. The organic layers were combined, concentrated under reduced pressure and subjected to column chromatography (hexane: ethyl acetate=5:1) to give 411 mg of 1-[2-(2,6-diethyl-4-methylphenyl)-2-oxoacetyl]-1-methyl-2-(phenylmethylidene)hydrazine ((40-b)-(15)-5).

Example 85

Production of 1-[2-(2,6-diethyl-4-methylphenyl)-2-oxoacetyl]-1-methylhydrazine (a compound of the formula (12-2) and No. (11)-39 in Table 27)

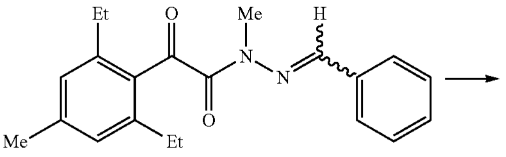

((40-b)-(15)-5)

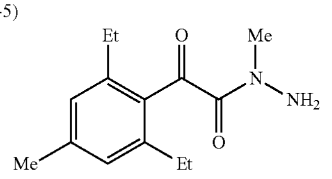

((12-2)-(11)-39)

To a 25 mL volume two-necked flask, 1.47 g of 1-[2-(2,6-diethyl-4-methylphenyl)-2-oxoacetyl]-1-methyl-2-(phenylmethylidene)hydrazine ((40-b)-(15)-5), 5.1 ml of 1,2-dimethoxyethane and 147 mg of 5 wt % Pd—C were added. The mixture was stirred under a hydrogen atmosphere at room temperature for 8 hours. An unsolved substance was removed by filtration and washed with 1,2-dimethoxyethane. The filtrates were combined and concentrated under reduced pressure to give 1.068 g of 1-[2-(2,6-diethyl-4-methylphenyl)-2-oxoacetyl]-1-methylhydrazine ((12-2)-(11)-39).

Example 86

Production of 1-[2-(2,6-diethyl-4-methylphenyl)-2-oxoacetyl]-1-methylhydrazine (a compound of the formula (12-2) and No. (11)-39 in Table 27)

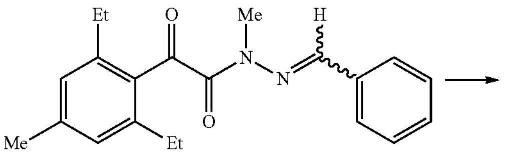

((40-b)-(15)-5)

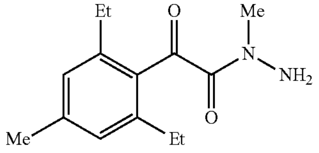

((12-2)-(11)-39)

To a test tube (outside diameter 21 mm ϕ×overall length 160 mm), 100 mg of 1-[2-(2,6-diethyl-4-methylphenyl)-2-oxoacetyl]-1-methyl-2-(phenylmethylidene)hydrazine ((40-b)-(15)-5), 0.5 ml of methanol, 10 mg of 10 wt % Pd-c and one drop of concentrated hydrochloric acid were added and the mixture was stirred at 0° C. for 7 hours under hydrogen atmosphere. An unsolved substance was removed by filtration and washed with methanol. The filtrates were combined and concentrated under reduced pressure to give 70 m g of 1-[2-(2,6-diethyl-4-methylphenyl)-2-oxoacetyl]-1-methylhydrazine ((12-2)-(11)-39)

Example 87

Production of 1-[2-(2,6-diethyl-4-methylphenyl)-2-oxoacetyl]-2-(2-methyl-1-propylidene)hydrazine (a compound of the formula (40-a) and No. (14)-4 in Table 38)

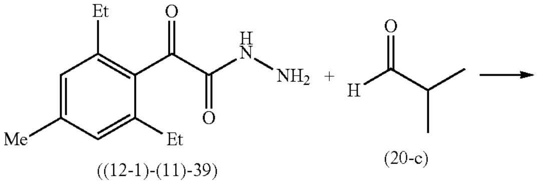

((12-1)-(11)-39) (20-c)

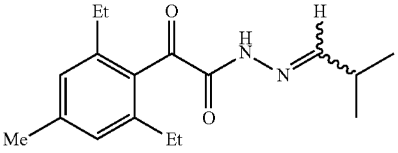

((40-a)-(14)-4)

To a 300 mL volume three-necked flask, 20.0 g of 2-(2,6-diethyl-4-methylphenyl)-2-oxoacetohydrazide ((12-1)-(11)-39), 76 ml of methanol and 12.3 g of isobutylaldehyde were added and the mixture was stirred at room temperature for 1.5 hours. The reaction mixture was concentrated under reduced pressure and then hexane was added thereto. The precipitated crystals were collected by filtration and dried under reduced pressure to give 23.2 g of 1-[2-(2,6-diethyl-4-methylphenyl)-2-oxoacetyl]-2-(2-methyl-1-propylidene)hydrazine ((40-a)-(14)-4).

Example 88

Production of 1-[2-(2,6-diethyl-4-methylphenyl)-2-oxoacetyl]-1-methyl-2-(2-methyl-1-propylidene) hydrazine (a compound of the formula (40-b) and No. (15)-4 in Table 39)

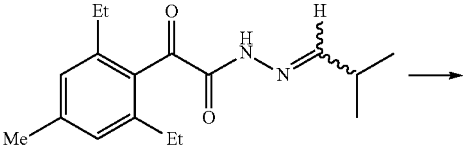

((40-a)-(14)-4)

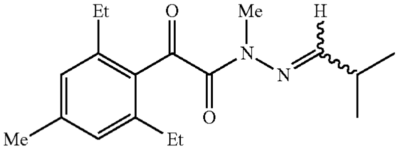

((40-b)-(15)-4)

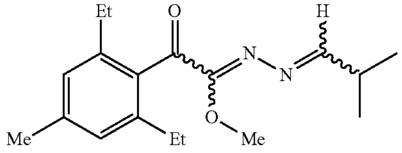

(x-2)

To a 50 mL volume three-necked flask, 5.0 g of 1-[2-(2,6-diethyl-4-methylphenyl)-2-oxoacetyl]-2-(2-methyl-1-propylidene)hydrazine ((40-a)-(14)-4), 19 ml of acetone, 7.19 g of potassium carbonate and 2.13 ml of dimethyl sulfate were added and the mixture was stirred at room temperature for 6 hours. Water and toluene were added to the reaction mixture and the resultant was extracted. Further, aqueous layer was extracted with toluene two times. The organic layers were combined and washed with saturated brine, dried over anhydrous magnesium sulfate and concentrated under reduced pressure. The resultant was subjected to column chromatography (hexane:ethyl acetate=6:1 to 2:1) to give 2.99 g of 1-[2-(2,6-diethyl-4-methylphenyl)-2-oxoacetyl]-1-methyl-2-(2-methyl-1-propylidene)hydrazine ((40-b)-(15)-4) and 0.28 g of methyl 2-(2,6-diethyl-4-methylphenyl)-N-(2-methyl-1-propylidene)-2-oxoethanehydrazonate (x-2).

1-[2-(2,6-diethyl-4-methylphenyl)-2-oxoacetyl]-1-methyl-2-(2-methyl-1-propylidene)hydrazine ((40-b)-(15)-4)

1H NMR ($CDCl_3$)

δ ppm: 7.04 (1H, d, J=5 Hz), 6.90 (2H, s), 3.27 (3H, s), 2.67 (4H, q, J=8 Hz), 2.55-2.42 (1H, m), 2.32 (3H, s), 1.19 (6H, t, J=7 Hz), 1.04 (6H, d, J=7 Hz).

methyl 2-(2,6-diethyl-4-methylphenyl)-N-(2-methyl-1-propylidene)-2-oxoethanehydrazonate (x-2)

1H NMR ($CDCl_3$)

δ ppm: 7.49 (1H, d, J=5 Hz), 6.88 (2H, s), 3.85 (3H, s), 2.59 (4H, q, J=8 Hz), 2.38-2.30 (4H, m), 1.18 (6H, t, J=8 Hz), 0.92 (6H, d, J=7 Hz).

Example 89

Production of 1-[2-(2,6-diethyl-4-methylphenyl)-2-oxoacetyl]-1-methyl-2-(2-methyl-1-propylidene) hydrazine (a compound of the formula (40-b) and No. (15)-4 in Table 39)

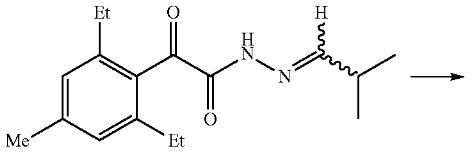

((40-a)-(14)-4)

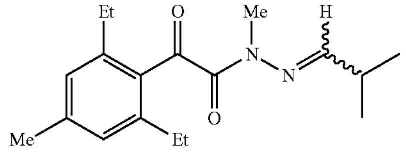

((40-b)-(15)-4)

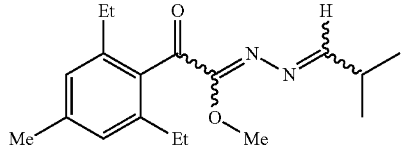

(x-2)

To a 50 mL volume three-necked flask, 5.0 g of 1-[2-(2,6-diethyl-4-methylphenyl)-2-oxoacetyl]-2-(2-methyl-1-propylidene)hydrazine ((40-a)-(14)-4), 16 ml of DMF, 7.19 g of potassium carbonate and 2.13 ml of dimethyl sulfate were added and the mixture was stirred at room temperature for 2.5 hours. Water and toluene were added to the reaction mixture and the resultant was extracted. Further, aqueous layer was extracted with toluene two times. The organic layers were combined and washed with saturated brine, dried over anhydrous magnesium sulfate and concentrated under reduced pressure. The resultant was subjected to column chromatography (hexane:ethyl acetate=6:1 to 2:1) to give 3.04 g of 1-[2-(2,6-diethyl-4-methylphenyl)-2-oxoacetyl]-1-methyl-2-(2-methyl-1-propylidene)hydrazine ((40-b)-(15)-4) and 0.74 g of methyl 2-(2,6-diethyl-4-methylphenyl)-N-(2-methyl-1-propylidene)-2-oxoethanehydrazonate (x-2).

Example 90

Production of 1-[2-(2,6-diethyl-4-methylphenyl)-2-oxoacetyl]-1-methylhydrazine (a compound of the formula (12-2) and No. (11)-39 in Table 27)

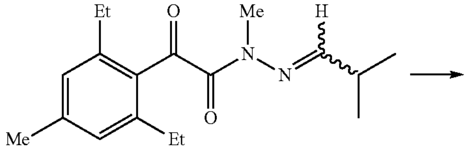

((40-b)-(15)-4)

-continued

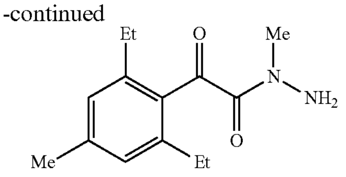

((12-2)-(11)-39)

To a 25 mL volume three-necked flask, 1.0 g of 1-[2-(2,6-diethyl-4-methylphenyl)-2-oxoacetyl]-1-methyl-2-(2-methyl-1-propylidene)hydrazine ((40-b)-(15)-4), 3.8 ml of methanol and 330 mg of 50 wt % hydroxylamine aqueous solution were added, and the mixture was stirred at 50° C. for 2.5 hours and then 60° C. for 14.5 hours. The reaction mixture was concentrated under reduced pressure and water and t-butyl methyl ether were added to the residue. The precipitated crystals were collected by filtration, washed with hexane and dried to give 0.63 g of 1-[2-(2,6-diethyl-4-methylphenyl)-2-oxoacetyl]-1-methylhydrazine ((12-2)-(11)-39).

Example 91

Production of 1-[2-(2,6-diethyl-4-methylphenyl)-2-oxoacetyl]-2-propylidenehydrazine (a compound of the formula (40-a) and No. (14)-3 in Table 38)

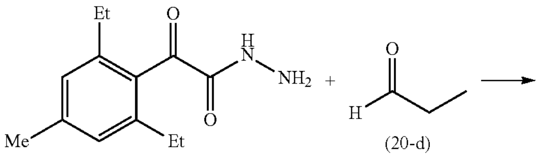

(20-d)

((12-2)-(11)-39)

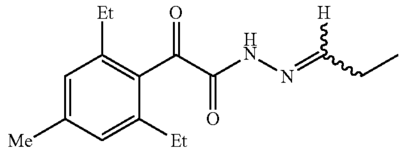

((40-a)-(14)-3)

To a 100 mL volume three-necked flask, 10.0 g of 2-(2,6-diethyl-4-methylphenyl)-2-oxoacetohydrazide ((12-1)-(11)-39), 38 ml of methanol and 6.16 ml of propanal were added and the mixture was stirred at room temperature for 2 hours. The reaction mixture was concentrated under reduced pressure. The residue was washed with hexane and dried under reduced pressure to give 9.44 g of 1-[2-(2,6-diethyl-4-methylphenyl)-2-oxoacetyl]-2-propylidenehydrazine ((40-a)-(14)-3).

Example 92

Production of 1-[2-(2,6-diethyl-4-methylphenyl)-2-oxoacetyl]-1-methyl-2-propylidenehydrazine (a compound of the formula (40-b) and No. (15)-3 in Table 39)

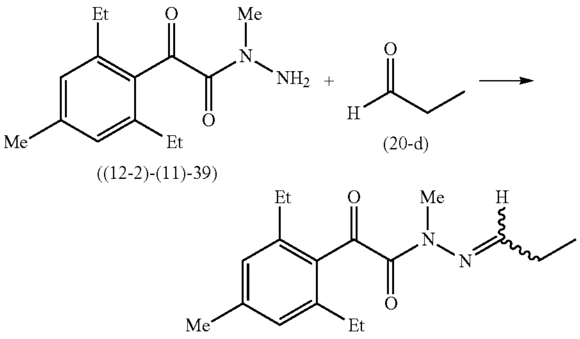

((12-2)-(11)-39) (20-d)

((40-b)-(15)-3)

To a test tube (outside diameter 21 mmϕ×overall length 160 mm), 100 mg of 1-[2-(2,6-diethyl-4-methylphenyl)-2-oxoacetyl]-1-methylhydrazine ((12-2)-(11)-39), 380 mg of methanol and 58 μl of propanal were added and the mixture was stirred at room temperature for 1.5 hours. Water was added to the reaction mixture and the resultant was extracted with chloroform three times. The organic layers were combined, dried over anhydrous magnesium sulfate and concentrated under reduced pressure to give 127 mg of 1-[2-(2,6-diethyl-4-methylphenyl)-2-oxoacetyl]-1-methyl-2-propylidenehydrazine ((40-b)-(15)-3).

1H NMR ($CDCl_3$)

δ ppm: 7.13 (1H, t, J=5 Hz), 6.90 (2H, s), 3.27 (3H, s), 2.68 (4H, q, J=7 Hz), 2.32 (3H, s), 2.30-2.23 (2H, m), 1.19 (6H, t, J=7 Hz), 1.03 (3H, t, J=8 Hz).

Example 93

Production of 2-ethylidene-1-[2-(2,6-diethyl-4-methylphenyl)-2-oxoacetyl]hydrazine (a compound of the formula (40-a) and No. (14)-2 in Table 38)

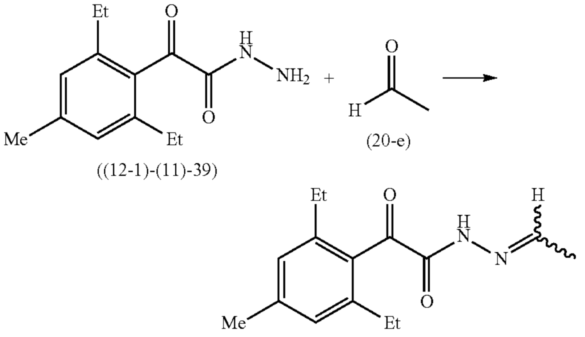

((12-1)-(11)-39) (20-e)

((40-a)-(14)-2)

To a 100 mL volume three-necked flask, 10.0 g of 2-(2,6-diethyl-4-methylphenyl)-2-oxoacetohydrazide ((12-1)-(11)-39), 38 ml of methanol and 4.79 ml of acetaldehyde were added and the mixture was stirred at room temperature for 1 hour. The reaction mixture was concentrated under reduced pressure, and the residue was washed with hexane and dried under reduced pressure to give 9.71 g of 2-ethylidene-1-[2-(2,6-diethyl-4-methylphenyl)-2-oxoacetyl]hydrazine ((40-a)-(14)-2) as a mixture (5:1) of geometrical isomer.

Example 94

Production of 1-[2-(2,6-diethyl-4-methylphenyl)-2-oxoacetyl]-2-ethylidene-1-methylhydrazine (a compound of the formula (40-b) and No. (15)-2 in Table 39)

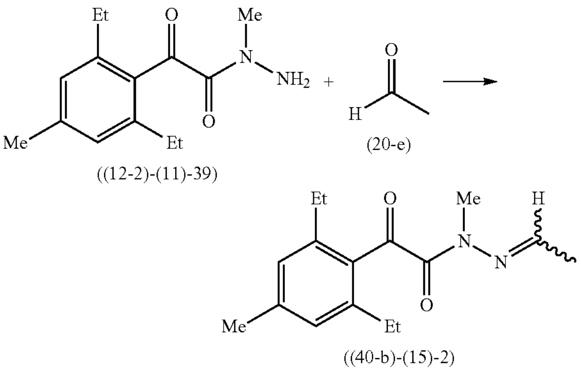

((12-2)-(11)-39) (20-e)

((40-b)-(15)-2)

To a test tube (outside diameter 21 mmϕ×overall length 160 mm), 100 mg of 1-[2-(2,6-diethyl-4-methylphenyl)-2-oxoacetyl]-1-methylhydrazine ((12-2)-(11)-39), 380 mg of methanol and 45 μl of acetaldehyde were added and the mixture was stirred at room temperature for 2 hours. Water was added to the reaction mixture and the resultant was extracted with chloroform three times. The organic layers were combined, dried over anhydrous magnesium sulfate and concentrated under reduced pressure to give 103 mg of 1-[2-(2,6-diethyl-4-methylphenyl)-2-oxoacetyl]-2-ethylidene-1-methylhydrazine ((40-b)-(15)-2).

1H NMR ($CDCl_3$)

δ ppm: 7.12 (1H, q, J=5 Hz), 6.90 (2H, s), 3.26 (3H, s), 2.69 (4H, q, J=7 Hz), 2.32 (3H, s), 1.92 (3H, d, J=5 Hz), 1.20 (6H, t, J=7 Hz).

Example 95

Production of 1-[2-(2,6-diethyl-4-methylphenyl)-2-oxoacetyl]-2-methylidenehydrazine (a compound of the formula (40-a) and No. (14)-1 in Table 38)

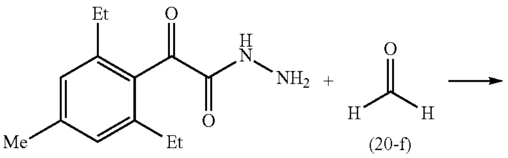

((12-1)-(11)-39) (20-f)

-continued

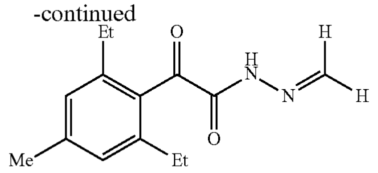

((40-a)-(14)-1)

To a 100 mL volume three-necked flask, 10.0 g of 2-(2,6-diethyl-4-methylphenyl)-2-oxoacetohydrazide ((12-1)-(11)-39), 38 ml of methanol and 6.93 g of 37 wt % formalin aqueous solution were added and the mixture was stirred at room temperature for 5 hours. Methanol was added to the reaction mixture and cooled on ice-bath. The precipitated crystals were collected by filtration, washed with cool methanol, and dried under reduced pressure to give 1.22 g of 1-[2-(2,6-diethyl-4-methylphenyl)-2-oxoacetyl]-2-methylidenehydrazine ((40-a)-(14)-1).

1H NMR ($CDCl_3$)

δ ppm: 9.44 (1H, s), 6.91 (2H, s), 4.53 (2H, br s), 2.44 (4H, q, J=7 Hz), 2.33 (3H, s), 1.13 (6H, t, J=7 Hz).

Example 96

Production of 1-[2-(2,6-diethyl-4-methylphenyl)-2-oxoacetyl]-1-methyl-2-methylidenehydrazine (a compound of the formula (40-b) and No. (15)-1 in Table 39)

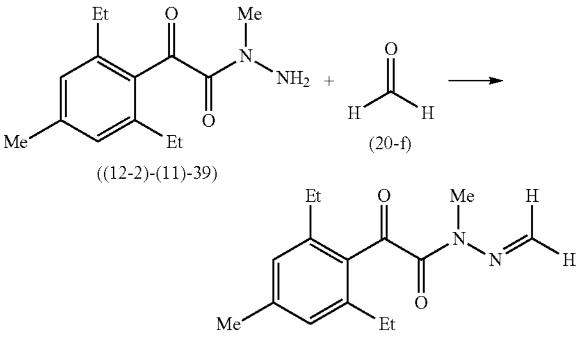

((12-2)-(11)-39) (20-f)

((40-b)-(15)-1)

To a test tube (outside diameter 21 mmϕ×overall length 160 mm), 100 mg of 1-[2-(2,6-diethyl-4-methylphenyl)-2-oxoacetyl]-1-methylhydrazine ((12-2)-(11)-39), 380 mg of methanol and 130 μl of 37 wt % formalin aqueous solution were added and the mixture was stirred at room temperature for 2.5 hours. Water was added to the reaction mixture and the resultant was extracted with chloroform three times. The organic layers were combined, dried over anhydrous magnesium sulfate and concentrated under reduced pressure to give 97 mg of 1-[2-(2,6-diethyl-4-methylphenyl)-2-oxoacetyl]-1-methyl-2-methylidenehydrazine ((40-b)-(15)-1).

1H NMR ($CDCl_3$)

δ ppm: 6.91 (2H, s), 6.74 (1H, d, J=10 Hz), 6.50 (1H, d, J=10 Hz), 3.28 (3H, s), 2.67 (4H, q, J=7 Hz), 2.32 (3H, s), 1.19 (6H, t, J=7 Hz).

The invention claimed is:

1. A method for producing a compound of the formula (2):

(2)

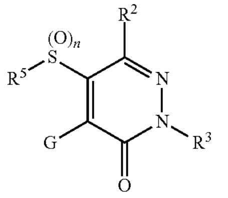

which comprises reacting a compound of the formula (4):

(4)

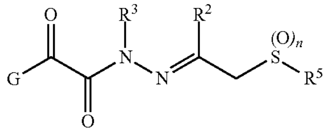

with a base;

wherein the symbols in the formulae (2) and (4) are defined as follows:

$R^2$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio)C1-C6 alkyl group, a (C1-C6 alkylsulfinyl)C1-C6 alkyl group, a (C1-C6 alkylsulfonyl) C1-C6 alkyl group, a phenyl group, or a 5- or 6-membered heteroaryl group;

wherein the C1-C6 alkyl group, the (C1-C6 alkoxy) C1-C6 alkyl group, the C2-C6 alkenyl group, the C2-C6 alkynyl group, the C3-C6 cycloalkyl group, the (C1-C6 alkylthio)C1-C6 alkyl group, the (C1-C6 alkylsulfinyl)C1-C6 alkyl group, and the (C1-C6 alkylsulfonyl)C1-C6 alkyl group may be optionally substituted with one or more halogens, provided that when they are substituted with two or more halogens, then the halogens may be same or different; and the phenyl group and the 5- or 6-membered heteroaryl group may optionally have one or more substituents selected from Group 2, provided that when they have two or more substituents, then the substituents may be same or different;

the Group 2 consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group;

in the Group 2, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different;

$R^3$ represents hydrogen, a C1-C6 alkyl group, a (C1-C6 alkoxy)C1-C6 alkyl group, a C2-C6 alkenyl group, a C2-C6 alkynyl group, a C3-C6 cycloalkyl group, a (C1-C6 alkylthio)C1-C6 alkyl group, a C1-C6 alkylsulfonyl group, a (C1-C6 alkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a phenyl group, a benzyl group, or a phenylsulfonyl group;

wherein the C1-C6 alkyl group, the (C1-C6 alkoxy) C1-C6 alkyl group, the C2-C6 alkenyl group, the C2-C6 alkynyl group, the C3-C6 cycloalkyl group, the (C1-C6 alkylthio)C1-C6 alkyl group, the C1-C6 alkylsulfonyl group, the (C1-C6 alkyl)carbonyl group, and the (C1-C6 alkoxy)carbonyl group may be optionally substituted with one or more halogens, provided that when they are substituted with two or more halogens, then the halogens may be same or different; and the phenyl group, the benzyl group, and the phenylsulfonyl group may optionally have one or more substituents selected from Group 3, provided that when they have two or more substituents, then the substituents may be same or different;

the Group 3 consists of halogen, a C1-C6 alkyl group, a C1-C6 alkoxy group, and a (C1-C6 alkoxy)C1-C6 alkyl group;

in the Group 3, the C1-C6 alkyl group, the C1-C6 alkoxy group, and the (C1-C6 alkoxy)C1-C6 alkyl group may be optionally substituted with one or more halogens, provided that when they are substituted with two or more halogens, then the halogens may be same or different;

$R^5$ represents a C1-C6 alkyl group or a phenyl group;

wherein the C1-C6 alkyl group may be optionally substituted with one or more halogens, provided that when it is substituted with two or more halogens, then the halogens may be same or different; and the phenyl group may optionally have one or more substituents selected from Group 5, provided that when it has two or more substituents, then the substituents may be same or different;

the Group 5 consists of halogen, a C1-C6 alkyl group, and a C1-C6 alkoxy group;

in the Group 5, the C1-C6 alkyl group and the C1-C6 alkoxy group may be optionally substituted with one or more halogens, provided that when they are substituted with two or more halogens, then the halogens may be same or different;

G represents a C6-C10 aryl group, a 5- or 6-membered heteroaryl group, or an 8- to 10-membered fused heteroaryl group;

wherein the C6-C10 aryl group, the 5- or 6-membered heteroaryl group, and the 8- to 10-membered fused heteroaryl group may optionally have one or more substituents selected from Group $R^4$, provided that when they have two or more substituents, then the substituents may be same or different;

the Group $R^4$ consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, a tri(C1-C6 alkyl)silyl group, a C6-C10 aryl group, and a 5- or 6-membered heteroaryl group;

in the Group $R^4$, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and the C6-C10 aryl group and the 5- or 6-membered heteroaryl group may optionally have one or more substituents selected from Group 4, provided that when they have two or more substituents, then the substituents may be same or different;

the Group 4 consists of halogen, a cyano group, a nitro group, a formyl group, a C1-C6 alkyl group, a C1-C6 alkoxy group, a (C1-C6 alkoxy)C1-C6 alkyl group, a C2-C6 alkenyl group, a C2-C6 alkynyl group, a C3-C6 cycloalkyl group, a C1-C6 alkylthio group, a C1-C6 alkylsulfinyl group, a C1-C6 alkylsulfonyl group, a C1-C6 alkylamino group, a di(C1-C6 alkyl)amino group, a C3-C6 cycloalkylamino group, a (C1-C6 alkyl)carbonyl group, a (C3-C6 cycloalkyl)carbonyl group, a (C1-C6 alkoxy)carbonyl group, a (C1-C6 alkylamino)carbonyl group, a di(C1-C6 alkyl)aminocarbonyl group, a (C3-C6 cycloalkylamino)carbonyl group, and a tri(C1-C6 alkyl)silyl group;

in the Group 4, the C1-C6 alkyl group, the C1-C6 alkoxy group, the (C1-C6 alkoxy)C1-C6 alkyl group, the C2-C6 alkenyl group, the C2-C6 alkynyl group, the C3-C6 cycloalkyl group, the C1-C6 alkylthio group, the C1-C6 alkylsulfinyl group, the C1-C6 alkylsulfonyl group, the (C1-C6 alkyl)carbonyl group, the (C3-C6 cycloalkyl)carbonyl group, and the (C1-C6 alkoxy)carbonyl group may be optionally substituted with one or more halogens, provided that when they are substituted with two or more halogens, then the halogens may be same or different; and n represents an integer of 0, 1 or 2.

2. The method according to claim 1, wherein G is a phenyl group wherein the phenyl group may optionally have one or more substituents selected from the Group $R^4$, provided that when it has two or more substituents, then the substituents may be same or different.

3. The method according to claim 1, wherein the Group $R^4$ is Group $R^{4-3}$;

wherein the Group $R^{4-3}$ consists of halogen, a cyano group, a nitro group, a C1-C6 alkyl group, a C1-C6 alkoxy group, a C3-C6 cycloalkyl group, a C2-C6 alkynyl group, and a phenyl group;

in the Group $R^{4-3}$, the C1-C6 alkyl group, the C1-C6 alkoxy group, the C3-C6 cycloalkyl group, and the C2-C6 alkynyl group may be optionally substituted with one or more halogens, provided that when they are substituted with two or more halogens, then the halogens may be same or different; and the phenyl group may optionally have one or more substituents selected from Group 4-3, provided that when it has two or more substituents, then the substituents may be same or different;

the Group 4-3 consists of halogen and a C1-C6 alkyl group;

in the Group 4-3, the C1-C6 alkyl group may be optionally substituted with one or more halogens, provided that when it is substituted with two or more halogens, then the halogens may be same or different.

4. The method according to claim 3, wherein $R^2$ is hydrogen, a C1-C6 alkyl group or a phenyl group wherein the C1-C6 alkyl group may be optionally substituted with one or more halogens, provided that when it is substituted with two or more halogens, then the halogens may be same or different, and the phenyl group may optionally have one or more halogens, provided that when it has two or more halogens, then the halogens may be same or different;

$R^3$ is hydrogen, a C1-C6 alkyl group, a (C1-C6 alkoxy)C1-C6 alkyl group, or a benzyl group wherein the C1-C6 alkyl group and the (C1-C6 alkoxy)C1-C6 alkyl group may be optionally substituted with one or more halogens, provided that when they are substituted with two or more halogens, then the halogens may be same or different; and the benzyl group may optionally have one or more substituents selected from the group consisting of halogen, a C1-C6 alkyl group, and C1-C6 alkoxy group, provided that when it has two or more substituents, then the substituents may be same or different;

$R^5$ is a C1-C6 alkyl group or a phenyl group wherein the C1-C6 alkyl group may be optionally substituted with one or more halogens, provided that when it is substituted with two or more halogens, then the halogens may be same or different; and the phenyl group may optionally have a C1-C6 alkyl group, provided that when it has two or more C1-C6 alkyl groups, then the C1-C6 alkyl groups may be same or different; and G is a phenyl group, a pyridyl group, an indolyl group or a pyrazolyl group wherein the phenyl group, the pyridyl group, the indolyl group and the pyrazolyl group may optionally have one or more substituents selected from Group $R^{4-3}$, provided that when they have two or more substituents, then the substituents may be same or different.

5. The method according to claim 1, wherein $R^2$ is a methyl group, a 4-fluorophenyl group or a trifluoromethyl group, $R^3$ is a methyl group or a benzyl group, $R^5$ is a methyl group or a 4-methylphenyl group, and G is a 2,4,6-triethylphenyl group, a 2-ethyl-5-(4-chlorophenyl)phenyl group, a 1-methylindol-3-yl group or a 2,6-diethyl-4-methylphenyl group.

* * * * *